US012565496B2

(12) United States Patent
Schulze et al.

(10) Patent No.: US 12,565,496 B2
(45) Date of Patent: Mar. 3, 2026

(54) SUBSTITUTED 1H-PYRROLO[3,2-B]PYRIDINE COMPOUNDS AND METHODS OF USE THEREOF

(71) Applicants: Bayer Aktiengesellschaft, Leverkusen (DE); The Broad Institute, Inc., Cambridge, MA (US); Dana-Farber Cancer Institute, Inc., Boston, MA (US)

(72) Inventors: Volker Schulze, Hohen Neuendorf (DE); Anne Mengel, Berlin (DE); Adelaide Clara Faria Alvares De Lemos, Berlin (DE); Sven Christian, East Boston, MA (US); Ulf Bömer, Glienicke (DE); Roman Hillig, Berlin (DE); Christian Lechner, Berlin (DE); Jérémie Xavier Mortier, Berlin (DE); Stefan Kaulfuss, Berlin (DE); Steven Corsello, Boston, MA (US); Katarzyna Handing, Framingham, MA (US); Amael Madec, Boston, MA (US); Laura Furst, Somerville, MA (US); Mrinal Shekhar, Quincy, MA (US); Markus Berger, Berlin (DE); Rajesha Rupaimoole, North Billerica, MA (US); Philip Lienau, Leverkusen (DE); Douglas Orsi, Watertown, MA (US); David McKinney, Cambridge, MA (US); Krzysztof Brzezinka, Berlin (DE)

(73) Assignees: Bayer Aktiengesellschaft, Leverkusen (DE); The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 435 days.

(21) Appl. No.: 18/018,221

(22) PCT Filed: Jul. 27, 2021

(86) PCT No.: PCT/EP2021/070998
§ 371 (c)(1),
(2) Date: Jan. 26, 2023

(87) PCT Pub. No.: WO2022/023341
PCT Pub. Date: Feb. 3, 2022

(65) Prior Publication Data

US 2023/0339939 A1 Oct. 26, 2023

Related U.S. Application Data

(60) Provisional application No. 63/058,239, filed on Jul. 29, 2020.

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
CPC ............................ C07D 471/04; C07D 487/04
See application file for complete search history.

(56) References Cited

U.S. PATENT DOCUMENTS

| | | | |
|---|---|---|---|
| 8,084,395 | B2 * | 12/2011 | Selles et al. |
| 8,546,413 | B2 | 10/2013 | Marchionni et al. |
| 12,227,501 | B2 | 2/2025 | Schulze et al. |
| 2004/0209897 | A1 | 10/2004 | Vernier et al. |
| 2016/0176871 | A1 | 6/2016 | Fink et al. |
| 2023/0046077 | A1 | 2/2023 | Schulze et al. |
| 2023/0322767 | A1 | 10/2023 | Schulze et al. |
| 2023/0365554 | A1 | 11/2023 | Schulze et al. |
| 2023/0391769 | A1 | 12/2023 | Schulze et al. |

FOREIGN PATENT DOCUMENTS

| | | | |
|---|---|---|---|
| WO | WO-99/20624 | A1 | 4/1999 |
| WO | WO-2005/013986 | A1 | 2/2005 |
| WO | WO-2007/067506 | A2 | 6/2007 |
| WO | WO-2008/132434 | A2 | 11/2008 |
| WO | WO-2010/046215 | A2 | 4/2010 |
| WO | WO-2010/070237 | A1 | 6/2010 |
| WO | WO-2010/070238 | A1 | 6/2010 |
| WO | WO-2011/053476 | A1 | 5/2011 |
| WO | WO-2015/073763 | A1 | 5/2015 |
| WO | WO-2015/195880 | A1 | 12/2015 |
| WO | WO-2016/100166 | A1 | 6/2016 |
| WO | WO-2016/120196 | A1 | 8/2016 |
| WO | WO-2017/079558 | A1 | 5/2017 |
| WO | WO-2020/161257 | A1 | 8/2020 |
| WO | WO-2022/023337 | A1 | 2/2022 |
| WO | WO-2022/023339 | A1 | 2/2022 |
| WO | WO-2022/023340 | A1 | 2/2022 |
| WO | WO-2022/023341 | A1 | 2/2022 |
| WO | WO-2023/147015 | A1 | 8/2023 |

OTHER PUBLICATIONS

International Search Report For International Application No. PCT/EP2020/053020 dated May 6, 2020.
Golub et al., "Molecular classification of cancer: class discovery and class prediction by gene expression monitoring." Science 286 (1999): 531-537.
Lala et al., "Role of nitric oxide in tumor progression: lessons from experimental tumors." Cancer and Metastasis Reviews 17 (1998): 91-106.
MedlinePlus, "Cancer" (2007): 10 pages.
(Continued)

*Primary Examiner* — Brandon J Fetterolf
(74) *Attorney, Agent, or Firm* — Foley Hoag LLP; David P. Halstead; David S. Surry

(57) ABSTRACT

Compounds of formula (I), process for their production and their use as pharmaceuticals.

17 Claims, No Drawings

Specification includes a Sequence Listing.

(56) References Cited

OTHER PUBLICATIONS

Bibian, Mathieu, et al. Development of highly selective casein kinase 1delta/1epsilon (CK1delta/epsilon) inhibitors with potent antiproliferative properties. Bioorganic & medicinal chemistry letters, 2013, 23.15: 4374-4380.
Huart, Anne-Sophie, et al. A Casein kinase 1/Checkpoint kinase 1 pyrazolo-pyridine protein kinase inhibitor as novel activator of the p53 pathway. Bioorganic & medicinal chemistry letters, 2013, 23.20: 5578-5585.
International Search Report and Written Opinion for Application No. PCT/US2023/011694 dated Apr. 27, 2023.
International Search Report and Written Opinion for International Application No. PCT/EP2021/070992 dated Nov. 3, 2021.
International Search Report and Written Opinion for International Application No. PCT/EP2021/070994 dated Oct. 27, 2021.
International Search Report and Written Opinion for International Application No. PCT/EP2021/070996 dated Nov. 19, 2021.
International Search Report and Written Opinion for International Application No. PCT/EP2021/070998 dated Oct. 20, 2021.
Jaras, Marcus, et al. Csnk1a1 inhibition has p53-dependent therapeutic efficacy in acute myeloid leukemia. Journal of Experimental Medicine, 2014, 211.4: 605-612. DOI: <10.1084/jem.20131033>. Published: Mar. 10, 2014.
Knippschild, Uwe, et al. The CK1 family: contribution to cellular stress response and its role in carcinogenesis. Frontiers in oncology, 2014, 4: 96. Published: May 19, 2014.
Shanware, Naval P., et al. Non-specific in vivo inhibition of CK1 by the pyridinyl imidazole p38 inhibitors SB 203580 and SB 202190. BMB reports, 2009, 42.3: 142. doi: 10.5483/bmbrep.2009.42.3.142. Published: Mar. 31, 2009.
Extended European Search Report for EP Application No. 24196936.9 dated Jan. 28, 2025.
Extended European Search Report for EP Application No. 24206778.3 dated Mar. 21, 2025.

* cited by examiner

SUBSTITUTED 1H-PYRROLO[3,2-B]PYRIDINE COMPOUNDS AND METHODS OF USE THEREOF

RELATED APPLICATIONS

This application is a § 371 national-stage application based on PCT/EP21/70998, filed Jul. 27, 2021, the specification of which is hereby incorporated by reference in its entirety, which claims the benefit of U.S. Provisional Patent Application Ser. No. 63/058,239, filed Jul. 29, 2020.

REFERENCE TO A SEQUENCE LISTING

This application contains a Sequence Listing in computer readable form. The computer readable form is incorporated herein by reference. Said ASCII copy, created on Sep. 2, 2025, is named BRH-04701_SL.txt and is 2,117 bytes in size.

INTRODUCTION

The invention relates to substituted 2-[2-(acylamino)pyridin-4-yl]-1H-pyrrolo[3,2-b]pyridin compounds, a process for their production and uses thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The members of the casein kinase 1 (CSNK1) family are highly conserved and are expressed in many eukaryotes ranging from yeast to humans. Mammalian CSNK1 isoforms (α, β, γ, δ, ε) and their splice variants are involved in diverse cellular processes including membrane trafficking, circadian rhythm, cell cycle progression, chromosome segregation, apoptosis and cellular differentiation. Mutations and deregulation of CSNK1 expression and activity have been linked to proliferative diseases such as cancer (Knippschild, Onkologie 2005; 28:508-514).

CSNK1 substrates are enzymes, transcription factors, splice factors, cytoskeleton proteins, receptors, membrane-associated proteins and cell signaling proteins. Since recognition motifs for CSNK1 are found on most cellular proteins, more than 140 in vitro and in vivo substrates have been reported thus far (Knippschild et al., Front Oncol. 2014 May 19; 4:96). Several known substrates especially of the CSNK1a and 5 isoforms are involved in oncogenic signaling pathways as Wnt/β-catenin (β-catenin; dishevelled (DVL); adenomatous polyposis coli (APC); nuclear factor of activated Tcells, cytoplasmic 3 (NFATC3)), p53 (p53; p53/E3 ubiquitin-protein ligase Mdm2 (MDM2)), P13K/AKT (forkhead box protein 01 (Foxo1)), death receptor signaling (Fas-associated death domain protein (FADD); and BH3-interactive domain death agonist (BID)) (Schittek and Sinnberg Molecular Cancer 2014, 13:231). A distinctive feature of CSNK1 family members is their exclusive need of ATP to phosphorylate their substrates and their independency of other co-factors.

CSNK1a plays a role in the mitotic spindle formation during cell division and in DNA repair mechanisms, and participates in RNA metabolism. Antibodies specific for CSNK1a block cell cycle progression during M phase in mouse oocytes, which indicates that CSNK1a is required for proper cell cycle progression in these cells. CSNK1a can be found at the centrosomes, microtubule asters and the kinetochore. Similarly, CSNK1a regulates apoptotic signaling pathways, however, there seems to be cell type-specific differences. CSNK1a has been shown to have an anti-apoptotic function in the extrinsic apoptosis pathway. Its inhibition increased Fas-induced apoptosis in Hela cells, whereas the overexpression of CSNK1a delayed cell death, caused by the phosphorylation of BID, prevented the caspase 8 dependent cleavage of BID. In addition, CSNK1a inhibits TRAIL induced apoptosis by modification of the TNF receptor or FADD at the death-inducing signaling complex (DISC). Therefore downregulation of CSNK1a leads to an enhancement of TRAIL-induced cell death. Likewise, CSNK1a promotes cell survival by interacting with the retinoid X receptor (RXR). Downregulation of CSNK1a enhances the apoptotic effect of RXR agonists (Schittek and Sinnberg, Molecular Cancer 2014, 13:231).

Knockdown or downregulation of CSNK1a in the intestinal epithelium of mice, in human colon cancers or in leukemia cells triggers p53 activation. Similarly, one study showed that CSNK1a stably associates with MDM2, stimulates MDM2-p53 binding, and cooperates with MDM2 to inactivate p53. These data suggest that inhibition of CSNK1a activity increases p53 activity. The knockdown of CSNK1a induces p53 transcriptional activity by reducing the inhibitory effect of MDM2 for p53 since MDM2 phosphorylation is necessary for interaction with p53 (Schittek and Sinnberg, Molecular Cancer 2014, 13:231).

Ribosomal protein S6 (RPS6) is a critical component of the 40S ribosomal subunit that mediates translation initiation. RPS6 activity is regulated by phosphorylation by CSNK1α, which phosphorylates serine residue 247, enhancing the phosphorylation of upstream sites (Hutchinson et al., JBC, 2011, 286, 10, 8688). CSNK1a inhibition leads to dramatic reduction in RPS6 phosphorylation and activation of p53, resulting in selective elimination of solid tumor and AML cells. Pharmacological inhibition of CSNK1α in p53 wt colon and lung carcinoma as well as in AML induces p53 accumulation along with apoptosis. Targeting of CSNK1a provides a potential approach to the therapeutic activation of p53 in AML, a disorder predominantly associated with non-mutated p53 (Jaras et al., J. Exp. Med. 2014, 211, 4, 605).

CSNK1α is an essential participant in the aberrant NF-kB activity required for ABC DLBCL subtype survival. CSNK1α knockdown is specifically lethal to ABC DLBCL cells (Bidere, Nature, 458, 5 Mar. 2009). Pharmacological inhibition of CSNK1α will specifically kill ABC-DLBCL due to the blocking of the CARD11-Bcl-10-MALT1 complex (CBM complex).

Thus, pharmacological inhibition of CSNK1α represents a new approach for the treatment of proliferative disorders, including solid tumors such as carcinomas, sarcomas, leukaemias and lymphoid malignancies or other disorders, associated with uncontrolled cellular proliferation.

Due to the fact that especially cancer disease, being expressed by uncontrolled proliferative cellular processes in tissues of different organs of the human- or animal body is still not considered to be a controlled disease in that sufficient drug therapies do not already exist, there is a strong need to provide further new therapeutically useful drugs, preferably those inhibiting new targets and providing new therapeutic options.

Therefore, inhibitors of Casein kinase 1 alpha and/or delta represent valuable compounds as single agent therapies that in some instances, can complement other therapeutic options either as single agents or in combination with other drugs.

WO 2016/120196 discloses 4H-pyrrolo[3,2-c]pyridin-4-one derivatives, which may be useful as Bub1 kinase inhibitors.

WO 2008/132434 relates to a method of preventing and/or controlling fungal infection in plants and/or plant propagation material comprising applying to the plant or plant propagation material a fungicidally effective amount of a compound, and to such pyrrolopyridine compounds.

SUMMARY OF THE INVENTION

The invention provides compounds that inhibit Casein kinase 1 alpha and/or Casein kinase 1 delta.

It has now been found that compounds of the present invention have surprising and advantageous properties. In particular, compounds of the present invention have surprisingly been found to effectively inhibit CSNK1A1. Furthermore, in certain embodiments, compounds of the present invention additionally show low inhibition of wild type-EGFR kinase.

In certain embodiments, compounds of the present invention display an $IC_{50}$ below 100 nM in a CSNK1A1 kinase assay in the presence of 1 μM ATP and are less potent than 600 nM in a wild type-EGFR kinase assay in the presence of 2 mM ATP.

In certain embodiments, compounds of the present invention display an $IC_{50}$ below 125 nM in a CSNK1A1 kinase assay in the presence of 1 mM ATP and are less potent than 100 nM in a wild type-EGFR kinase assay in the presence of 2 mM ATP.

In general, reduced or no inhibition of other kinases and specifically reduced or no inhibition of wild type EGFR kinase, in particular in a high ATP assay (e.g. with a concentration of 2 mM ATP), is considered to be relevant in the clinical setting to avoid/reduce unwanted side effects associated with the inhibition of said wild type EGFR kinase, such as, for example, skin rash and GI toxicity.

DESCRIPTION OF THE INVENTION

In accordance with a first aspect, the invention relates to compounds of formula (I), (I)

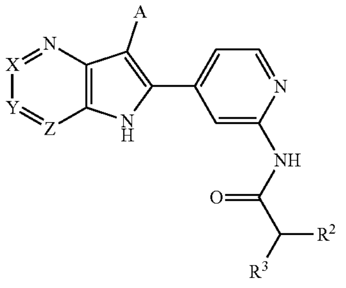

in which:

A represents a group selected from:

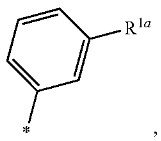
,
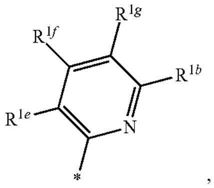
,
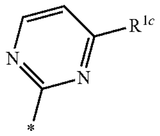
and
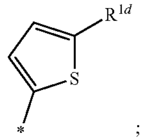
;

X represents N, C—H, C—F, C—Cl, or C-Me;
Y represents N, or C—$R^{4a}$;
Z represents N, or C—$R^{4b}$,
wherein none or one of X, Y, and Z represents N;
$R^{1a}$ represents hydrogen or fluoro;
$R^{1b}$ represents hydrogen or halogen;
$R^{1c}$ represents hydrogen or fluoro;
$R^{1d}$ represents hydrogen or halogen;
$R^{1e}$ represents hydrogen or halogen;
$R^{1f}$ represents hydrogen or fluoro;
$R^{1g}$ represents hydrogen or fluoro;
$R^2$ represents hydrogen, halogen, methoxy, cyano, $C_1$-$C_3$-alkyl, or $C_1$-$C_3$-alkoxy-$C_1$-$C_3$-alkyl-;
$R^3$ represents phenyl, wherein said phenyl is independently optionally substituted, one or more times, with halogen, methyl, methoxy, $C_1$-$C_2$-haloalkyl, or $C_1$-$C_2$-haloalkoxy;
$R^{4a}$ represents hydrogen, halogen, $C_1$-$C_3$-alkyl, $C_2$-$C_3$-alkenyl, methoxy, difluoromethoxy, trifluoromethoxy, $C_3$-$C_4$-cycloalkyl, 4- to 5-membered heterocycloalkyl, cyclopropyloxy, 4- to 5-membered heterocycloalkyl-O—, or $R^{5a}R^{6a}N$— wherein said 4- to 5-membered heterocycloalkyl and 4- to 5-membered heterocycloalkyl-O— are optionally substituted, one or two times, with methyl; $R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_6$-cycloalkyl, $C_3$-$C_6$-cycloalkyl-$C_1$-$C_4$-alkyl, $C_3$-$C_6$-cycloalkyl-O—, $C_3$-$C_6$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl, $C_1$-$C_4$-hydroxyalkyl-O—, or 3- to 6-membered heterocycloalkyl-$C_1$-$C_3$-alkyl-, wherein said $C_3$-$C_6$-cycloalkyl, $C_3$-$C_6$-cycloalkyl-$C_1$-$C_4$-alkyl, $C_3$-$C_6$-cycloalkyl-O—, $C_3$-$C_6$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl, $C_1$-$C_4$-hydroxyalkyl-O— and 3- to 6-membered heterocycloalkyl-$C_1$-$C_3$-alkyl groups are optionally substituted, one, two or three times, with halogen, methyl, methoxy, or trifluoromethoxy;

$R^{5a}$ represents hydrogen, methyl, cyclopropyl, methoxyethyl, or 3- to 5-membered heterocycloalkyl;

$R^{6a}$ represents hydrogen or methyl, or $R^{5a}$ and $R^{6a}$, together with the nitrogen atom to which they are attached, represent a 4- to 5-membered heterocyclic ring, wherein said heterocyclic ring is optionally substituted, one or two times, with methyl;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

A represents a group selected from:

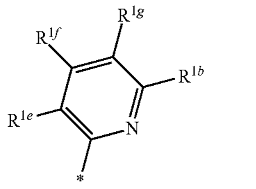

and

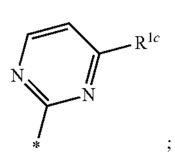

;

X represents N, C—H, C—F, C—Cl, or C-Me;

Y represents N, or C—$R^{4a}$;

Z represents N, or C—$R^{4a}$, wherein none or one of X, Y, and Z represents N;

$R^{1b}$ represents hydrogen or halogen;

$R^{1c}$ represents hydrogen or fluoro;

$R^{1e}$ represents hydrogen or fluoro;

$R^{1f}$ represents hydrogen or fluoro;

$R^{1g}$ represents hydrogen or fluoro;

$R^2$ represents hydrogen, halogen, methoxy, cyano, $C_1$-$C_2$-alkyl, or $C_1$-$C_3$-alkoxy-$C_1$-$C_3$-alkyl-;

$R^3$ represents phenyl, wherein said phenyl is independently optionally substituted, one or more times, with halogen, methyl, methoxy, $C_1$-$C_2$-haloalkyl, or $C_1$-$C_2$-haloalkoxy;

$R^{4a}$ represents hydrogen, halogen, $C_1$-$C_3$-alkyl, $C_2$-alkenyl, methoxy, difluoromethoxy, $C_3$-cycloalkyl, 4-membered heterocycloalkyl, cyclopropyloxy, 4-membered heterocycloalkyl-O—, or $R^{5a}R^{6a}N$—;

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_5$-cycloalkyl, $C_3$-$C_5$-cycloalkyl-$C_1$-$C_2$-alkyl, $C_3$-$C_5$-cycloalkyl-O—, $C_3$-$C_5$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_1$-$C_3$-alkyl-, $C_1$-$C_3$-alkoxy-$C_2$-$C_3$-alkoxy-, or $C_1$-$C_4$-hydroxyalkyl, $C_1$-$C_4$-hydroxyalkyl-O—, wherein said $C_3$-$C_5$-cycloalkyl, $C_3$-$C_5$-cycloalkyl-$C_1$-$C_2$-alkyl, $C_3$-$C_5$-cycloalkyl-O—, $C_3$-$C_5$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl and $C_1$-$C_4$-hydroxyalkyl-O— groups are optionally substituted one, two or three times with halogen, methyl, or methoxy;

$R^{5a}$ represents hydrogen or methyl;

$R^{6a}$ represents hydrogen or methyl, or $R^{5a}$ and $R^{6a}$, together with the nitrogen atom to which they are attached, represent a 4-membered heterocyclic ring, wherein said heterocyclic ring is optionally substituted with methyl;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

A represents a group selected from:

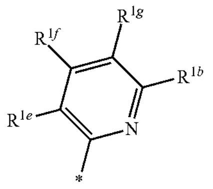

and

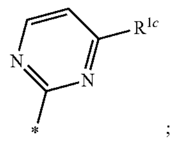

;

X represents N, C—H, C—F, or $C_1$-$C_1$;

Y represents N or C—$R^{4a}$;

Z represents N or C—$R^{4b}$, wherein none or one of X, Y and Z represents N; $R^{1b}$ represents hydrogen or fluoro; $R^{1c}$ represents hydrogen; $R^{1e}$ represents hydrogen; $R^{1f}$ represents hydrogen or fluoro; $R^{1g}$ represents hydrogen or fluoro;

$R^2$ represents hydrogen, $C_1$-$C_2$-alkyl, or $C_1$-$C_2$-alkoxy-$C_1$-$C_2$-alkyl-;

$R^3$ represents phenyl, wherein said phenyl is independently optionally substituted, one or more times, with halogen, methyl, or Cr-haloalkyl;

$R^{4a}$ represents hydrogen, halogen, $C_1$-alkyl, $C_2$-alkenyl, $C_3$-cycloalkyl, 4-membered heterocycloalkyl, or $R^{5a}R^{6a}N$—;

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—, wherein said $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_2$-$C_3$-alkoxy-, $C_1$-$C_4$-hydroxyalkyl and $C_1$-$C_4$-hydroxyalkyl-O— groups are optionally substituted, one or two times, with halogen or methyl;

$R^{5a}$ represents hydrogen or methyl;

$R^{6a}$ represents hydrogen or methyl, or $R^{5a}$ and $R^{6a}$, together with the nitrogen atom to which they are attached, represent a 4-membered heterocyclic ring;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

A represents:

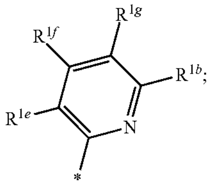

X represents C—H, C—F;

Y represents N or C—$R^{4a}$;

Z represents N or C—$R^{4b}$;

wherein none or one of Y and Z represents N;

$R^{1b}$ represents hydrogen or fluoro;

$R^{1e}$ represents hydrogen;

$R^{1f}$ represents hydrogen;

$R^{1g}$ represents hydrogen or fluoro;

$R^2$ represents hydrogen, methyl, or C-alkoxy-$C_1$-$C_2$-alkyl-;

$R^3$ represents phenyl, wherein said phenyl is independently optionally substituted, one or more times, with halogen or methyl;

$R^{4a}$ represents hydrogen, halogen, or methyl;

$R^{4b}$ represents hydrogen, halogen, $C_1$-$C_4$-alkyl, $C_1$-$C_3$-haloalkyl-$CH_2$—, $C_1$-$C_3$-alkoxy, $C_1$-$C_3$-haloalkoxy, $C_3$-cycloalkyl, $C_3$-cycloalkyl-$C_1$-$C_2$-alkyl, $C_3$-cycloalkyl-O—, $C_3$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

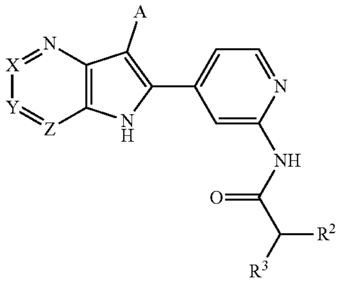

(I)

in which:

A represents a group selected from:

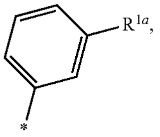 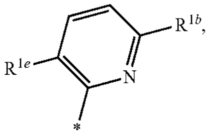 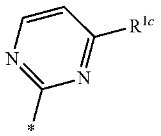 and 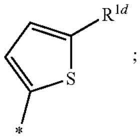 ;

X represents N, C—H, C—F, C—Cl, or C-Me;

Y represents N or C—$R^{4a}$;

Z represents N or C—$R^{4a}$, wherein none or one of X, Y, and Z represents N;

$R^{1a}$ represents hydrogen or fluoro;

$R^{1b}$ represents hydrogen or halogen;

$R^{1c}$ represents hydrogen or fluoro;

$R^{1d}$ represents hydrogen or halogen;

$R^{1e}$ represents hydrogen, halogen, or methyl;

$R^2$ represents hydrogen, halogen, methoxy, cyano, or $C_1$-$C_3$-alkyl;

$R^3$ represents phenyl, wherein said phenyl is independently optionally substituted, one or more times, with halogen, methyl, methoxy, $C_1$-$C_2$-haloalkyl, or $C_1$-$C_2$-haloalkoxy;

$R^{4a}$ represents hydrogen, halogen, $C_1$-$C_3$-alkyl, $C_2$-$C_3$-alkenyl, methoxy, trifluoromethoxy, $C_3$-$C_4$-cycloalkyl, 4- to 5-membered heterocycloalkyl, cyclopropyloxy, 4- to 5-membered heterocycloalkyl-O—, or $R^{5a}R^{6a}$N—, wherein said 4- to 5-membered heterocycloalkyl and 4- to 5-membered heterocycloalkyl-O— are optionally substituted, one or two times, with methyl;

$R^{4b}$ represents hydrogen, halogen, $C_1$-$C_4$-alkyl, $C_2$-$C_4$-alkenyl, $C_1$-$C_4$-haloalkyl, $C_1$-$C_3$-alkoxy, $C_1$-$C_3$-haloalkoxy, $C_3$-$C_6$-cycloalkyl, $C_3$-$C_5$-cycloalkyl-C, —$C_4$-alkyl, $C_3$-$C_6$-cycloalkyl-O—, $C_3$-$C_5$-cycloalkyl-$CH_2$—O—, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, or 3- to 6-membered heterocycloalkyl-$CH_2$—O—, wherein said $C_3$-$C_6$-cycloalkyl, $C_3$-$C_6$-cycloalkyl-$C_1$-$C_4$-alkyl, $C_3$-$C_5$-cycloalkyl-O—, $C_3$-$C_5$-cycloalkyl-$CH_2$—O—, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, and 3- to 6-membered heterocycloalkyl-$CH_2$—O— groups are optionally substituted, one, two or three times, with halogen, methyl, methoxy, or trifluoromethoxy; $R^{5a}$ represents hydrogen, methyl, cyclopropyl, methoxyethyl, or 3- to 5-membered heterocycloalkyl;

$R^{5a}$ represents hydrogen or methyl, or $R^{5a}$ and $R^{6a}$, together with the nitrogen atom to which they are attached, represent a 4- to 5-membered heterocyclic ring, wherein said heterocyclic ring is optionally substituted, one or two times, with methyl;

or an N-oxide, a salt, a tautomer or a stereoisomer of said compound, or a salt of said N-oxide, tautomer or stereoisomer.

One aspect of the invention are compounds of formula (I) as described in the examples, as characterized by their names in the title, as claimed in claim 5, and/or their structures as well as the subcombinations of all residues specifically disclosed in the compounds of the examples.

Another aspect of the present invention are the intermediates used for their synthesis.

One special aspect of the invention are intermediates (VII-A), or a salt thereof:

(VII-A)

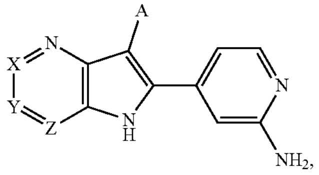

in which A, X, Y and Z are as defined herein for the compound of general formula (I).

Another aspect of the invention relates to the use of intermediates (VII-A), or a salt thereof:

(VII-A)

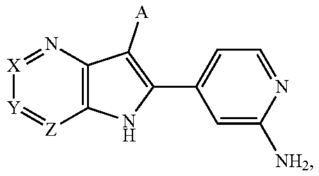

in which A, X, Y and Z are as defined herein for the compound of general formula (I), for preparing a compound of formula (I) as defined herein or an N-oxide, a salt, a tautomer or a stereoisomer of said compound, or a salt of said N-oxide, tautomer or stereoisomer.

One special aspect of the invention are intermediates (IX-Q), or a salt thereof:

(IX-Q)

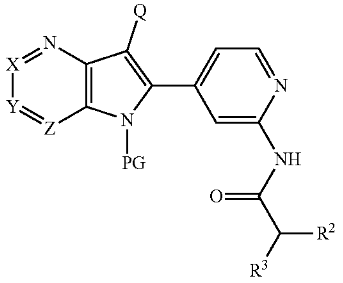

in which $R^2$, $R^3$, X, Y and Z are as defined herein for the compound of general formula (I) and Q represents a chloro, a bromo or an iodo, and PG represents a protecting group.

Another aspect of the invention relates to the use of intermediates (IX-Q), or a salt thereof:

(IX-Q)

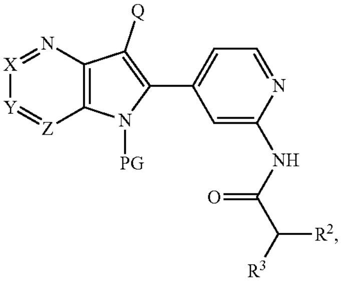

in which $R^2$, $R^3$, X, Y and Z are as defined for the compound of general formula (I) and Q represents a chloro, a bromo or an iodo, and PG represents a protecting group, for the preparation of a compound of formula (I) as defined herein or an N-oxide, a salt, a tautomer or a stereoisomer of said compound, or a salt of said N-oxide, tautomer or stereoisomer.

One special aspect of the invention are intermediates (IX-A), or a salt thereof:

(IX-A)

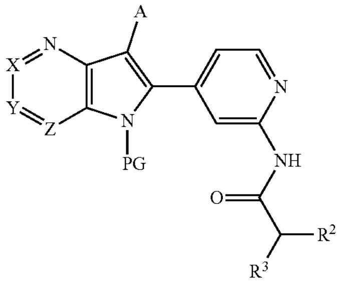

in which $R^2$, $R^3$, A, X, Y and Z are as defined herein for the compound of general formula (I) and PG represents a protecting group.

Another aspect of the invention relates to the use of intermediates (IX-A), or a salt thereof:

(IX-A)

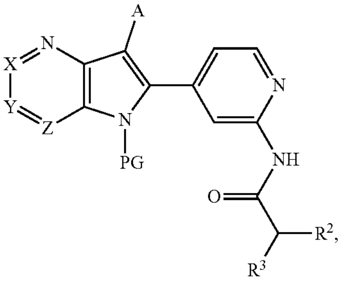

in which $R^2$, $R^3$, A, X, Y and Z are as defined for the compound of general formula (I) and PG represents a protecting group, for the preparation of a compound of formula (I) as defined herein or an N-oxide, a salt, a tautomer or a stereoisomer of said compound, or a salt of said N-oxide, tautomer or stereoisomer.

One special aspect of the invention are intermediates (XIV-Q), or a salt thereof:

(XIV-Q)

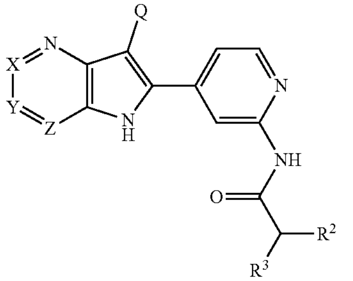

in which $R^2$, $R^3$, X, Y and Z are as defined for the compound of general formula (I) and Q represents a chloro, a bromo or an iodo.

Another aspect of the invention relates to the use of intermediates (XIV-Q), or a salt thereof:

(XIV-Q)

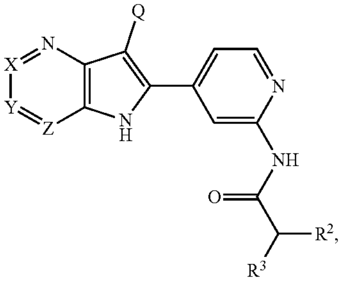

in which $R^2$, $R^3$, X, Y and Z are as defined for the compound of general formula (I) and Q represents a chloro, a bromo or an iodo for the preparation of a compound of formula (I) as defined herein or an N-oxide, a salt, a tautomer or a stereoisomer of said compound, or a salt of said N-oxide, tautomer or stereoisomer.

One special aspect of the invention are intermediates (XVII), or a salt thereof:

(XVII)

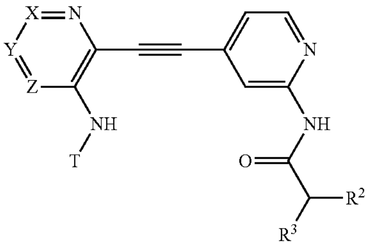

in which $R^2$, $R^3$, X, Y and Z are as defined for the compound of general formula (I), and T represents $CF_3$—C(O)—, mesylate, tosylate or Ph-$SO_2$—, wherein Ph can be substituted one, two or three times with halogen or a methyl group or a nitro group.

Another aspect of the invention relates to the use of intermediates (XVII), or a salt thereof:

(XVII)

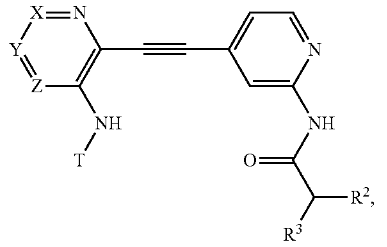

in which $R^2$, $R^3$, X, Y and Z are as defined for the compound of general formula (I), and T represents $CF_3$—C(O)—, mesylate, tosylate or Ph-$SO_2$—, wherein Ph can be substituted one, two or three times with halogen or a methyl group or a nitro group, for the preparation of a compound of formula (I) as defined herein or an N-oxide, a salt, a tautomer or a stereoisomer of said compound, or a salt of said N-oxide, tautomer or stereoisomer.

Another aspect of the invention relates to the use of any of the intermediates described herein for preparing a compound of formula (I) as defined herein or an N-oxide, a salt, a tautomer or a stereoisomer of said compound, or a salt of said N-oxide, tautomer or stereoisomer.

In further embodiments of the above-mentioned aspects, the invention relates to compounds of formula (I), wherein:

A represents a group selected from:

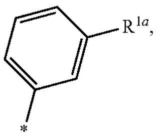 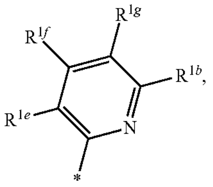

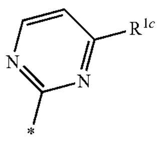 and 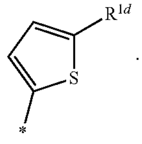 .

In further embodiments of the above-mentioned aspects, the invention relates to compounds of formula (I), wherein:

A represents a group selected from:

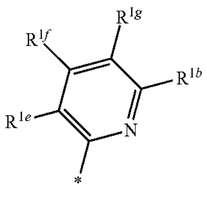 and 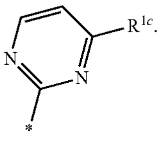

In further embodiments of the above-mentioned aspects, the invention relates to compounds of formula (I), wherein:

A represents a group selected from:

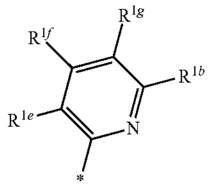 and 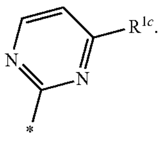

In further embodiments of the above-mentioned aspects, the invention relates to compounds of formula (I), wherein:

A represents:

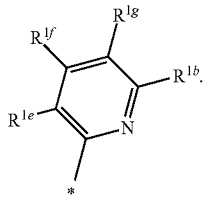

In further embodiments of the above-mentioned aspects, the invention relates to compounds of formula (I), wherein:

A represents:

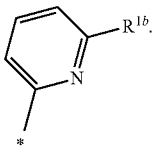

In further embodiments of the above-mentioned aspects, the invention relates to compounds of formula (I), wherein:

X represents N, C—H, C—F, $C_1$-$C_1$, or C-Me.

In further embodiments of the above-mentioned aspects, the invention relates to compounds of formula (I), wherein:

X represents N, C—H, C—F, or C—Cl.

In further embodiments of the above-mentioned aspects, the invention relates to compounds of formula (I), wherein:

X represents C—H or C—F.

In further embodiments of the above-mentioned aspects, the invention relates to compounds of formula (I), wherein:

X represents C—F.

In further embodiments of the above-mentioned aspects, the invention relates to compounds of formula (I), wherein:

X represents N.

In further embodiments of the above-mentioned aspects, the invention relates to compounds of formula (I), wherein:

Y represents N or C—$R^{4a}$.

In further embodiments of the above-mentioned aspects, the invention relates to compounds of formula (I), wherein:

Y represents C—$R^4$.

In further embodiments of the above-mentioned aspects, the invention relates to compounds of formula (I), wherein:

Y represents N.

In further embodiments of the above-mentioned aspects, the invention relates to compounds of formula (I), wherein:

Z represents N or C—$R^{4b}$.

In further embodiments of the above-mentioned aspects, the invention relates to compounds of formula (I), wherein:

Z represents N.

In further embodiments of the above-mentioned aspects, the invention relates to compounds of formula (I), wherein:

Z represents C—$R^{4b}$.

In further embodiments of the above-mentioned aspects, the invention relates to compounds of formula (I), wherein:

$R^{1a}$ represents hydrogen or fluoro.

In further embodiments of the above-mentioned aspects, the invention relates to compounds of formula (I), wherein:

$R^{1b}$ represents hydrogen or halogen.

In further embodiments of the above-mentioned aspects, the invention relates to compounds of formula (I), wherein:

$R^{1b}$ represents hydrogen or fluoro.

In further embodiments of the above-mentioned aspects, the invention relates to compounds of formula (I), wherein:

$R^{1b}$ represents hydrogen.

In further embodiments of the above-mentioned aspects, the invention relates to compounds of formula (I), wherein:

$R^{1c}$ represents hydrogen or fluoro.

In further embodiments of the above-mentioned aspects, the invention relates to compounds of formula (I), wherein:

$R^{1c}$ represents hydrogen.

In further embodiments of the above-mentioned aspects, the invention relates to compounds of formula (I), wherein:

$R^{1d}$ represents hydrogen or halogen.

In further embodiments of the above-mentioned aspects, the invention relates to compounds of formula (I), wherein:

$R^{1e}$ represents hydrogen, halogen, or methyl.

In further embodiments of the above-mentioned aspects, the invention relates to compounds of formula (I), wherein:

$R^{1e}$ represents hydrogen or halogen.

In further embodiments of the above-mentioned aspects, the invention relates to compounds of formula (I), wherein:

$R^{1e}$ represents hydrogen or fluoro.

In further embodiments of the above-mentioned aspects, the invention relates to compounds of formula (I), wherein:

$R^{1e}$ represents hydrogen.

In further embodiments of the above-mentioned aspects, the invention relates to compounds of formula (I), wherein:

$R^{1f}$ represents hydrogen or fluoro.

In further embodiments of the above-mentioned aspects, the invention relates to compounds of formula (I), wherein:

$R^{1f}$ represents hydrogen.

In further embodiments of the above-mentioned aspects, the invention relates to compounds of formula (I), wherein:

$R^{1g}$ represents hydrogen or fluoro.

In further embodiments of the above-mentioned aspects, the invention relates to compounds of formula (I), wherein:

$R^2$ represents hydrogen, halogen, methoxy, cyano, $C_1$-$C_3$-alkyl, or $C_1$-$C_3$-alkoxy-$C_1$-$C_3$-alkyl-.

In further embodiments of the above-mentioned aspects, the invention relates to compounds of formula (I), wherein:

$R^2$ represents hydrogen, $C_1$-$C_2$-alkyl, or $C_1$-$C_2$-alkoxy-$C_1$-$C_2$-alkyl-.

In further embodiments of the above-mentioned aspects, the invention relates to compounds of formula (I), wherein:

$R^2$ represents hydrogen, halogen, methoxy, cyano, or $C_1$-$C_2$-alkyl.

In further embodiments of the above-mentioned aspects, the invention relates to compounds of formula (I), wherein:

$R^2$ represents hydrogen, methyl, or C-alkoxy-$C_1$-$C_2$-alkyl-.

In further embodiments of the above-mentioned aspects, the invention relates to compounds of formula (I), wherein:

$R^2$ represents hydrogen or $C_1$-$C_2$-alkyl.

In further embodiments of the above-mentioned aspects, the invention relates to compounds of formula (I), wherein:

$R^2$ represents hydrogen or methyl.

In further embodiments of the above-mentioned aspects, the invention relates to compounds of formula (I), wherein:

$R^2$ represents hydrogen.

In further embodiments of the above-mentioned aspects, the invention relates to compounds of formula (I), wherein:

$R^2$ represents methyl.

In further embodiments of the above-mentioned aspects, the invention relates to compounds of formula (I), wherein:

$R^3$ represents phenyl, wherein said phenyl is independently optionally substituted, one or more times, with halogen, methyl, methoxy, $C_1$-$C_2$-haloalkyl, or $C_1$-$C_2$-haloalkoxy.

In further embodiments of the above-mentioned aspects, the invention relates to compounds of formula (I), wherein:

$R^3$ represents phenyl, wherein said phenyl is independently optionally substituted, one or more times, with halogen, methyl, or C-haloalkyl.

In further embodiments of the above-mentioned aspects, the invention relates to compounds of formula (I), wherein:

$R^3$ represents phenyl, wherein said phenyl is independently optionally substituted, one or more times, with halogen or methyl.

In further embodiments of the above-mentioned aspects, the invention relates to compounds of formula (I), wherein:

$R^{4a}$ represents hydrogen, halogen, $C_1$-$C_3$-alkyl, $C_2$-$C_5$-alkenyl, methoxy, difluoromethoxy, trifluoromethoxy, $C_3$-$C_4$-cycloalkyl, 4- to 5-membered heterocycloalkyl, cyclopropyloxy, 4- to 5-membered heterocycloalkyl-O—, or $R^{5a}R^{6a}N$— wherein said 4- to 5-membered heterocycloalkyl and 4- to 5-membered heterocycloalkyl-O— are optionally substituted, one or two times, with methyl.

In further embodiments of the above-mentioned aspects, the invention relates to compounds of formula (I), wherein:

$R^{4a}$ represents hydrogen, halogen, $C_1$-$C_3$-alkyl, $C_2$-alkenyl, methoxy, difluoromethoxy, $C_3$-cycloalkyl, 4-membered heterocycloalkyl, cyclopropyloxy, 4-membered heterocycloalkyl-O—, or $R^{5a}R^{6a}N$—.

In further embodiments of the above-mentioned aspects, the invention relates to compounds of formula (I), wherein:

$R^{4a}$ represents hydrogen, halogen, C-alkyl, $C_2$-alkenyl, $C_3$-cycloalkyl, 4-membered heterocycloalkyl, or $R^{5a}R^{6a}N$—.

In further embodiments of the above-mentioned aspects, the invention relates to compounds of formula (I), wherein:

$R^{4a}$ represents hydrogen, halogen, or a methyl group-.

In further embodiments of the above-mentioned aspects, the invention relates to compounds of formula (I), wherein:

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_6$-cycloalkyl, $C_3$-$C_6$-cycloalkyl-$C_1$-$C_4$-alkyl, $C_3$-$C_6$-cycloalkyl-O—, $C_3$-$C_6$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_1$-$C_3$-alkyl-, $C_1$-$C_3$-alkoxy-$C_2$-$C_5$-alkoxy-, $C_1$-$C_4$-hydroxyalkyl, $C_1$-$C_4$-hydroxyalkyl-O—, or 3- to 6-membered heterocycloalkyl-$C_1$-$C_3$-alkyl-, wherein said $C_3$-$C_6$-cycloalkyl, $C_3$-$C_5$-cycloalkyl-$C_1$-$C_4$-alkyl, $C_5$-$C_8$-cycloalkyl-O—, $C_3$-$C_6$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_1$-$C_3$-alkyl-, $C_1$-$C_3$-alkoxy-$C_2$-$C_5$-alkoxy-, $C_1$-$C_4$-hydroxyalkyl, $C_1$-$C_4$-hydroxyalkyl-O— and 3- to 6-membered heterocycloalkyl-$C_1$-$C_3$-alkyl groups are optionally substituted, one, two or three times, with halogen, methyl, methoxy, or trifluoromethoxy.

In further embodiments of the above-mentioned aspects, the invention relates to compounds of formula (I), wherein:

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_5$-cycloalkyl, $C_3$-$C_5$-cycloalkyl-$C_1$-$C_2$-alkyl, $C_3$-$C_5$-cycloalkyl-O—, $C_3$-$C_5$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_1$-$C_3$-alkyl-, $C_1$-$C_3$-alkoxy-$C_2$-$C_3$-alkoxy-, or $C_1$-$C_4$-hydroxyalkyl, $C_1$-$C_4$-hydroxyalkyl-O—, wherein said $C_3$-$C_5$-cycloalkyl, $C_3$-$C_5$-cycloalkyl-$C_1$-$C_2$-alkyl, $C_3$-$C_5$-cycloalkyl-O—, $C_3$-$C_5$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl and $C_1$-$C_4$-hydroxyalkyl-O— groups are optionally substituted one, two or three times with halogen, methyl, or methoxy.

In further embodiments of the above-mentioned aspects, the invention relates to compounds of formula (I), wherein:

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—, wherein said $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_2$-$C_3$-alkoxy-, $C_1$-$C_4$-hydroxyalkyl and $C_1$-$C_4$-hydroxyalkyl-O— groups are optionally substituted, one or two times, with halogen or methyl.

In further embodiments of the above-mentioned aspects, the invention relates to compounds of formula (I), wherein:

$R^{4b}$ represents hydrogen, halogen, $C_1$-$C_4$-alkyl, $C_1$-$C_3$-haloalkyl-$CH_2$—, $C_1$-$C_3$-alkoxy, $C_1$-$C_3$-haloalkoxy, $C_3$-cycloalkyl, $C_3$-cycloalkyl-$C_1$-$C_2$-alkyl, $C_3$-cycloalkyl-O—, $C_3$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—.

In further embodiments of the above-mentioned aspects, the invention relates to compounds of formula (I), wherein:

$R^{5a}$ represents hydrogen, methyl, cyclopropyl, methoxyethyl, or 3- to 5-membered heterocycloalkyl.

In further embodiments of the above-mentioned aspects, the invention relates to compounds of formula (I), wherein:

$R^{5a}$ represents hydrogen or methyl.

In further embodiments of the above-mentioned aspects, the invention relates to compounds of formula (I), wherein:

$R^{6a}$ represents hydrogen or methyl.

In further embodiments of the above-mentioned aspects, the invention relates to compounds of formula (I), wherein:

$R^{5a}$ and $R^{6a}$, together with the nitrogen atom to which they are attached, represent a 4- to 5-membered heterocyclic ring, wherein said heterocyclic ring is optionally substituted, one or two times, with methyl.

In further embodiments of the above-mentioned aspects, the invention relates to compounds of formula (I), wherein:

$R^{5a}$ and $R^{6a}$, together with the nitrogen atom to which they are attached, represent a 4-membered heterocyclic ring, wherein said heterocyclic ring is optionally substituted with methyl.

In further embodiments of the above-mentioned aspects, the invention relates to compounds of formula (I), wherein:

$R^{5a}$ and $R^{6a}$, together with the nitrogen atom to which they are attached, represent a 4-membered heterocyclic ring.

A further aspect of the invention are compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In other embodiments of the invention, compounds are defined according to the claims as disclosed in the Claims section wherein the definitions are limited according to the preferred or more preferred definitions as disclosed below or specifically disclosed residues of the exemplified compounds and subcombinations thereof.

In certain embodiments, compounds of the present invention have surprising and advantageous properties.

In particular, compounds of the present invention have surprisingly been found to effectively inhibit Casein kinase 1 alpha and/or delta and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses. In particular, the disclosed compounds can be used for treatment or prophylaxis of diseases in which the uncontrolled cell growth, proliferation and/or survival, inappropriate cellular immune responses, or inappropriate cellular inflammatory responses is mediated by Casein kinase 1 alpha and/or delta, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours including esophageal, gastric and colorectal tumours, endocrine tumours, mammary and other gynaecological tumours, urological tumours including renal, bladder and prostate tumours, skin tumours, and sarcomas, and/or metastases thereof.

Definitions

Constituents which are optionally substituted as stated herein, may be substituted, unless otherwise noted, one or more times, independently of one another at any possible position.

When any variable occurs more than one time in any constituent, each definition is independent. For example, when in which $R^2$, $R^3$, $R^4$, $R^7$, and/or $R^8$, occur more than one time in any compound of formula (I) each definition of $R^2$, $R^3$, $R^4$, $R^7$, and $R^8$ is independent.

Should a constituent be composed of more than one part, e.g. $C_3$-$C_6$-cycloalkyl-$C_1$-$C_4$-alkyl-, unless stated otherwise, the position of a possible substituent can be at any of these parts at any suitable position (e.g. in the case of a substituted $C_3$-$C_6$-cycloalkyl-$C_1$-$C_4$-alkyl-group, substituents may be present at the $C_3$-$C_6$-cycloalkyl part of the group, at the $C_1$-$C_4$-alkyl part of the group or both). A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned above" or "mentioned above", "supra" within the description it is referred to any of the disclosures made within the specification in any of the preceding pages or above on the same page.

If it is referred to "as mentioned herein", "described herein", "provided herein" or "stated herein" within the description it is referred to any of the disclosures made within the specification in any of the preceding or subsequent pages.

"suitable" within the sense of the invention means chemically possible to be made by methods within the knowledge of a skilled person.

The terms as mentioned in the present text have preferably the following meanings: The term "halogen atom", "halo-" or "Hal-" is to be understood as meaning a fluorine, chlorine, bromine or iodine atom, preferably a fluorine, chlorine or bromine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof. Preferably, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more preferably 1, 2 or 3 carbon atoms ("$C_1$-$C_3$-alkyl"), e.g. a methyl, ethyl, n-propyl or iso-propyl group.

The term "$C_1$-$C_4$-haloalkyl" is to be understood as meaning a linear or branched, saturated, monovalent hydrocarbon group in which the term "$C_1$-$C_4$-alkyl" is defined supra, and in which one or more hydrogen atoms are replaced by a halogen atom, identically or differently, i.e. one halogen atom being independent from another. Preferably, said halogen atom is F. Said $C_1$-$C_4$-haloalkyl group is, for example, $—CF_3$, $—CHF_2$, $—CH_2F$, $—CF_2CF_3$, $—CH_2CH_2F$, $—CH_2CHF_2$, $—CH_2CF_3$, $—CH_2CH_2CF_3$, or $—CH(CH_2F)_2$. Preferably, said group has 1, 2, or 3 carbon atoms ("$C_1$-$C_3$-haloalkyl"). More preferably, said group has 1, or 2 carbon atoms ("$C_1$-$C_2$-haloalkyl").

The term "$C_1$-$C_5$-hydroxyalkyl" means a linear or branched, saturated, monovalent hydrocarbon group in which the term "$C_1$-$C_5$-alkyl" is defined supra, and in which 1 or 2 hydrogen atoms are replaced with a hydroxy group, e.g. a hydroxymethyl, 1-hydroxyethyl, 2-hydroxyethyl, 1,2-di-hydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl or 1-hydroxy-2-methyl-propyl group.

The term "$C_1$-$C_4$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, isopropoxy, n-butoxy, iso-butoxy, tert-butoxy or sec-butoxy group, or an isomer thereof.

The term "$C_1$-$C_4$-haloalkoxy" is to be understood as meaning a linear or branched, saturated, monovalent $C_1$-$C_4$-alkoxy group, as defined supra, in which one or more of the hydrogen atoms are replaced, identically or differently, by a halogen atom. Preferably, said halogen atom is F.

Said $C_1$-$C_4$-haloalkoxy group is, for example, $—OCF_3$, $—OCHF_2$, $—OCH_2F$, $—OCF_2CF_3$, or $—OCH_2CF_3$. Preferably, said group has 1, 2, or 3 carbon atoms ("$C_1$-$C_3$-haloalkoxy"). More particularly, said group has 1, or 2 carbon atoms ("$C_1$-$C_2$-haloalkoxy").

The term "$C_3$-$C_6$-cycloalkyl" is to be understood as meaning a saturated, monovalent, mono- or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "halocyclopropyl" is to be understood as meaning a cyclopropyl group in which one or more hydrogen atoms are replaced by a halogen atom, identically or differently, i.e. one halogen atom being independent from another. Particularly, said halogen atom is F.

The terms "3- to 6-membered heterocycloalkyl" and "4- to 5-membered heterocycloalkyl" mean a monocyclic, saturated heterocycle with 3, 4, 5, or 6 or, respectively, 4 or 5 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 3-membered ring, such as oxiranyl or aziridinyl, for example; or a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example.

Particularly, "3- to 6-membered heterocycloalkyl" means a 3- to 6-membered heterocycloalkyl as defined supra containing one ring nitrogen or oxygen atom and optionally one further ring heteroatom from the series: N, O, S. More particularly, "3- or 4-membered heterocycloalkyl" means a monocyclic, saturated heterocycle with 3 or 4 ring atoms in total, containing one ring nitrogen or oxygen atom.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), preferably 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used throughout this text, e.g. in the context of the definition of "$C_1$-$C_6$-alkyl" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_2$-$C_6$, $C_3$-$C_6$, $C_1$-$C_2$, $C_1$-$C_3$, particularly $C_1$-$C_2$, $C_1$-$C_3$, $C_1$-$C_4$, The term "$C_1$-$C_4$", as used throughout this text, e.g. in the context of the definition of "$C_1$-$C_4$-alkyl", "$C_1$-$C_4$-haloalkyl", "$C_1$-$C_4$-alkoxy", or "$C_1$-$C_4$-haloalkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_2$-$C_4$, $C_3$-$C_4$, $C_1$-$C_2$, $C_1$-$C_3$, preferably $C_1$-$C_2$, $C_1$-$C_3$, $C_1$-$C_4$, in the case of "$C_1$-$C_4$-haloalkyl" or "$C_1$-$C_4$-haloalkoxy" even more preferably $C_1$-$C_2$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$—C; preferably $C_3$-$C_6$.

The term "substituted" means that one or more hydrogens on the designated atom is replaced with a selection from the indicated group, provided that the substituted atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, preferably one, two, three or four, more particularly one, two or three, even more preferably one or two".

The compounds of general formula (I) may exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes of the elements that constitute such a compound.

The term "Isotopic variant of the compound of general formula (I)" is defined as a compound of general formula (I) exhibiting an unnatural proportion of one or more of the isotopes of the elements that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as 2H (deuterium), $^{3}H$ (tritium), $^{11}C$, $^{13}C$, $^{14}C$, $^{15}N$, $^{17}O$, $^{18}O$, $^{32}P$, $^{33}$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively. Accordingly, recitation of "hydrogen" or "H" should be understood to encompass $^{1}H$ (protium), $^{2}H$ (deuterium), and $^{3}H$ (tritium) unless otherwise specified.

With respect to the treatment and/or prophylaxis of the disorders specified herein, isotopic variant(s) of the compounds of general formula (I) preferably contain elevated levels of deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, e.g., by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. e.g., Pd, Pt, and Rh) in the presence of deuterium gas can be used to directly exchange deuterium for hydrogen in functional groups containing hydrocarbons (J. G. Atkinson et al., U.S. Pat. No. 3,966, 781). A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844,1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363.

The term "deuterium-containing compound of general formula (I)" is defined as a compound of general formula (I), in which one or more protium ($^{1}H$) atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., J. Am. Chem. Soc., 1963, 85, 2759; C. L. Perrin, et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and/or enhances the formation of a desired metabolite (e.g. Nevirapine: A. M.

Sharma et al., Chem. Res. Toxicol., 2013, 26, 410; Uetrecht et al., Chemical Research in Toxicology, 2008, 21, 9,1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels, i.e., reduced peak-trough variation. This could result in lower side effects and/or enhanced efficacy, depending on the particular compound's pharmacokinetic/pharmacodynamic relationship. Indiplon (A. J. Morales et al., Abstract 285, The $15^{th}$ North American Meeting of the International Society of Xenobiotics, San Diego, CA, Oct. 12-16, 2008), ML-337 (C. J. Wenthur et al., J. Med. Chem., 2013, 56, 5208), and Odanacatib (K. Kassahun et al., WO2012/112363) are examples of this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to include also a single compound, salt, polymorph, isomer, hydrate, solvate or the like.

By ou37 stable compound' or "stable structure" is meant a compound that is sufficiently robust to survive isolation to a useful degree of purity from a reaction mixture, and is capable of being subjected to further chemical transformation or, preferably, formulation into an efficacious therapeutic agent.

The compounds of this invention may contain one or more asymmetric centres, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds, (i.e., atropisomers).

Substituents on a non-planar ring may also be present in either cis or trans configurations. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art. Separated optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials or optically active catalysts.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

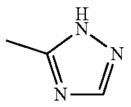

1H-tautomer

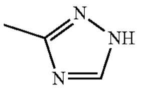

2H-tautomer

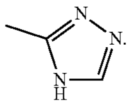

4H-tautomer

Specifically, the compound of formula (I) may exist, at least as the following tautomers:

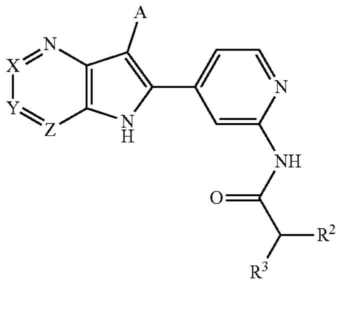

and

-continued

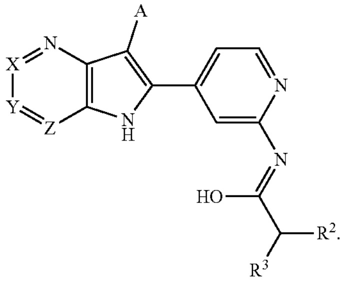

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, preferably water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention can be prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x $CF_3COOH$", "x $Na^+$", for example, are to be understood as not a stoichiometric specification, but simply as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl, 1,3-dioxolen-2-onylmethyl esters, e.g. 5-methyl-1,3-dioxolen-2-onylmethyl, and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents" includes but is not limited to: 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, 1-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]- octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

General Procedures

The compounds according to the invention can be prepared according to the following Schemes 1 through 7.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. In addition, interconversion of any of the substituents $R^{1a}$, $R^{1b}$, $R^{1c}$, $R^{1d}$, $R^{1e}$, $R^2$, $R^3$, $R^{4a}$, $R^{4b}$, $R^{5a}$, $R^{6a}$, A, X, Y, Z, Q, PG, and T can be achieved before and/or after the exemplified transformations. These modifications can be such as the introduction of protecting groups, cleavage of protecting groups, reduction or oxidation of functional groups, dehydrogenation, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art.

Specific examples are described in the subsequent paragraphs.

Scheme 1

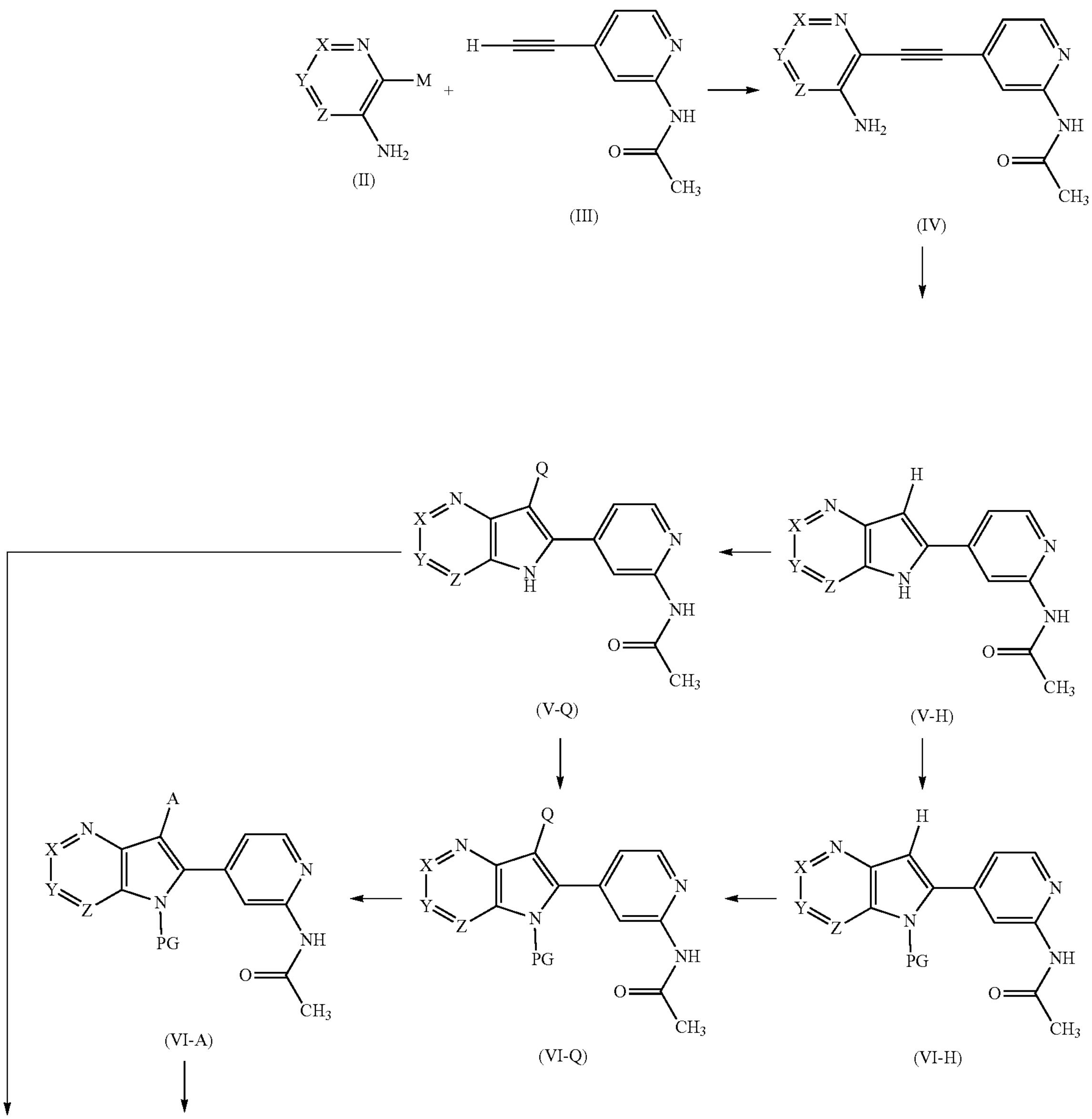

(II) (III) (IV) (V-Q) (V-H) (VI-A) (VI-Q) (VI-H)

-continued

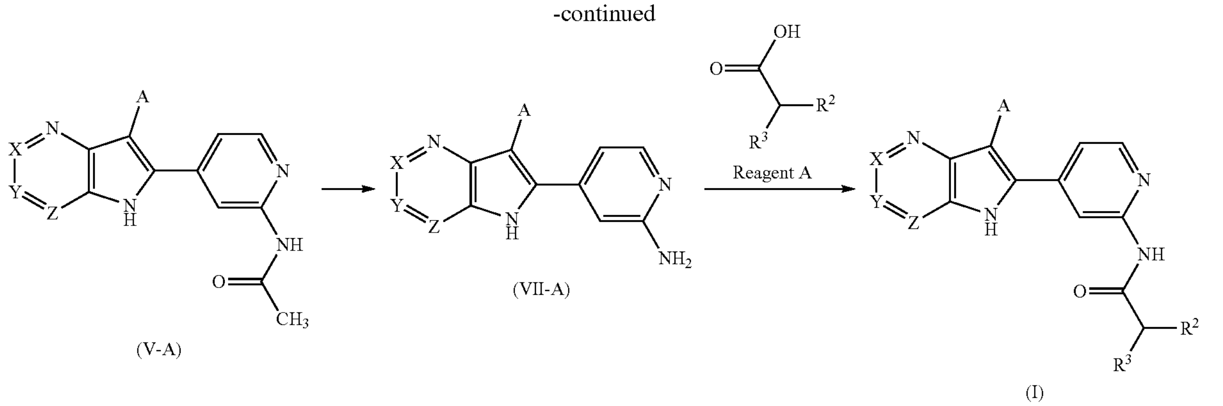

(V-A) (VII-A) (I)

Scheme 1: Route for the preparation of compounds of general formula (I), wherein $R^2$, $R^3$, A, X, Y and Z have the meaning as given for general formula (I), supra. Q represents a chloro, a bromo or an iodo, preferably a bromo or an iodo and M represents a chloro, a bromo or an iodo, preferably a bromo. In addition, interconversion of any of the substituents, $R^{1a}$, $R^{1b}$, $R^{1c}$, $R^{1d}$, $R^{1e}$, $R^2$, $R^3$, $R^4$, $R^{4b}$, $R^{5a}$, $R^{6a}$, A, X, Y, Z, Q, and PG can be achieved before and/or after the exemplified transformation.

Reagent A, is either commercially available or can be prepared according to procedures available from the public domain, as understandable to the person skilled in the art. Specific examples are described in the subsequent paragraphs An amino-aryl compound of general formula (II), such as, for example, 2-bromo-pyridin-3-amine or 2-bromo-6-fluoropyridin-3-amine, can be reacted with an alkyne of formula (III) with a catalyst system typically used for Sonogashira couplings as described in the literature (K. Sonogashira, Y. Tohda, N. Hagihara: Tetrahedron Lett. 1975, S. 4467-4470) like for example dichlorobis(triphenylphosphine)palladium (II) and copper(I) iodide in a suitable solvent system, such as, for example, triethylamine or a mixture of triethylamine and DMF or DMA or NMP, preferably DMF at temperatures ranging from 50° C. to 120° C., preferably at temperatures ranging from 70° C. to 90° C. to furnish intermediates of general formula (IV). Similar reactions have been performed before and are described in the literature (ACS Med. Chem. Lett. 2018, 9, 1117-1122).

Intermediates of general formula (IV) can be converted to intermediates of general formula (V-H) by reaction with a suitable base, such as, for example potassium 2-methylpropan-2-olate, in a suitable solvent system, such as, for example, NMP or DMA, preferably NMP at temperatures ranging from 50° C. to 120° C., preferably at temperatures ranging from 80° C. to 100° C. Alternatively the reaction can be carried out with copper(I)iodide in a suitable solvent system, such as, for example, NMP at a temperature between 100° C. and 150° C. preferably 120° C. to 140° C. to furnish compounds of general formula (V-H).

Intermediates of general formula (V-H) can be converted to intermediates of general formula (V-Q) by reaction with a halogenating agents like NBS in a suitable solvent system such as, for example, DMF or DMA, in a temperature range from 0° C. to 50° C., preferably at room temperature. Utilizing NBS as reagent will furnish intermediates of general formula (V-Q) where Q represents bromo. Utilizing NCS as reagent will furnish intermediates of general formula (V-Q) where Q represents chloro, and utilizing NIS as reagent will furnish intermediates of general formula (V-Q) where Q represents iodo.

Intermediates of general formula (V-H) can be reacted with a suitable base like for example sodium bicarbonate, sodium carbonate, potassium carbonate or sodium hydride, in a suitable solvent system such as for example DMF or DMA or NMP or dichloromethane or THF or mixtures of these solvents, preferably in DMF, and a suitable reagent to introduce a protecting group like for example SEM-Cl, in a temperature range from 0° C. to 50° C., preferably at room temperature to furnish Intermediates of general formula (VI-H). Appropriate protecting groups and their introduction and cleavage are well-known to the person skilled in the art (see for example T.W. Greene and P.G.M. Wutts in Protective Groups in Organic Synthesis, 3rd edition, Wiley 1999).

Likewise, intermediates of general formula (V-Q) can be reacted with a suitable base like for example, sodium bicarbonate, sodium carbonate, potassium carbonate or sodium hydride, in a suitable solvent system such as for example DMF or DMA or NMP or dichloromethane or THE or mixtures of these solvents, preferably in DMF, and a suitable reagent to introduce a protecting group like for example SEM-Cl, in a temperature range from 0° C. to 50° C., preferably at room temperature to furnish intermediates of general formula (VI-Q). Appropriate protecting groups and their introduction and cleavage are well-known to the person skilled in the art (see for example T.W. Greene and P.G.M. Wutts in Protective Groups in Organic Synthesis, 3rd edition, Wiley 1999).

Intermediates of general formula (VI-H) can be converted to intermediates of general formula (VI-Q) by reaction with a halogenating agents like NBS in a suitable solvent system such as, for example, DMF or DMA, in a temperature range from 0° C. to 50° C., preferably at room temperature. Utilizing NBS as reagent will furnish intermediates of general formula (VI-Q) where Q represents bromo. Utilizing NCS as reagent will furnish intermediates of general formula (VI-Q) where Q represents chloro, and utilizing NIS as reagent will furnish intermediates of general formula (VI-Q) where Q represents iodo.

Intermediates of general formula (VI-Q) can be converted to intermediates of general formula (VI-A) by reaction with a suitable stannane like for example 2-(tributylstannyl) pyridine or 2-fluoro-6-(tributylstannyl)pyridine or a suitable boronic acid like for example phenylboronic acid or a suitable boronic acid derivative in the presence of a suitable catalyst system, preferably a palladium catalyst, like for example tetrakis(triphenylphosphine)palladium(0) or tetrakis(triphenylphosphine)palladium(0) with lithium chloride as an additive or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably Pd-Xphos G3 in a suitable solvent system such as, for example, toluene, dioxane, DMF, DMA, or NMP or mixtures of the solvents, preferably in dioxane in a temperature range from 60° C. to 130° C., preferably in a temperature range from 80° C. to 100° C.

Intermediates of general formula (V-Q) can be converted to intermediates of general formula (V-A) by reaction with a suitable stannane like for example 2-(tributylstannyl) pyridine or 2-fluoro-6-(tributylstannyl)pyridine or a suitable boronic acid like for example phenylboronic acid or a suitable boronic acid derivative in the presence of a suitable catalyst system, preferably a palladium catalyst, like for example tetrakis(triphenylphosphine)palladium(0) or tetrakis(triphenylphosphine)palladium(0) with lithium chloride as an additive or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably tetrakis(triphenylphosphine)palladium(0) with lithium chloride as an additive in a suitable solvent system such as, for example, toluene, dioxane, DMF, DMA, or NMP or mixtures of these solvents, preferably in dioxane in a temperature range from 60° C. to 130° C., preferably in a temperature range from 90° C. to 110° C.

Intermediates of general formula (VI-A) can be converted to intermediates of general formula (V-A) by utilizing appropriate reagents for the cleavage of the applied protecting group which are well-known to the person skilled in the art (see for example T.W. Greene and P.G.M. Wutts in Protective Groups in Organic Synthesis, 3rd edition, Wiley 1999). Specifically, for intermediates in which PG represents SEM, the SEM group can be removed for example using acids like for example hydrochloric acid in a suitable solvent system like for example an alcohol like ethanol or 1-propanol in a temperature range from 60° C. to 130° C., preferably at the boiling temperature of the respective solvent. Alternatively, for intermediates in which PG represents SEM, the SEM group can be removed, for example by reaction of intermediates of general formula (VI-A) with boron trifluoride etherate in a suitable solvent system like for example acetonitrile in a temperature range from 0° C. to 40° C., preferably at room temperature followed by addition of exess aqeous ammonium hydroxide in a temperature range from 0° C. to 40° C., preferably at room temperature to furnish intermediates of general formula (V-A).

Intermediates of general formula (V-A) can be converted to intermediates of general formula (VII-A) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THE or tert-butanol or mixtures of these solvents, preferably in methanol or THE in a temperature range from 60° C. to 100° C., preferably in a temperature range from 70° C. to 90° C.

Intermediates of general formula (VII-A) are reacted with an acylating agent prepared from a reagent of general formula (Reagent A) or an acylating agent which can be generated in situ from a reagent of general formula (Reagent A) to furnish compounds of general formula (I).

These types of reactions are well-known (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187).

Not-limiting examples of these types of reagents are:

i) carboxylic acids with dehydrating reagents typically used in amide bond formation, such as, for example (HBTU, HATU, PyBOP, BOP, T3P, EDC, DIC, DCC)

ii) acid fluorides, acid chlorides or acid bromides, preferably in the presence of a base iii) acid anhydrides of the general formulae

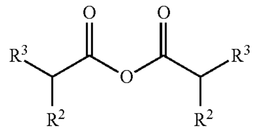

or

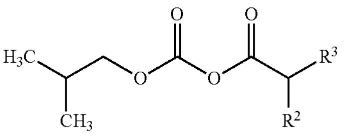

preferably in the presence of a base

Preferably the acylating reaction is carried out in a solvent like DMF, DMA, NMP, dichloromethane or THE or mixtures of these solvents, more preferably in a solvent like DMA or dichloromethane or mixtures of DMA and dichloromethane, to react intermediates of general formula (VII-A) with reagents of general formula (Reagent A) using a coupling reagent like for example HATU, PyBOP or BOP more preferably PyBOP and a base like for example potassium carbonate or triethylamine or Hünig base, preferably Hünig base in a temperature range from 0° C. to 40° C., preferably at room temperature to furnish compounds of general formula (I).

Said acylating agent can be in a protected form, containing a protecting group like Boc for example leading to a protected form of compounds of general formula (I) which furnishes compounds of general formula (I) after an additional deprotection step. Further protecting groups are well known to the person skilled in the art. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

Scheme 2

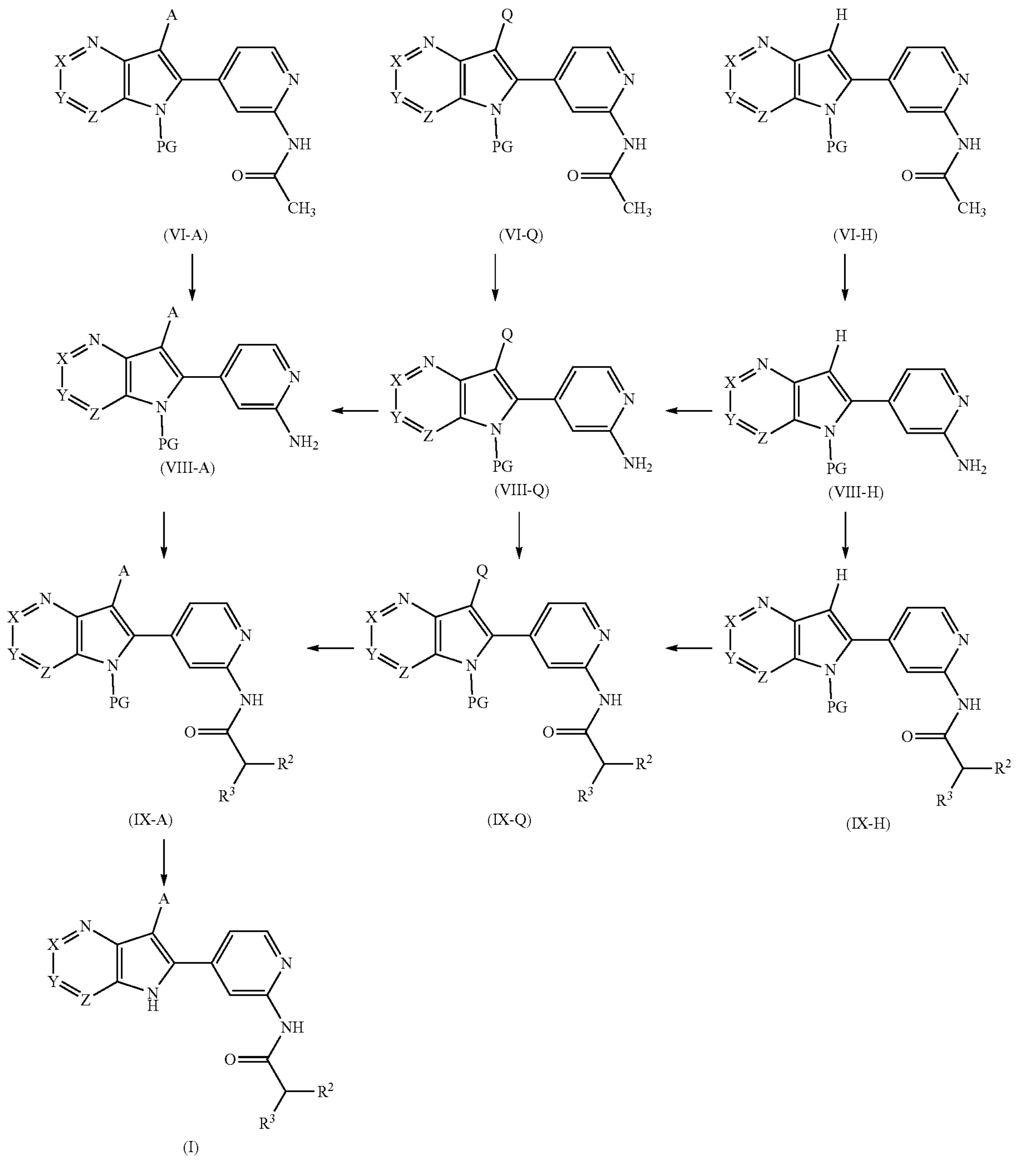

Scheme 2: Route for the preparation of compounds of general formula (I), wherein $R^2$, $R^3$, A, X, Y and Z have the meaning as given for general formula (I), supra. Q represents a chloro, a bromo or an iodo, preferably a bromo or an iodo. In addition, interconversion of any of the substituents, $R^{1a}$, $R^{1b}$, $R^{1c}$, $R^{1d}$, $R^{1e}$, $R^2$, $R^3$, $R^{4a}$, $R^{4b}$, $R^{5a}$, $R^{6a}$, A, X, Y, Z, Q, and PG can be achieved before and/or after the exemplified transformation.

Intermediates of general formula (VI-H) can be converted to intermediates of general formula (VIII-H) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THF or tert-butanol or mixtures of these solvents, preferably in methanol or THF in a temperature range from 60° C. to 100° C., preferably in a temperature range from 70° C. to 90° C.

Likewise, intermediates of general formula (VI-Q) can be converted to intermediates of general formula (VIII-Q) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THF or tert-butanol or mixtures of these solvents, preferably in methanol or THF in a temperature range from 60° C. to 100° C., preferably in a temperature range from 70° C. to 90° C.

Likewise, intermediates of general formula (VI-A) can be converted to intermediates of general formula (VIII-A) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THF or tert-butanol or mixtures of these solvents, preferably in methanol or THE in a temperature range from 60° C. to 100° C., preferably in a temperature range from 70° C. to 90° C.

Intermediates of general formula (VIII-H) can be converted to intermediates of general formula (IX—H) by an analogous procedure as described for the conversion of intermediates of general formula (VII-A) to compounds of general formula (I) supra.

Likewise, intermediates of general formula (VIII-Q) can be converted to intermediates of general formula (IX-Q) by an analogous procedure as described for the conversion of intermediates of general formula (VII-A) to compounds of general formula (I) supra.

Likewise, intermediates of general formula (VIII-A) can be converted to intermediates of general formula (IX-A) by an analogous procedure as described for the conversion of intermediates of general formula (VII-A) to compounds of general formula (I) supra.

Intermediates of general formula (VIII-H) can be converted to intermediates of general formula (VIII-Q) by an analogous procedure as described for the conversion of intermediates of general formula (VI-H) to compounds of general formula (VI-Q) supra.

Intermediates of general formula (VIII-Q) can be converted to intermediates of general formula (VIII-A) by an analogous procedure as described for the conversion of intermediates of general formula (VI-Q) to compounds of general formula (VI-A) supra.

Intermediates of general formula (IX—H) can be converted to intermediates of general formula (IX-Q) by an analogous procedure as described for the conversion of intermediates of general formula (V-H) to intermediates of general formula (V-Q) supra.

Intermediates of general formula (IX-Q) can be converted to intermediates of general formula (IX-A) by an analogous procedure as described for the conversion of intermediates of general formula (VI-Q) to intermediates of general formula (VI-A) supra.

Intermediates of general formula (IX-A) can be converted to compounds of general formula (I) by an analogous procedure as described for the conversion of intermediates of general formula (VI-A) to intermediates of general formula (V-A) supra.

Scheme 3

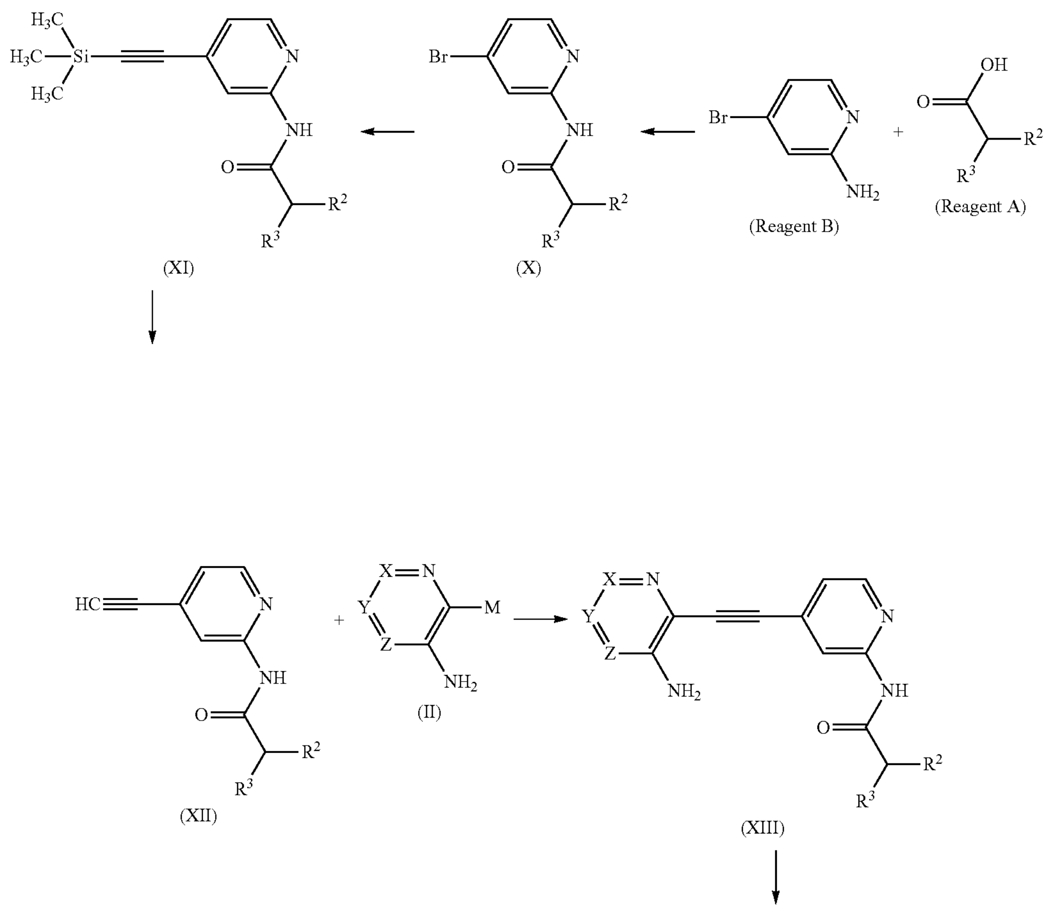

-continued

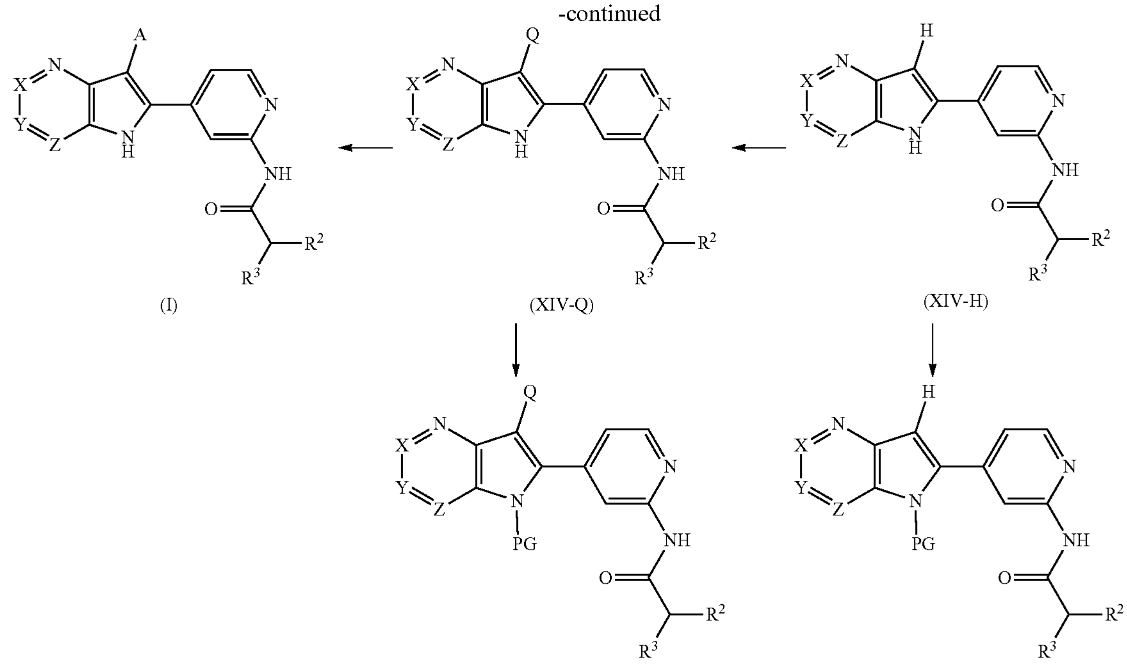

(I) (XIV-Q) (XIV-H)

(IX-Q) (IX-H)

Scheme 3: Route for the preparation of compounds of general formula (I), wherein $R^2$, $R^3$, A, X, Y and Z have the meaning as given for general formula (I), supra. Q represents a chloro, a bromo or an iodo, preferably a bromo or an iodo and M represents a chloro, a bromo or an iodo, preferably a bromo. In addition, interconversion of any of the substituents, $R^{1a}$, $R^{1b}$, $R^{1c}$, $R^{1d}$, $R^{1e}$, $R^2$, $R^3$, $R^{4a}$, $R^{4a}$, $R^{5a}$, Rea, A, X, Y, Z, Q, and PG can be achieved before and/or after the exemplified transformation.

Reagent B can be reacted with an acylating agent prepared from a reagent of general formula (Reagent A) or an acylating agent which can be generated in situ from a reagent of general formula (Reagent A) to furnish compounds of general formula (X). These types of reactions are well-known (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187).

Not-limiting examples of these types of reagents are:

i) carboxylic acids with dehydrating reagents typically used in amide bond formation, such as, for example (HBTU, HATU, PyBOP, BOP, T3P, EDC, DIC, DCC)

ii) acid fluorides, acid chlorides or acid bromides, preferably in the presence of a base iii) acid anhydrides of the general formulae

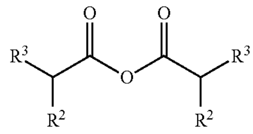

or

-continued

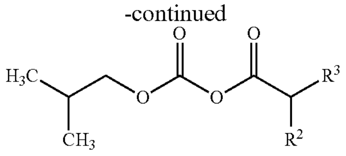

preferably in the presence of a base

Preferably the acylating reaction is carried out in a solvent like DMF, DMA, NMP, dichloromethane or THF or mixtures of these solvents, more preferably in a solvent like DMA or dichloromethane or mixtures of DMA and dichloromethane, to react Reagent B with reagents of general formula (Reagent A) using a coupling reagent like for example HATU, PyBOP or BOP more preferably HATU and a base like for example potassium carbonate or triethylamine or Hünig base, preferably Hünig base in a temperature range from 0° C. to 40° C., preferably at room temperature to furnish compounds of general formula (X).

Intermediates of general formula (X) can be converted to intermediates of general formula (XI) by reaction with ethynyl(trimethyl)silane with a catalyst system typically used for Sonogashira couplings as described in the literature (K. Sonogashira, Y. Tohda, N. Hagihara: Tetrahedron Lett. 1975, S. 4467-4470) like for example dichlorobis(triphenylphosphine)palladium(II) and copper(I) iodide in a suitable solvent system, such as, for example, triethylamine or a mixture of triethylamine and DMF or DMA or NMP, preferably DMF at temperatures ranging from 50° C. to 120° C., preferably at temperatures ranging from 70° C. to 90° C. to furnish intermediates of general formula (XI). Similar reactions have been performed before and are described in the literature (ACS Med. Chem. Lett. 2018, 9, 1117-1122; Org. Lett. 2014, 16, 708-711).

Intermediates of general formula (XI) can be converted to intermediates of general formula (XII) by reaction with a suitable base like for example, potassium carbonate or sodium hydroxide, preferably potassium carbonate, in a suitable solvent system such as for example methanol or ethanol or DMF or DMA or NMP or mixtures of these solvents, preferably in methanol or ethanol, in a temperature range from 0° C. to 50° C., preferably at room temperature to furnish Intermediates of general formula (XII). Appropriate protecting groups and their introduction and cleavage are well-known to the person skilled in the art (see for example T.W. Greene and P.G.M. Wutts in Protective Groups in Organic Synthesis, 3rd edition, Wiley 1999).

Intermediates of general formula (XII) can be converted to intermediates of general formula (XIII) by reaction with an amino-aryl compound of general formula (II), such as, for example, 2-bromo-pyridin-3-amine or 2-bromo-6-fluoro-pyridin-3-amine, with a catalyst system typically used for Sonogashira couplings as described in the literature (K. Sonogashira, Y. Tohda, N. Hagihara: Tetrahedron Lett. 1975, S. 4467-4470) like for example dichlorobis(triphenylphosphine)palladium(II) and copper(I) iodide in a suitable solvent system, such as, for example, triethylamine or a mixture of triethylamine and DMF or DMA or NMP, preferably DMF at temperatures ranging from 50° C. to 120° C., preferably at temperatures ranging from 70° C. to 110° C. to furnish intermediates of general formula (IV). Similar reactions have been performed before and are described in the literature (ACS Med. Chem. Lett. 2018, 9, 1117-1122).

Intermediates of general formula (XIII) can be converted to intermediates of general formula (XIV—H) by an analogous procedure as described for the conversion of intermediates of general formula (IV) to intermediates of general formula (V-H) supra.

Intermediates of general formula (XIV—H) can be converted to intermediates of general formula (XIV-Q) by an analogous procedure as described for the conversion of intermediates of general formula (V-H) to intermediates of general formula (V-Q) supra.

Intermediates of general formula (XIV—H) can be converted to intermediates of general formula (IX—H) by an analogous procedure as described for the conversion of intermediates of general formula (V-H) to intermediates of general formula (VI-H) supra.

Intermediates of general formula (XIV-Q) can be converted to intermediates of general formula (IX-Q) by an analogous procedure as described for the conversion of intermediates of general formula (V-Q) to intermediates of general formula (VI-Q) supra.

Intermediates of general formula (XIV-Q) can be converted to compounds of general formula (I) by reaction with a suitable stannane like for example 2-(tributylstannyl) pyridine or 2-fluoro-6-(tributylstannyl)pyridine or a suitable boronic acid like for example phenylboronic acid or a suitable boronic acid derivative in the presence of a suitable catalyst system, preferably a palladium catalyst, like for example tetrakis(triphenylphosphine)palladium(0) or tetrakis(triphenylphosphine)palladium(0) with lithium chloride as an additive or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably tetrakis(triphenylphosphine)palladium(0) with lithium chloride as an additive in a suitable solvent system such as, for example, toluene, dioxane, DMF, DMA, or NMP or mixtures of these solvents, preferably in dioxane in a temperature range from 60° C. to 130° C., preferably in a temperature range from 90° C. to 110° C.

Scheme 4

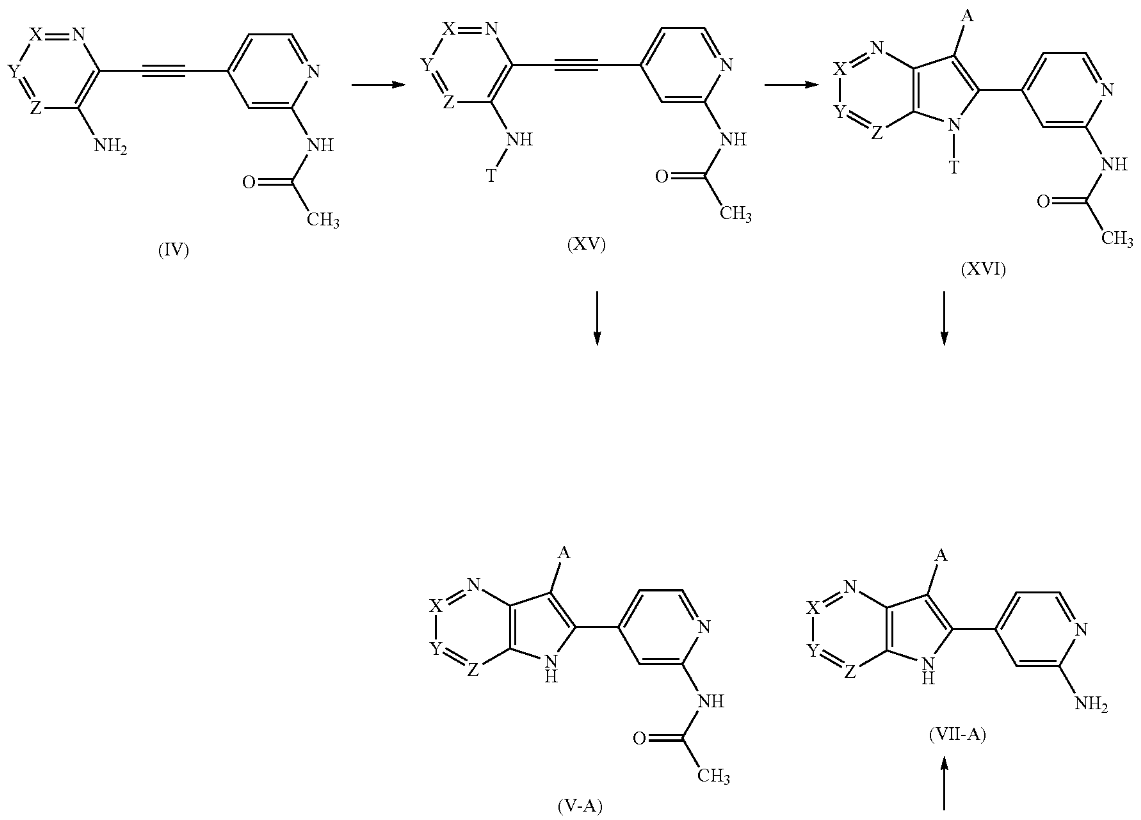

(IV) (XV) (XVI) (V-A) (VII-A)

-continued

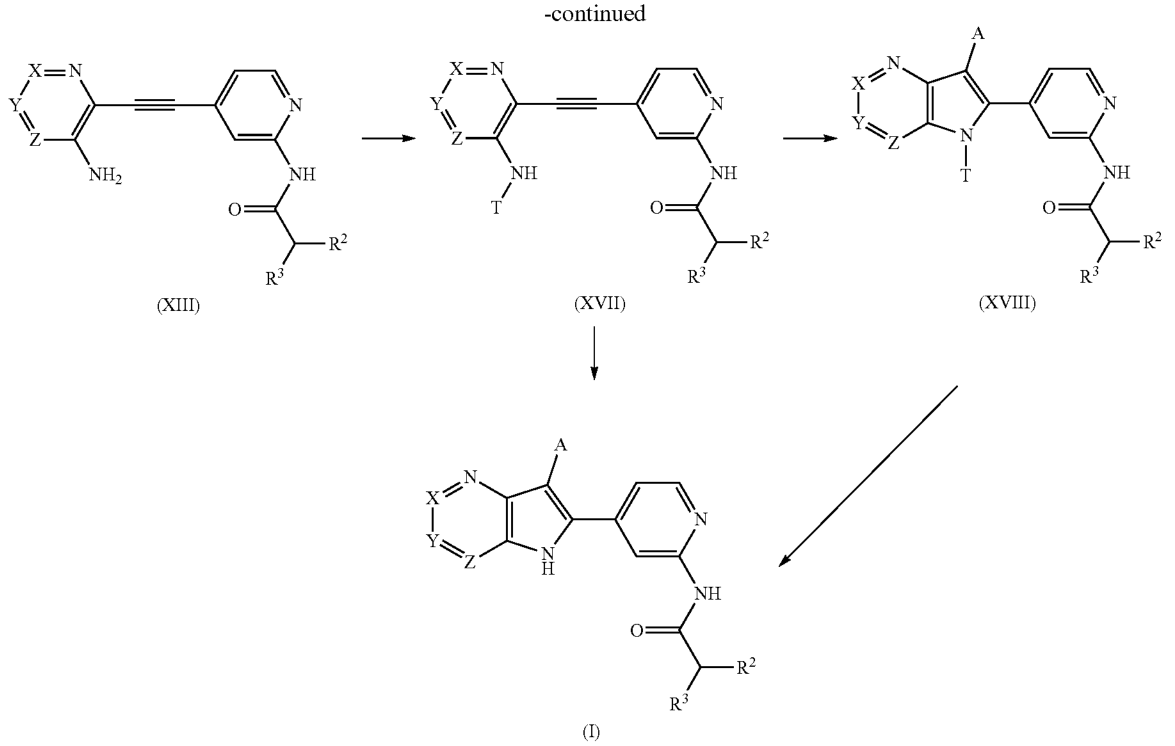

Scheme 4: Route for the preparation of compounds of general formula (I), wherein $R^2$, $R^3$, A, X, Y and Z have the meaning as given for general formula (I), supra; T represents $CF_3$—C(O)—, mesylate, tosylate or Ph-$SO_2$—, wherein Ph can be substituted one, two or three times with halogen or a methyl-group or a nitro-group. Interconversion of any of the substituents, $R^{1a}$, $R^{1b}$, $R^{1c}$, $R^{1d}$, $R^{1e}$, $R^2$, $R^3$, $R^{4a}$, $R^{4b}$, $R^{5a}$, $R^{6a}$, A, X, Y, Z, and T can be achieved before and/or after the exemplified transformation.

Intermediates of general formula (IV) can be converted to intermediates of general formula (XV) in which T represents $CF_3$—C(O)— by reaction with reagent like trifluoroacetic anhydride in a suitable solvent system such as dichloromethane, THF or acetonitrile or mixtures or mixtures of these solvents, preferably in dichloromethane or acetonitrile, and a base like for example potassium carbonate or triethylamine or Hünig base, preferably triethylamine or Hünig base in a temperature range from −10° C. to 40° C., preferably in a temperature range from 0° C. to room temperature to furnish intermediates of general formula (XV) in which T represents $CF_3$—C(O)—.

Intermediates of general formula (IV) can be converted to intermediates of general formula (XV) in which T represents mesylate, tosylate or Ph-$SO_2$—, wherein Ph can be substituted one, two or three times with halogen or a methyl-group or a nitro-group, by reaction with a suitable reagent like for example Mesylchloride or tosylchloride or nosylchloride in a suitable solvent system such as dichloromethane, THF or acetonitrile or mixtures or mixtures of these solvents, preferably in dichloromethane or acetonitrile, and a base like for example potassium carbonate or triethylamine or Hünig base or pyridine, preferably triethylamine, pyridine or Hünig base in a temperature range from −10° C. to 40° C., preferably in a temperature range from 0° C. to room temperature to furnish intermediates of general formula (XV) in which T represents mesylate, tosylate or Ph-$SO_2$—, wherein Ph can be substituted one, two or three times with halogen or a methyl-group or a nitro-group.

Intermediates of general formula (XV) in which T represents $CF_3$—C(O)— can be converted to intermediates of general formula (V-A) by reaction by reaction with a suitable halogen compound like for example 2-bromopyridine or 2-iodopyridine or iodobenzene in the presence of a suitable catalyst system, preferably a palladium catalyst, like for example tetrakis(triphenylphosphine)palladium(0) or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably Pd-Xphos G3 in a suitable solvent system such as, for example, acetonitrile, toluene, dioxane, DMF, DMA, or NMP or mixtures of these solvents, preferably in acetonitrile or dioxane in the presence of a base like dicaesium carbonate, or tripotassium phosphate in a temperature range from 60° C. to 130° C., preferably in a temperature range from 80° C. to 100° C. to furnish intermediates of general formula (V-A). Intermediates of general formula (XV) in which T represents mesylate, tosylate or Ph-$SO_2$—, wherein Ph can be substituted one, two or three times with halogen or a methyl-group or a nitro-group, can be converted to intermediates of general formula (XVI) in which T represents mesylate, tosylate or Ph-$SO_2$—, wherein Ph can be substituted one, two or three times with halogen or a methyl-group or a nitro-group, by reaction by reaction with a suitable halogen compound like for example 2-bromopyridine or 2-iodopyridine or iodobenzene in the presence of a suitable catalyst system, preferably a palladium catalyst, like for example tetrakis(triphenylphosphine)palladium(0) or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably Pd-Xphos G3 in a suitable solvent system such as, for example, acetonitrile, toluene, dioxane, DMF, DMA, or NMP or mixtures of these solvents, preferably in acetonitrile or dioxane in the presence of a base like dicaesium carbonate, or tripotassium phosphate in a temperature range from 60° C. to 130° C., preferably in a temperature range from 80° C. to 100° C. to furnish intermediates of general formula (XVI) in which T represents mesylate, tosylate or Ph-$SO_2$—, wherein Ph can be substituted one, two or three times with halogen or a methyl-group or a nitro-group.

Intermediates of general formula (XVI) in which T represents mesylate, tosylate or Ph-$SO_2$—, wherein Ph can be substituted one, two or three times with halogen or a methyl-group or a nitro-group can be converted to intermediates of general formula (VII-A) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THF or tert-butanol or mixtures of these solvents, preferably in methanol or THF in a temperature range from 60° C. to 100° C., preferably in a temperature range from 70° C. to 90° C. to furnish intermediates of general formula (VII-A).

Intermediates of general formula (XIII) can be converted to intermediates of general formula (XVII) in which T represents $CF_3$—C(O)— by reaction with reagent like trifluoroacetic anhydride in a suitable solvent system such as dichloromethane, THF or acetonitrile or mixtures or mixtures of these solvents, preferably in dichloromethane or acetonitrile, and a base like for example potassium carbonate or triethylamine or Hünig base, preferably triethylamine or Hünig base in a temperature range from −10° C. to 40° C., preferably in a temperature range from 0° C. to room temperature to furnish intermediates of general formula (XVII) in which T represents CFs-C(O).

Intermediates of general formula (XIII) can be converted to intermediates of general formula (XVII) in which T represents mesylate, tosylate or Ph-$SO_2$—, wherein Ph can be substituted one, two or three times with halogen or a methyl-group or a nitro-group, by reaction with a suitable reagent like for example Mesylchloride or tosylchloride or nosylchloride in a suitable solvent system such as dichloromethane, THE or acetonitrile or mixtures or mixtures of these solvents, preferably in dichloromethane or acetonitrile, and a base like for example potassium carbonate or triethylamine or Hünig base or pyridine, preferably triethylamine, pyridine or Hünig base in a temperature range from −10° C. to 40° C., preferably in a temperature range from 0° C. to room temperature to furnish intermediates of general formula (XVII) in which T represents mesylate, tosylate or Ph-$SO_2$—, wherein Ph can be substituted one, two or three times with halogen or a methyl-group or a nitro-group.

Intermediates of general formula (XVII) in which T represents $CF_3$—C(O)— can be converted to compounds of general formula (I) by reaction by reaction with a suitable halogen compound like for example 2-bromopyridine or 2-iodopyridine or iodobenzene in the presence of a suitable catalyst system, preferably a palladium catalyst, like for example tetrakis(triphenylphosphine)palladium(0) or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably Pd-Xphos G3 in a suitable solvent system such as, for example, acetonitrile, toluene, dioxane, DMF, DMA, or NMP or mixtures of these solvents, preferably in acetonitrile or dioxane in the presence of a base like dicaesium carbonate, or tripotassium phosphate in a temperature range from 60° C. to 130° C., preferably in a temperature range from 80° C. to 100° C. to furnish compounds of general formula (I).

Intermediates of general formula (XVII) in which T represents mesylate, tosylate or Ph-$SO_2$—, wherein Ph can be substituted one, two or three times with halogen or a methyl-group or a nitro-group, can be converted to intermediates of general formula (XVIII) in which T represents mesylate, tosylate or Ph-$SO_2$—, wherein Ph can be substituted one, two or three times with halogen or a methyl-group or a nitro-group, by reaction by reaction with a suitable halogen compound like for example 2-bromopyridine or 2-iodopyridine or iodobenzene in the presence of a suitable catalyst system, preferably a palladium catalyst, like for example tetrakis(triphenylphosphine)palladium(0) or for example a palladium catalyst prepared from a palladium source like palladium acetate or $Pd_2dba_3$ and XPhos as a ligand or a palladium-XPhos precatalyst like Pd-Xphos G2 or Pd-Xphos G3, preferably Pd-Xphos G3 in a suitable solvent system such as, for example, acetonitrile, toluene, dioxane, DMF, DMA, or NMP or mixtures of these solvents, preferably in acetonitrile or dioxane in the presence of a base like dicaesium carbonate, or tripotassium phosphate in a temperature range from 60° C. to 130° C., preferably in a temperature range from 80° C. to 100° C. to furnish intermediates of general formula (XVIII) in which T represents mesylate, tosylate or Ph-$SO_2$—, wherein Ph can be substituted one, two or three times with halogen or a methyl-group or a nitro-group.

Intermediates of general formula (XVIII) in which T represents mesylate, tosylate or Ph-$SO_2$—, wherein Ph can be substituted one, two or three times with halogen or a methyl-group or a nitro-group can be converted to intermediates of general formula (VII-A) by reaction with a suitable base, such as, for example an aqueous solution of sodium hydroxide or an aqueous solution of potassium hydroxide or an aqueous solution of lithium hydroxide, preferably an aqueous solution of sodium hydroxide, in a suitable solvent system, such as, for example, methanol or ethanol or THE or tert-butanol or mixtures of these solvents, preferably in methanol or THE in a temperature range from 60° C. to 100° C., preferably in a temperature range from 70° C. to 90° C. to furnish intermediates of general formula (VII-A).

Intermediates of general formula (XVIII) in which T represents mesylate, tosylate or Ph-$SO_2$—, wherein Ph can be substituted one, two or three times with halogen or a methyl-group or a nitro-group can be converted to compounds of general formula (I) by reaction with a suitable base, such as, for example an aqueous solution of potassium carbonate or an aqueous solution of cesium carbonate or an aqueous solution of lithium hydroxide, preferably an aqueous solution of potassium carbonate, in a suitable solvent system, such as, for example, methanol or ethanol or THE or tert-butanol or mixtures of these solvents, preferably in methanol or THE in a temperature range from 60° C. to 100° C., preferably in a temperature range from 70° C. to 90° C. to furnish compounds of general formula (I).

Scheme 5

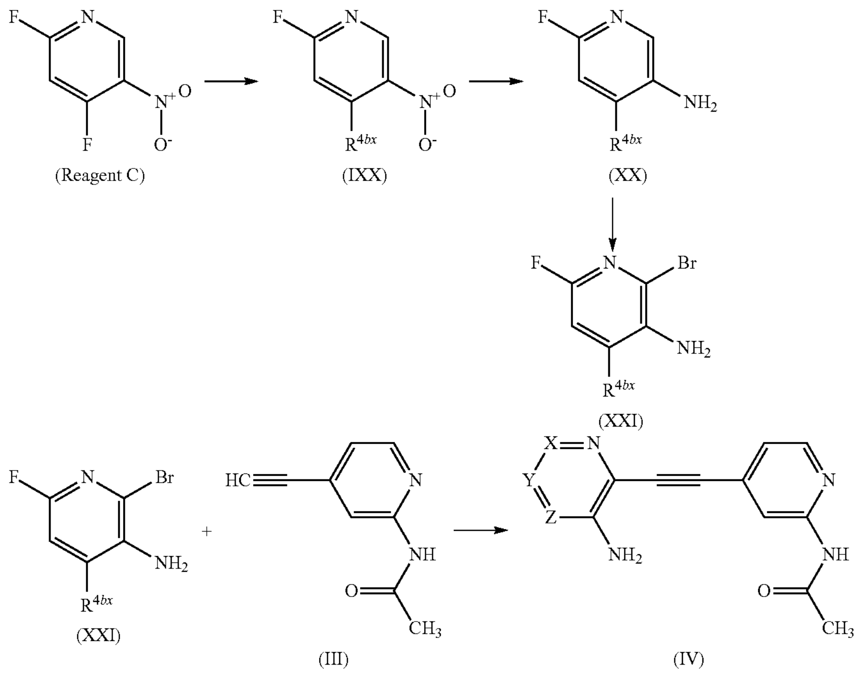

(Reagent C) (IXX) (XX) (XXI) (XXI) (III) (IV)

Scheme 5: Route for the preparation of Intermediates of general formula (IV), wherein X represents C—F, Y represents C—H, Z represents C—$R^{4bx}$, wherein $R^{4bx}$ represents a group selected from $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O—, or 3- to 6-membered heterocycloalkyl-$CH_2$—O—, wherein said $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O—, groups are optionally substituted one, two or three times with halogen, methyl, methoxy, or trifluoromethoxy. In addition, interconversion of the substituent, $R^{4bx}$ can be achieved before and/or after the exemplified transformation.

Reagent C is commercially available and can be converted to intermediates of general formula (IXX) wherein C—$R^{4bx}$, represents a group selected from $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O—, wherein said $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O— groups are optionally substituted one, two or three times with halogen, methyl, methoxy, or trifluoromethoxy, by reaction with a suitable reagent H—$R^{4bx}$, in a suitable solvent system such as, for example, acetonitrile, THF, dioxane, DMF, DMA, or NMP or mixtures of these solvents, preferably in THE or dioxane, most preferably in THE in the presence of a suitable base, such as, for example triethylamine, Hünig Base, potassium carbonate or cesium carbonate, preferably Hünig Base, in a temperature range from −10° C. to 100° C., preferably in a temperature range from rt to 80° C., most preferably in a temperature range from 50° C. to 70° C.

Intermediates of general formula (IXX) can be converted to intermediates of general formula (XX) by hydrogenation in the presence of a suitable catalyst such as palladium on carbon, or Raney nickel, preferably palladium on carbon in a suitable solvent system such as, for example, methanol or ethanol or dichlorometnane or mixtures of these solvents, preferably in ethanol, in a temperature range from 0° C. to 50° C., preferably at room temperature, or by reduction with other suitable reducing agents, such as iron powder in a solvent like methanol or ethanol in the prescence of an acid like concentrated hydrochloric acid, in a temperature range from 0° C. to 50° C., preferably at room temperature.

Intermediates of general formula (XX) can be converted to intermediates of general formula (XXI) by reaction with a halogenating agent like NBS in a suitable solvent system such as, for example, DMF or DMA, in a temperature range from 0° C. to 50° C., preferably at room temperature. Alternatively, and preferably, intermediates of general formula (XX) can be converted to intermediates of general formula (XXI) by reaction with a halogenating agent like bromine in a suitable solvent system such as, for example, acetic acid or dichloromethane or mixtures of these solvents, preferably in acetic acid, in a temperature range from −10° C. to 50° C., preferably in a temperature range from −5° C. to room temperature, more preferably in a temperature range from 0° C. to 10° C. to furnish intermediates of general formula (XXI).

Intermediates of general formula (XXI), can be reacted with an alkyne of formula (III) with a catalyst system typically used for Sonogashira couplings as described in the literature (K.

Sonogashira, Y. Tohda, N. Hagihara: Tetrahedron Lett. 1975, S. 4467-4470) like for example dichlorobis(triphenylphosphine)palladium(II) and copper(I) iodide in a suitable solvent system, such as, for example, triethylamine or a mixture of triethylamine and DMF or DMA or NMP, preferably DMF at temperatures ranging from 50° C. to 120° C., preferably at temperatures ranging from 70° C. to 90° C. to furnish intermediates of general formula (IV) wherein Z represents C—$R^{4bx}$, wherein $R^{4bx}$ represents a group selected from $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— or 3- to 6-membered heterocycloalkyl-$CH_2$—O—, wherein said $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O—, groups are optionally substituted one, two or three times with halogen, methyl, methoxy, or trifluoromethoxy. Similar reactions have been performed before and are described in the literature (ACS Med. Chem. Lett. 2018, 9, 1117-1122).

Scheme 6

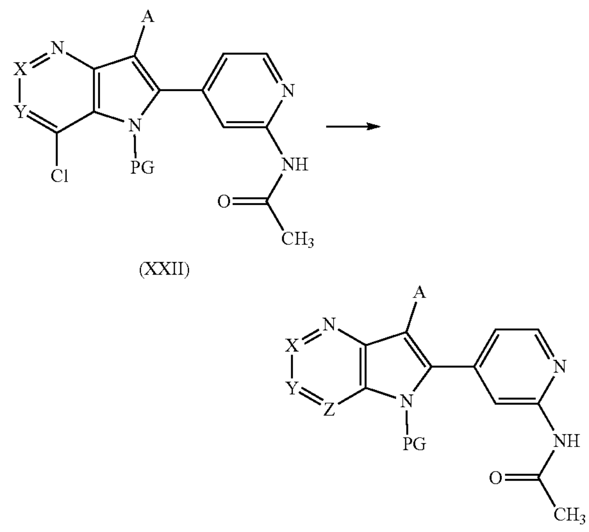

(XXII)

(VI-A)

Scheme 6: Route for the preparation of Intermediates of general formula (VI-A), wherein X, Y, and A have the meaning as given for general formula (I), supra. Z represents C—$R^{4bz}$, wherein $R^{4bz}$ represents a group selected from $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— or 3- to 6-membered heterocycloalkyl-$CH_2$—O—, wherein said $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O—, groups are optionally substituted one, two or three times with halogen, methyl, methoxy, or trifluoromethoxy.

In addition, interconversion of any of the substituents, $R^{4bz}$ can be achieved before and/or after the exemplified transformation.

Intermediates of general formula (XXII) can be converted to intermediates of general formula (VI-A) wherein Z represents C—$R^{4bz}$, wherein $R^{4bz}$ represents a group selected from $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— or 3- to 6-membered heterocycloalkyl-$CH_2$—O—, wherein said $C_1$-$C_3$-alkoxy, $C_1$-$C_3$-haloalkoxy, pyrrolidin-2-one, piperidin-2-one, morpholin-3-one, 4-methylpiperazin-2-one, $C_3$-$C_6$-cycloalkyl-O—, $C_3$-$C_6$-cycloalkyl-$CH_2$—O—, 3- to 6-membered heterocycloalkyl-O— and 3- to 6-membered heterocycloalkyl-$CH_2$—O—, groups are optionally substituted one, two or three times with halogen, methyl, methoxy, or trifluoromethoxy, by reaction with a suitable reagent H—$R^{4bz}$, in the presence of a suitable catalyst system, preferably a palladium catalyst, like for example a palladium catalyst prepared from a palladium source like palladium acetate or $Pd_2dba_3$ and 5-(Di-t-butylphosphino)-1',3',5'-triphenyl-1,4'-bi-1H-pyrazole in a suitable solvent system such as, for example, acetonitrile, toluene, dioxane, DMF, DMA, or NMP or mixtures of these solvents, preferably in toluene in the presence of a suitable base, such as, for example cesium carbonate in a temperature range from 60° C. to 130° C., preferably in a temperature range from 90° C. to 110° C.

These modifications can be such as the introduction of protecting groups, cleavage of protecting groups, reduction or oxidation of functional groups, halogenation, metallation, substitution or It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000. The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC may be applied. The compounds of the present invention which possess a sufficiently basic or acidic functionality, may result as a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of the compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, free acid, solvate, inclusion complex) of a compound of the present invention as isolated and described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds or optically active catalysts in synthesis or by separating enantiomeric and diasteriomeric mixtures obtained in synthesis.

Enantiomeric and diastereomeric mixtures can be separated into the pure enantiomers and pure diastereomers by methods known to the person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be separated using chiral separating columns in chromatography. Another suitable method for the isolation of enantiomers is the enzymatic separation.

One preferred aspect of the invention is the process for the preparation of the compounds of claims 1 to 4 according to the examples as well as the intermediates used for their preparation.

The intermediates used for the synthesis of the compounds of claims of formula (I) as described herein, as well as their use for the synthesis of the compounds of formula (I), are one further aspect of the present invention. Preferred intermediates are the Intermediate Examples as disclosed herein.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit Casein kinase 1 alpha and/or delta finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses. In particular, the disclosed compounds can be used for the treatment or prophylaxis of diseases in which the uncontrolled cell growth, proliferation and/or survival, inappropriate cellular immune responses, or inappropriate cellular inflammatory responses are mediated by Casein kinase 1 alpha and/or delta, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins lymphoma, chronic and acute myeloid leukemia (CML/AML), acute lymphoblastic leukemia (ALL), Hodgkins lymphoma, multiple myeloma and T-cell lymphoma. Also included are myelodysplastic syndrome, plasma cell neoplasia, paraneoplastic syndromes, and cancers of unknown primary site as well as AIDS related malignancies.

The term "inappropriate" within the context of the present invention, in particular in the context of "inappropriate cellular immune responses, or inappropriate cellular inflammatory responses", as used herein, is to be understood as preferably meaning a response which is associated with, responsible for, or results in, the pathology of said diseases.

Preferably, the use is in the treatment or prophylaxis of diseases, especially the treatment, wherein the diseases are haematological tumours, solid tumours and/or metastases thereof. Another aspect is the use of a compound of formula (I) for the prophylaxis and/or treatment of cervical tumours, lung tumours (such as lung carcinoma), colon tumours (such as colorectal carcinoma), or lymphoma (such as diffuse large B-cell lymphoma) and/or metastases thereof, especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is a cervical tumour, a lung tumour (such as lung carcinoma), a colon tumour (such as colorectal carcinoma), or a lymphoma (such as diffuse large B-cell lymphoma and/or metastases thereof.

Methods of treating hyper-proliferative disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as cancer.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes.

Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels.

These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death, e.g., apoptosis, of such cell types.

Preferably, the diseases of said method are haematological tumours, solid tumour and/or metastases thereof.

The compounds of the present invention can be used in particular in therapy and prevention, e.g., prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R.G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include, but are not limited to acetic acid, citric acid, fumaric acid, hydrochloric acid, nitric acid);

alkalinizing agents (examples include, but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include, but are not limited to powdered cellulose and activated charcoal); aerosol propellants (examples include, but are not limited to carbon dioxide, $CCl_2F_2$, $F_2ClC$—$CClF_2$ and $CClF_3$);

air displacement aqents—examples include, but are not limited to nitrogen and argon; antifungal preservatives (examples include, but are not limited to benzoic acid, butylparaben, ethylparaben, methylparaben, propylparaben, sodium benzoate);

antimicrobial preservatives (examples include, but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include, but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include, but are not limited to block polymers, natural and synthetic rubber, polyacrylates, polyurethanes, silicones, polysiloxanes and styrene-butadiene copolymers);

buffering agents (examples include, but are not limited to potassium metaphosphate, dipotassium phosphate, sodium acetate, sodium citrate anhydrous and sodium citrate dihydrate);

carrying agents (examples include, but are not limited to acacia syrup, aromatic syrup, aromatic elixir, cherry syrup, cocoa syrup, orange syrup, corn oil, mineral oil, peanut oil, sesame oil, bacteriostatic sodium chloride injection and bacteriostatic water for injection);

chelating agents (examples include, but are not limited to edetate disodium and edetic acid);

colourants (examples include, but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include, but are not limited to bentonite);

emulsifying agents (examples include, but are not limited to acacia, cetomacrogol, cetyl alcohol, glyceryl monostearate, lecithin, sorbitan monooleate, polyoxyethylene 50 monostearate); encapsulating agents (examples, include but are not limited to gelatin and cellulose acetate phthalate);

flavourants (examples include, but are not limited to anise oil, cinnamon oil, cocoa, menthol, orange oil, peppermint oil and vanillin);

humectants (examples include, but are not limited to glycerol, propylene glycol and sorbitol);

levigatinq agents (examples include, but are not limited to mineral oil and glycerin); oils (examples include, but are not limited to arachis oil, mineral oil, olive oil, peanut oil, sesame oil and vegetable oil);

ointment bases (examples include, but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include, but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include, but are not limited to diethyl phthalate and glycerol);

solvents (examples include, but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include, but are not limited to cetyl alcohol, cetyl esters wax, microcrystalline wax, paraffin, stearyl alcohol, white wax and yellow wax);

suppository bases (examples include, but are not limited to cocoa butter and polyethylene glycols (mixtures));

surfactants (examples include, but are not limited to benzalkonium chloride, nonoxynol 10, oxtoxynol 9, polysorbate 80, sodium lauryl sulfate and sorbitan mono-palmitate);

suspending agents (examples include, but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include, but are not limited to aspartame, dextrose, glycerol, mannitol, propylene glycol, saccharin sodium, sorbitol and sucrose);

tablet anti-adherents (examples include, but are not limited to magnesium stearate and talc);

tablet binders (examples include, but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include, but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include, but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include, but are not limited to dibasic calcium phosphate);

tablet disintegrants (examples include, but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include, but are not limited to colloidal silica, corn starch and talc); tablet lubricants (examples include, but are not limited to calcium stearate, magnesium stearate, mineral oil, stearic acid and zinc stearate);

tablet/capsule opaquants (examples include, but are not limited to titanium dioxide);

tablet polishing agents (examples include, but are not limited to carnuba wax and white wax);

thickening agents (examples include, but are not limited to beeswax, cetyl alcohol and paraffin);

tonicity agents (examples include, but are not limited to dextrose and sodium chloride);

viscosity increasing agents (examples include, but are not limited to alginic acid, bentonite, carbomers, carboxymethylcellulose sodium, methylcellulose, polyvinyl pyrrolidone, sodium alginate and tragacanth); and wetting agents (examples include, but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, “drug holidays” in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al, publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Experimental Part

Table 1 lists the abbreviations used in this paragraph and in the Intermediates and Examples sections as far as they are not explained within the text body.

TABLE 1

| Abbreviation | Meaning |
|---|---|
| AcOH | acetic acid (ethanoic acid) |
| aq. | aqueous |
| Boc | t-butoxycarbonyl |
| BOP | (benzotriazol-1-yloxy)tris(dimethylamino)phosphonium hexafluorophosphate |
| br | broad |
| CI | chemical ionisation |
| $Cs_2CO_3$ | caesium carbonate |
| d | doublet |
| DAD | diode array detector |
| DBU | 1,8-diazabicyclo(5.4.0)undec-7-ene |
| DCC | N,N'-dicyclohexylcarbodiimide |
| DCM | dichloromethane |
| dd | double-doublet |
| DIC | N,N'-diisopropylcarbodiimide |
| DIPEA | diisopropylethylamine |
| DMA | Dimethylacetamide |
| DMF | N,N-dimethylformamide |
| DMSO | dimethyl sulfoxide |
| dt | double-triplet |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour |
| HATU | 1-[bis(dimethylamino)methylene]-1H-1,2,3-triazolo[4,5-b]pyridinium 3-oxid hexafluorophosphate |
| HBTU | (o-benzotriazole-10yl)-N,N,N',N,-tetramethyluronium hexafluorophosphate |
| HCl | hydrochloric acid |
| HPLC | high performance liquid chromatography |
| $K_2CO_3$ | potassium carbonate |
| LC-MS | liquid chromatography mass spectrometry |
| m | multiplet |
| mCPBA | meta-Chloroperbenzoic acid |
| min | minute |
| MeCN | acetonitrile |
| MeOH | methanol |
| MS | mass spectrometry |
| MTBE | methyl-tert-butyl ether |
| NaCl | sodium chloride |
| $NaHCO_3$ | sodium hydrogen carbonate or sodium bicarbonate |
| NMR | nuclear magnetic resonance spectroscopy: chemical shifts (δ) are given in ppm. The chemical shifts were corrected by setting the DMSO signal to 2.50 ppm unless otherwise stated. |
| $Na_2SO_4$ | sodium sulfate |
| PDA | Photo Diode Array |
| Pd/C | palladium on activated charcoal |
| PyBOP | (benzotriazol-1-yloxy)tripyrrolidinophosphonium hexafluorophosphate |
| q | quartet |
| r.t. or rt or RT | room temperature |
| Rt | retention time (as measured either with HPLC or UPLC) in minutes |
| s | singlet |
| sat. | saturated |
| SFC | supercritical fluid chromatography |
| SIBX | stabilized 2-iodoxybenzoic acid |
| SM | starting material |
| SQD | Single-Quadrupole-Detector |
| T3P | propylphosphonic anhydride |
| t | triplet |
| td | triple-doublet |
| TEA | triethylamine |
| TFA | trifluoroacetic acid |
| THF | tetrahydrofuran |
| UPLC | ultra performance liquid chromatography |
| XPhos Pd G3; or XPhos-Pd-G3 | (2-Dicyclohexylphosphino-2',4',6'-triisopropyl-1,1'-biphenyl)[2-(2'-amino-1,1'-biphenyl)]palladium(II) methanesulfonate |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered.

Reactions employing microwave irradiation may be run with a Biotage Initiator® microwave oven optionally equipped with a robotic unit. The reported reaction times employing microwave heating are intended to be understood as fixed reaction times after reaching the indicated reaction temperature.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example pre-packed silica gel cartridges, e.g. from Separtis such as Isolute®

Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula and introduced into reaction vessels through rubber septa. Commercial grade reagents and solvents were used without further purification. The term "concentrated in vacuo" refers to the use of a Buchi rotary evaporator at a minimum pressure of approximately 15 mm of Hg. All temperatures are reported uncorrected in degrees Celsius (° C.).

In order that this invention may be better understood, the following examples are set forth.

These examples are for the purpose of illustration only, and are not to be construed as limiting the scope of the invention in any manner. All publications mentioned herein are incorporated by reference in their entirety.

Analytical Conditions

UPLC-MS Standard Procedures

UPLC-MS-data given in the subsequent specific experimental descriptions refer (unless otherwise noted) to the following conditions:

Method 1:

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µL |
| Detection: | DAD scan range 210-400 nm<br>MS ESI+, ESI−, scan range 160-1000 m/z<br>ELSD |

Method 2:

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µL |
| Detection: | DAD scan range 210-400 nm<br>MS ESI+, ESI−, scan range 160-1000 m/z<br>ELSD |

Method 3:

| | | | | |
|---|---|---|---|---|
| Instrument | | SHIMADZU LCMS-2020; | | |
| Software | | LabSolution Version 5.97SP1 | | |
| HPLC | Column | Kinetex ® EVO C18 2.1 × 30 mm 5 um | | |
| | Mobile Phase | A: 0.0375% TFA in water (v/v)<br>B: 0.01875% TFA in Acetonitrile (v/v) | | |
| | Gradient | Time(min) | B(%) | Flow(mL/min) |
| | | 0.0 | 5 | 0.8 |
| | | 3.0 | 95 | 0.8 |
| | | 3.60 | 95 | 0.8 |
| | | 3.61 | 5 | 0.8 |
| | | 4.00 | 5 | 0.8 |
| | Column Temp | 40° C. | | |
| | Detector | PDA (220 nm&254 nm) | | |
| MS | Ionization source | ESI | | |
| | Drying Gas | N2 | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |

Method 4:

Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.5 min 5% B, 0.5-4.0 min 5-95% B, 4.0-4.5 min 95% B; 4.5-5.0 min 5% B; flow: 0.65 mL/min; temperature: 50° C.; DAD scan: 200-500 nm.

Method A:

Instrument: SHIMADZU LCMS-2020 SingleQuad; Column: Chromolith® Flash RP-18E 25-2 MM; eluent A: water+0.0375 vol % trifluoroacetic acid, eluent B: acetonitrile+0.01875 vol % trifluoroacetic acid; gradient: 0-0.8 min 0-60% B, 0.8-1.2 min 60% B; flow 1.5 ml/min; temperature: 50° C.; PDA: 220 nm & 254 nm.

Method B:

Instrument: Agilent 1100G1956A SingleQuad; Column: Kinetex® Sum EVO C18 30*2.1 mm; eluent A: water+0.0375 vol % trifluoroacetic acid, eluent B: acetonitrile+0.01875 vol % trifluoroacetic acid; gradient: 0-0.8 min 0-60% B, 0.8-1.2 min 60% B; flow 1.5 ml/min; temperature: 50° C.; PDA: 220 nm & 254 nm.

Method C:

Instrument: SHIMADZU LCMS-2020 SingleQuad; Column: Chromolith® Flash RP-18E 25-2 MM; eluent A: water+0.0375 vol % trifluoroacetic acid, eluent B: acetonitrile+0.01875 vol % trifluoroacetic acid; gradient: 0-0.8 min, 5-95% B, 0.8-1.2 min 95% B; flow 1.5 ml/min; temperature: 50° C.; PDA: 220 nm & 254 nm.

Method D:

Instrument: Agilent 1100G1956A SingleQuad; Column: Kinetex® 5 μm EVO C18 30*2.1 mm; eluent A: water+0.0375 vol % trifluoroacetic acid, eluent B: acetonitrile+0.01875 vol % trifluoroacetic acid; gradient: 0-0.8 min 5-95% B, 0.8-1.2 min 95% B; flow 1.5 ml/min; temperature: 50° C.; PDA: 220 nm & 254 nm.

Method E:

Instrument: Agilent 1200G6110A SingleQuad; Column: XBridge C18 2.1*50 mm, 5 μm; eluent A: water+0.025 vol % ammonium hydroxide, eluent B: acetonitrile; gradient: 0-1.2 min 10-80% B, 1.2-1.6 min 80% B; flow 1.2 ml/min; temperature: 40° C.; DAD: 220 nm & 254 nm.

Method F:

Instrument: Agilent 1200G6110A SingleQuad; Column: XBridge C18 2.1*50 mm, 5 μm; eluent A: water+0.025 vol % ammonium hydroxide, eluent B: acetonitrile; gradient: 0-1.2 min 0-60% B, 1.2-1.6 min 60% B; flow 1.0 ml/min; temperature: 40° C.; DAD: 220 nm & 254 nm.

Method G:

Instrument: SHIMADZU LCMS-2020 SingleQuad; Column: Kinetex EVO C18 2.1*30 mm, 5 μm; eluent A: water+0.025 vol % ammonium hydroxide, eluent B: acetonitrile; gradient: 0-0.8 min, 5-95% B, 0.8-1.2 min 95% B; flow 1.5 ml/min; temperature: 40° C.; PDA: 220 nm & 254 nm.

Method H:

Instrument: SHIMADZU LCMS-2020 SingleQuad; Column: Kinetex EVO C18 2.1*30 mm, 5 μm; eluent A: water+0.025 vol % ammonium hydroxide, eluent B: acetonitrile; gradient: 0-1.2 min, 0-60% B, 1.2-1.6 min, 60% B; flow 1.0 ml/min; temperature: 40° C.; PDA: 220 nm & 254 nm.

Method I:

Instrument: SHIMADZU LCMS-2020 SingleQuad; Column: Kinetex EVO C18 2.1*30 mm, 5 μm; eluent A: water+0.025 vol % ammonium hydroxide, eluent B: acetonitrile; gradient: 0-0.8 min, 5-95% B, 0.8-1.2 min, 95% B; flow 1.5 ml/min; temperature: 40° C.; PDA: 220 nm & 254 nm.

Method J:

Instrument: SHIMADZU LCMS-2020 SingleQuad; Column: Kinetex EVO C18 2.1*30 mm, 5 μm; eluent A: water+0.025 vol % ammonium hydroxide, eluent B: acetonitrile; gradient: 0-0.8 min, 0-60% B, 0.8-1.2 min, 60% B; flow 1.5 ml/min; temperature: 40° C.; PDA: 220 nm & 254 nm.

Preparative HPLC Conditions

"Purification by preparative HPLC" in the subsequent experimental descriptions refers to the following conditions (unless otherwise noted):

Method K

Istrument: Labomatic HD-5000, pump head HDK-280, gradient module NDB-1000, fraction collector Labomatic Labocol Vario 2000, Knauer UV detector Azura UVD 2.1S, Prepcon 5 software. Column: Chromatorex C18 10 μM 120×30 mm; Eluent A: 0.1% ammonia in water; Eluent B: acetonitrile; gradient: given for intermediates and examples, rate 150 mL/min, temperature 25° C.; UV 250 nm Method L Instrument: Labomatic HD-5000, pump head HDK-280, gradient module NDB-1000, fraction collector Labomatic Labocol Vario 2000, Knauer UV detector Azura UVD 2.1S, Prepcon 5 software. Column: Chromatorex C18 10 μM 120×30 mm; Eluent A: water+0.1% formic acid; Eluent B: acetonitrile; gradient: given for intermediates and examples, rate 150 mL/min, temperature 25° C.; UV 220 nm Flash Column Chromatography Conditions "Purification by (flash) column chromatography" as stated in the subsequent specific experimental descriptions refers to the use of a Biotage Isolera purification system. For technical specifications see "Biotage product catalogue" on www.biotage.com.

Chemical names were generated using the ACD/Name software from ACD/Labs. In some cases generally accepted names of commercially available reagents were used in place of ACD/Name generated names.

Optical rotations were measured using a JASCO P2000 Polarimeter. Typical, a solution of the compound with a concentration of 1 mg/mL to 15 mg/mL was used for the measurement. The specific rotation $[\alpha]_D$ was calculated according to the following formula:

$$[\alpha]D = \frac{\alpha}{\beta \times d}$$

In this equation, α is the measured rotation in degrees; d is the path length in decimetres and β is the concentration in g/mL.

Experimental Section-Intermediates

Intermediate 1

N-{4-[(3-amino-6-fluoropyridin-2-yl)ethynyl]pyridin-2-yl}acetamide

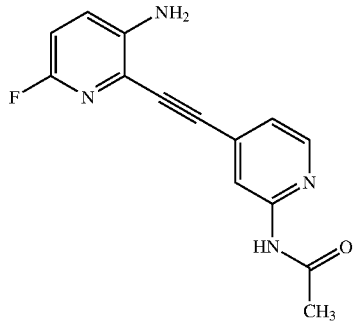 [SMILES: CC(=O)Nc1cc(C#Cc2nc(F)ccc2N)ccn1]

N-(4-Ethynylpyridin-2-yl)acetamide (799 mg, 4.99 mmol, CAS-RN:[1445876-40-3]), 2-bromo-6-fluoropyridin-3-amine (1.00 g, 5.24 mmol, CAS-RN:[1068976-51-1]), bis(triphenylphosphine) palladium(II) dichloride (350 mg, 499 μmol; CAS-RN:[13965-03-2]), copper(I)-iodide (19.0 mg, 99.7 μmol; CAS-RN:[7681-65-4]) and triethylamine (6.3 mL, 45 mmol) were dissolved in 2.1 mL DMF and stirred at 80° C. for 1.5 hours under Argon atmosphere. The reaction mixture was concentrated under reduced pressure and purified by flash chromatography (55 g column, aminophase; dichloromethane/ethanol 0%-5%) to provide the target compound in 65% purity: 168 mg.

LC-MS (Method 1): $R_t$=0.84 min; MS (ESIpos): m/z=271 $[M+H]^+$ $^1$H-NMR (400 MHz, DMSO-d6): δ [ppm]=2.11 (s, 3H), 5.87 (s, 2H), 6.99 (dd, 1H), 7.31-7.34 (m, 1H), 7.36 (dd, 1H), 8.23 (s, 1H), 8.35 (dd, 1H), 10.63 (s, 1H).

Intermediate 2

N-{2-[(2-acetamidopyridin-4-yl)ethynyl]-6-fluoro-pyridin-3-yl}-2,2,2-trifluoroacetamide

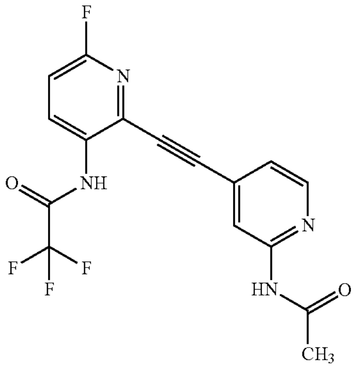 [SMILES: CC(=O)Nc1cc(C#Cc2nc(F)ccc2NC(=O)C(F)(F)F)ccn1]

N-{4-[(3-Amino-6-fluoropyridin-2-yl)ethynyl]pyridin-2-yl}acetamide (see Intermediate 1, 830 mg) and triethylamine (1.3 mL, 9.2 mmol) were suspended in 13 mL dichloromethane and cooled down with an ice bath. Then trifluoroacetic anhydride (640 μL, 4.6 mmol) was added portion wise. The reaction mixture was stirred at 0° C. for 2 hours under Argon atmosphere. To the reaction mixture aqueous saturated sodium hydrogencarbonte solution and dichloromethane were added. The undissolved precipitate was filtered off, washed with water and dichloromethane/isopropanole (7:3) and dried at 50° C. under vacuo to provide the target compound in 85% puritiy: 304 mg.

LC-MS (Method 2): Rt=0.51 min; MS (ESIpos): m/z=368 $[M+H]^+$

1H-NMR (400 MHz, DMSO-d6) δ[ppm]=2.09-2.15 (m, 3H), 7.19 (dd, 1H), 7.44 (dd, 1H), 8.17 (dd, 1H), 8.24 (s, 1H), 8.41 (dd, 1H), 10.71 (s, 1H), 11.66 (br s, 1H).

Intermediate 3

N-{4-[5-fluoro-3-(pyridin-2-yl)-1H-pyrrolo[3,2-b]pyridin-2-yl]pyridin-2-yl}acetamide

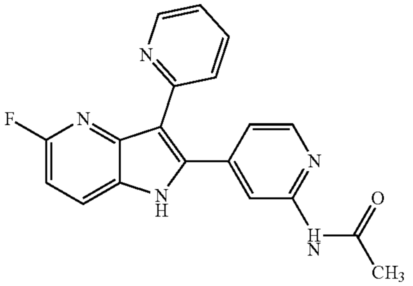 [SMILES: CC(=O)Nc1cc(-c2[nH]c3ccc(F)nc3c2-c2ccccn2)ccn1]

N-{2-[(2-Acetamidopyridin-4-yl)ethynyl]-6-fluoropyridin-3-yl}-2,2,2-trifluoroacetamide (see Intermediate 2, 250 mg), 2-bromopyridine (75 μL, 790 μmol), tetrakis(triphenylphosphine)palladium (39.4 mg, 34.1 μmol; CAS-RN: [14221-01-3]) and cesiumcarbonate 645 mg, 1.98 mmol) were dissolved in 5.7 mL acetonitrile and stirred at 100° C. under Argon atmosphere in a sealed vessel for 1 h. The reaction mixture was combined with another batch started from N-{2-[(2-Acetamidopyridin-4-yl)ethynyl]-6-fluoro-pyridin-3-yl}-2,2,2-trifluoroacetamide (see Intermediate 2, 50 mg). The undissolved precipitated was filtered off and washed with dichloromethane and methanol. The filtrate was concentrated under reduced pressure and purified by HPLC chromatography under basic conditions in 2 portions. The product containing fractions were concentrated under reduced pressure and treated with dichloromethane and ethanol. The undissolved precipitate was filtered off, washed with dichloromethane and dried at 50° C. under vacuo to provide the target compound in 88% purity: 26 mg.

LC-MS (Method 2): $R_t$=0.89 min; MS (ESIpos): m/z=348 $[M+H]^+$ $^1$H-NMR (400 MHz, DMSO-d6) δ[ppm]=2.08 (s, 3H), 7.00 (dd, 1H), 7.12 (dd, 1H), 7.27 (ddd, 1H), 7.83-7.97 (m, 2H), 8.05 (dd, 1H), 8.24-8.33 (m, 2H), 8.45 (d, 1H), 10.56 (s, 1H), 12.15-12.50 (m, 1H).

Intermediate 4

4-[5-fluoro-3-(pyridin-2-yl)-1H-pyrrolo[3,2-b]pyridin-2-yl]pyridin-2-amine

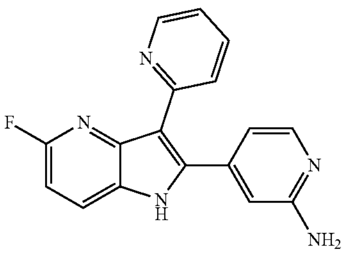 [SMILES: Nc1cc(-c2[nH]c3ccc(F)nc3c2-c2ccccn2)ccn1]

N-{4-[5-Fluoro-3-(pyridin-2-yl)-1H-pyrrolo[3,2-b]pyridin-2-yl]pyridin-2-yl}acetamide (see Intermediate 3, 180 mg) was dissolved in 39 mL methanol and treated with aqueous sodium hydroxide solution (5.2 mL, 1.0 M, 5.2 mmol). The reaction mixture was stirred at 80° C. for 1.5 hours under Argon atmosphere. Further aqueous sodium hydroxide solution (2.1 mL, 2.0 M, 4.1 mmol) were added and it was stirred at 80° C. for 6.5 hours under Argon atmosphere. The reaction mixture was concentrated under reduced pressure and diluted with water. The undissolved precipitate was filtered off and washed with water until the filtrate was not basic anymore. The residue was dried at 50° C. under vacu to provide the analytically pure target compound: 139 mg.

LC-MS (Method 2): $R_t$=0.85 min; MS (ESIpos): m/z=306 $[M+H]^+$ $^1$H-NMR (400 MHz, DMSO-d6) δ[ppm]=6.02 (s, 2H), 6.50 (dd, 1H), 6.59 (s, 1H), 6.96 (dd, 1H), 7.23-7.32 (m, 1H), 7.81-7.92 (m, 3H), 7.99 (dd, 1H), 8.51 (dt, 1H), 11.81-12.54 (m, 1H).

Intermediate 5

N-(4-bromopyridin-2-yl)-2-(4-fluorophenyl)acetamide

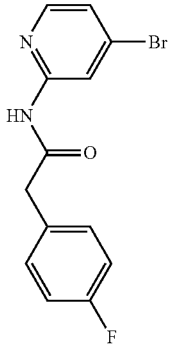 [SMILES: O=C(Cc1ccc(F)cc1)Nc1cc(Br)ccn1]

To a solution of (4-fluorophenyl)acetic acid (16.0 g, 104 mmol) in dichloromethane (200 ml) was added 2-(7-azabenzotriazol-1-yl)-N,N,N',N'-tetramethyluronium hexafluorophosphate (42.9 g, 113 mmol) and N,N-diisopropylethylamine (30 ml). Then 4-bromopyridin-2-amine (15.0 g, 86.7 mmol) was added to the mixture. The mixture was stirred at room temperature for 16 hours. The mixture was poured into water, the organic layer was separated. The aqueous layer was extracted with dichloromethane. The combined organic layer was washed with brine, dried over anhydrous sodium sulfate, filtered and concentrated to give a residue. The residue was purified by flash silica gel chromatography (80 g, ethyl acetate in petroleum ether=0% to 30%) to give N-(4-bromopyridin-2-yl)-2-(4-fluorophenyl)acetamide (15.0 g, 56% yield) as yellow oil.

$^1$H NMR (400 MHz, $CDCl_3$): δ [ppm]=8.51 (d, J=1.2 Hz, 1H), 8.29 (s, 1H), 8.04 (d, J=5.6 Hz, 1H), 7.34-7.30 (m, 2H), 7.22 (dd, J=5.6, 2.0 Hz, 1H), 7.11-7.06 (m, 2H), 3.74 (s, 2H).

Intermediate 6

2-(4-fluorophenyl)-N-{4-[(trimethylsilyl)ethynyl]pyridin-2-yl}acetamide

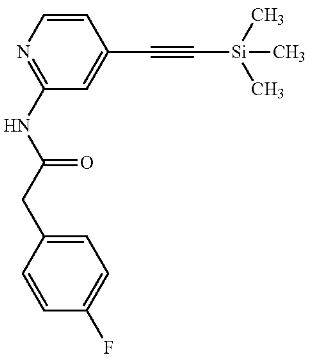 [SMILES: C[Si](C)(C)C#Cc1ccnc(NC(=O)Cc2ccc(F)cc2)c1]

A mixture of N-(4-bromopyridin-2-yl)-2-(4-fluorophenyl)acetamide (see Intermediate 5, 15.0 g, 48.5 mmol), ethynyl(trimethyl)silane (7.15 g, 72.8 mmol), dichlorobis(triphenylphosphine)palladium(II) (681 mg, 0.97 mmol) and copper(I) iodide (370 mg, 1.94 mmol) in triethylamine (75 ml, 540 mmol) and N,N-dimethylformamide (150 ml) was puraged with nitrogen. The mixture was stirred at 80° C. for 2 hours. The mixture was diluted with ethyl acetate, then washed with water. The organic layer was concentrated to give a residue.

The residue (combined with Intermediate 6) was purified by silica gel chromatography (petroleum ether:ethyl acetate=20:1, then 10:1, then 5:1, then 3:1) to give 2-(4-fluorophenyl)-N-{4-[(trimethylsilyl)ethynyl]pyridin-2-yl}acetamide (9.50 g, 60% yield) as a yellow solid.

LC-MS (Method C): Rt=1.004 min; MS (ESIpos): m/z=327.2 $[M+H]^+$.

$^1$H NMR (400 MHz, CDC): 6 [ppm]=8.30 (s, 1H), 8.17 (s, 1H), 7.87 (s, 1H), 7.34-7.30 (m, 2H), 7.12-7.07 (m, 3H), 3.74 (s, 2H), 0.27 (s, 9H).

Intermediate 7

N-(4-ethynylpyridin-2-yl)-2-(4-fluorophenyl)acetamide

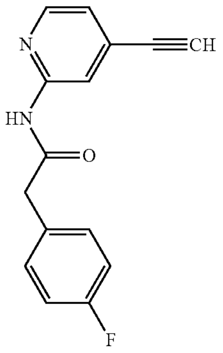 [SMILES: C#Cc1ccnc(NC(=O)Cc2ccc(F)cc2)c1]

To a solution of 2-(4-fluorophenyl)-N-{4-[(trimethylsilyl)ethynyl]pyridin-2-yl}acetamide (see Intermediate 6, 9.50 g, 29.1 mmol) in methanol (100 ml) was added potassium carbonate (58 ml, 1.0 M, 58 mmol). The mixture was stirred at room temperature for 2 hours. The mixture was concentrated. The residue was purified by silica gel chromatography (200-300 mesh, petroleum ether:ethyl acetate=20:1, then 10:1, then 3:1) to give N-(4-ethynylpyridin-2-yl)-2-(4-fluorophenyl)acetamide (6.50 g, 88% yield) as a yellow solid.

LC-MS (Method C): $R_t$=0.767 min; MS (ESIpos): m/z=255.1 $[M+H]^+$.

Intermediate 8

N-{4-[(3-aminopyridin-2-yl)ethynyl]pyridin-2-yl}-2-(4-fluorophenyl)acetamide

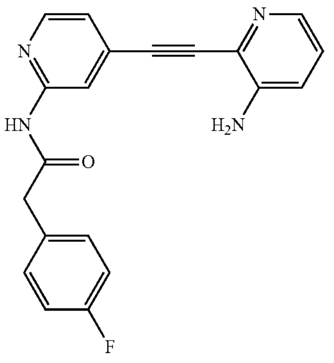 [SMILES: Nc1cccnc1C#Cc1ccnc(NC(=O)Cc2ccc(F)cc2)c1]

A mixture of N-(4-ethynylpyridin-2-yl)-2-(4-fluorophenyl)acetamide (see Intermediate 7, 2.90 g, 11.4 mmol), 2-bromopyridin-3-amine (3.95 g, 22.8 mmol), dichlorobis (triphenylphosphine)palladium(II) (400 mg, 0.57 mmol; and copper(I) iodide (217 mg, 1.14 mmol) in trimethylamine (18 ml, 130 mmol) and N,N-dimethylformamide (45 ml) was puraged with nitrogen. The mixture was stirred at 100° C. for 2 hours. The mixture was cooled to room temperature. The solid was filtered off, and the filtrate was concentrated. The residue was diluted with ethyl acetate and then washed with water. The organic layer was concentrated. The crude product was purified by flash silica gel chromatography (24 g, ethyl acetate in petroleum ether=0% to 80%) to give N-{4-[(3-aminopyridin-2-yl)ethynyl]pyridin-2-yl}-2-(4-fluorophenyl)acetamide (2.7 g, 68% yield) as a yellow solid.

LC-MS (Method C): $R_t$=0.777 min; MS (ESIpos): m/z=347.2 $[M+H]^+$.

$^1$H NMR (400 MHz, DMSO-$d_6$): δ [ppm]=10.86 (s, 1H), 8.37 (d, J=4.8 Hz, 1H), 8.22 (s, 1H), 7.82-7.80 (m, 1H), 7.41-7.35 (m, 3H), 7.18-7.12 (m, 4H), 5.81 (s, 2H), 3.74 (s, 2H).

Intermediate 9

2,2,2-trifluoro-N-[2-({2-[2-(4-fluorophenyl)acetamido]pyridin-4-yl}ethynyl)pyridin-3-yl]acetamide

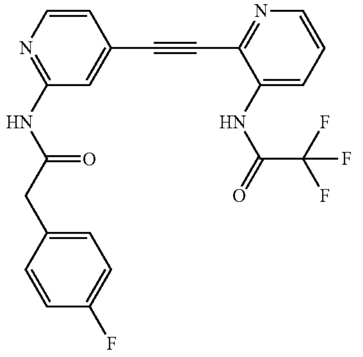 [SMILES: O=C(Cc1ccc(F)cc1)Nc1cc(C#Cc2ncccc2NC(=O)C(F)(F)F)ccn1]

To a suspension of N-{4-[(3-aminopyridin-2-yl)ethynyl]pyridin-2-yl}-2-(4-fluorophenyl)acetamide (see Intermediate 8, 2.70 g, 7.33 mmol) in dichloromethane (50 ml) was added trimethylamine (20 ml, 15 mmol), and the mixture was cooled to 0° C. Trifluoroacetic anhydride (1.6 ml, 11 mmol) was slowly added. The reaction mixture was stirred at 0° C. for 0.5 hour. The mixture was diluted with dichloromethane. The solution was washed with saturated sodium hydrogen carbonate and brine, then the mixture was extracted with dichloromethane and the combined organic layer was washed with brine, dried over anhydrous sodium sulfate, filtered and concentrated by evaporation in vacuum. The residue was purified by trituration with dichloromethane (15 ml) to give 2,2,2-trifluoro-N-[2-({2-[2-(4-fluorophenyl)acetamido]pyridin-4-yl}ethynyl)pyridin-3-yl]acetamide (2.70 g, 99% purity, 82% yield) as light yellow solid.

LC-MS (Method C): $R_t$=0.902 min; MS (ESIpos): m/z=443.1 $[M+H]^+$.

Intermediate 10

N-{4-[(3-aminopyridin-2-yl)ethynyl]pyridin-2-yl}acetamide

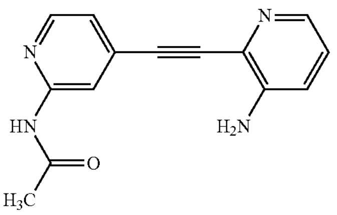 [SMILES: CC(=O)Nc1cc(C#Cc2ncccc2N)ccn1]

To a stirred solution of N-(4-ethynylpyridin-2-yl)acetamide (CAS 1445876-40-3, 2.00 g, 12.5 mmol) and 2-bromopyridin-3-amine (CAS 39856-58-1, 2.59 g, 15.0 mmol) in DMF (34 mL) was added triethylamine (7.0 ml, 50 mmol; CAS-RN:[121-44-8]), $Pd(PPh_2)_3Cl_2$ (438 mg, 624 μmol; CAS-RN:[13965-03-2]) and CuI (238 mg, 1.25 mmol; CAS-RN:[7681-65-4]) and the flask was twice degased and backfilled with argon. The mixture was stirred at 80° C. for 1 h. Ethyl acetate was added and the mixture was washed with half-saturated sodium chloride solution (three times), dried (sodium sulfate), filtered and the solvent was removed in vacuum. Silicagel chromatography (Gradient: dichloromethane/ethanol 0-25%) gave 1.72 g of the title compound.

LC-MS (Method 1): Rt=0.59 min; MS (ESIpos): m/z=253 $[M+H]^+$ $^1$H-NMR (400 MHz, DMSO-$d_6$): δ [ppm]=10.62 (s, 1H), 8.35 (d, 1H), 8.23 (s, 1H), 7.81 (br s, 1H), 7.35 (dd, 1H), 7.18-7.08 (m, 2H), 5.83 (s, 2H), 2.11 (s, 3H).

Intermediate 11

N-{2-[(2-acetamidopyridin-4-yl)ethynyl]pyridin-3-yl}-2,2,2-trifluoroacetamide

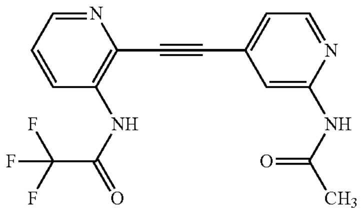 [SMILES: CC(=O)Nc1cc(C#Cc2ncccc2NC(=O)C(F)(F)F)ccn1]

A stirred solution of N-{4-[(3-aminopyridin-2-yl)ethynyl]pyridin-2-yl}acetamide (see Intermediate 10, 560 mg, 2.22 mmol), and triethylamine (620 μl, 4.4 mmol; CAS-RN:[121-44-8]) in dichloromethane (25 ml) was cooled to 0° C., trifluoroacetic anhydride (470 μl, 3.3 mmol; CAS-RN:[407-25-0]) was slowly added and the mixture was stirred at 0° C. for 2 h. Dichloromethane and an aqueous solution of sodium bicarbonate were added and the mixture was extracted with a mixture of dichloromethane and methanol. The organic phase was washed with saturated sodium chloride solution, dried (sodium sulfate), filtered and the solvent was removed in vacuum. The residue was triturated with a mixture of dichloromethane and hexane. The mixture was filtered, the solid was discarded and the solution was concentrated to drynes to give 256 mg (68% purity) of the title compound.

LC-MS (Method 1): $R_t$=0.88 min; MS (ESIpos): m/z=349 $[M+H]^+$

Intermediate 12

N-{4-[3-(pyridin-2-yl)-1H-pyrrolo[3,2-b]pyridin-2-yl]pyridin-2-yl)acetamide

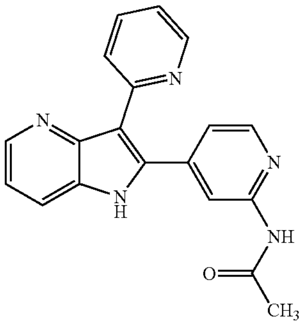 [SMILES: CC(=O)Nc1cc(-c2[nH]c3cccnc3c2-c2ccccn2)ccn1]

To a stirred solution of N-{2-[(2-acetamidopyridin-4-yl)ethynyl]pyridin-3-yl}-2,2,2-trifluoroacetamide (see Intermediate 11, 250 mg, 65% purity, 467 μmol) and 2-bromopyridine (67 μl, 700 μmol; CAS-RN:[109-04-6]) in acetonitrile (2.6 mL) in a sealed tube was added dicaesium carbonate (456 mg, 1.40 mmol; CAS-RN:[534-17-8]) and tetrakis(triphenylphosphin)palladium (27.0 mg, 23.3 μmol; CAS-RN:[14221-01-3]) and the flask was twice degased and backfilled with argon. The mixture was heated to 80° C. for 3 h and then to 100° C. for 1 h. Water was added, the mixture was extracted with a mixture of dichloromethane and methanol. The organic phase was dried (sodium sulfate), filtered and the solvent was removed in vacuum. Silicagel chromatography (Gradient: dichloromethane/ethanol 0-25%) gave 26.0 mg of the title compound.

LC-MS (Method 1): $R_t$=0.59 min; MS (ESIpos): m/z=330 $[M+H]^+$ $^{1}$H-NMR (400 MHz, DMSO-d6): δ [ppm]=12.09 (s, 1H), 10.55 (s, 1H), 8.48-8.41 (m, 2H), 8.31 (s, 1H), 8.30-8.27 (m, 1H), 8.15-8.10 (m, 1H), 7.91-7.83 (m, 2H), 7.29-7.22 (m, 2H), 7.15 (dd, 1H), 2.08 (s, 3H).

Intermediate 13

4-[3-(pyridin-2-yl)-1H-pyrrolo[3,2-b]pyridin-2-yl]pyridin-2-amine

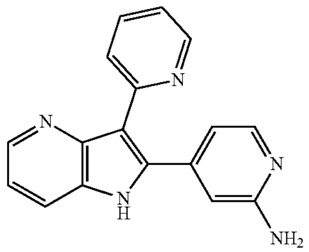 [SMILES: Nc1cc(-c2[nH]c3cccnc3c2-c2ccccn2)ccn1]

To a stirred solution of N-{4-[3-(pyridin-2-yl)-1H-pyrrolo[3,2-b]pyridin-2-yl]pyridin-2-yl}acetamide (see Intermediate 12, 25.0 mg, 75.9 μmol) in methanol (5.8 ml) was added an aqueous solution of sodium hydroxide (760 μl, 1.0 M, 760 μmol; CAS-RN:[1310-73-2]) and the mixture was stirred at 80° C. for 3 h. The mixture was concentrated in vacuum. Water was added and the precipitate was collected by filtration to give 21.0 mg of the title compound.

LC-MS (Method 2): Rt=0.73 min; MS (ESIpos): m/z=288 $[M+H]^+$ $^{1}$H-NMR (400 MHz, DMSO-d6) δ[ppm]: 1.231 (1.34), 2.084 (0.74), 2.518 (12.32), 2.523 (8.29), 3.372 (1.51), 5.995 (16.00), 6.511 (8.09), 6.515 (8.49), 6.525 (8.10), 6.528 (8.77), 6.620 (10.35), 6.622 (12.25), 6.624 (11.64), 7.207 (7.71), 7.219 (7.66), 7.228 (7.84), 7.234 (5.17), 7.237 (6.52), 7.240 (8.83), 7.246 (4.71), 7.249 (5.30), 7.253 (5.58), 7.256 (4.84), 7.265 (5.32), 7.268 (4.88), 7.813 (7.93), 7.817 (9.14), 7.822 (4.63), 7.826 (4.81), 7.834 (8.65), 7.838 (8.53), 7.841 (7.64), 7.846 (7.30), 7.860 (4.63), 7.865 (5.18), 7.872 (9.90), 7.885 (9.50), 8.028 (5.70), 8.031 (9.22), 8.033 (5.81), 8.048 (4.82), 8.051 (7.59), 8.404 (7.91), 8.408 (8.64), 8.415 (8.16), 8.419 (7.99), 8.476 (4.99), 8.479 (5.68), 8.481 (5.85), 8.483 (5.16), 8.488 (5.27), 8.491 (6.08), 8.493 (5.68), 8.495 (4.84), 11.934 (4.71).

Intermediate 14

N-{4-[(3-amino-5-fluoropyridin-2-yl)ethynyl]pyridin-2-yl}acetamide

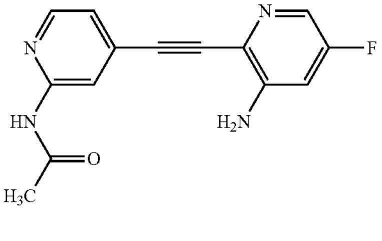 [SMILES: CC(=O)Nc1cc(C#Cc2ncc(F)cc2N)ccn1]

To a stirred solution of N-(4-ethynylpyridin-2-yl)acetamide (699 mg, 4.36 mmol) and 2-bromo-5-fluoropyridin-3-amine (1.00 g, 5.24 mmol) in DMF (12 mL) was added triethylamine (2.4 ml, 17 mmol; CAS-RN:[121-44-8]), $Pd(PPh_2)_3Cl_2$ (153 mg, 218 μmol; CAS-RN:[13965-03-2]) and CuI (83.1 mg, 436 μmol; CAS-RN:[7681-65-4]) and the flask was twice degased and backfilled with argon. The mixture was stirred at 80° C. for 1 h. A mixture of dichloromethane and methanol (7:3; 1000 mL) was added and the mixture was washed with a half-saturated sodium chloride solution. The organic phase was dried (sodium sulfate), filtered and the solvent was removed in vacuum. The residue was triturated with a mixture of dichloromethane and methanol (9:1) to give 784 mg of the title compound.

LC-MS (Method 1): $R_t$=0.79 min; MS (ESIpos): m/z=271 $[M+H]^+$ $^1$H-NMR (400 MHz, DMSO-$d_6$): δ [ppm]=10.62 (s, 1H), 8.35 (br d, 1H), 8.23 (s, 1H), 7.78 (d, 1H), 7.35 (dd, 1H), 6.94 (dd, 1H), 6.19 (s, 2H), 2.11 (s, 3H)

Intermediate 15

N-{2-[(2-acetamidopyridin-4-yl)ethynyl]-5-fluoropyridin-3-yl}-2,2,2-trifluoroacetamide

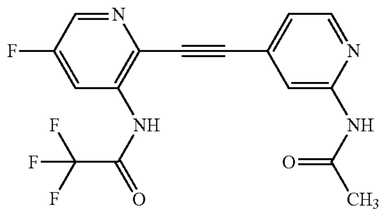 [SMILES: CC(=O)Nc1cc(C#Cc2ncc(F)cc2NC(=O)C(F)(F)F)ccn1]

A stirred solution of N-{4-[(3-amino-5-fluoropyridin-2-yl)ethynyl]pyridin-2-yl}acetamide (see Intermediate 14, 300 mg, 1.11 mmol), and triethylamine (390 μl, 2.8 mmol; CAS-RN:[121-44-8]) in acetonitrile (5 ml) was twice degased and the flask was backfilled with argon. The mixture was cooled to 0° C., trifluoroacetic anhydride (240 μl, 1.7 mmol; CAS-RN:[407-25-0]) was slowly added and the mixture was stirred at 0° C. for 30 min. The solvent was removed in vacuum. Silicagel chromatography (Gradient: dichloromethane/ethanol 0-30%) gave a solid that was triturated with a mixture of dichloromethane and hexane to give 222 mg of the title compound.

LC-MS (Method 1): $R_t$=1.04 min; MS (ESIpos): m/z=367 $[M+H]^+$ $^1$H-NMR (400 MHz, DMSO-$d_6$): δ [ppm]=11.77 (s, 1H), 10.69 (s, 1H), 8.70 (d, 1H), 8.40 (br d, 1H), 8.24 (s, 1H), 8.09 (dd, 1H), 7.18 (dd, 1H), 2.11 (s, 3H).

Intermediate 16

N-{4-[6-fluoro-3-(pyridin-2-yl)-1H-pyrrolo[3,2-b]pyridin-2-yl]pyridin-2-yl}acetamide

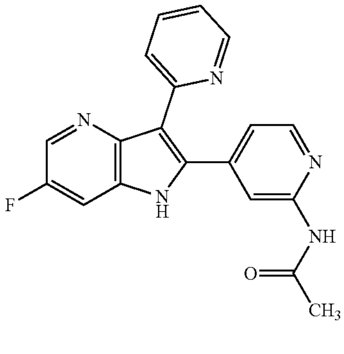 [SMILES: CC(=O)Nc1cc(-c2[nH]c3cc(F)cnc3c2-c2ccccn2)ccn1]

To a stirred solution of N-{2-[(2-acetamidopyridin-4-yl)ethynyl]-5-fluoropyridin-3-yl}-2,2,2-trifluoroacetamide (see Intermediate 15, 760 mg, 2.07 mmol) and 2-bromopyridine (300 p1, 3.1 mmol; CAS-RN:[109-04-6]) in acetonitrile (12 mL) in a sealed tube was added dicaesium carbonate (2.03 g, 6.22 mmol; CAS-RN:[534-17-8]) and tetrakis(triphenylphosphin)palladium (120 mg, 104 μmol; CAS-RN:[14221-01-3]) and the flask was twice degased and backfilled with argon. The mixture was heated to 100° C. for 1 h. Water was added, the mixture was extracted with a mixture of dichloromethane and methanol. The organic phase was dried (sodium sulfate), filtered and the solvent was removed in vacuum. Silicagel chromatography (Gradient: dichloromethane/ethanol 0-35%) gave a solid that was triturated with dichloromethane to give 425 mg (59% yield) of the title compound. In addition 153 mg of Intermediate 17 were obtained.

LC-MS (Method 1): Rt=0.62 min; MS (ESIpos): m/z=348 $[M+H]^+$ $^1$H-NMR (400 MHz, DMSO-$d_6$): δ [ppm]=12.23 (s, 1H), 10.55 (s, 1H), 8.48-8.43 (m, 2H), 8.30 (s, 1H), 8.28 (dd, 1H), 8.04 (dt, 1H), 7.86 (td, 1H), 7.75 (dd, 1H), 7.27 (ddd, 1H), 7.13 (dd, 1H), 2.08 (s, 3H).

Intermediate 17

4-[6-fluoro-3-(pyridin-2-yl)-1H-pyrrolo[3,2-b]pyridin-2-yl]pyridin-2-amine

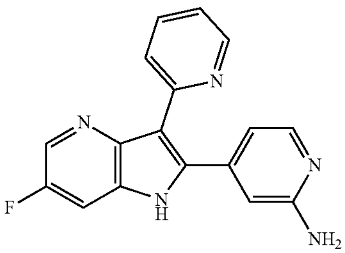 [SMILES: Nc1cc(-c2[nH]c3cc(F)cnc3c2-c2ccccn2)ccn1]

To a stirred solution of N-{4-[6-fluoro-3-(pyridin-2-yl)-1H-pyrrolo[3,2-b]pyridin-2-yl]pyridin-2-yl}acetamide (see Intermediate 16, 420 mg, 1.21 mmol) in methanol (10 ml) was added an aqueous solution of sodium hydroxide (12 ml, 1.0 M, 12 mmol; CAS-RN:[1310-73-2]) and the mixture was stirred at 80° C. for 4 h. The mixture was concentrated in vacuum. A mixture of ethyl acetate and methanol was added and the mixture was washed with half-saturated sodium chloride solution. The organic phase was dried (sodium sulfate), filtered and the solvent was removed in vacuum to give 334 mg of the title compound that was used without further purification.

LC-MS (Method 1): $R_t$=0.53 min; MS (ESIpos): m/z=306 $[M+H]^+$ $^1$H-NMR (400 MHz, DMSO-$d_6$): 5 [ppm]=12.18 (s, br, 1H), 8.50 (ddd, 1H), 8.41 (dd, 1H), 7.96 (dt, 1H), 7.89-7.81 (m, 2H), 7.70 (dd, 1H), 7.27 (ddd, 1H), 6.68-6.57 (m, 1H), 6.51 (dd, 1H), 6.00 (s, 2H)

Intermediate 18

N-[4-(6-fluoro-3-phenyl-1H-pyrrolo[3,2-b]pyridin-2-yl)pyridin-2-yl]acetamide

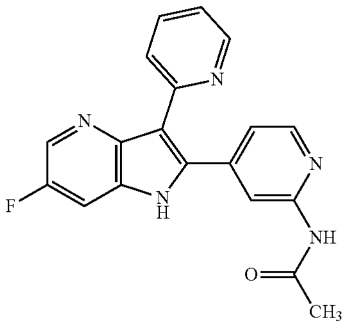

To a stirred solution of N-{2-[(2-acetamidopyridin-4-yl)ethynyl]-5-fluoropyridin-3-yl}-2,2,2-trifluoroacetamide (see Intermediate 15, 1.29 g, 3.51 mmol) and iodobenzene (590 μl, 5.3 mmol; CAS-RN:[591-50-4]) in acetonitrile (20 mL) in a sealed tube was added dicaesium carbonate (3.43 g, 10.5 mmol; CAS-RN:[534-17-8]) and tetrakis(triphenylphosphin)palladium (203 mg, 175 μmol; CAS-RN:[14221-01-3]) and the flask was twice degased and back-filled with argon. The mixture was heated to 100° C. for 1 h. Water was added, the mixture was extracted with a mixture of dichloromethane and methanol. The organic phase was dried (sodium sulfate), filtered and the solvent was removed in vacuum. Silicagel chromatography (Gradient: dichloromethane/ethanol 0-35%) gave 375 mg of the title compound. In addition 220 mg of Intermediate 14 were obtained.

LC-MS (Method 2): Rt=1.05 min; MS (ESIpos): m/z=347 $[M+H]^+$ $^1$H-NMR (400 MHz, DMSO-$d_6$): δ [ppm]=12.11 (s, 1H), 10.59 (s, 1H), 8.41 (dd, 1H), 8.33 (s, 1H), 8.26 (d, 1H), 7.72 (dd, 1H), 7.50-7.45 (m, 2H), 7.41-7.35 (m, 2H), 7.33-7.28 (m, 1H), 7.02 (dd, 1H), 2.09 (s, 3H)

Intermediate 19

4-(6-fluoro-3-phenyl-1H-pyrrolo[3,2-b]pyridin-2-yl)pyridin-2-amine

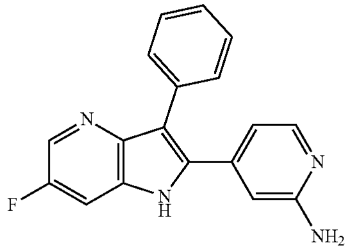 [SMILES: Nc1cc(-c2[nH]c3cc(F)cnc3c2-c2ccccc2)ccn1]

To a stirred solution of N-[4-(6-fluoro-3-phenyl-1H-pyrrolo[3,2-b]pyridin-2-yl)pyridin-2-yl]acetamide (see Intermediate 18, 370 mg, 1.07 mmol) in methanol (40 ml) was added an aqueous solution of sodium hydroxide (11 ml, 1.0 M, 11 mmol; CAS-RN:[1310-73-2]) and the mixture was stirred at 80° C. for 6 h. The mixture was concentrated in vacuum. A saturated potassium carbonate solution was added and then the mixture was extracted with a mixture of chloroform and methanol (3:1). The organic phase was dried (sodium sulfate), filtered and the solvent was removed in vacuum to give 273 mg (approx. 75 purity) of the title compound that was used without further purification.

LC-MS (Method 2): Rt=1.00 min; MS (ESIpos): m/z=305 $[M+H]^+$

Intermediate 20

N-[4-(3-phenyl-1H-pyrrolo[3,2-b]pyridin-2-yl)pyridin-2-yl]acetamide

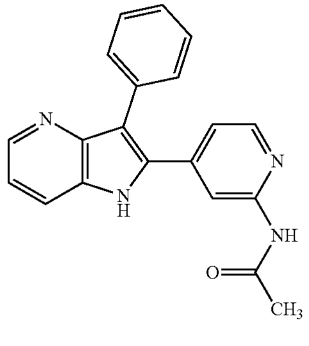 [SMILES: CC(=O)Nc1cc(-c2[nH]c3cccnc3c2-c2ccccc2)ccn1]

A mixture of N-{2-[(2-acetamidopyridin-4-yl)ethynyl]pyridin-3-yl}-2,2,2-trifluoroacetamide (8.00 g, 23.0 mmol, see Intermediate 12), iodobenzene (7.03 g, 34.5 mmol) and dicaesium carbonate (22.5 g, 68.9 mmol) in 1-Methyl-2-pyrrolidinone (80 ml) was purged with nitrogen. Then methanesulfonato(2-dicyclohexylphosphino-2',4',6'-tri-i-propyl-1,1'-biphenyl)(2'-amino-1,1'-biphenyl-2-yl)palladium(II) (1.94 g, 2.30 mmol) was added to the mixture and the mixture was purged with nitrogen at room temperature. The mixture was then heated to 100° C. for 16 h. The mixture was poured into water and the mixture was extracted with ethyl acetate. The combined organic phasees were washed with saturated sodium chloride solution, dried over anhydrous sodium sulfate, filtered and concentrated to give a residue. The residue was purified by silicagel chromatography (Petroleum ether/Ethyl acetate=0-100%) to give 1.70 g of the title compound as a yellow oil.

LC-MS (Method C): $R_t$=0.596 min; MS (ESIpos): m/z=329.1 [M+H]$^+$.

Intermediate 21

4-(3-phenyl-1H-pyrrolo[3,2-b]pyridin-2-yl)pyridin-2-amine

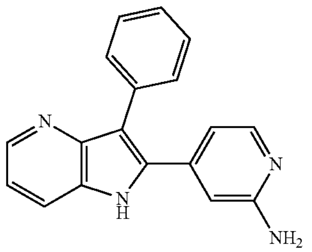 [SMILES: Nc1cc(-c2[nH]c3cccnc3c2-c2ccccc2)ccn1]

A mixture of N-[4-(3-phenyl-1H-pyrrolo[3,2-b]pyridin-2-yl)pyridin-2-yl]acetamide (2.70 g, 8.22 mmol, see Intermediate 20) and sodium hydroxide in tetrahydrofuran and water was stirred at 80° C. for 20 hours. The mixture was filtered and a filter cake was obtained. The filtrate was extracted with ethyl acetate three times and the combined organic phase was dried over anhydrous sodium sulfate, filtered and concentrated in vacuum. The residue and filter cake were dissolved with acetonitrile and from the mixture was removed most solvent. Water was added and the mixture was sonicated and the resulting mixture was oil pump freeze-dried to give 982 mg of the title compound as a yellow solid.

LC-MS (Method A): Rt=0.703 min; MS (ESIpos): m/z=287.3 [M+H]$^+$ $^1$H NMR (400 MHz, DMSO-$d_6$): δ [ppm]=11.80 (s, 1H), 8.38 (dd, J=4.4, 1.2 Hz, 1H), 7.90 (d, J=5.2 Hz, 1H), 7.80 (dd, J=8.0, 1.2 Hz, 1H), 7.55 (d, J=7.2 Hz, 2H), 7.37 (t, J=7.6 Hz, 2H), 7.26 (t, J=7.6 Hz, 1H), 7.20 (dd, J=8.0, 4.4 Hz, 1H), 6.59 (s, 1H), 6.50 (dd, J=5.2, 1.2 Hz, 1H), 6.03 (s, 2H).

Intermediate 22

N-[4-(1H-pyrrolo[3,2-b]pyridin-2-yl)pyridin-2-yl] acetamide

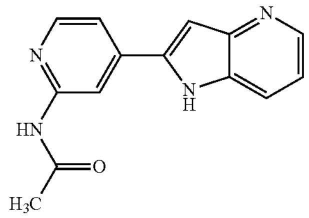 [SMILES: CC(=O)Nc1cc(-c2cc3ncccc3[nH]2)ccn1]

To a stirred solution of N-{4-[(3-aminopyridin-2-yl)ethynyl]pyridin-2-yl}acetamide see Intermediate 11, 2.48 g, 9.83 mmol) in NMP (25 mL) was added potassium 2-methylpropan-2-olate (2.21 g, 19.7 mmol; CAS-RN:[865-47-4]) and the mixture was stirred at 90° C. for 2 h. Ethyl acetate was added and the mixture was washed with half-saturated sodium chloride solution (three times). The aqueous phase was extracted with a mixture of chloroform and methanol (3:1). The combined organic phases were dried (sodium sulfate), filtered and the solvent was removed in vacuum. Silicagel chromatography (Gradient: dichloromethane/ethanol 0-10%) gave a solid that was triturated with dichloromethane 1.61 g of the title compound.

LC-MS (Method 1): $R_t$=0.49 min; MS (ESIpos): m/z=253 [M+H]$^+$ $^1$H-NMR (400 MHz, DMSO-$d_6$): δ [ppm]=12.04 (d, 1H), 10.59 (s, 1H), 8.52 (s, 1H), 8.39 (d, 1H), 8.37 (dd, 1H), 7.81 (dt, 1H), 7.60 (dd, 1H), 7.21-7.13 (m, 2H), 2.14 (s, 3H).

Intermediate 23

N-[4-(3-bromo-1H-pyrrolo[3,2-b]pyridin-2-yl)pyridin-2-yl]acetamide

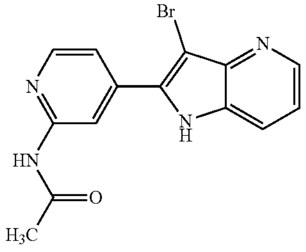 [SMILES: CC(=O)Nc1cc(-c2[nH]c3cccnc3c2Br)ccn1]

To a stirred solution of N-[4-(1H-pyrrolo[3,2-b]pyridin-2-yl)pyridin-2-yl]acetamide (see Intermediate 22 Intermediate 22, 2.32 g, 9.20 mmol) in DMF (22 mL) was added NBS (2.46 g, 13.8 mmol; CAS-RN:[128-08-5]) and the mixture was stirred at r.t. for 1 h. An aqueous solution of sodium bicarbonate and an aqueous solution of disodium sulfurothioate was added and the mixture was stirred for 30 minutes. A solid precipitated and was collected by filtration to give 2.67 g of the title compound.

LC-MS (Method 2): Rt=0.79 min; MS (ESIpos): m/z=333 [M+H]$^+$ $^1$H-NMR (400 MHz, DMSO-$d_6$): δ [ppm]=12.33 (s, 1H), 10.69 (s, 1H), 8.76 (s, 1H), 8.55-8.41 (m, 2H), 7.87 (dd, 1H), 7.59 (dd, 1H), 7.29 (dd, 1H), 2.14 (s, 3H).

Intermediate 24

N-{4-[(3-aminopyrazin-2-yl)ethynyl]pyridin-2-yl}-2-(4-fluorophenyl)acetamide

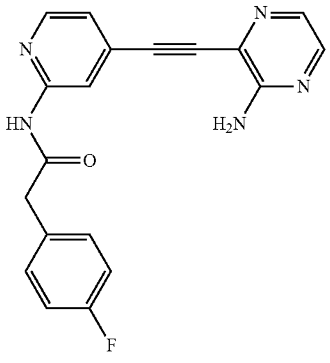 [SMILES: Nc1nccnc1C#Cc1ccnc(NC(=O)Cc2ccc(F)cc2)c1]

A mixture of N-(4-ethynylpyridin-2-yl)-2-(4-fluorophenyl)acetamide (see Intermediate 7, 2.00 g, 7.87 mmol), 3-bromopyrazin-2-amine (2.05 g, 11.8 mmol), dichlorobis(triphenylphosphine)palladium(II) (276 mg, 0.39 mmol) and copper(I) iodide (150 mg, 0.79 mmol) in triethylamine (4.0 ml, 29 mmol) and N,N-dimethylformamide (20 ml) was puraged with nitrogen. The mixture was stirred at 100° C. for 2 hours. The mixture was diluted with water, then extracted with ethyl acetate. The organic layer was washed by saturated brine, dried over sodium sulfate and filtered, the filtrate was concentrated in vacuum to give a residue. The residue was purified by silica gel chromatography (100-200 mesh, eluting with petroleum ether/ethyl acetate=3:1, then 1:1, then 0:1) to give N-{4-[(3-aminopyrazin-2-yl)ethynyl]pyridin-2-yl}-2-(4-fluorophenyl)acetamide (2.40 g, 88% yield) as a yellow solid.

LC-MS (Method C): $R_t$=0.851 min; MS (ESIpos): m/z=348.2 $[M+H]^+$.

$^1H$ NMR (400 MHz, DMSO-$d_6$): δ [ppm]=10.88 (s, 1H), 8.39 (d, J=4.8 Hz, 1H), 8.27 (s, 1H), 8.01 (d, J=2.4 Hz, 1H), 7.81 (d, J=2.4 Hz, 1H), 7.42-7.36 (m, 3H), 7.15 (t, J=8.8 Hz, 2H), 6.87 (s, 2H), 3.74 (s, 2H).

Intermediate 25

2-(4-fluorophenyl)-N-[4-(5H-pyrrolo[2,3-b]pyrazin-6-yl)pyridin-2-yl]acetamide

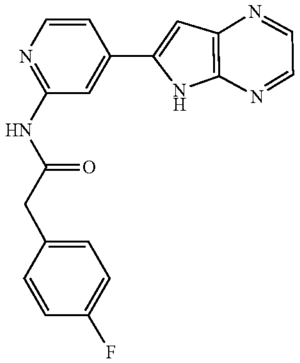 [SMILES: O=C(Cc1ccc(F)cc1)Nc1cc(-c2cc3nccnc3[nH]2)ccn1]

To a solution of N-{4-[(3-aminopyrazin-2-yl)ethynyl]pyridin-2-yl}-2-(4-fluorophenyl)acetamide (see Intermediate 24, 1.30 g, 3.74 mmol) in 1-methyl-2-pyrrolidinone (13 ml) was added potassium tert-butoxide (840 mg, 7.49 mmol) at 20° C., the mixture was stirred at 90° C. for 2 hours. The mixture (combined with a batch starting from 100 mg of Intermediate 24) was poured into the water. The mixture was extracted with ethyl acetate and the combined organic phase was washed with brine, dried over anhydrous sodium sulfate, filtered and concentrated in vacuum. The crude product was purified by flash silica gel chromatography (Petroleum ether/Ethyl acetate=0%-100%) to give 2-(4-fluorophenyl)-N-[4-(5H-pyrrolo[2,3-b]pyrazin-6-yl)pyridin-2-yl]acetamide (980 mg, 75% yield) as a yellow solid.

LC-MS (Method C): Rt=0.720 min; MS (ESIpos): m/z=348.1 $[M+H]^+$.

$^1H$ NMR (400 MHz, DMSO-$d_6$): δ [ppm]=12.81 (s, 1H), 10.87 (s, 1H), 8.58 (s, 1H), 8.46-8.43 (m, 2H), 8.30 (d, J=2.4 Hz, 1H), 7.70 (dd, J=5.2, 1.2 Hz, 1H), 7.43-7.39 (m, 2H), 7.23-7.14 (m, 3H), 3.78 (s, 2H).

Intermediate 26

N-[4-(7-bromo-5H-pyrrolo[2,3-b]pyrazin-6-yl)pyridin-2-yl]-2-(4-fluorophenyl)acetamide

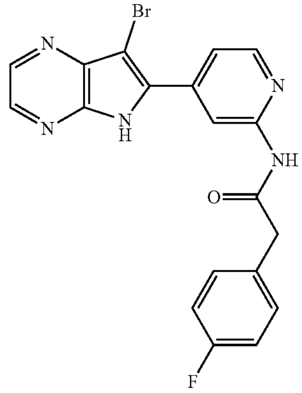 [SMILES: O=C(Cc1ccc(F)cc1)Nc1cc(-c2[nH]c3nccnc3c2Br)ccn1]

To a solution of 2-(4-fluorophenyl)-N-[4-(5H-pyrrolo[2,3-b]pyrazin-6-yl)pyridin-2-yl]acetamide (see Intermediate 25, 900 mg, 2.59 mmol) in N,N-dimethylformamide (20 ml) was added N-bromosuccinimide (415 mg, 2.33 mmol) in portions at room temperature. The reaction mixture was stirred at room temperature for 2 hours. The reaction mixture was concentrated in reduced pressure to give a residue. The residue was diluted with water and extracted with ethyl acetate. The organic phase was washed with brine, dried over anhydrous sodium sulfate and filtered. The filtrate was concentrated and purified by column chromatography on silica gel (200-300 mesh, petroleum ether:ethyl acetate=5:1) to give N-(4-(3-bromo-1H-pyrrolo[3,2-c]pyridin-2-yl)pyridin-2-yl)-2-(4-fluorophenyl)acetamide (860 mg, 77%) as a white solid.

LC-MS (Method C): $R_t$=0.755 min; MS (ESIpos): m/z=426.0 $[M+H]^+$.

Intermediate 27

N-{4-[(4-amino-6-chloropyridazin-3-yl)ethynyl]pyridin-2-yl}-2-(4-fluorophenyl)acetamide

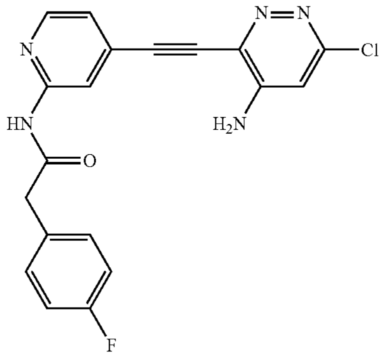 [SMILES: Nc1cc(Cl)nnc1C#Cc1ccnc(NC(=O)Cc2ccc(F)cc2)c1]

A mixture of N-(4-ethynylpyridin-2-yl)-2-(4-fluorophenyl)acetamide (see Intermediate 7, 1.71 g, 6.71 mmol), 3,6-dichloropyridazin-4-amine (1.00 g, 6.10 mmol), dichlorobis(triphenylphosphine)palladium(II) (128 mg, 0.18 mmol) and copper(I) iodide (58.1 mg, 0.31 mmol) in triethylamine (4.2 ml, 30 mmol) and acetonitrile (20 ml) was puraged with nitrogen. The mixture was stirred at 60° C. for 16 hours. The mixture was concentrated by evaporation in vacuum. The residue was purified by silica gel column chromatography (100-200 mesh, petroleum ether:ethyl acetate=10:1, 5:1, 3:1, 1:1, 0:1) to give N-{4-[(4-amino-6-chloropyridazin-3-yl)ethynyl]pyridin-2-yl}-2-(4-fluorophenyl)acetamide (1.30 g, 51% yield) as a yellow solid.

LC-MS (Method C): Rt=0.849 min; MS (ESIpos): m/z=382.2 $[M+H]^+$.

$^1H$ NMR (400 MHz, DMSO-d6): δ [ppm]=10.93 (s, 1H), 8.42 (d, J=5.2 HZ, 1H), 8.31 (s, 1H), 7.43-7.42 (m, 1H), 7.40-7.37 (m, 2H), 7.18-7.13 (m, 3H), 6.85 (s, 1H), 3.74 (s, 2H).

Intermediate 28

N-[4-(3-chloro-5H-pyrrolo[3,2-c]pyridazin-6-yl)pyridin-2-yl]-2-(4-fluorophenyl)acetamide

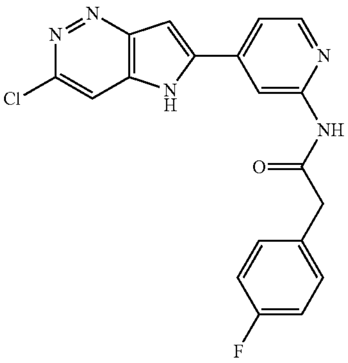 [SMILES: O=C(Cc1ccc(F)cc1)Nc1cc(-c2cc3nnc(Cl)cc3[nH]2)ccn1]

A mixture of N-{4-[(4-amino-6-chloropyridazin-3-yl)ethynyl]pyridin-2-yl}-2-(4-fluorophenyl)acetamide (see Intermediate 27, 600 mg, 1.57 mmol) and Copper(I) iodide (59.9 mg, 0.31 mmol) in N,N-Dimethylformamide (10 ml) was stirred at 130° C. for 4 hours. The mixture was poured into water and the mixture was filtered. The filter cake was slurried with ethyl acetate to give N-[4-(3-chloro-5H-pyrrolo[3,2-c]pyridazin-6-yl)pyridin-2-yl]-2-(4-fluorophenyl)acetamide (400 mg, crude) as a brown solid.

Intermediate 29

2-(4-fluorophenyl)-N-[4-(5H-pyrrolo[3,2-c]pyridazin-6-yl)pyridin-2-yl]acetamide

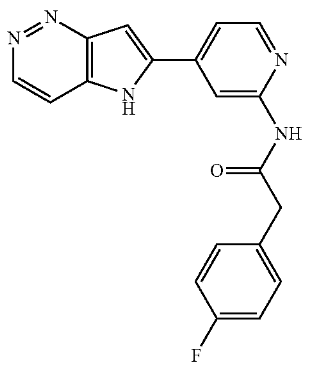 [SMILES: O=C(Cc1ccc(F)cc1)Nc1cc(-c2cc3nnccc3[nH]2)ccn1]

A mixture of N-[4-(3-chloro-5H-pyrrolo[3,2-c]pyridazin-6-yl)pyridin-2-yl]-2-(4-fluorophenyl)acetamide (see Intermediate 28, 400 mg, 1.05 mmol) and trimethylamine (0.29 ml, 2.1 mmol) in methanol (20 ml) was added palladium 10% on activated carbon (111 mg, 10% purity, 0.11 mmol) at room temperature, then the mixture was stirred at 50° C. for 16 hours under hydrogen atmosphere (50 psi). The mixture was filtered and filtrate was concentrated by evaporation in vacuum. A mixture of N-[4-(3-chloro-5H-pyrrolo[3,2-c]pyridazin-6-yl)pyridin-2-yl]-2-(4-fluorophenyl)acetamide and triethylamine (0.292 ml) in methanol (20 ml) was added palladium 10% on activated carbon (212.027 mg) at room temperature, then the mixture was stirred at 50° C. for 16 hours under hydrogen atmosphere (15 psi). The combined mixture was filtered and filtrate was concentrated by evaporation in vacuum. The residue was purified by silica gel column chromatography (100-200 mesh, petroleum ether:ethyl acetate=10:1, 5:1, 3:1, 1:1, 0:1) to give 2-(4-fluorophenyl)-N-[4-(5H-pyrrolo[3,2-c]pyridazin-6-yl)pyridin-2-yl]acetamide (50 mg) as a brown solid.

$^1H$ NMR (400 MHz, DMSO-d6): δ [ppm]=10.92 (s, 1H), 8.93 (d, J=4.8 Hz, 1H), 8.58 (s, 1H), 8.47 (d, J=5.2 Hz, 1H), 7.72-7.70 (m, 1H), 7.64-7.62 (m, 1H), 7.52 (s, 1H), 7.13-7.39 (m, 2H), 7.20-7.13 (m, 2H), 3.78 (s, 2H).

Intermediate 30

N-[4-(7-bromo-5H-pyrrolo[3,2-c]pyridazin-6-yl)pyridin-2-yl]-2-(4-fluorophenyl)acetamide

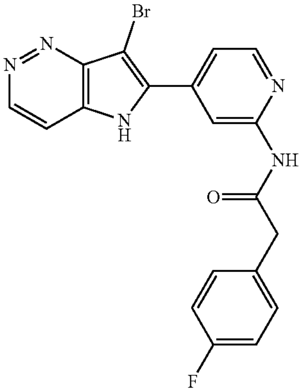 [SMILES: O=C(Cc1ccc(F)cc1)Nc1cc(-c2[nH]c3ccnnc3c2Br)ccn1]

To a solution of 2-(4-fluorophenyl)-N-[4-(5H-pyrrolo[3,2-c]pyridazin-6-yl)pyridin-2-yl]acetamide (see Intermediate 29, 50.0 mg, 0.14 mmol) in N,N-dimethylformamide (5.0 ml) was added N-bromosuccinimide (23.1 mg, 0.13 mmol) in portions at room temperature. The reaction mixture was stirred at room temperature for 2 hours. The reaction was poured into water and the mixture was extracted with ethyl acetat. The organic phase was dried over anhydrous sodium sulfate, filtered and concentrated to give a residue. The residue was purified by silica gel chromatography (100-200 mesh, petroleum ether:ethyl acetate=1:1 to ethyl acetate: methanol=10:1) to give N-[4-(7-bromo-5H-pyrrolo[3,2-c]pyridazin-6-yl)pyridin-2-yl]-2-(4-fluorophenyl)acetamide (60 mg, 98% yield) as a yellow solid.

LC-MS (Method C): Rt=0.798 min; MS (ESIpos): m/z=426.1 $[M+H]^+$.

Intermediate 31

N-[4-(7-bromo-5-{[2-(trimethylsilyl)ethoxy]methyl}-5H-pyrrolo[3,2-c]pyridazin-6-yl)pyridin-2-yl]-2-(4-fluorophenyl)acetamide

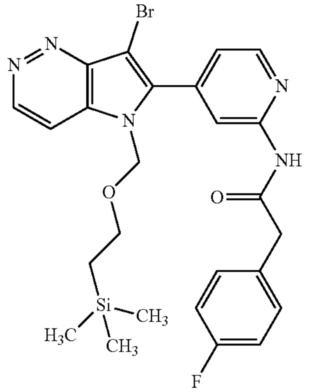 [SMILES: C[Si](C)(C)CCOCn1c(-c2ccnc(NC(=O)Cc3ccc(F)cc3)c2)c(Br)c2nnccc21]

To a solution of N-[4-(7-bromo-5H-pyrrolo[3,2-c]pyridazin-6-yl)pyridin-2-yl]-2-(4-fluorophenyl)acetamide (see Intermediate 30, 200 mg, 0.47 mmol) in N,N-dimethylformamide (10 ml) was added potassium carbonate (324 mg, 2.35 mmol) in portions at room temperature. After stirring for 30 minutes, [2-(chloromethoxy)ethyl](trimethyl)silane (0.17 ml, 0.94 mmol) was added in one portion. The reaction mixture was stirred at room temperature for 2 hours. The mixture was poured into water and extracted with ethyl acetate. The organic phase was washed with brine, dried over anhydrous sodium sulfate, filtered and concentrated to give a residue. The residue was purified by flash silica gel chromatography (12 g, ethyl acetate:methanol=10:1 in petroleum ether=0% to 38%) to give N-[4-(7-bromo-5-{[2-(trimethylsilyl)ethoxy]methyl}-5H-pyrrolo[3,2-c]pyridazin-6-yl)pyridin-2-yl]-2-(4-fluorophenyl)acetamide (150 mg, 57% yield) as a yellow solid.

LC-MS (Method C): Rt=0.928 min; MS (ESIpos): m/z=556.0 $[M+H]^+$.

Intermediate 32

2-(4-fluorophenyl)-N-{4-[7-(pyridin-2-yl)-5-{[2-(trimethylsilyl)ethoxy]methyl}-5H-pyrrolo[3,2-c]pyridazin-6-yl]pyridin-2-yl}acetamide

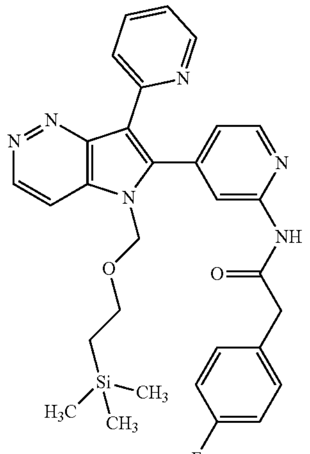

To a solution of N-[4-(7-bromo-5-{[2-(trimethylsilyl)ethoxy]methyl}-5H-pyrrolo[3,2-c]pyridazin-6-yl)pyridin-2-yl]-2-(4-fluorophenyl)acetamide (see Intermediate 31, 150 mg, 0.27 mmol) and 2-(tributylstannyl)pyridine (198 mg, 0.54 mmol) in 1,4-dioxane (5.0 ml) was added bis(triphenylphosphine)palladium(II) chloride (18.9 mg, 0.027 mmol), sodium carbonate (85.7 mg, 0.81 mmol) and copper (I) iodide (5.13 mg, 0.027 mmol) at room temperature. The reaction mixture was stirred at 100° C. for 16 hours under nitrogen atmosphere. The organic phase was washed with brine, dried over anhydrous sodium sulfate, filtered and concentrated to give a residue. The residue was purified by flash silica gel chromatography (12 g, ethyl acetate methanol=10:1 in petroleum ether=0% to 38%) to give 2-(4-fluorophenyl)-N-{4-[7-(pyridin-2-yl)-5H-pyrrolo[3,2-c]pyridazin-6-yl]pyridin-2-yl}acetamide (50 mg, 33% yield) as a yellow solid.

LC-MS (Method C): Rt=0.888 min; MS (ESIpos): m/z=555.1 $[M+H]^+$.

Intermediate 33

N-{4-[(3-amino-4-chloropyridin-2-yl)ethynyl]pyridin-2-yl}-2-(4-fluorophenyl)acetamide

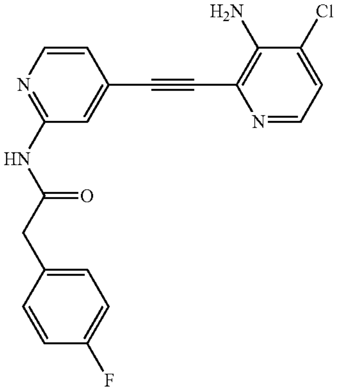 [SMILES: Nc1c(Cl)ccnc1C#Cc1ccnc(NC(=O)Cc2ccc(F)cc2)c1]

A mixture of N-(4-ethynylpyridin-2-yl)-2-(4-fluorophenyl)acetamide (see Intermediate 7, 2.70 g, 10.6 mmol), 2,4-dichloropyridin-3-amine (1.73 g, 10.6 mmol), dichlorobis(triphenylphosphine)palladium(II) (373 mg, 0.53 mmol) and copper(I) iodide (202 mg, 1.06 mmol) in trimethylamine (12 ml, 86 mmol) and N,N-dimethylformamide (30 ml) was puraged with nitrogen at 25° C. The mixture was stirred at 100° C. for 2 hours. The mixture was cooled to room temperature. The mixture was poured into water and the mixture was extracted with ethyl acetate. The organic layer was dried over anhydrous sodium sulfate, filtered and concentrated to afford crude product. The crude product was purified by flash column chromatography (40 g, ethyl acetate:methanol=10:1 in petroleum ether=10% to 40%) to give N-{4-[(3-amino-4-chloropyridin-2-yl)ethynyl]pyridin-2-yl}-2-(4-fluorophenyl)acetamide (1.3 g, 32% yield) as a brown solid.

LC-MS (Method C): Rt=0.779 min; MS (ESIpos): m/z=381.1 $[M+H]^+$.

Intermediate 34

N-[4-chloro-2-({2-[2-(4-fluorophenyl)acetamido]pyridin-4-yl}ethynyl)pyridin-3-yl]-2,2,2-trifluoroacetamide

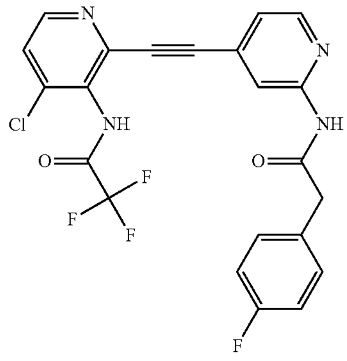 [SMILES: O=C(Cc1ccc(F)cc1)Nc1cc(C#Cc2nccc(Cl)c2NC(=O)C(F)(F)F)ccn1]

To a suspension of N-{4-[(3-amino-4-chloropyridin-2-yl)ethynyl]pyridin-2-yl}-2-(4-fluorophenyl)acetamide (see Intermediate 33, 1.10 g, 2.89 mmol) in dichloromethane (50 ml) was added trimethylamine (810 μl, 5.8 mmol), and the mixture was cooled to 0° C.

Trifluoroacetic anhydride (610 μl, 4.332 mmol) was slowly added. The reaction mixture was stirred at 0° C. for 0.5 hour. The mixture was separated and the organic phase was dried over anhydrous sodium sulfate, filtered and concentrated to give a residue. The residue was purified by flash column chromatography (40 g, ethyl acetate:methanol=10:1 in petroleum ether=10% to 40%) to give N-[6-chloro-2-({2-[2-(4-fluorophenyl)acetamido]pyridin-4-yl}ethynyl)pyridin-3-yl]-2,2,2-trifluoroacetamide (300 mg, 22% yield) as a yellow solid.

Intermediate 35

N-{4-[(3-amino-6-chloropyridin-2-yl)ethynyl]pyridin-2-yl}-2-(4-fluorophenyl)acetamide

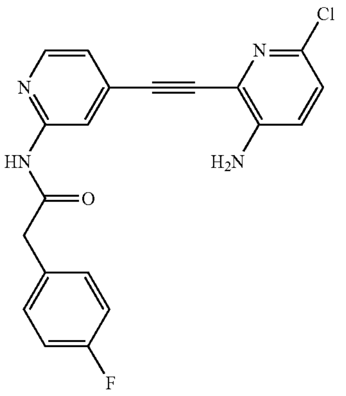 [SMILES: Nc1ccc(Cl)nc1C#Cc1ccnc(NC(=O)Cc2ccc(F)cc2)c1]

A mixture of N-(4-ethynylpyridin-2-yl)-2-(4-fluorophenyl)acetamide (see Intermediate 7, 3.00 g, 11.8 mmol), 2-bromo-6-chloropyridin-3-amine (2.94 g, 14.2 mmol), dichlorobis(triphenylphosphine)palladium(II) (414 mg, 0.59 mmol) and copper(I) iodide (225 mg, 1.18 mmol) in triethylamine (30 ml) and N,N-dimethylformamide (30 ml) was puraged with nitrogen. The mixture was stirred at 100° C. for 16 hours. The reaction mixture was diluted with water and extracted with ethyl acetate. Then the organic layer was washed by saturated brine, dried over anhydrous sodium sulfate, filtered and the filtrate was concentrated in vacuum to give a residue. The residue was purified by silica gel chromatography (100-200 mesh, petroleum ether:ethyl acetate=1:0, 3:1, 1:1 and 1:2) to give N-{4-[(3-amino-6-chloropyridin-2-yl)ethynyl]pyridin-2-yl}-2-(4-fluorophenyl)acetamide (3 g, 66.7% yield) as a yellow solid.

LC-MS (Method C): Rt=0.806 min; MS (ESIpos): m/z=381.0 $[M+H]^+$.

$^1$H NMR (400 MHz, DMSO-$d_6$): δ [ppm]=10.86 (s, 1H), 8.37 (d, J=5.2 Hz, 1H), 8.23 (s, 1H), 7.40-7.36 (m, 3H), 7.23-7.12 (m, 4H), 6.07 (s, 2H), 3.74 (s, 2H).

Intermediate 36

N-[4-(5-chloro-1H-pyrrolo[3,2-b]pyridin-2-yl)pyridin-2-yl]-2-(4-fluorophenyl)acetamide

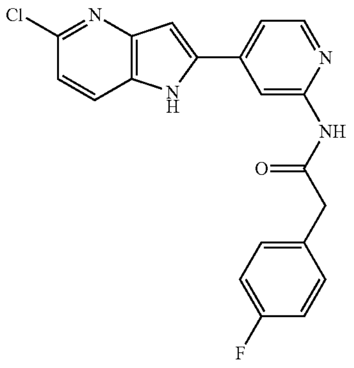 [SMILES: O=C(Cc1ccc(F)cc1)Nc1cc(-c2cc3nc(Cl)ccc3[nH]2)ccn1]

To a solution of N-{4-[(3-amino-6-chloropyridin-2-yl)ethynyl]pyridin-2-yl}-2-(4-fluorophenyl)acetamide (see Intermediate 35, 1.00 g, 2.63 mmol) in 1-methyl-2-pyrrolidinone (10 ml) was added copper(I) iodide (100 mg, 0.53 mmol) in one portion. The reaction mixture was stirred at 130° C. for 16 hours. The reaction mixture was diluted with water and extracted with ethyl acetate. The organic layer was washed by saturated brine, dried over sodium sulfate, filtered and the filtrate was concentrated under reduced pressure to give a residue. The residue was purified by silical gel column (100-200 mesh, petroleum ether:ethyl acetate=20:1, 10:1, 5:1, 2:1) to give N-[4-(5-chloro-1H-pyrrolo[3,2-b]pyridin-2-yl)pyridin-2-yl]-2-(4-fluorophenyl)acetamide (800 mg, 80% yield) as a yellow solid.

LC-MS (Method C): Rt=0.881 min; MS (ESIpos): m/z=381.2 $[M+H]^+$.

$^1$H NMR (400 MHz, DMSO-$d_6$): δ [ppm]=12.30 (s, 1H), 10.87 (s, 1H), 8.51 (s, 1H), 8.42 (d, J=5.2 Hz, 1H), 7.84 (dd, J=8.4, 0.8 Hz, 1H), 7.54-7.44 (m, 2H), 7.43-7.38 (m, 2H), 7.21-7.14 (m, 3H), 3.77 (s, 2H).

Intermediate 37

N-[4-(3-bromo-5-chloro-1H-pyrrolo[3,2-b]pyridin-2-yl)pyridin-2-yl]-2-(4-fluorophenyl)acetamide

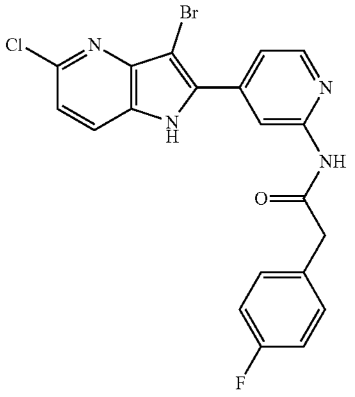 [SMILES: O=C(Cc1ccc(F)cc1)Nc1cc(-c2[nH]c3ccc(Cl)nc3c2Br)ccn1]

A solution of N-[4-(5-chloro-1H-pyrrolo[3,2-b]pyridin-2-yl)pyridin-2-yl]-2-(4-fluorophenyl)acetamide (see Intermediate 36, 500 mg, 1.31 mmol) in N,N-dimethylformamide (5.0 ml) was added N-bromosuccinimide (187 mg, 1.05 mmol) at 0° C., the mixture was stirred at room temperature for 0.5 hour. The reaction mixture was quenched by saturated solution of sodium hydrogen carbonate and saturated solution of sodium thiosulfate, the mixture was extracted with ethyl acetate. The combined organic phase was washed with brine, dried over anhydrous sodium sulfate, filtered and concentrated to give a residue. The residue was purified by flash column chromatography (4 g, ethyl acetate in petroleum ether was 0%-33%) to give N-[4-(3-bromo-5-chloro-1H-pyrrolo[3,2-b]pyridin-2-yl)pyridin-2-yl]-2-(4-fluorophenyl)acetamide (320 mg, 53% yield) as a yellow solid.

LC-MS (Method C): Rt=0.829 min; MS (ESIpos): m/z=460.9 $[M+H]^+$.

$^1$H NMR (400 MHz, DMSO-$d_6$): δ [ppm]=12.58 (s, 1H), 10.95 (s, 1H), 8.73 (s, 1H), 8.51 (d, J=5.6 Hz, 1H), 7.92 (d, J=8.8 Hz, 1H), 7.61 (dd, J=5.2, 1.6 Hz, 1H), 7.42-7.36 (m, 2H), 7.32 (d, J=8.4 Hz, 1H), 7.16 (t, J=8.8 Hz, 1H), 3.77 (s, 2H).

Intermediate 38

N-{4-[(3-amino-4-chloropyridin-2-yl)ethynyl]pyridin-2-yl}acetamide

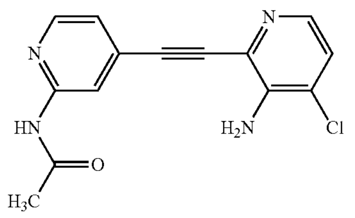 [SMILES: CC(=O)Nc1cc(C#Cc2nccc(Cl)c2N)ccn1]

A mixture of N-(4-ethynylpyridin-2-yl)acetamide (2.00 g, 12.5 mmol), 2,4-dichloropyridin-3-amine (2.04 g, 12.5 mmol), dichlorobis(triphenylphosphine)palladium(II) (438 mg, 0.624 mmol) and copper(I) iodide (238 mg, 1.25 mmol) in trimethylamine (8.0 ml, 57 mmol) and N,N-dimethylformamide (20 ml) was puraged with nitrogen at 25° C. The mixture was stirred at 100° C. for 2 hours. The mixture was cooled to room temperature. The mixture was poured into water and the mixture was extracted with ethyl acetate. The organic layer was dried over anhydrous sodium sulfate, filtered and concentrated to afford crude product. The crude product was purified by flash column chromatography (40 g, ethyl acetate:methanol=10:1 in petroleum ether=10% to 40%) to give N-{4-[(3-amino-4-chloropyridin-2-yl)ethynyl]pyridin-2-yl}acetamide (1.1 g, 31% yield) as a yellow solid.

LC-MS (Method C): Rt=0.698 min; MS (ESIpos): m/z=286.9 $[M+H]^+$.

Intermediate 39

N-{2-[(2-acetamidopyridin-4-yl)ethynyl]-4-chloropyridin-3-yl}-2,2,2-trifluoroacetamide

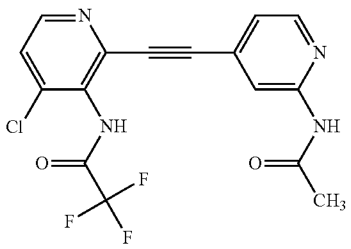 [SMILES: CC(=O)Nc1cc(C#Cc2nccc(Cl)c2NC(=O)C(F)(F)F)ccn1]

To a suspension of N-{4-[(3-amino-4-chloropyridin-2-yl)ethynyl]pyridin-2-yl}acetamide (see Intermediate 38, 1.80 g, 6.28 mmol) in dichloromethane (30 ml) was added trimethylamine (1.8 ml, 13 mmol), and the mixture was cooled to 0° C. Trifluoroacetic anhydride (1.3 ml, 9.4 mmol) was slowly added. The reaction mixture was stirred at 0° C. for 0.5 hour. The mixture was separated and the organic phase was dried over anhydrous sodium sulfate, filtered and concentrated to give a residue. The residue was purified by flash column chromatography (40 g, ethyl acetate:methanol=10:1 in petroleum ether=10% to 40%) to give N-{2-[(2-acetamidopyridin-4-yl)ethynyl]-4-chloropyridin-3-yl}-2,2,2-trifluoroacetamide (1.5 g, 62% yield) as a yellow solid.

LC-MS (Method C): Rt=0.815 min; MS (ESIpos): m/z=383.2 $[M+H]^+$.

Intermediate 40

N-{4-[7-chloro-3-(pyridin-2-yl)-1H-pyrrolo[3,2-b]pyridin-2-yl]pyridin-2-yl}acetamide

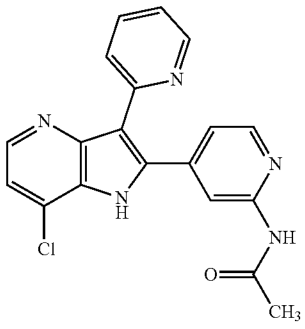 [SMILES: CC(=O)Nc1cc(-c2[nH]c3c(Cl)ccnc3c2-c2ccccn2)ccn1]

A mixture of N-{2-[(2-acetamidopyridin-4-yl)ethynyl]-4-chloropyridin-3-yl}-2,2,2-trifluoroacetamide (see Intermediate 39, 1.20 g, 3.14 mmol), 2-iodopyridine (771 mg, 3.76 mmol), Methanesulfonato(2-dicyclohexylphosphino-2',4',6'-tri-i-propyl-1,1'-biphenyl)(2'-amino-1,1'-biphenyl-2-yl)palladium(II) (265 mg, 0.314 mmol) and cesium carbonate (3.06 g, 9.41 mmol) in 1-methyl-2-pyrrolidinone (20 ml) was purged with nitrogen. The mixture was stirred at 100° C. for 16 hours under nitrogen. The combined mixture (combined with a batch starting from 300 mg Intermediate 39) was poured into water and the mixture was extracted with ethyl acetate. The organic phase was dried over anhydrous sodium sulfate, filtered and concentrated to give a residue. The residue was purified by flash column chromatography (40 g, ethyl acetate methanol=10:1 in petroleum ether=10% to 40%) to give N-{4-[7-chloro-3-(pyridin-2-yl)-1H-pyrrolo[3,2-b]pyridin-2-yl]pyridin-2-yl}acetamide (357.3 mg, 96.4% purity) as a yellow solid.

LC-MS (Method C): Rt=0.703 min; MS (ESIpos): m/z=364.0 $[M+H]^+$.

$^1$H NMR (400 MHz, DMSO-$d_6$): δ [ppm]=12.46 (s, 1H), 10.55 (s, 1H), 8.43-8.39 (m, 2H), 8.31-8.29 (m, 2H), 8.08 (d, J=8.0 Hz, 1H), 7.86 (dt, J=7.6, 2.0 Hz, 1H), 7.43 (d, J=4.8 Hz, 1H), 7.28-7.24 (m, 1H), 7.17 (dd, J=5.2 Hz, 1.6 Hz, 1H), 2.09 (s, 3H).

Intermediate 41

2-fluoro-5-hydrazinyl-3-methylpyridine

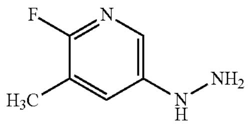

6-Fluoro-5-methylpyridin-3-amine (1.00 g, 7.93 mmol, CAS-RN:[186593-48-6]) was dissolved in aqueous hydrochloric acid (20 mL, 6.0 M, 120 mmol) and cooled to 0° C. At this temperature sodium nitrite (547 mg, 7.93 mmol) in 21 mL water was added dropwise. After 30 min. under cooling a solution of tin(II)chloride dihydrate (4.47 g, 19.8 mmol) in aqueous hydrochloric acid (20 mL, 6.0 M, 120 mmol) was added slowly. The reaction mixture was stirred at 0° C. for 1.5 h. To the mixture aqueous potassium hydroxide (24 mL, 40% purity, 240 mmol) was added until the pH value turned basic. The aqueous mixture was extracted with ethyl acetate for three times. The combined organic layers were dried using a water resistant filter and concentrated under reduced pressure to provide 766 mg of the target compound in 86% purity.

LC-MS (Method 2): $R_t$=0.55 min; MS (ESIpos): m/z=142 $[M+H]^+$ $^1$H-NMR (400 MHz, DMSO-$d_6$) 5 [ppm]2.14 (s, 3H), 4.06 (br s, 2H), 6.78 (s, 1H), 7.02-7.29 (m, 1H), 7.46 (t, 1H).

Intermediate 42

5-{-2-[1-(2-bromopyridin-4-yl)-2-(pyridin-2-yl)ethylidene]hydrazinyl}-2-fluoro-3-methylpyridine

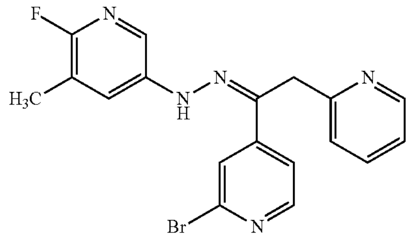 [SMILES: Cc1cc(N/N=C(/Cc2ccccn2)c2ccnc(Br)c2)cnc1F]

2-Fluoro-5-hydrazinyl-3-methylpyridine (Intermediate 41, 50.0 mg) was dissolved in 2.6 mL ethyl acetate. Propane phosphonic acidanhydride (230 μL, 50% in ethyl acetate, 390 μmol; CAS-RN:[68957-94-8]) and 1-(2-bromopyridin-4-yl)-2-(pyridin-2-yl)ethan-1-one (98.2 mg, 354 μmol, CAS-RN:[656257-84-0]) were added. The mixture was stirred for 1 min. at rt and then heated at 120° C. for 15 minutes in the microwave. The reaction mixture was diluted with ethyl acetate and saturated aqueous sodium hydrogencarbonate-solution. The layers were separated and the organic layer was dried using a water resistant filter. The clear filtrate was concentrated under reduced pressure to provide 145 mg. the target compound in 65% purity.

LC-MS (Method 2): Rt=1.28 min; MS (ESIpos): m/z=402 $[M+H]^+$ $^1$H-NMR (400 MHz, DMSO-d6) δ[ppm]=2.26 (s, 3H), 4.39 (s, 2H), 7.25 (ddd, 1H), 7.39 (d, 1H), 7.62-8.06 (m, 5H), 8.29 (d, 1H), 8.39-8.55 (m, 1H), 10.58 (s, 1H).

Intermediate 1

2-(2-bromopyridin-4-yl)-5-fluoro-6-methyl-3-(pyridin-2-yl)-1H-pyrrolo[3,2-b]pyridine

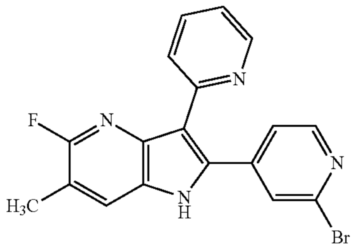 [SMILES: Cc1cc2[nH]c(-c3ccnc(Br)c3)c(-c3ccccn3)c2nc1F]

5-{2-[1-(2-Bromopyridin-4-yl)-2-(pyridin-2-yl)ethylidene]hydrazinyl}-2-fluoro-3-methylpyridine (see Intermediate 42, 124 mg) was dissolved in 2.2 mL sulfolane and zinc chloride (46.5 mg, 341 μmol) was added. The mixture was heated at 170° C. for 4 hours. The reaction mixture was diluted with ethyl acetate. It was washed with half-saturated aqueous sodium chloride-solution for three-times. The organic layer was dried using a water resistant filter. The clear filtrate was concentrated under reduced pressure. The crude product was diluted with dichloromethane. A beige solid precipitated. It was filtered off under vacuo to provide 56 mg of the target compound in 87% purity.

LC-MS (Method 2): $R_t$=1.08 min; MS (ESIpos): m/z=383 $[M+H]^+$ $^1$H-NMR (400 MHz, DMSO-$d_6$) 5 [ppm]2.38 (s, 3H), 7.31 (ddd, 1H), 7.50 (dd, 1H), 7.80 (d, 1H), 7.87-7.98 (m, 2H), 7.99-8.08 (m, 1H), 8.37 (d, 1H), 8.45-8.55 (m, 1H), 12.30 (s, 1H).

Intermediate 44

2-(4-fluorophenyl)propanamide

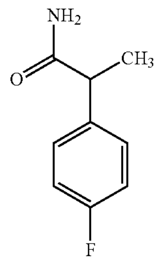

2-(4-Fluorophenyl)propanoic acid (2.00 g, 11.9 mmol) was dissolved in 69 mL dichloromethane and cooled down with an ice bath. Oxalyl chloride (1.2 mL, 14 mmol) was added, followed by 65 μL DMF. The reaction mixture was stirred at rt for 1 hour under nitrogen atmosphere. The mixture was cooled down again and treated with aqueous ammonia (26 mL, 33% purity, 150 mmol) drop wise. It was stirred at rt over night under nitrogen atmosphere. To the reaction mixture water was added. The aqueous layer was extracted with a mixture of dichloromethane/isopropanole (7:3) three times. The combined organic layers were dried using a water resistant filter and concentrated under reduced pressure to provide 1.99 g of the target compound in 94% purity.

LC-MS (Method 2): Rt=0.76 min; MS (ESIpos): m/z=168 $[M+H]^+$ $^1$H-NMR (400 MHz, DMSO-d6) δ[ppm]=1.28 (d, 3H), 3.57 (q, 1H), 6.83 (br s, 1H), 7.07-7.17 (m, 2H), 7.29-7.37 (m, 2H), 7.40 (br s, 1H).

Intermediate 45

N-{4-[5-fluoro-3-(5-fluoropyridin-2-yl)-1H-pyrrolo[3,2-b]pyridin-2-yl]pyridin-2-yl}acetamide

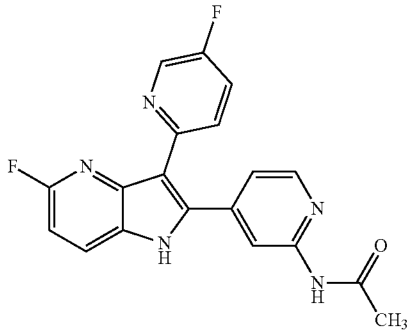 [SMILES: CC(=O)Nc1cc(-c2[nH]c3ccc(F)nc3c2-c2ccc(F)cn2)ccn1]

N-{2-[(2-Acetamidopyridin-4-yl)ethynyl]-6-fluoropyridin-3-yl}-2,2,2-trifluoroacetamide (Intermediate 2, 1.42 g, 3.87 mmol), 5-fluoro-2-iodopyridine (1.0 g, 4.48 mmol), tetrakis(triphenylphosphine) palladium (223 mg, 193 μmol; CAS-RN:[14221-01-3]) and cesium carbonate (3.65 g, 11.2 mmol) were suspended in 32 mL acetonitrile and stirred at 100° C. under an Argon atmosphere in a sealed vessel for 3 hours. The undissolved precipitate was filtered off and washed with DCM and methanol. The filtrate was concentrated under reduced pressure and purified by flash chromatography (silica gel, gradient: EtOAc/EtOH 0%-50%) to afford 865 mg of a row product which was sonicated in DCM to yield 762 mg (91% purity, 49% yield) of the title compound after filtration.

LC-MS (Method 2): Rt=0.93 min; MS (ESIpos): m/z=366 $[M+H]^+$ $^1$H NMR (400 MHz, DMSO-$d_6$) δ [ppm]2.08 (s, 3H), 7.01 (dd, 1H), 7.14 (dd, 1H), 7.83 (td, 1H), 8.00 (dd, 1H), 8.05 (dd, 1H), 8.25 (s, 1H), 8.31 (d, 1H), 8.46 (d, 1H), 10.56 (s, 1H), 12.35 (s, 1H).

Intermediate 46

4-[5-fluoro-3-(5-fluoropyridin-2-yl)-1H-pyrrolo[3,2-b]pyridin-2-yl]pyridin-2-amine

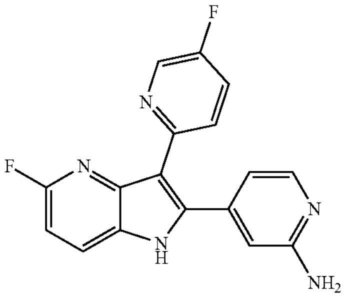 [SMILES: Nc1cc(-c2[nH]c3ccc(F)nc3c2-c2ccc(F)cn2)ccn1]

N-{4-[5-fluoro-3-(5-fluoropyridin-2-yl)-1H-pyrrolo[3,2-b]pyridin-2-yl]pyridin-2-yl}acetamide (Intermediate 45, 760 mg, 2.08 mmol) was dissolved in methanol (84 ml) and treated with aqueous sodium hydroxide solution (21 ml, 1.0M, 21 mmol). The reaction mixture was stirred at 80° C. for 16 hours under a nitrogen atmosphere. The reaction mixture was concentrated under reduced pressure and diluted with water. The precipitate was filtered off and washed with water until the filtrate was not basic anymore. The residue was dried at 50° C. under vacuum to provide 667 mg (86% purity, 85% yield) of the target compound.

LC-MS (Method 2): Rt=0.89 min; MS (ESIpos): m/z=324 $[M+H]^+$ $^1$H NMR (400 MHz, DMSO-$d_6$) δ [ppm]6.03 (br s, 2H), 6.51 (dd, 1H), 6.55 (s, 1H), 6.97 (dd, 1H), 7.81 (dt, 1H), 7.90-7.95 (m, 2H), 8.00 (dd, 1H), 8.51 (d, 1H), 12.19 (br s, 1H).

Intermediate 42

N-{4-[7-chloro-3-(pyridin-2-yl)-1-{[2-(trimethylsilyl)ethoxy]methyl}-1H-pyrrolo[3,2-b]pyridin-2-yl]pyridin-2-yl}acetamide

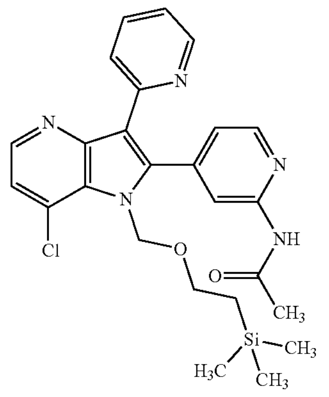 [SMILES: CC(=O)Nc1cc(-c2c(-c3ccccn3)c3nccc(Cl)c3n2COCC[Si](C)(C)C)ccn1]

To a solution of N-{4-[7-chloro-3-(pyridin-2-yl)-1H-pyrrolo[3,2-b]pyridin-2-yl]pyridin-2-yl}acetamide (see Intermediate 40, 750 mg, 2.06 mmol) in N,N-dimethylformamide (11 ml) was added potassium carbonate (1.42 g, 10.3 mmol) in portions at room temperature. After stirring for 30 minutes, (chloromethoxy)ethyl](trimethyl)silane (0.730 ml, 4.1 mmol) was added in one portion to above reaction mixture. The reaction mixture was stirred at room temperature for 2 hours. The mixture was poured into water and extracted with ethyl acetate. The organic phase was washed with brine, dried over anhydrous sodium sulfate, filtered and concentrated to give a residue. The residue was purified by flash silica gel chromatography (petroleum ether: 10% methanol in ethyl acetate=1:0 to 3:1) to give N-{4-[7-chloro-3-(pyridin-2-yl)-1-{[2-(trimethylsilyl)ethoxy]methyl}-1H-pyrrolo[3,2-b]pyridin-2-yl]pyridin-2-yl}acetamide (500 mg, 49% yield) as a yellow solid.

Intermediate 48

N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide

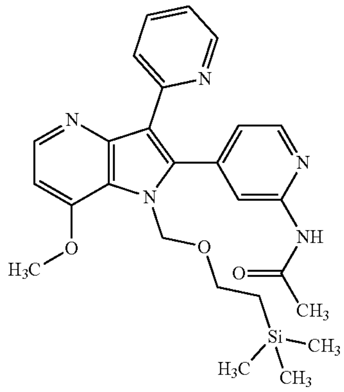

To a solution of N-{4-[7-chloro-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 47, 250 mg, 0.51 mmol) and methanol (0.061 ml, 5.06 mmol) in toluene (5.0 ml) were added cesium carbonate (330 mg, 1.01 mmol), 5-(di-t-butylphosphino)-1',3',5'-triphenyl-1,4'-bi-1H-pyrazole (t-Bu-BippyPhos) (51.3 mg, 0.10 mmol) and palladium (II) acetate (11.4 mg, 0.05 mol) in one portion at room temperature.

After stirring at 100° C. for 16 hours under nitrogen atmosphere, the mixture was poured into water and extracted with ethyl acetate. The organic phase was washed with brine, dried over anhydrous sodium sulfate, filtered and concentrated to give a residue. The residue was purified purified by flash silica gel chromatography (petroleum ether: 10% methanol in ethyl acetate=1:0 to 3:7) to give N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide (70 mg, 28% yield) as a yellow solid.

Intermediate 49

4-[7-methoxy-3-(pyridin-2-yl)-1-{[2-(trimethylsilyl)ethoxy]methyl}-1H-pyrrolo[3,2-b]pyridin-2-yl]pyridin-2-amine

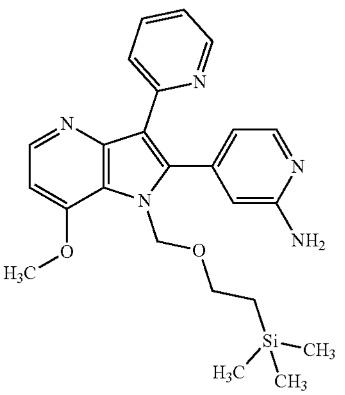 [SMILES: COc1ccnc2c(-c3ccccn3)c(-c3ccnc(N)c3)n(COCC[Si](C)(C)C)c12]

A mixture of N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 48, 70.0 mg, 0.143 μmol) and sodium hydroxide (57.2 mg, 1.43 mmol) in a mixed solvent of methanol (2.0 ml) and water (2.0 ml) was stirred at 50° C. for 16 hours. The mixture was concentrated by evaporation in vacuum. The residue was purified by flash silica gel chromatography (petroleum ether: 10% methanol in ethyl acetate=1:0 to 1:4) to give 4-[7-methoxy-3-(pyridin-2-yl)-1-{[2-(trimethylsilyl)ethoxy]methyl}-1H-pyrrolo[3,2-b]pyridin-2-yl]pyridin-2-amine (50 mg, 78% yield) as a yellow solid.

Intermediate 50

2-(4-fluorophenyl)-N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide

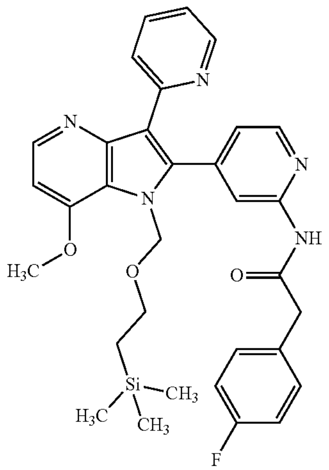 [SMILES: COc1ccnc2c(-c3ccccn3)c(-c3ccnc(NC(=O)Cc4ccc(F)cc4)c3)n(COCC[Si](C)(C)C)c12]

To a solution of 4-[7-methoxy-3-(pyridin-2-yl)-1-{[2-(trimethylsilyl)ethoxy]methyl}-1H-pyrrolo[3,2-b]pyridin-2-yl]pyridin-2-amine (see Intermediate 49, 40.0 mg, 0.089 mmol) and (4-fluorophenyl)acetic acid (27.5 mg, 0.18 mmol) in N,N-dimethylformamide were added propanephosphonic anhydride (3.0 ml, 50% purity in N,N-dimethylformamide) and N,N-diisopropylethylamine (3.0 ml) at 25° C. After stirring at 80° C. for 16 hours, the mixture was poured into water and extracted with ethyl acetate. The combined organic layers were washed with brine, dried over anhydrous sodium sulfate, filtered and concentrated to give a residue. The residue was purified by flash silica gel chromatography (petroleum ether: 10% methanol in ethyl acetate=1:0 to 1:4) to give 2-(4-fluorophenyl)-N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide (50 mg) as a yellow solid.

Intermediate 51

N-{4-[(3-amino-6-chloropyridin-2-yl)ethynyl]pyridin-2-yl}acetamide

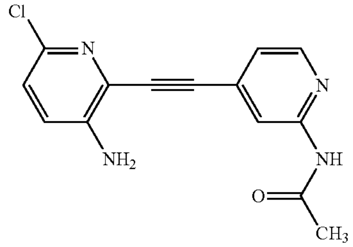 [SMILES: CC(=O)Nc1cc(C#Cc2nc(Cl)ccc2N)ccn1]

A mixture of N-(4-ethynylpyridin-2-yl)acetamide (CAS 1445876-40-3, 5.00 g, 31.2 mmol), 2-bromo-6-chloropyridin-3-amine (7.12 g, 34.3 mmol), dichlorobis(triphenylphosphine)palladium(II) (1.10 g, 1.56 mmol), copper(I) iodide (595 mg, 3.12 mmol) and trimethylamine (20 mL, 140 mmol) in N,N-dimethylformamide (50 mL) was purged with nitrogen. After stirring at 100° C. for 16 hours under nitrogen protection, the reaction mixture was poured into water, extracted with ethyl acetate. The combined organic layers were dried over anhydrous sodium sulfate, filtered and concentrated to give a residue. The residue was purified by silica gel chromatography (100-200 mesh, petroleum ether:ethyl acetate=1:1 to 0:1) to give N-{4-[(3-amino-6-chloropyridin-2-yl)ethynyl]pyridin-2-yl}acetamide (5.90 g, 66% yield) as a yellow solid.

Intermediate 52

N-[4-(5-chloro-1H-pyrrolo[3,2-b]pyridin-2-yl)pyridin-2-yl]acetamide

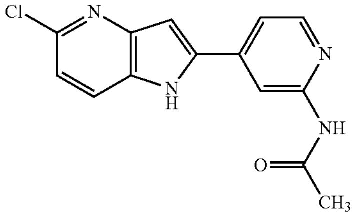 [SMILES: CC(=O)Nc1cc(-c2cc3nc(Cl)ccc3[nH]2)ccn1]

To a solution of N-{4-[(3-amino-6-chloropyridin-2-yl)ethynyl]pyridin-2-yl}acetamide (see Intermediate 51, 5.90 g, 20.6 mmol) in 1-methyl-2-pyrrolidinone (50 mL) was added copper(I) iodide (784 mg, 4.12 mmol) at 25° C. After stirring at 130° C. for 16 hours, the reaction mixture was diluted with water and extracted with ethyl acetate. The organic layer was washed with brine, dried over anhydrous sodium sulfate, filtered, concentrated to give a residue. The residue was purified by silical gel column (100-200 mesh, petroleum ether:ethyl acetate=1:1 to 1:2) to give N-[4-(5-chloro-1H-pyrrolo[3,2-b]pyridin-2-yl)pyridin-2-yl]acetamide (2.60 g, 44% yield) as a yellow solid.

Intermediate 53

N-[4-(3-bromo-5-chloro-1H-pyrrolo[3,2-b]pyridin-2-yl)pyridin-2-yl]acetamide

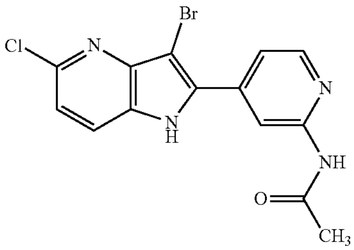 [SMILES: CC(=O)Nc1cc(-c2[nH]c3ccc(Cl)nc3c2Br)ccn1]

To a solution of N-[4-(5-chloro-1H-pyrrolo[3,2-b]pyridin-2-yl)pyridin-2-yl]acetamide (see Intermediate 52, 2.40 g, 8.37 mmol) in N,N-dimethylformamide (29 mL) was added N-bromosuccinimide (1.34 g, 7.53 mmol) at 0° C. After stirring at room temperature for 0.5 hour, the reaction mixture (combined with a batch starting from 200 mg Intermediate 52) was quenched with saturated sodium hydrogen carbonate and saturated sodium thiosulfate, extracted with ethyl acetate. The organic layer was washed with brine, dried over sodium sulfate, filtered, concentrated to give a residue. The residue was triturated with ethyl acetate to give N-[4-(3-bromo-5-chloro-1H-pyrrolo[3,2-b]pyridin-2-yl)pyridin-2-yl]acetamide (2.7 g) as a yellow solid.

Intermediate 54

N-[4-(3-bromo-5-chloro-1-{[2-(trimethylsilyl)ethoxy]methyl}-1H-pyrrolo[3,2-b]pyridin-2-yl)pyridin-2-yl]acetamide

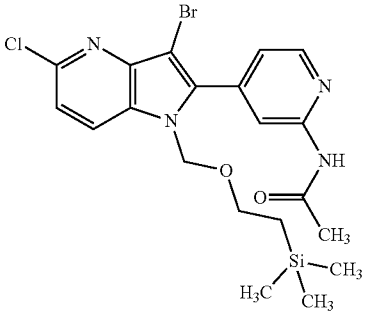 [SMILES: CC(=O)Nc1cc(-c2c(Br)c3nc(Cl)ccc3n2COCC[Si](C)(C)C)ccn1]

To a solution of N-[4-(3-bromo-5-chloro-1H-pyrrolo[3,2-b]pyridin-2-yl)pyridin-2-yl]acetamide (see Intermediate 53, 2.50 g, 6.84 mmol) in N,N-dimethylformamide (25 mL) was added potassium carbonate (2.8 g, 20.51 mmol) at 25° C. After stirring at room temperature for 10 minutes, [2-(chloromethoxy)ethyl](trimethyl)silane (1.71 g, 10.3 mmol) was added into the reaction mixture. After stirring at room temperature for 2 hours, the reaction mixture (combined with a batch starting from 200 mg Intermediate 53) was diluted with water, extracted with ethyl acetate. The organic layer was washed with brine, dried over anhydrous sodium sulfate and filtered. The filtrate was concentrated to give a residue. The residue was purified by silical gel column (100-200 mesh, petroleum ether:ethyl acetate=10:1 to 3:1) to give N-[4-(3-bromo-5-chloro-1-{[2-(trimethylsilyl)ethoxy]methyl}-1H-pyrrolo[3,2-b]pyridin-2-yl)pyridin-2-yl]acetamide (3 g) as yellow gum.

Intermediate 55

N-{4-[5-chloro-3-(pyridin-2-yl)-1-{[2-(trimethylsilyl)ethoxy]methyl}-1H-pyrrolo[3,2-b]pyridin-2-yl]pyridin-2-yl}acetamide

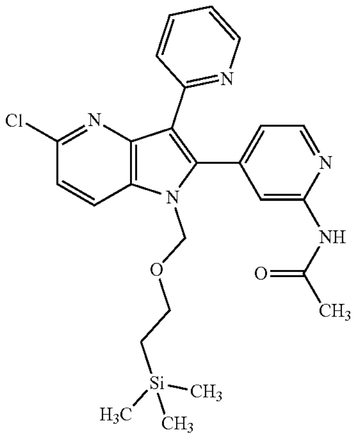 [SMILES: CC(=O)Nc1cc(-c2c(-c3ccccn3)c3nc(Cl)ccc3n2COCC[Si](C)(C)C)ccn1]

To a mixture of N-[4-(3-bromo-5-chloro-1-{[2-(trimethylsilyl)ethoxy]methyl}-1H-pyrrolo[3,2-b]pyridin-2-yl)pyridin-2-yl]acetamide (see Intermediate 54, 2.50 g, 5.04 mmol), 2-(tributylstannyl)pyridine (2.23 g, 6.05 mmol) in 1,4-dioxane (30 mL) was added dichlorobis(triphenylphosphine)palladium(II) (354 mg, 0.5 mmol) in one portion at room temperature. After stirring at 100° C. for 16 hours under nitrogen atmosphere, the reaction mixture (combined with two batches starting from 50 mg and 500 mg Intermediate 54) was concentrated to give a residue. The residue was purified by flash chromatography (petroleum ether:ethyl acetate=3:1) to give N-{4-[5-chloro-3-(pyridin-2-yl)-1-{[2-(trimethylsilyl)ethoxy]methyl}-1H-pyrrolo[3,2-b]pyridin-2-yl]pyridin-2-yl}acetamide (940 mg) as yellow gum.

A crude product of N-{4-[5-chloro-3-(pyridin-2-yl)-1-{[2-(trimethylsilyl)ethoxy]methyl)-1H-pyrrolo[3,2-b]pyridin-2-yl]pyridin-2-yl}acetamide (see Intermediate 55, 400 mg, 0.81 mmol) was purified by preparative HPLC (Instrument: ACSWH-GX-Q; Column: Shim-pack C18 150*25*10 μm; eluent A: water (0.225% formic acid), eluent B: acetonitrile; gradient: 0-14 min 32-60% B; flow 25 mL/min; temperature: room temperature; Detector: UV 220/254 nm) to give N-{4-[5-chloro-3-(pyridin-2-yl)-1-{[2-(trimethylsilyl)ethoxy]methyl}-1H-pyrrolo[3,2-b]pyridin-2-yl]pyridin-2-yl}acetamide (138 mg, 98% purity) as a white solid.

LC-MS (Method C): $R_t$=0.78 min; MS (ESIpos): m/z=494 $[M+H]^+$.

$^1$H NMR (400 MHz, DMSO-$d_6$): δ [ppm]=10.61 (s, 1H), 8.36 (d, J=5.2 Hz, 1H), 8.32-8.34 (m, 1H), 8.27 (d, J=8.8 Hz, 1H), 8.15 (s, 1H), 7.84 (td, J=7.8, 2.0 Hz, 1H), 7.43 (d, J=8.8 Hz, 1H), 7.22-7.19 (m, 1H), 7.10 (dd, J=5.2, 1.6 Hz, 1H), 5.51 (s, 2H), 2.06 (s, 3H), 0.75-0.69 (m, 2H), −0.14 (s, 10H).

Intermediate 56

N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide

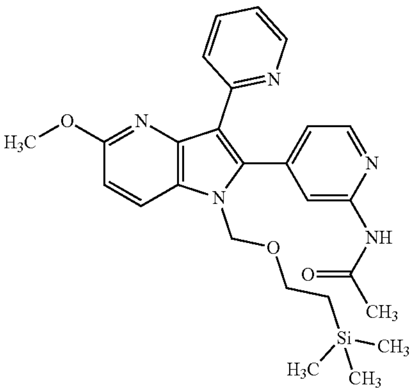

To a solution of N-{4-[5-chloro-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 55, 150 mg, 0.30 mmol) and methanol (0.12 ml) in toluene (15 ml) were added cesium carbonate (297 mg, 0.91 mmol), 5-(di-t-butylphosphino)-1',3',5'-triphenyl-1,4'-bi-1H-pyrazole (30.8 mg, 0.06 mmol) and palladium(II) acetate (6.82 mg, 0.03 mmol) in one portion at room temperature. After stirring at 100° C. for 16 hours under nitrogen atmosphere, the reaction mixture was concentrated to give a residue. The residue was diluted with water and extracted with ethyl acetate. The organic phase was washed with brine, dried over anhydrous sodium sulfate, filtered and concentrated to give a residue. The residue was purified by preparative HPLC (Instrument: Gilson-281; Column: Phenomenex Synergi C18 150*25*10 μm; eluent A: water (0.225% formic acid), eluent B: acetonitrile; gradient: 0-10 min 18-48% B; flow 25 ml/min; temperature: room temperature; Detector: UV 220/254 nm) to give N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide (60 mg, 90% purity) as a yellow solid.

Intermediate 57

4-[5-methoxy-3-(pyridin-2-yl)-1-{[2-(trimethylsilyl)ethoxy]methyl}-1H-pyrrolo[3,2-b]pyridin-2-yl]pyridin-2-amine

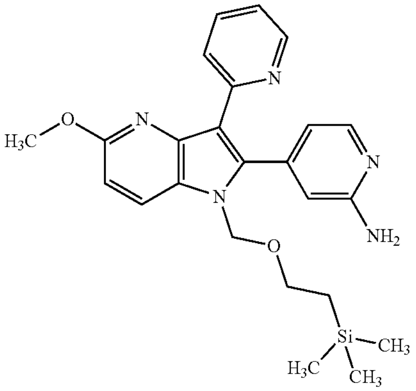

A mixture of N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 56, 60.0 mg, 0.12 mmol) and sodium hydroxide (49.0 mg, 1.23 mmol) in a mixed solvent of methanol (3 ml) and water (3 ml) was stirred at 50° C. for 16 hours. The reaction mixture was concentrated to give a residue. The residue was diluted with water and extracted with ethyl acetate. The organic phase was washed with brine, dried over anhydrous sodium sulfate and filtered. The filtrate was concentrated to give 45.0 mg (82% yield) of the title compound as a crude product and a yellow solid, that was used without further purification.

LC-MS (Method C): $R_t$=0.807 min; MS (ESIpos): m/z=448.0 $[M+H]^+$.

Intermediate 58

2-(4-fluorophenyl)-N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide

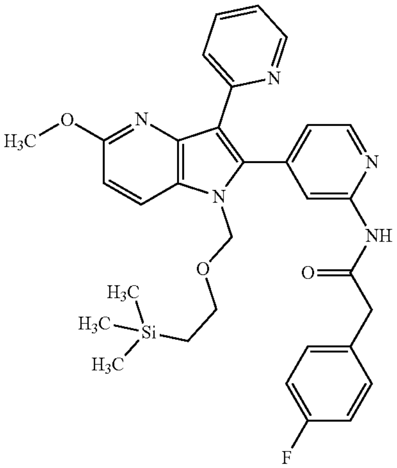 [SMILES: COc1ccc2c(n1)c(-c1ccccn1)c(-c1ccnc(NC(=O)Cc3ccc(F)cc3)c1)n2COCC[Si](C)(C)C]

To a solution of (4-fluorophenyl)acetic acid (31.0 mg, 0.20 mmol) and [dimethylamino(triazolo[4,5-b]pyridin-3-yloxy)methylidene]-dimethylazanium; hexafluorophosphate (115 mg, 0.30 mmol) in N,N-dimethylformamide (1.7 ml) was added N,N-diisopropylethylamine (0.07 ml, 0.40 mmol) at 25° C. After stirring at 25° C. for 0.5 hour, 4-[5-methoxy-3-(pyridin-2-yl)-1-{[2-(trimethylsilyl)ethoxy]methyl}-1H-pyrrolo[3,2-b]pyridin-2-yl]pyridin-2-amine (see Intermediate 57, 45.0 mg, 0.10 mmol) was added into the mixture at room temperature. After stirring at 25° C. for 16 hours, the reaction mixture was concentrated to give a residue. The residue was diluted with water and extracted with ethyl acetate. The organic phase was washed with brine, dried over anhydrous sodium sulfate, filtered and concentrated to give a residue. The residue was purified by preparative HPLC (Instrument: Gilson-281; Column: Phenomenex Synergi C18 150*25*10 µm; eluent A: water (0.225% formic acid), eluent B: acetonitrile; gradient: 0-10 min 18-48% B; flow 25 ml/min; temperature: room temperature; Detector: UV 220/254 nm) to give 2-(4-fluorophenyl)-N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide (36.0 mg, 61% yield) as a yellow solid.

LC-MS (Method C): Rt=0.940 min; MS (ESIpos): m/z=584.1 $[M+H]^+$.

Intermediate 59

N-{4-[7-ethenyl-3-(pyridin-2-yl)-1-{[2-(trimethylsilyl)ethoxy]methyl}-1H-pyrrolo[3,2-b]pyridin-2-yl]pyridin-2-yl}acetamide

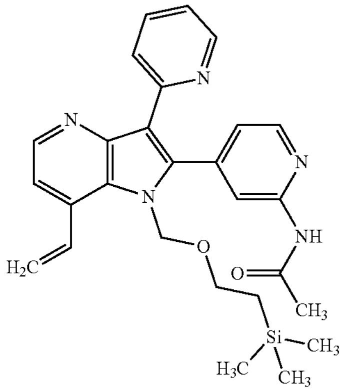 [SMILES: C=Cc1ccnc2c(-c3ccccn3)c(-c3ccnc(NC(C)=O)c3)n(COCC[Si](C)(C)C)c12]

A mixture of N-{4-[7-chloro-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 47, 300 mg, 0.607 mmol), potassium ethenyl(trifluorido)borate (813 mg, 6.07 mmol), cesium carbonate (989 mg, 3.04 mmol) and methanesulfonato(2-dicyclohexylphosphino-2',4',6'-tri-i-propyl-1,1'-biphenyl)(2'-amino-1,1'-biphenyl-2-yl)palladium(II) (51.3 mg, 0.0607 mmol) in dioxane (5.0 ml) and water (0.2 ml) was stirred at 100° C. for 16 hours. The mixture was poured into water and the mixture was extracted with ethyl acetate. The organic phase was dried over anhydrous sodium sulfate, filtered and concentrated to give a residue. The residue was purified by flash column chromatography (20 g, petroleum ether: 10% methanol in ethyl acetate=9:1 to 0:1) to give N-{4-[3-(pyridin-2-yl)-1-{

[2-(trimethylsilyl)ethoxy]methyl}-7-vinyl-1H-pyrrolo[3,2-b]pyridin-2-yl]pyridin-2-yl}acetamide (200 mg, 95% yield) as a yellow solid.

Intermediate 60

4-[7-ethenyl-3-(pyridin-2-yl)-1H-pyrrolo[3,2-b]pyridin-2-yl]pyridin-2-amine

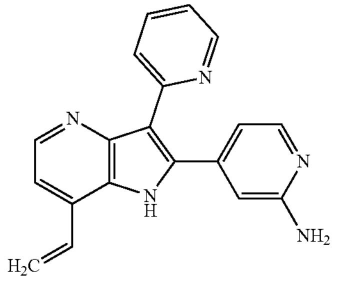 [SMILES: C=Cc1ccnc2c(-c3ccccn3)c(-c3ccnc(N)c3)[nH]c12]

A mixture of N-{4-[7-ethenyl-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 59, 280 mg, 0.577 mmol) in hydrochloric acid (10 ml, 4 M in methanol) was stirred at 50° C. for 16 hours. The residue was diluted with ethyl acetate and saturated potassium carbonate in water, and the mixture was stirred at room temperature for 30 minutes. The organic layer was washed with brine, dried over anhydrous sodium sulfate, filtered and concentrated to give a residue. The residue was purified by flash silica gel chromatography (20 g, petroleum ether: 10% methanol in ethyl acetate=1:0 to 0:1) to give 4-[3-(pyridin-2-yl)-7-vinyl-1H-pyrrolo[3,2-b]pyridin-2-yl]pyridin-2-amine (150 mg, 71% yield) as a yellow solid.

Intermediate 61

N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}acetamide

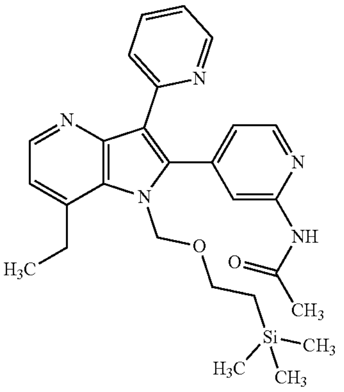 [SMILES: CCc1ccnc2c(-c3ccccn3)c(-c3ccnc(NC(C)=O)c3)n(COCC[Si](C)(C)C)c12]

A mixture of N-{4-[7-ethenyl-3-(pyridin-2-yl)-1-{[2-(trimethylsilyl)ethoxy]methyl)-1H-pyrrolo[3,2-b]pyridin-2-yl]pyridin-2-yl}acetamide (see Intermediate 59, 192 mg, 0.40 mmol), palladium on activated carbon (42.1 mg, contained 50% water, 10% purity) and ammonium formate in ethanol (10.0 ml) was stirred at room temperature for 16 hours under nitrogen. The reaction mixture (combined with a batch starting from 20 mg Intermediate 59) was filtered. The filtrate was concentrated by evaporation in vacuum. The residue was dissolved with ethyl acetate, washed with water. The organic phase was dried over anhydrous sodium sulfate, filtered, concentrated to give N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}acetamide (200 mg, crude) as yellow oil. The crude product was used for next step directly without further purification.

Intermediate 62

4-[7-ethyl-3-(pyridin-2-yl)-1-{[2-(trimethylsilyl)ethoxy]methyl}-1H-pyrrolo[3,2-b]pyridin-2-yl]pyridin-2-amine

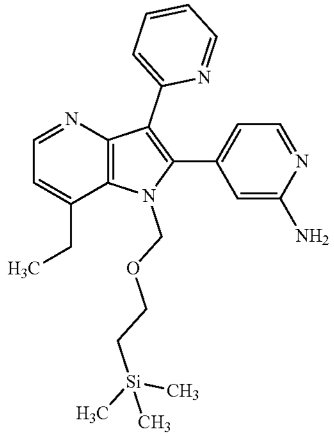 [SMILES: CCc1ccnc2c(-c3ccccn3)c(-c3ccnc(N)c3)n(COCC[Si](C)(C)C)c12]

A mixture of N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 61, 200 mg, 0.41 mmol) and sodium hydroxide (164 mg, 4.10 mmol) in a mixed solvent of methanol (3.0 ml) and water (3.0 ml) was stirred at 50° C. for 16 hours. The mixture was concentrated, diluted with ethyl acetate, washed with water. The organic phase was dried over anhydrous sodium sulfate and filtered. The filtrate was concentrated to give 132 mg (72% yield) of the title compound as a crude product and a yellow solid, that was used without further purification.

Intermediate 63

N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide

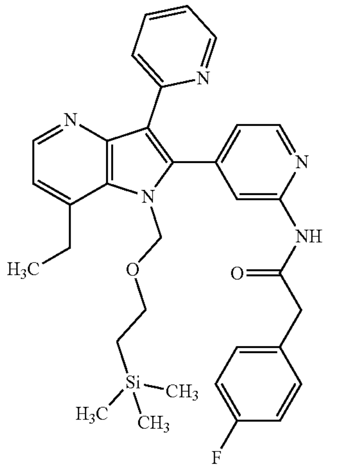 [SMILES: CCc1ccnc2c(-c3ccccn3)c(-c3ccnc(NC(=O)Cc4ccc(F)cc4)c3)n(COCC[Si](C)(C)C)c12]

To a solution of 4-[7-ethyl-3-(pyridin-2-yl)-1-{[2-(trimethylsilyl)ethoxy]methyl}-1H-pyrrolo[3,2-b]pyridin-2-yl]pyridin-2-amine (see Intermediate 62, 132 mg, 0.30 mmol) and (4-fluorophenyl)acetic acid (54.8 mg, 0.36 mmol) in N,N-dimethylformamide (5.0 ml) were added 2-(7-azabenzotriazol-1-yl)-N,N,N',N'-tetramethyluronium hexafluorophosphate (HATU) (225 mg, 0.59 mmol) and N,N-diisopropylethylamine (0.210 ml, 1.2 mmol). After stirring at room temperature for 16 hours, the mixture was poured into water, extracted with ethyl acetate. The organic layer was washed with brine, dried over anhydrous sodium sulfate, filtered and concentrated to give a residue. The residue was purified by flash column chromatography (20 g, 10% methanol in ethyl acetate:petroleum ether=0:1 to 10:1) to give N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide (100 mg, 97% purity, 56% yield) as a yellow solid.

LC-MS (Method C): Rt=0.911 min; MS (ESIpos): m/z=582.2 $[M+H]^+$.

Intermediate 64

N-{4-[7-cyclopropyl-3-(pyridin-2-yl)-1-{[2-(trimethylsilyl)ethoxy]methyl}-1H-pyrrolo[3,2-b]pyridin-2-yl]pyridin-2-yl}acetamide

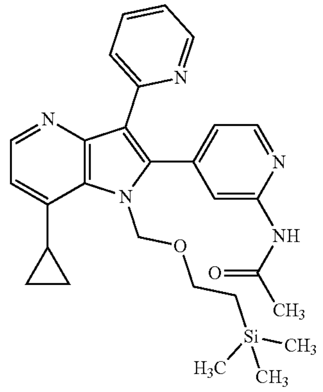 [SMILES: CC(=O)Nc1cc(-c2c(-c3ccccn3)c3nccc(C4CC4)c3n2COCC[Si](C)(C)C)ccn1]

A mixture of N-{4-[7-chloro-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 47, 500 mg, 1.01 mmol), cyclopropylboronic acid (435 mg, 5.06 mmol), cesium carbonate (989 mg, 3.04 mmol), 2-(dicyclohexylphosphino)-2',4',6'-tri-i-propyl-1,1'-biphenyl (Xphos) (94.6 mg, 0.202 mmol) and palladium(II) acetate (45.4 mg, 0.202 mmol) in a mixed solvent of toluene (10 ml) and water (1 ml) was stirred at 100° C. for 16 hours. The mixture was poured into water, extracted with ethyl acetate. The organic phase was dried over anhydrous sodium sulfate, filtered and concentrated to give a residue. The residue was purified by flash column chromatography (10% methanol in ethyl acetate:petroleum ether=1:9 to 1:0) to give N-{4-[3-(pyridin-2-yl)-1-{[2-(trimethylsilyl)ethoxy]methyl}-7-vinyl-1H-pyrrolo[3,2-b]pyridin-2-yl]pyridin-2-yl}acetamide (100 mg, 93% purity, 18% yield) as a yellow solid.

Intermediate 65

4-[7-cyclopropyl-3-(pyridin-2-yl)-1-{[2-(trimethylsilyl)ethoxy]methyl}-1H-pyrrolo[3,2-b]pyridin-2-yl]pyridin-2-amine

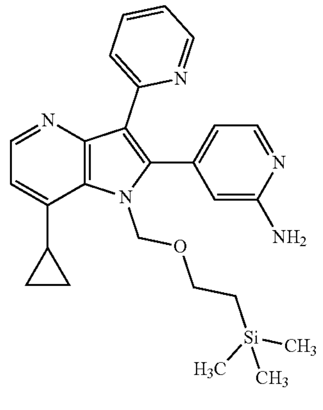 [SMILES: C[Si](C)(C)CCOCn1c(-c2ccnc(N)c2)c(-c2ccccn2)c2nccc(C3CC3)c21]

A mixture of N-{4-[7-cyclopropyl-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 64, 100 mg, 0.2 mmol) and sodium hydroxide (40.0 mg, 1.00 mmol) in a mixed solvent of methanol (3.0 ml) and water (3.0 ml) was stirred at 50° C. for 16 hours. The mixture was concentrated, purified by flash silica gel chromatography (10% methanol in ethyl acetate:petroleum ether=0:1 to 4:1) to give 4-[7-cyclopropyl-3-(pyridin-2-yl)-1-{[2-(trimethylsilyl)ethoxy]methyl}-1H-pyrrolo[3,2-b]pyridin-2-yl]pyridin-2-amine (70 mg, 76% yield) as a yellow solid.

Intermediate 66

N-{4-[7-cyclopropyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide

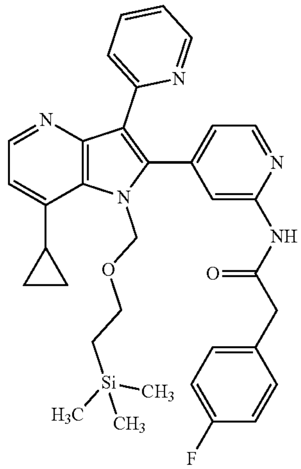 [SMILES: C[Si](C)(C)CCOCn1c(-c2ccnc(NC(=O)Cc3ccc(F)cc3)c2)c(-c2ccccn2)c2nccc(C3CC3)c21]

To a solution of 4-[7-cyclopropyl-3-(pyridin-2-yl)-1-{[2-(trimethylsilyl)ethoxy]methyl}-1H-pyrrolo[3,2-b]pyridin-2-yl]pyridin-2-amine (see Intermediate 65, 70.0 mg, 0.153 mmol) and 4-fluorophenyl)acetic acid (70.7 mg, 0.459 mmol) in N,N-dimethylformamide (2.0 ml) were added 2-(7-azabenzotriazol-1-yl)-N,N,N',N'-tetramethyluronium hexafluorophosphate (HATU) (233 mg, 0.612 mmol) and N,N-diisopropylethylamine (0.213 ml, 1.2 mmol). The mixture was stirred at room temperature for 16 hours. The mixture was concentrated, purified by preparative-TLC (petroleum ether:ethyl acetate=1:2) to give 40 mg of the title compound as a crude product and a yellow solid, that was used without further purification.

Intermediate 67

Mixture of 4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-amine and 4-[7-ethenyl-3-(pyridin-2-yl)-1-{[2-(trimethylsilyl)ethoxy]methyl}-1H-pyrrolo[3,2-b]pyridin-2-yl]pyridin-2-amine

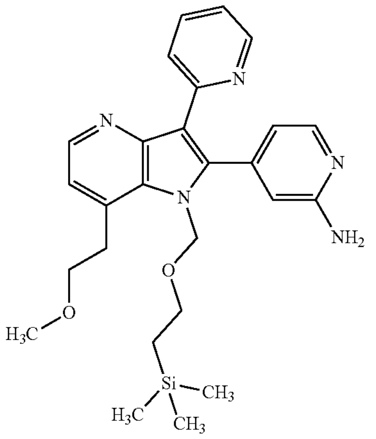

+

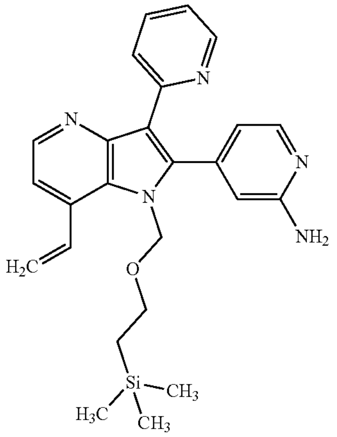

A mixture of N-{4-[7-ethenyl-3-(pyridin-2-yl)-1-{[2-(trimethylsilyl)ethoxy]methyl}-1H-pyrrolo[3,2-b]pyridin-2-yl]pyridin-2-yl}acetamide (200 mg, 0.41 mmol, see Intermediate 59) and sodium hydroxide (82.4 mg, 2.06 mmol) in a mixed solvent of methanol (2.0 ml) and water (2.0 ml) was stirred at 50° C. for 16 hours. The mixture was concentrated, purified by flash silica gel chromatography (10% methanol in ethyl acetate:petroleum ether=0:1 to 5:1) to give a mixture of 4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-amine and 4-[7-ethenyl-3-(pyridin-2-yl)-1-{[2-(trimethylsilyl)ethoxy]methyl)-1H-pyrrolo[3,2-b]pyridin-2-yl]pyridin-2-amine (130 mg, ratio of both products:approx.: 1:1) as a yellow solid.

Intermediate 68

Mixture of 2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide and N-{4-[7-ethenyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide

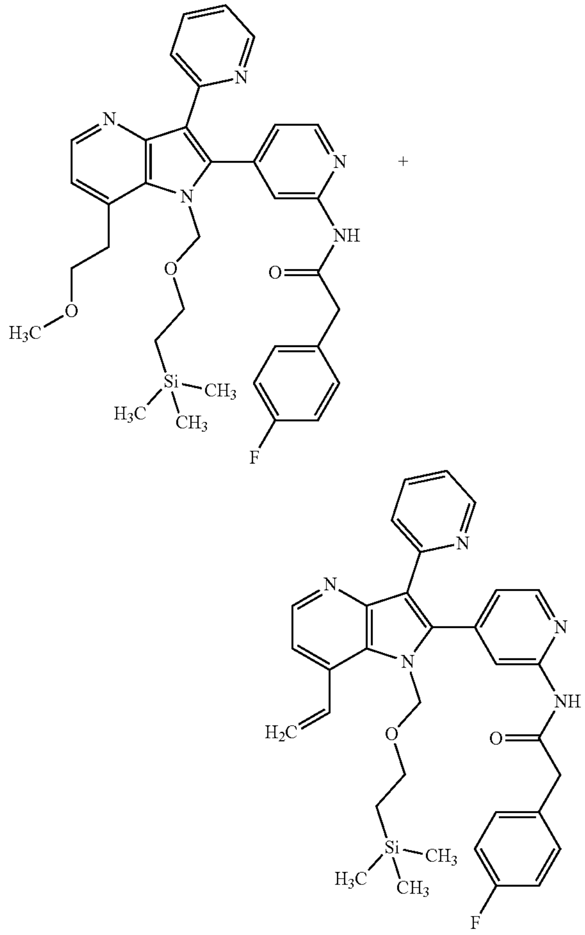

To a solution of a mixture of 4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-amine and 4-[7-ethenyl-3-(pyridin-2-yl)-1-{12-(trimethylsilyl)ethoxy]methyl}-1H-pyrrolo[3,2-b]pyridin-2-yl]pyridin-2-amine (see Intermediate 67, 120 mg, 0.26 mmol) and (4-fluorophenyl) acetic acid (80.5 mg, 0.52 mmol) in N,N-dimethylformamide (5.0 ml) were added 2-(7-azabenzotriazol-1-yl)-N,N,N',N'-tetramethyluronium hexafluorophosphate (HATU) (298 mg, 0.78 mmol) and N,N-diisopropylethylamine (0.230 ml, 1.30 mmol). After stirring at room temperature for 32 hours, the mixture was poured into water, extracted with ethyl acetate. The organic layer was washed with brine, dried over anhydrous sodium sulfate, filtered and concentrated to give a residue. The residue was purified by preparative HPLC (Instrument: ACSWH-GX-L; Column: Unisil 3-100 $C_{18}$ Ultra 150*50 mm*3 µm; eluent A: water (0.225% formic acid), eluent B: acetonitrile; gradient: 0-10 min 10-30% B; flow 25 ml/min; temperature: room temperature; Detector: UV 220/254 nm) to give a residue. The residue was purified three times by preparative-TLC (ethyl acetate) to give 2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide containing a small amount of and N-{4-[7-ethenyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide as an impurity (70 mg, crude) as a yellow solid. The crude product was used for next step directly without further purification.

Intermediate 69

Mixture of 2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide and N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide

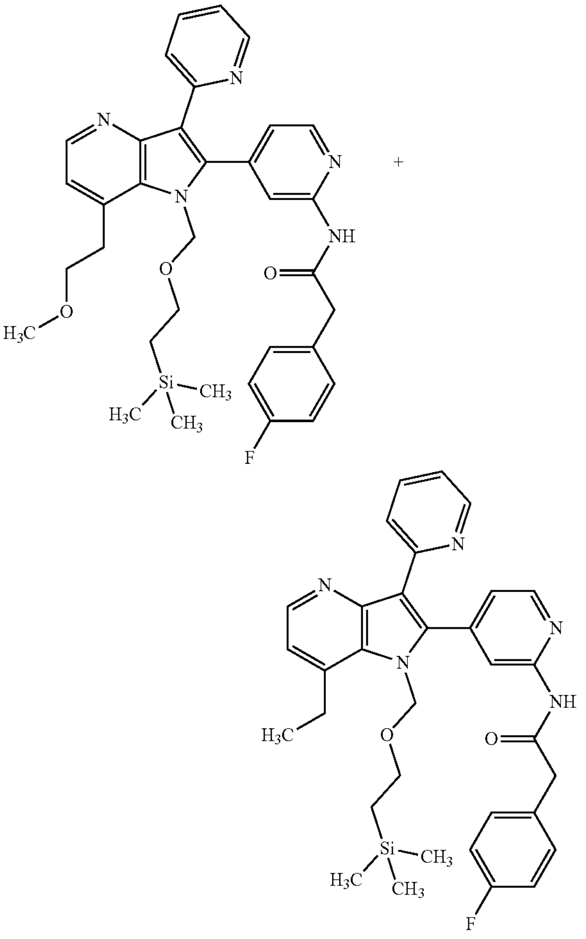

A mixture of 2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide containing a small amount of and N-{4-[7-ethenyl-3-(pyridin-2-yl)-1-{[2-(trimethylsilyl)ethoxy]

methyl}-1H-pyrrolo[3,2-b]pyridin-2-yl]pyridin-2-yl}-2-(4-fluorophenyl)acetamide as an impurity (crude product, see Intermediate 68, 50.0 mg, 0.084 mmol), palladium on activated carbon (8.93 mg, contained 50% water, 10% purity) and ammonium formate (52.9 mg, 0.839 mmol) in ethanol (5.0 ml) was stirred at room temperature for 16 hours under nitrogen. The mixture was filtered, concentrated, diluted with ethyl acetate and washed with water. The organic phase was dried over anhydrous sodium sulfate, filtered, concentrated by evaporation in vacuum to give 2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide containing a small amount of N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide as an impurity (30 mg, crude) a yellow oil. The crude product was used for next step directly without further purification.

Intermediate 70 tert-butyl (6-fluoropyridin-3-yl)carbamate

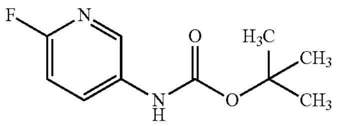

A mixture of 6-fluoropyridin-3-amine (50.0 g, 446 mmol), tert-butanol (25 ml), di-tert-butyl dicarbonate (200 ml) was stirred at 40° C. for 4 hours. The mixture was diluted with hexanes, cooled to 0° C. and stranded for two hours to precipitate out the crystal. The crystal was filtered, washed with hexanes, and dried in vacuo to give 80.0 g (85% yield) of the title compound as a crude product and a pink solid, that was used without further purification.

$^1$H NMR (400 MHz, DMSO-$d_6$): δ [ppm]=9.62 (brs, 1H), 8.25 (s, 1H), 8.00 (td, J=8.0, 2.4 Hz, 1H), 7.10 (dd, J=8.8, 3.2 Hz, 1H), 1.47 (s, 9H).

Intermediate 71 tert-butyl (4-bromo-6-fluoropyridin-3-yl)carbamate

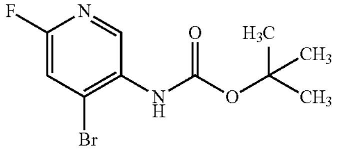 [SMILES: CC(C)(C)OC(=O)Nc1cnc(F)cc1Br]

A solution of tert-butyl (6-fluoropyridin-3-yl)carbamate (see Intermediate 70, 20.0 g, 94.2 mmol) in tetrahydrofuran (150 ml) was added tert-butyllithium (217 ml, 1.3 M solution in pentane, 283 mmol) at −70° C. After stirring at −40° C. for 1 hour, a solution of 1,2-dibromoethane (53.1 g, 283 mmol) in tetrahydrofuran (100 ml) was added at −70° C. After stirring at −78° C. for 2 hours, the reaction mixture was warmed to room temperature and stirred for 12 hours. The mixture was diluted with saturated ammonium chloride, extracted with ethyl acetate. The combined organic layers were dried over sodium sulfate, filtered, and concentrated to give a residue. The residue was purified by flash column chromatography (petroleum ether:ethyl acetate=1:0~20:1) to give tert-butyl (4-bromo-6-fluoropyridin-3-yl)carbamate (8.0 g, 29% yield) as yellow solid.

$^1$H NMR (400 MHz, DMSO-$d_6$): δ [ppm]=8.97 (s, 1H), 8.21 (s, 1H), 7.69 (d, J=2.4 Hz, 1H), 1.45 (s, 9H).

Intermediate 72 tert-butyl [4-(cyclopropylmethyl)-6-fluoropyridin-3-yl]carbamate

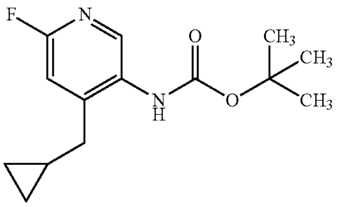 [SMILES: CC(C)(C)OC(=O)Nc1cnc(F)cc1CC1CC1]

A mixture of tert-butyl (4-bromo-6-fluoropyridin-3-yl) carbamate (see Intermediate 71, 8.09 g, 27.8 mmol), potassium (cyclopropylmethyl)(trifluorido)borate (9.00 g, 55.6 mmol), cesium carbonate (27.2 g, 83.3 mmol), methanesulfonato(2-dicyclohexylphosphino-2',6'-di-i-propoxy-1,1'-biphenyl)(2'-amino-1,1'-biphenyl-2-yl)palladium(II) (1.16 g, 1.389 mmol) and water (8.0 ml) in toluene (80 ml) was stirred at 80° C. for 16 hours under nitrogen atmosphere. The mixture (combined with two batches starting from 500 mg Intermediate 121) was poured into water and extracted with ethyl acetate. The combined organic phase was washed with brine, dried over anhydrous sodium sulfate, filtered and concentrated to give a residue. The residue was purified by flash column chromatography (petroleum ether:ethyl acetate=7:1) to give 7.3 g (54% purity) of the title compound as a crude product and a yellow oil, that was used without further purification.

$^1$H NMR (400 MHz, DMSO-$d_6$): δ [ppm]=8.75 (s, 1H), 8.05 (s, 1H), 7.17 (d, J=2.0 Hz, 1H), 2.53 (d, J=7.2 Hz, 2H), 1.44 (s, 9H), 1.02-0.95 (m, 1H), 0.53-0.48 (m, 2H), 0.20-0.17 (m, 2H).

Intermediate 73

4-(cyclopropylmethyl)-6-fluoropyridin-3-amine hydrogen chloride

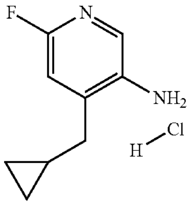

To a solution of tert-butyl [4-(cyclopropylmethyl)-6-fluoropyridin-3-yl]carbamate (see Intermediate 72, 7.30 g, 54% purity, 14.8 mmol) in ethyl acetate (50 ml) was added hydrochloric acid (20 ml, 80 mmol, 4 M in ethyl acetate). After stirring at room temperature for 4 hours, the mixture was concentrated to give 5.0 g (54% purity) of the title compound as a crude product and a yellow solid, that was used without further purification.

$^1$H NMR (400 MHz, DMSO-$d_6$): δ [ppm]=7.94 (s, 1H), 7.17 (s, 1H), 2.55 (d, J=6.8 Hz, 2H), 1.13-1.06 (m, 1H), 0.58-0.53 (m, 2H), 0.23-0.19 (m, 2H).

Intermediate 74

4-(cyclopropylmethyl)-2-fluoro-5-hydrazinylpyridine

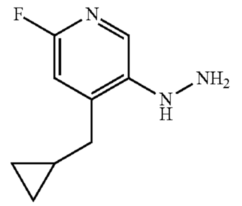 [SMILES: NNc1cnc(F)cc1CC1CC1]

To a solution of 4-(cyclopropylmethyl)-6-fluoropyridin-3-amine hydrogen chloride (see Intermediate 73, 4.50 g, 22.2 mmol) in hydrochloric acid (50 ml, 6 M in water, 300 mmol) was added a solution of sodium nitrite (2.30 g, 33.3 mmol) in water (5.0 ml) at −10° C. After addition, the reaction mixture was warmed to 0° C. and stirred for 0.5 hour. Then tin (II) chloride dehydrate (12.5 g, 55.5 mmol) was added to the reaction mixture at −10° C. and stirred at 0° C. for 1 hour. Potassium hydroxide (40%) was added into reaction to adjusted pH ~11. The reaction mixture was extracted with ethyl acetate. The organic layers were dried over sodium sulfate, filtered and concentrated to give 3.1 g of the title compound as a crude product, that was used without further purification.

Intermediate 75

2-bromo-N-methoxy-N-methylpyridine-4-carboxamide

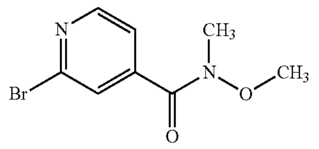

To a solution of 2-bromopyridine-4-carboxylic acid (10.0 g, 49.5 mmol) in dichloromethane (100 ml) was added 1,1-carbonyldiimidazole (12.0 g, 74.3 mmol) at 25° C. After stirring at room temperature for 2 hours, N,O-dimethylhydroxylamine hydrochloride (5.31 g, 54.5 mmol) was added into the above mixture at 25° C. After stirring at room temperature for 16 hours, the reaction mixture was quenched with sodium hydroxide (0.1 M), extracted with dichloromethane. The combined organic phase was washed with brine, dried over magnesium sulfate, filtered and concentrated to give a residue. The residue was purified by flash column chromatography (petroleum ether:ethyl acetate=10:1 to 4:1) to give 2-bromo-N-methoxy-N-methylisonicotinamide (10.3 g, 85% yield) as colorless oil.

$^1$H NMR (400 MHz, DMSO-$d_6$): δ [ppm]=8.50 (dd, J=5.2, 0.8 Hz, 1H), 7.78 (d, J=0.8 Hz, 1H), 7.58 (dd, J=5.2, 1.2 Hz, 1H), 3.56 (s, 3H), 3.27 (s, 3H).

Intermediate 76

1-(2-bromopyridin-4-yl)-2-(pyridin-2-yl)ethanol

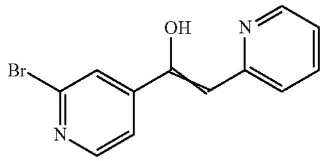 [SMILES: OC(=Cc1ccccn1)c1ccnc(Br)c1]

To a solution of 2-methylpyridine (3.26 g, 35.0 mmol) in tetrahydrofuran (100 ml) was added sodium bis(trimethylsilyl)amide (42 ml, 1M in tetrahydrofuran, 42 mmol) at −78° C. After stirring at −78° C. for 1 hour, a solution of 2-bromo-N-methoxy-N-methylpyridine-4-carboxamide (see Intermediate 75, 10.3 g, 42.0 mmol) in tetrahydrofuran (50 ml) was added at −78° C. After stirring at 25° C. for 16 hours, the mixture was quenched with saturated ammonium chloride, extracted with ethyl acetate. The combined organic phase was dried over sodium sulfate, filtered, and concentrated to give a residue. The residue was purified by flash column chromatography (petroleum ether:ethyl acetate=1:0 to 2:1) to give 1-(2-bromopyridin-4-yl)-2-(pyridin-2-yl) ethanol (5.91 g, 51% yield) as a yellow solid.

$^1$H NMR (400 MHz, DMSO-$d_6$): δ [ppm]=15.52 (br.s, 1H), 8.46 (d, J=4.2 Hz, 2H), 7.97 (d, J=0.8 Hz, 1H), 7.89 (td, J=8.0, 1.2 Hz, 1H), 7.81 (dd, J=4.2, 1.2 Hz, 1H), 7.36 (d, J=8.0 Hz, 1H), 7.26-7.23 (m, 1H), 6.68 (s, 1H).

Intermediate 77

5-(2-(1-(2-bromopyridin-4-yl)-2-(pyridin-2-yl)ethylidene)hydrazinyl)-4-(cyclopropylmethyl)-2-fluoropyridine

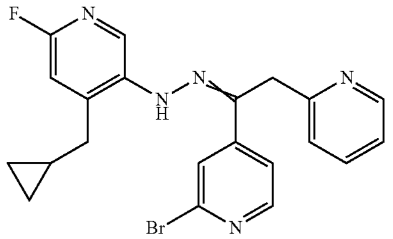 [SMILES: Fc1cc(CC2CC2)c(NN=C(Cc2ccccn2)c2ccnc(Br)c2)cn1]

A mixture of 4-(cyclopropylmethyl)-2-fluoro-5-hydrazinylpyridine (3.10 g, 17.1 mmol, Intermediate 74), 1-(2-bromopyridin-4-yl)-2-(pyridin-2-yl)ethanol (2.37 g, 8.55 mmol, Intermediate 76), acetic acid (cat. 0.098 ml) in ethanol (62 ml) was stirred at 78° C. for 24 hours.

The reaction mixture was concentrated. The residue was purified by flash column (petroleum ether:ethyl acetate=3:1) to give 5-(2-(1-(2-bromopyridin-4-yl)-2-(pyridin-2-yl)ethylidene)hydrazinyl)-4-(cyclopropylmethyl)-2-fluoropyridine (2.00 g, 27% yield) as yellow solid.

$^1$H-NMR (400 MHz, DMSO-$d_6$): δ [ppm]=10.93 (s, 1H), 8.50 (d, J=4.0 Hz, 1H), 8.36 (d, J=5.2 Hz, 1H), 8.30 (s, 1H), 8.07 (d, J=1.2 Hz, 1H), 7.95 (dd, J=5.2, 1.6 Hz, 1H), 7.86 (td, J=7.6, 2.0 Hz, 1H), 7.62 (d, J=8.0 Hz, 1H), 7.34 (dd, J=6.8, 4.8 Hz, 1H), 7.15 (d, J=1.6 Hz, 1H), 4.40 (s, 2H), 2.73 (d, J=6.8 Hz, 2H), 1.18-1.09 (m, 1H), 0.60-0.55 (m, 2H), 0.29-0.25 (m, 2H).

Intermediate 78

2-(2-bromopyridin-4-yl)-7-(cyclopropylmethyl)-5-fluoro-3-(pyridin-2-yl)-1H-pyrrolo[3,2-b]pyridine

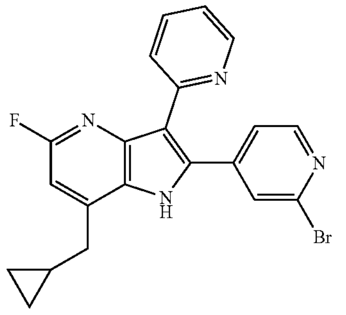 [SMILES: Fc1cc(CC2CC2)c2[nH]c(-c3ccnc(Br)c3)c(-c3ccccn3)c2n1]

A mixture of 5-(2-(1-(2-bromopyridin-4-yl)-2-(pyridin-2-yl)ethylidene)hydrazinyl)-4-(cyclopropylmethyl)-2-fluoropyridine (see Intermediate 77, 100 mg, 0.227 mmol), zinc dichloride (34.1 mg, 0.250 mmol) in tetramethylene sulfone (2.0 ml) was stirred at 180° C. for 4 hours under air (open system). The reaction mixture (combined with a batch starting from 100 mg Intermediate 127) was poured into water and extracted with ethyl acetate. The combined organic phase was washed with brine, dried over anhydrous sodium sulfate, filtered and concentrated to give a residue. The residue was purified by flash column chromatography (petroleum ether:ethyl acetate=3:1) to give yellow oil. The yellow oil was triturated with ethyl acetate to give 2-(2-bromopyridin-4-yl)-7-(cyclopropylmethyl)-5-fluoro-3-(pyridin-2-yl)-1H-pyrrolo[3,2-b]pyridine (710 mg) as a white solid.

$^1$H NMR (400 MHz, DMSO-$d_6$): δ [ppm]=12.16 (s, 1H), 8.46 (d, J=4.0 Hz, 1H), 8.38 (d, J=5.2 Hz, 1H), 8.03 (d, J=8.0 Hz, 1H), 7.91 (td, J=7.6, 2.0 Hz, 1H), 7.84 (s, 1H), 7.48 (dd, J=5.2, 1.6 Hz, 1H), 7.30 (dd, J=6.4, 4.8 Hz, 1H), 7.01 (s, 1H), 2.94 (d, J=7.2 Hz, 2H), 1.25-0.19 (m, 1H), 0.58-0.53 (m, 2H), 0.35-0.29 (m, 2H).

Intermediate 79

2-(4-fluorophenyl)acetamide

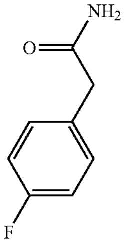

To a solution of (4-fluorophenyl)acetonitrile (25.0 g, 185 mmol) in dimethyl sulfoxide (500 ml) was added potassium carbonate (25.6 g, 185 mmol) at 25° C. Then hydrogen peroxide (38 ml, 30% purity, 370 mmol) was added 0° C. After stirring at 25° C. for 16 hours, saturated sodium thiosulfate was added at 25° C. After stirring at 25° C. for 0.5 hour, the reaction mixture was extracted with ethyl acetate. The combined organic phase was washed with brine, dried over anhydrous sodium sulfate, filtered and concentrated to give 26.0 g (92% yield) of the title compound as a crude product and a white solid, that was used without further purification.

Intermediate 30

4-[7-(4-methylpiperazin-1-yl)-3-(pyridin-2-yl)-1H-pyrrolo[3,2-b]pyridin-2-yl]pyridin-2-amine

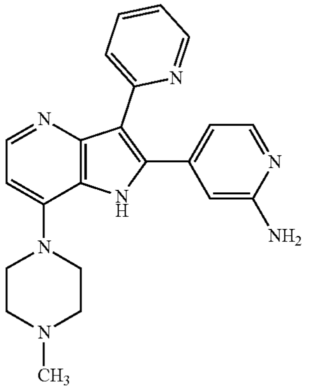 [SMILES: CN1CCN(c2ccnc3c(-c4ccccn4)c(-c4ccnc(N)c4)[nH]c23)CC1]

A mixture of N-{4-[7-chloro-3-(pyridin-2-yl)-1H-pyrrolo[3,2-b]pyridin-2-yl]pyridin-2-yl}acetamide (see Intermediate 40, 150 mg, 0.412 mmol) and 1-methylpiperazine (165 mg, 1.65 mmol) in 1,2-ethanediol (2.0 ml) was stirred at 100° C. 72 hours. The mixture was concentrated to give a residue. The residue was purified by flash column chromatography (10% methanol in ethyl acetate:petroleum ether=1:9~1:0, then ethyl acetate:methanol=5:1) to give 4-[7-(4-methylpiperazin-1-yl)-3-(pyridin-2-yl)-1H-pyrrolo[3,2-b]pyridin-2-yl]pyridin-2-amine (100 mg, 63% yield) as a yellow solid.

Intermediate 81

2-(2-aminopyridin-4-yl)-N-methyl-N-(1-methylpiperidin-4-yl)-3-(pyridin-2-yl)-1H-pyrrolo[3,2-b]pyridin-7-amine

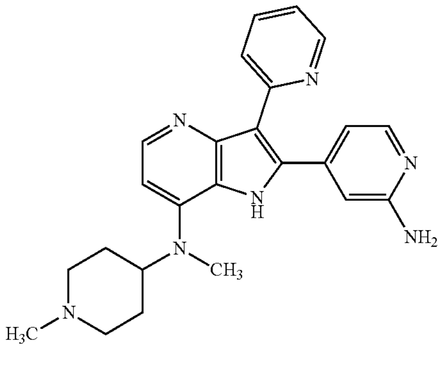 [SMILES: CN1CCC(N(C)c2ccnc3c(-c4ccccn4)c(-c4ccnc(N)c4)[nH]c23)CC1]

A mixture of N-{4-[7-chloro-3-(pyridin-2-yl)-1H-pyrrolo[3,2-b]pyridin-2-yl]pyridin-2-yl}acetamide (see Intermediate 40, 150 mg, 0.41 mmol) and N-1-dimethylpiperidin-4-amine (264 mg, 2.06 mmol) was stirred at 200° C. for 2 hours in microwave. The reaction mixture was concentrated to give a residue. The residue was purified by reversed phase (Instrument: Agela HP1000; Column: Welch Ultimate XB_C18 150*400 mm 20/40 μm; eluent A: water, eluent B: acetonitrile; gradient: 0-35 min 30-84% B; flow 65 ml/min; temperature: room temperature; Detector: UV 220/254 nm) to give a crude product. The crude product was dissolved with methanol and added into a saturated sodium hydroxide. After stirring at 50° C. for 16 hours, the mixture was concentrated to give a residue. The residue was dissolved with ethyl acetate and washed with water. The organic phase was dried over anhydrous sodium sulfate and filtered. The filtrate was concentrated to give 70 mg (77% purity, 32% yield) of the title compound as a crude product and a yellow solid, that was used without further purification.

LC-MS (Method A): Rt=0.692 min; MS (ESIpos): m/z=414.4 $[M+H]^+$.

Intermediate 82

4-{[2-(2-acetamidopyridin-4-yl)-3-(pyridin-2-yl)-1H-pyrrolo[3,2-b]pyridin-7-yl]amino}butanoic acid

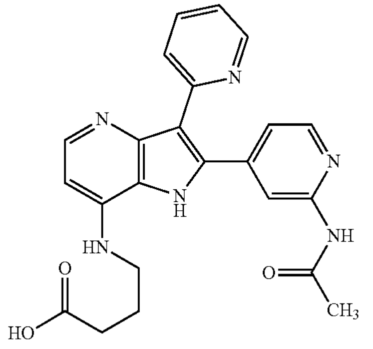 [SMILES: CC(=O)Nc1cc(-c2[nH]c3c(NCCCC(=O)O)ccnc3c2-c2ccccn2)ccn1]

To a solution of N-{4-[7-chloro-3-(pyridin-2-yl)-1H-pyrrolo[3,2-b]pyridin-2-yl]pyridin-2-yl}acetamide (see Intermediate 40, 300 mg, 0.82 mmol) in 1-Methyl-2-pyrrolidinone (1.0 ml) was added a solution of methyl 4-aminobutanoate hydrogen chloride (1/1) (190 mg, 1.24 mmol) and N,N-diisopropylethylamine (1.4 ml, 8.2 mmol) in 1-Methyl-2-pyrrolidinone (1.0 ml) at 160° C. After stirring at 160° C. for 6 hours, the mixture was directly purified by reversed phase (Instrument: Agela HP1000; Column: Welch Ultimate XB_C18*150*400 mm 20/40 μm; eluent A: water, eluent B: acetonitrile; gradient: 0-35 min 30-84% B; flow 65 ml/min; temperature: room temperature; Detector: UV 220/254 nm) to give to give 4-{[2-(2-acetamidopyridin-4-yl)-3-(pyridin-2-yl)-1H-pyrrolo[3,2-b]pyridin-7-yl]amino}butanoic acid (100 mg, 28% yield) as a yellow solid.

LC-MS (Method C): Rt=0.710 min; MS (ESIpos): m/z=413.4 $[M+H]^+$.

Intermediate 83

N-{4-[7-(2-oxopyrrolidin-1-yl)-3-(pyridin-2-yl)-1H-pyrrolo[3,2-b]pyridin-2-yl]pyridin-2-yl}acetamide

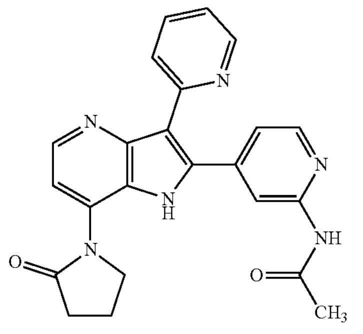 [SMILES: CC(=O)Nc1cc(-c2[nH]c3c(N4CCCC4=O)ccnc3c2-c2ccccn2)ccn1]

To a solution of 4-{[2-(2-acetamidopyridin-4-yl)-3-(pyridin-2-yl)-1H-pyrrolo[3,2-b]pyridin-7-yl]amino}butanoic acid (see Intermediate 82, 85 mg, 0.20 mmol) in N,N-dimethylformamide (2 ml) were added 2-(7-azabenzotriazol-1-yl)-N,N,N',N'-tetramethyluronium hexafluorophosphate (HATU) (113 mg, 0.30 mmol) and N,N-diisopropylethylamine (0.14 ml, 0.79 mmol) at 25° C. After stirring at room temperature for 16 hours, the mixture was concentrated to give a residue. The residue was purified by flash silica gel chromatography (20 g, 10% methanol in ethyl acetate:petroleum ether=0:1 to 4:1, and then 10% methanol and 5% ammonium hydroxide in ethyl acetate) to give 63 mg (86% purity) of the title compound as a white solid, that was used without further purification.

LC-MS (Method C): $R_t$=0.714 min; MS (ESIpos): m/z=413.2 $[M+H]^+$.

Intermediate 44

1-[2-(2-aminopyridin-4-yl)-3-(pyridin-2-yl)-1H-pyrrolo[3,2-b]pyridin-7-yl]pyrrolidin-2-one

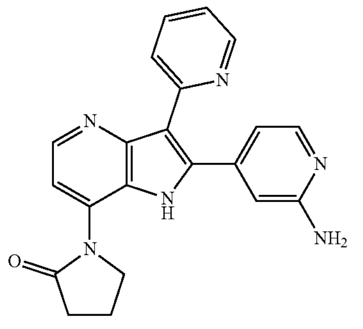 [SMILES: Nc1cc(-c2[nH]c3c(N4CCCC4=O)ccnc3c2-c2ccccn2)ccn1]

A solution of N-{4-[7-(2-oxopyrrolidin-1-yl)-3-(pyridin-2-yl)-1H-pyrrolo[3,2-b]pyridin-2-yl]pyridin-2-yl}acetamide (see Intermediate 83, 48 mg, 0.12 mmol) in hydrochloric acid (5 ml, 4.0 M in methanol) was stirred at room temperature for 20 hours. The mixture was adjusted pH ~9 by trimethylamine and concentrated to give a residue. The residue was dissolved with ethyl acetate:methanol=10:1 and stirred at room temperature for 10 minutes. The mixture was filtered and the filtrate was concentrated to give 100 mg of the title compound as a crude product and a white solid, that was used without further purification.

LC-MS (Method C): Rt=0.695 min; MS (ESIpos): m/z=371.1 $[M+H]^+$.

Intermediate 55

(2RS)-methyl 2-(4-fluorophenyl)-3-methoxypropanoate (Racemate)

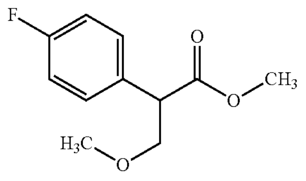

Methyl 2-(4-fluorophenyl)acetate (2.0 g, 11.9 mmol, CAS-RN: [34837-84-8]) was dissolved in THE (20 mL) and cooled to −78° C. A solution of lithium diisopropylamide (11.9 mL, 2.0 M, 23.8 mmol, CAS-RN: [4111-54-0]). A solution of bromo(methoxy)methane (2.23 g, 17.8 mmol, CAS-RN: 13057-17-5) in THE (10 mL) was added dropwise. The reaction mixture was allowed to slowly warm from −78° C. to 25° C. over 12 h. The reaction mixture was quenched by the addition of 80 mL of a saturated aqueous solution of ammonium chloride and extracted with ethyl acetate three times. The combined organic layers were washed with brine three times, dried over sodium sulfate, filtered, and concentrated in vacuo. The residue was purified by flash column chromatography (Silica gel, petroleum ether/ethyl acetate=1%-18%) to provide 1.65 g of the target compound (95% purity, 65% yield).

Intermediate 66

(2RS)—2-(4-fluorophenyl)-3-methoxypropanoic acid (Racemate)

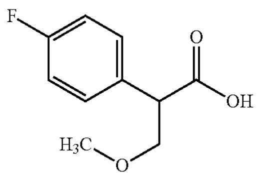

Methyl 2-(4-fluorophenyl)-3-methoxy-propanoate (see Intermediate 85, 400 mg, 1.88 mmol) was dissolved in MeOH (5 mL). Lithium hydroxide-monohydrate (158 mg, 3.77 mmol, CAS-RN: 1310-66-3) was added. The reaction mixture was stirred at 25° C. for 1 h. The reaction mixture was concentrated under reduced pressure, and the resulting crude residue was diluted with water. The pH of the resulting mixture was adjusted to 4 with a aqueous HCl solution (2.0 M), and then extracted with ethyl acetate three times. The combined organic layers were washed with brine three times, dried over sodium sulfate, filtered, and concentrated under reduced pressure to provide 350 mg of the title compound as a crude product, that was used without further purification.

$^1$H NMR (400 MHz, DMSO-$d_6$) δ [ppm]7.41-7.34 (m, 2H), 7.21-7.13 (m, 2H), 3.90-3.77 (m, 2H), 3.52 (dd, J=4.8, 8.4 Hz, 2H), 3.25 (s, 4H).

Intermediate 77

(2RS)—2-(4-fluorophenyl)-4-methoxybutanoic acid (Racemate)

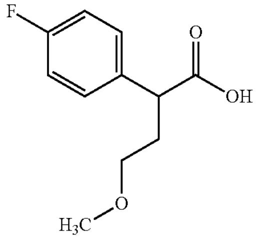

1-Bromo-2-methoxy-ethane (3.31 g, 23.8 mmol, CAS-RN: [6482-24-2]) was dissolved in THF (20 mL) at 0° C. A dispersion of sodium hydride in mineral oil (951 mg, 23.8 mmol, 60% purity, CAS-RN: [7646-69-7]) was added by portions. The reaction mixture was stirred at 0° C. for 1 h. Then methyl 2-(4-fluorophenyl)acetate (2 g, 11.9 mmol, CAS-RN: [34837-84-8]) was added, the reaction mixture was allowed to warm from 0° C. to 25° C., and stirred at 25° C. for 12 h. The reaction mixture was quenched by the addition of water and extracted with ethyl acetate three times. The combined organic layers were washed with brine three times, dried over sodium sulfate, and concentrated under reduced pressure. The residue was purified by flash chromatography ($SiO_2$, Petroleum ether/Ethyl acetate=0%-18%) to provide: 900 mg of the title compound (95% purity, 36% yield).

$^1$H NMR (400 MHz, DMSO-d6) δ[ppm]12.38 (br s, 1H), 7.38-7.26 (m, 2H), 7.20-7.09 (m, 2H), 3.64 (t, J=7.6 Hz, 1H), 3.57 (s, 1H), 3.20 (s, 1H), 3.18 (s, 3H), 2.25-2.13 (m, 1H), 1.90-1.76 (m, 1H).

Intermediate 88 tert-butyl (4-bromopyridin-2-yl)carbamate

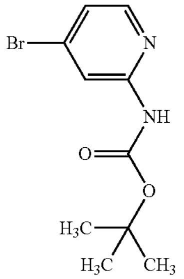

4-Bromopyridine-2-amine (5.00 g, 28.9 mmol, 1 eq, CAS-RN: [84249-14-9]) was dissolved in 150 mL of DCM. Triethylamine (6.03 mL, 43.3 mmol, 1.5 eq, CAS-RN: [121-44-8]), Di-tert-butyl decarbonate (6.31 g, 28.9 mmol, 1 eq, CAS-RN: [24424-99-5]), and 4-dimethylaminopyridine (176.5 mg, 1.44 mmol, 0.05 eq, CAS-RN: [1122-58-3]) were added sequentially. The reaction mixture was allowed to stir at 25° C. for 12 h. The reaction mixture was quenched by the addition of 50 mL of a saturated aqueous solution of $NH_4Cl$, and then extracted with DCM (50 mL×3). The combined organic layers were washed with brine (50 mL×3), dried over $Na_2SO_4$, filtered, and concentrated in vacuo. The residue was purified by flash column chromatography (ISCO®; 60 g SepaFlash® Silica Flash Column, Eluent of 0~5% Ethyl acetate/Petroleum ether, gradient 5® 50 mL/min) to provide the target compound in >95% purity: 6.5 g, 21.3 mmol, 74% yield.

$^1$H NMR (400 MHz, DMSO-d6) δ[ppm]6=10.08 (s, 1H), 8.14 (d, J=5.6 Hz, 1H), 8.04 (d, J=1.6 Hz, 1H), 7.27 (dd, J=1.6, 5.4 Hz, 1H), 1.47 (s, 9H)

Intermediate 99 tert-butyl {4-[(trimethylsilyl)ethynyl]pyridin-2-yl}carbamate

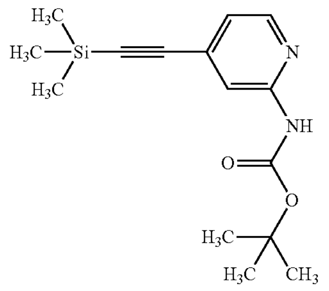 [SMILES: CC(C)(C)OC(=O)Nc1cc(C#C[Si](C)(C)C)ccn1]

Tert-butyl N-(4-bromo-2-pyridyl)carbamate (1.00 g, 3.66 mmol, 1 eq), ethynyl(trimethyl)silane (576.4 mg, 5.49 mmol, 1.5 eq, CAS-RN: [1066-54-2]), copper(I) iodide (27.9 mg, 0.146 mmol, 0.04 eq, CAS-RN: [7681-65-4]), and bis(triphenylphosphine)palladium(II) dichloride (51.4 mg, 0.073 mmol, 0.02 eq, CAS-RN: [13965-03-2]) were dissolved in 10 mL of triethylamine. The mixture was placed under a nitrogen atmosphere, and stirred at 75° C. for 2 h. The reaction was then filtered through celite, and the filtrate concentrated in vacuo. The crude material was used without further purification. Recovered 1.00 g of crude material as a red oil.

Intermediate 90 tert-butyl (4-ethynylpyridin-2-yl)carbamate

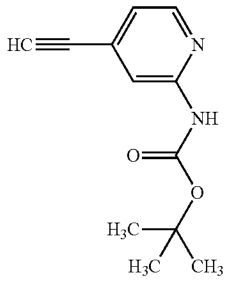 [SMILES: C#Cc1ccnc(NC(=O)OC(C)(C)C)c1]

Crude tert-butyl N-[4-(2-trimethylsilylethynyl)-2-pyridyl]carbamate (1.00 g, 3.44 mmol, 1 eq) was dissolved in 10 mL of THF. 8.61 mL of a 1 M solution of TBAF in THE (8.61 mmol, 2.5 eq, CAS-RN: [429-41-4]) was added via syringe, and the mixture was stirred at 25° C. for 2 h. The reaction mixture was quenched by the addition of 10 mL of a saturated solution of NH4Cl, and then extracted with EtOAc (10 mL×3). The combined organic layers were washed with brine (10 mL×5), dried over Na2SO4, filtered, and concentrated in vacuo. The crude residue was purified by normal phase flash column chromatography on silica gel (SiO2, petroleum ether/ethyl acetate=10/1 to 5/1) to provide the target compound in 94% purity: 760 mg, 3.27 mmol, 95% yield.

LC-MS (Method 3): Rt=0.533 min; MS (ESIpos): m/z=163.1 [M+H]$^+$

Intermediate 91 tert-butyl {4-[(3-aminopyridin-2-yl)ethynyl]pyridin-2-yl}carbamate

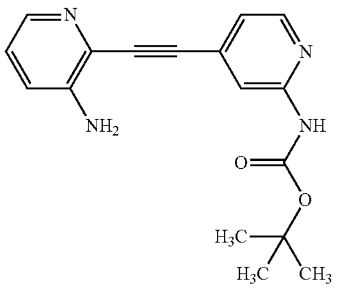 [SMILES: CC(C)(C)OC(=O)Nc1cc(C#Cc2ncccc2N)ccn1]

Tert-butyl N-(4-ethynyl-2-pyridyl)carbamate (0.70 g, 3.21 mmol, 1 eq) and 2-bromopyridin-3-amine (0.665 g, 3.85 mmol, 1.2 eq, CAS-RN: [39856-58-1]) were dissolved in 14 mL of DMF. Copper(I) iodide (61.1 mg, 0.320 mmol, 0.1 eq, CAS-RN: [7681-65-4]), bis(triphenylphosphine)palladium(II) dichloride (225 mg, 0.320 mmol, 0.1 eq, CAS-RN: [13965-03-2]) and triethylamine (4.46 mL, 32.07 mmol, 10 eq, CAS-RN: [121-44-8]) were added sequentially. The mixture was stirred at 70° C. for 12 h. The reaction mixture was quenched by the addition of 15 mL of a saturated solution of NH4Cl, and then extracted with EtOAc (15 mL×3). The combined organic layers were washed with brine (15 mL×3), dried over Na2SO4, filtered, and concentrated in vacuo. The crude residue was purified by normal phase flash column chromatography on silica gel (SiO2, petroleum ether/ethyl acetate=1/1) to provide the target compound: 800 mg, 2.58 mmol, 80.3% yield.

LC-MS (Method 3): Rt=0.374 min; MS (ESIpos): m/z=255.1 [M+H]$^+$

Intermediate 92 tert-butyl (4-{[3-(2,2,2-trifluoroacetamido)pyridin-2-yl]ethynyl}pyridin-2-yl)carbamate

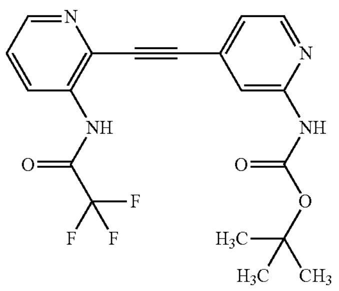 [SMILES: CC(C)(C)OC(=O)Nc1cc(C#Cc2ncccc2NC(=O)C(F)(F)F)ccn1]

tert-butyl N-[4-[2-(3-amino-2-pyridyl)ethynyl]-2-pyridyl]carbamate (0.80 g, 2.58 mmol, 1 eq) was dissolved in 25 mL of DCM and cooled to 0° C. Triethylamine (0.716 mL, 5.16 mmol, 2 eq, CAS-RN: [121-44-8]) and trifluoroacetic anhydride (0.537 mL, 3.87 mmol, 1.5 eq, CAS-RN: [407-25-0]) were added. The mixture was stirred at 0° C. for 6 h. The reaction mixture was quenched by the addition of 30 mL of a saturated solution of $NaHCO_3$, and then extracted with EtOAc (30 mL×3). The combined organic layers were washed with brine (30 mL×3), dried over Na2SO4, filtered, and concentrated in vacuo. The crude residue was purified by normal phase flash column chromatography on silica gel (ISCO®; 10 g SepaFlash® Silica Flash Column, Eluent of 0-50% ethyl acetate/petroleum ether, gradient@50 mL/min) to provide the target compound: 760 mg, 1.29 mmol, 50.1% yield.

$^1$H NMR (400 MHz, 6d-DMSO) δ=11.58 (s, 1H), 10.01 (s, 1H), 8.67-8.61 (m, 1H), 8.34 (d, J=5.0 Hz, 1H), 7.95 (s, 1H), 7.64-7.55 (m, 2H), 7.10 (dd, J=1.2, 5.2 Hz, 1H), 1.49 (s, 9H).

LC-MS (Method 3): $R_t$=0.936 min; MS (ESIpos): m/z=456.1 $[M+H]^+$

Intermediate 93

4-[3-(pyrimidin-2-yl)-1H-pyrrolo[3,2-b]pyridin-2-yl]pyridin-2-amine

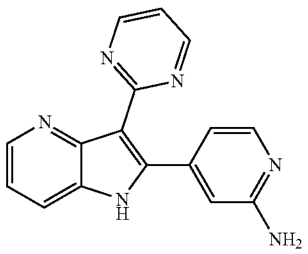 [SMILES: Nc1cc(-c2[nH]c3cccnc3c2-c2ncccn2)ccn1]

To a 30 mL sealed tube was added tert-butyl N-[4-[2-[3-[(2,2,2-trifluoroacetyl)amino]-2-pyridyl]ethynyl]-2-pyridyl]carbamate (0.850 g, 2.09 mmol, 1 eq) and 2-iodopyridine (0.268 mL, 2.09 mmol, 1 eq, CAS-RN: [5029-67-4]). The mixture was dissolved in 18 mL of MeCN. Then Xphos-Pd-G3 (177 mg, 0.209 mmol, 0.1 eq, CAS-RN: [1445085-55-1]) and Cs2CO3 (2.04 g, 6.28 mmol, 3 eq, CAS-RN: [534-17-8]) were added in one portion, and the reaction was placed under a nitrogen atmosphere. The mixture was stirred at 100° C. for 12 h. The reaction mixture was concentrated in vacuo. The crude residue was purified by reverse phase preparative HPLC (column: Phenomenex Gemini 150*25 mm*10 μm; mobile phase: [water (0.05% NH3H2O)-ACN]; B %: 15%-45%, 10 min) to provide the target compound: 170 mg, 0.531 mmol, 25.4% yield.

$^1$H NMR (400 MHz, DMSO-d6) δ[ppm]=8.82 (d, J=4.8 Hz, 2H), 8.35-8.30 (m, 1H), 7.86 (d, J=5.2 Hz, 1H), 7.81 (dd, J=1.2, 8.0 Hz, 1H), 7.39-7.33 (m, 1H), 7.16 (dd, J=4.6, 8.0 Hz, 1H), 6.56 (s, 1H), 6.48 (dd, J=1.2, 5.2 Hz, 1H), 6.40-6.40 (m, 1H), 6.32 (s, 1H), 5.94 (s, 2H), 1.99 (s, 2H), 1.18 (t, J=7.2 Hz, 2H).

Intermediate 94

3-chloro-5-hydrazinylpyridine

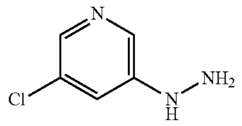

5-Chloropyridin-3-amine (340 mg, 2.64 mmol) was dissolved in 6N HCl (6.6 ml, 40 mmol) and cooled with an ice bath. A solution of sodium nitrate (182 mg, 2.64 mmol) in water (7.1 ml) was added dropwise. The reaction was stirred at this temperature for 30 minutes under N2 atmosphere, then a solution of $SnCl_2$ dihydrate (1.49 g, 6.61 mmol) dissolved in 6N HCl (6.6 ml, 40 mmol) was added slowly and the reaction was stirred for 1.5 hours at 0° C. The reaction was quenched by dropwise addition of 40% aqueous KOH solution (8 ml) until the pH was adjusted to 12. The reaction was extracted three times with ethyl acetate. The combined organic layers were washed once with water and brine, filtered through a silicone coated filter and concentrated under reduced pressure. A precipitate formed in the aqueous layer was collected by filtration and washed with water and ethyl acetate. The collected precipitate was combined with the organic extract to afford the title compound as a crude product (327 mg, 86% yield) which was used in the subsequent reaction without further purification.

LC-MS (Method 2): $R_t$=0.59 min; MS (ESIpos): m/z=144 $[M+H]^+$

Intermediate 95

2-bromo-4-[1-[2-(5-chloropyridin-3-yl)hydrazinylidene]-2-(pyridin-2-yl)ethyl]pyridine

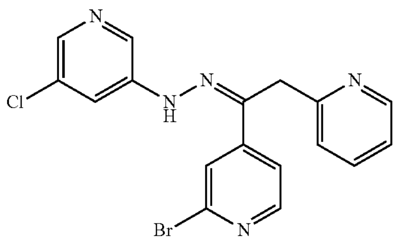 [SMILES: Clc1cncc(N/N=C(/Cc2ccccn2)c2ccnc(Br)c2)c1]

A mixture of (5-chloro-3-pyridyl)hydrazine (Intermediate 94, 320 mg, 2.23 mmol), 1-(2-bromopyridin-4-yl)-2-(pyridin-2-yl)ethan-1-one (618 mg, 2.23 mmol, CAS-RN: [656257-84-0]), ethyl acetate (16.4 ml) and propanephosphonic anhydride, 50% in EtOAc (1.46 ml, 2.45 mmol) was stirred at 120° C. for 15 minutes in the microwave reactor under nitrogen atmosphere. The reaction mixture was cooled to room temperature and diluted with ethyl acetate and saturated $NaHCO_3$ solution and extracted three times with ethyl acetate. The combined organic layer was filtered through a silicone coated filter and concentrated under reduced pressure to afford the title compound (923 mg, quantitative yield) which was used without further purification.

LC-MS (Method 2): Rt=1.28 min; MS (ESIpos): m/z=402 $[M+H]^+$ $^1$H NMR (400 MHz, DMSO-$d_6$) δ [ppm]4.42 (s, 2H), 7.22-7.28 (m, 1H), 7.42 (d, 1H), 7.76-7.78 (m, 1H), 7.85 (dd, 1H), 7.89-7.92 (m, 1H), 8.10 (d, 1H), 8.31 (d, 1H), 8.32 (d, 1H), 8.44-8.48 (m, 1H), 8.53 (d, 1H), 10.76 (s, 1H).

Intermediate 96

2-(2-bromopyridin-4-yl)-6-chloro-3-(pyridin-2-yl)-1H-pyrrolo[3,2-b]pyridine

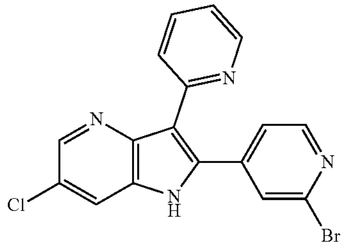 [SMILES: Clc1cnc2c(-c3ccccn3)c(-c3ccnc(Br)c3)[nH]c2c1]

A mixture of 2-bromo-4-[1-[2-(5-chloropyridin-3-yl)hydrazinylidene]-2-(pyridin-2-yl)ethyl]pyridine (Intermediate 95, 720 mg, 1.79 mmol) and zinc(II)chloride (268 mg, 1.97 mmol) in sulfolane (13 ml) was stirred at 170° C. for 2 hours under Ar atmosphere. The reaction mixture was cooled to room temperature and diluted with ethyl acetate. The mixture was washed with 50% saturated NaCl solution to remove the sulfolane and the organic layer was filtered through a silicone coated filter, then concentrated under reduced pressure. The residue was partially purified by flash chromatography over silica gel using a mixture of ethyl acetate and ethanol to afford the title compound 281 mg (41% yield) as a mixture with the side product 2-(2-chloropyridin-4-yl)-6-chloro-3-(pyridin-2-yl)-1H-pyrrolo[3,2-b]pyridine. This mixture was used in the following reaction without further purification.

LC-MS (Method 2): Rt=1.11 min; MS (ESIpos): m/z=385 $[M+H]^+$ $^1$H NMR (400 MHz, DMSO-$d_6$) δ [ppm]7.33 (ddd, 1H), 7.52 (dd, 1H), 7.82-7.83 (m, 1H), 7.91 (dt, 1H), 8.02 (d, 1H), 8.13 (d, 1H), 8.41 (d, 1H), 8.48-8.51 (m, 2H), 12.46 (s, 1H).

EXPERIMENTAL SECTION—EXAMPLES

Example 1

2-(4-fluorophenyl)-N-{4-[5-fluoro-3-(pyridin-2-yl)-1H-pyrrolo[3,2-b]pyridin-2-yl]pyridin-2-yl}propanamide (Racemate)

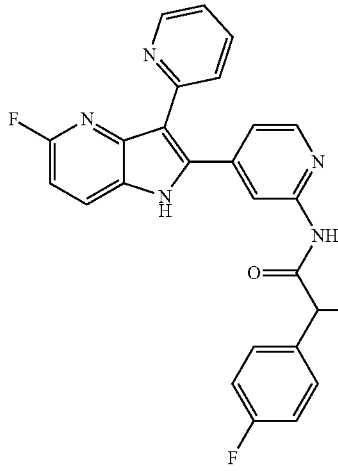

4-[5-Fluoro-3-(pyridin-2-yl)-1H-pyrrolo[3,2-b]pyridin-2-yl]pyridin-2-amine (see Intermediate 4, 155 mg), 2-(4-fluorophenyl)propanoic acid (Racemate) (128 mg, 762 μmol), N,N-diisopropylethylamine (530 μL, 3.0 mmol), PyBOP (793 mg, 1.52 mmol) were dissolved in 2.9 mL DMA stirred at rt under Argon atmosphere over night. The reaction mixture was diluted with dichloromethane, water and aqueous saturated sodium hydrogencarbonate. It was stirred for 10 minutes and the organic layer was filtered through a silicone coated filter and concentrated under reduced pressure. The crude product was purified by HPLC chromatography under basic conditions in 2 portions to provide the target compound in 98% purity: 92 mg.

LC-MS (Method 2): Rt=1.20 min; MS (ESIpos): m/z=456 $[M+H]^+$ $^1$H-NMR (400 MHz, DMSO-d6) δ[ppm]=1.38 (d, 3H) 4.04 (q, 1H) 7.00 (dd, 1H) 7.08 (dd, 1H) 7.14-7.23 (m, 2H) 7.27 (ddd, 1H) 7.38-7.48 (m, 2H) 7.83-7.90 (m, 1H) 7.92-7.97 (m, 1H) 8.03 (dd, 1H) 8.26 (dd, 1H) 8.34 (d, 1H) 8.38-8.49 (m, 1H) 10.78 (s, 1H) 12.31 (s, 1H). -contains ethanol.

Example 2

(−)-2-(4-fluorophenyl)-N-{4-[5-fluoro-3-(pyridin-2-yl)-1H-pyrrolo[3,2-b]pyridin-2-yl]pyridin-2-yl}propanamide (Enantiomer 1)

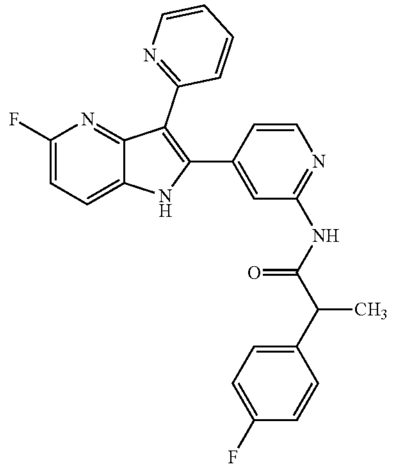 [SMILES: CC(C(=O)Nc1cc(-c2[nH]c3ccc(F)nc3c2-c2ccccn2)ccn1)c1ccc(F)cc1]

The racemic compound (see Example 1, 92 mg) was separated into enantiomers by preparative chiral HPLC to give enantiomer 1 (38 mg, 99.1% ee, see Example 2) and enantiomer 2 (33 mg, 98.4% ee, see Example 3).

Preparative chiral HPLC method: Instrument: Sepiatec: Prep SFC100; Column: Chiralpak IG 5μ 250×30 mm; eluent A: carbon dioxide; eluent B: methanol+0.2 vol % aqueous ammonia (32%); isocratic: 30% B; flow: 100 mL/min; temperature: 40° C.; BPR: 150 bar; UV: 230 nm; Analytical chiral HPLC method: Instrument: Agilent: 1260, Aurora SFC-Modul; Column: Chiralpak IG 5μ 100×4.6 mm; eluent A: carbon dioxide; eluent B: methanol+0.2 vol % aqueous ammonia (32%); isocratic: 30% B; flow: 4 mL/min; temperature: 37.5° C.; BPR: 100 bar; UV: 254 nm;

Analytical Chiral HPLC (method see Example 2): $R_t$=3.88 min.

$[\alpha]_D$=−149.3° (from solution in DMSO, c=6.4 mg/mL)

1H-NMR (400 MHz, DMSO-$d_6$) δ [ppm]=1.38 (d, 3H), 4.04 (q, 1H), 7.00 (dd, 1H), 7.08 (dd, 1H), 7.12-7.23 (m, 2H), 7.27 (ddd, 1H), 7.38-7.48 (m, 2H), 7.84-7.92 (m, 1H), 7.92-7.98 (m, 1H), 8.03 (dd, 1H), 8.22-8.29 (m, 1H), 8.34 (d, 1H), 8.38-8.49 (m, 1H), 10.77 (s, 1H), 12.31 (s, 1H). impurities in the aliphatic range.

Example 3

(+)-2-(4-fluorophenyl)-N-{4-[5-fluoro-3-(pyridin-2-yl)-1H-pyrrolo[3,2-b]pyridin-2-yl]pyridin-2-yl}propanamide (Enantiomer 2)

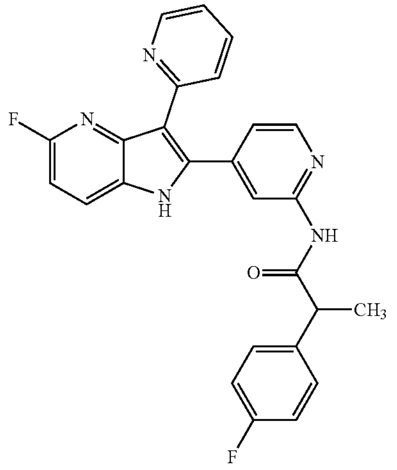 [SMILES: CC(C(=O)Nc1cc(-c2[nH]c3ccc(F)nc3c2-c2ccccn2)ccn1)c1ccc(F)cc1]

For the preparation of the racemic title compound see Example 1. Separation of enantiomers by preparative chiral HPLC (method see Example 2) gave the title compound (33 mg).

Analytical Chiral HPLC (method see Example 2): $R_t$=5.18 min.

$[\alpha]_D$=132.2° (from solution in DMSO, c=4.7 mg/mL)

1H-NMR (400 MHz, DMSO-$d_6$) δ [ppm]=1.38 (d, 3H), 4.04 (q, 1H), 7.00 (dd, 1H), 7.08 (dd, 1H), 7.14-7.22 (m, 2H), 7.27 (ddd, 1H), 7.39-7.47 (m, 2H), 7.83-7.90 (m, 1H), 7.91-7.97 (m, 1H), 8.03 (dd, 1H), 8.23-8.29 (m, 1H), 8.34 (s, 1H), 8.38-8.48 (m, 1H), 10.77 (s, 1H), 12.31 (s, 1H). impurities in the aliphatic range.

Example 4

2-(4-fluorophenyl)-N-{4-[5-fluoro-3-(pyridin-2-yl)-1H-pyrrolo[3,2-b]pyridin-2-yl]pyridin-2-yl)acetamide

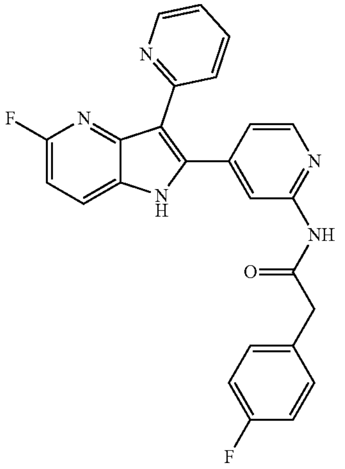 [SMILES: O=C(Cc1ccc(F)cc1)Nc1cc(-c2[nH]c3ccc(F)nc3c2-c2ccccn2)ccn1]

4-[5-Fluoro-3-(pyridin-2-yl)-1H-pyrrolo[3,2-b]pyridin-2-yl]pyridin-2-amine (see Intermediate 4, 155 mg), (4-fluorophenyl)acetic acid (117 mg, 762 µmol), N,N-diisopropylethylamine (530 µL, 3.0 mmol) and PyBOP (793 mg, 1.52 mmol) were dissolved in 2.9 mL DMA and stirred at rt under Argon atmosphere over night. The reaction mixture was diluted with dichloromethan, aqueous saturated sodium hydrogencarbonte solution and water. It was stirred for 10 minutes, the organic layer was filtered through a silicone coated filter and concentrated under reduced pressure. The crude product was purified by HPLC chromatography under basic conditions in 2 portions to provide the target compound in 95% purity: 90 mg.

LC-MS (Method 2): Rt=1.12 min; MS (ESIpos): m/z=442 $[M+H]^+$ $^1$H NMR (400 MHz, DMSO-$d_6$): δ [ppm]=3.71 (s, 2H), 6.99 (dd, 1H), 7.08-7.21 (m, 3H), 7.26 (ddd, 1H), 7.34-7.42 (m, 2H), 7.82-7.90 (m, 1H), 7.91-7.98 (m, 1H), 8.02 (dd, 1H), 8.25-8.34 (m, 2H), 8.40-8.46 (m, 1H), 10.83 (s, 1H), 12.31 (s, 1H).

Example 5

2-(4-fluorophenyl)-N-{4-[3-(pyridin-2-yl)-1H-pyrrolo[3,2-b]pyridin-2-yl]pyridin-2-yl}acetamide

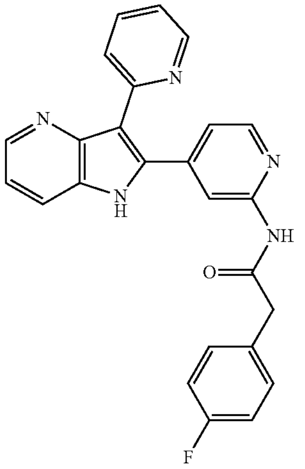 [SMILES: O=C(Cc1ccc(F)cc1)Nc1cc(-c2[nH]c3cccnc3c2-c2ccccn2)ccn1]

A mixture of 2,2,2-trifluoro-N-[2-({2-[2-(4-fluorophenyl)acetamido]pyridin-4-yl}ethynyl)pyridin-3-yl]acetamide (150 mg, 99% purity, 0.34 mmol, see Intermediate 9), 2-iodopyridine (103 mg, 0.50 mmol) and dicaesium carbonate (328 mg, 1.01 mmol) in 1-methyl-2-pyrrolidinone (3.0 ml) was purged with nitrogen. Then methanesulfonato(2-dicyclohexylphosphino-2',4',6'-tri-i-propyl-1,1'-biphenyl)(2'-amino-1,1'-biphenyl-2-yl)palladium(II) (19 mg, 0.017 mmol) was added to the mixture and the mixture was purged with nitrogen at room temperature. The mixture was then heated at 100° C. for 16 hours. The mixture was cooled to room temperature. The mixture was poured into water, the resulting mixture was extracted with ethyl. acetate, the organic layer was dried over anhydrous sodium sulfate, filtered, the filtrate was concentrated. The residue was combined with a second batch starting from 30 mg of Intermediate 9 was purified by silica gel chromatography (100-200 mesh, petroleum ether:ethyl acetate=10:1, then 3:1, then 1:1, then 0:1) to give a crude product. The crude product was then purified by preparative HPLC [Instrument: ACSWH-GX-L; Column: Unisil 3-100 C18 Ultra 150*50 mm*3 µm; eluent A: water (0.225% formic acid in water), eluent B: acetonitrile; gradient: 10 minutes 15-35% B; flow 25 ml/minute; temperature: room temperature; Detector: UV 220/254 nm] and then lyophilization to give 2-(4-fluorophenyl)-N-{4-[3-(pyridin-2-yl)-1H-pyrrolo[3,2-b]pyridin-2-yl]pyridin-2-yl}acetamide (72.2 mg, 94% purity, 48% yield, NMR contained 0.42 eq formic acid) as a yellow solid.

LC-MS (Method C): Rt=0.856 min; MS (ESIpos): m/z=424.3 $[M+H]^+$.

$^1$H NMR (400 MHz, DMSO-$d_6$): δ [ppm]=12.08 (s, 1H), 10.82 (s, 1H), 8.44 (dd, J=12.8, 3.6 Hz, 2H), 8.34 (s, 1H), 8.30 (d, J=5.2 Hz, 1H), 8.20 (s, 0.42H) 8.15-8.13 (m, 1H), 7.88-7.85 (m, 2H), 7.40-7.37 (m, 2H), 7.28-7.24 (m, 2H), 7.20-7.15 (m, 3H), 3.73 (s, 2H).

Example 6

2-(4-fluorophenyl)-N-{4-[3-(pyridin-2-yl)-1H-pyrrolo[3,2-b]pyridin-2-yl]pyridin-2-yl}propanamide (Racemate)

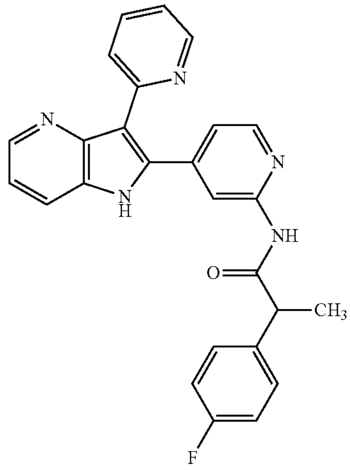 [SMILES: CC(C(=O)Nc1cc(-c2[nH]c3cccnc3c2-c2ccccn2)ccn1)c1ccc(F)cc1]

To a stirred solution of 4-[3-(pyridin-2-yl)-1H-pyrrolo[3,2-b]pyridin-2-yl]pyridin-2-amine (see Intermediate 13, 200 mg, 696 µmol) in DMA (1.2 mL) was added N,N-diisopropylethylamine (730 µl, 4.2 mmol; CAS-RN:[7087-68-5]), (rac)-2-(4-fluorophenyl)propanoic acid (293 mg, 1.74 mmol) and PyBOP (1.45 g, 2.78 mmol; CAS-RN:[128625-52-5]). The mixture was stirred at r.t. for 48 h. An aqueous solution of sodium bicarbonate was added, the mixture was stirred for 5 minutes and the mixture was extracted with ethyl acetate. The organic phase was washed with half-saturated sodium chloride solution (three times), dried (sodium sulfate), filtered and the solvent was removed in vacuum. Silicagel chromatography (Gradient: dichloromethane/ethanol 0-25%) followed by aminophase-silicagel chromatography (Gradient: dichloromethane/ethanol 0-25%) gave a solid that was triturated with a mixture of dichloromethane and hexane to give 149 mg of the title compound.

LC-MS (Method 2): $R_t$=1.06 min; MS (ESIpos): m/z=438 $[M+H]^+$ $^1$H-NMR (400 MHz, DMSO-$d_6$): δ [ppm]=12.08 (s, 1H), 10.76 (s, 1H), 8.45 (dd, 1H), 8.42-8.37 (m, 1H), 8.36 (d, 1H), 8.26 (d, 1H), 8.13 (dt, 1H), 7.91-7.83 (m, 2H), 7.46-7.39 (m, 2H), 7.29-7.23 (m, 2H), 7.21-7.13 (m, 2H), 7.11 (dd, 1H), 4.05 (q, 1H), 1.39 (d, 3H).

Example 7

(+)-2-(4-fluorophenyl)-N-{4-[3-(pyridin-2-yl)-1H-pyrrolo[3,2-b]pyridin-2-yl]pyridin-2-yl}propanamide (Enantiomer 1)

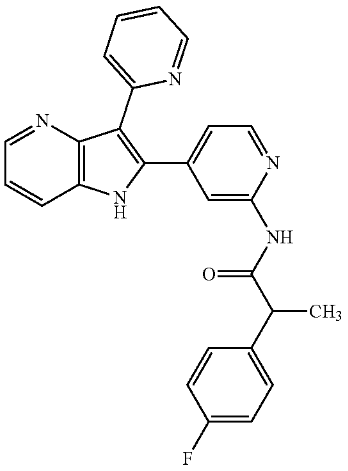 [SMILES: CC(C(=O)Nc1cc(-c2[nH]c3cccnc3c2-c2ccccn2)ccn1)c1ccc(F)cc1]

The racemic compound (see Example 6, 141 mg) was separated into enantiomers by preparative chiral HPLC. Crude enantiomer 1 was triturated with a mixture of dichloromethane and hexane to give enantiomer 1 (45 mg, >99% ee, see Example 7). Crude enantiomer 2 was triturated with a mixture of dichloromethane and hexane to give enantiomer 2 (46 mg, 97.8% ee, see Example 8).

Preparative Chiral HPLC Method:

Instrument: PrepCon Labomatic HPLC-3; Column: Chiralcel OD-H 5p, 250×20; eluent A: hexane+0.1 vol % diethylamine; eluent B: ethanol+0.1 vol % diethylamine; isocratic: 70% A+30% B; flow: 10 mL/min; temperature: 25° C.; UV: 254 nm Analytical chiral HPLC method: Instrument: Waters Alliance 2695; Column: Chiralcel OD-H 5p, 100×4.6; eluent A: hexane+0.1 vol % diethylamine; eluent B: ethanol; isocratic: 70% A+30% B; flow: 1.4 ml/min; temperature: 25° C.; UV: 254 nm Analytical Chiral HPLC (method see Example 7 Intermediate 7): $R_t$=4.13 min.

$[\alpha]_D$=+171.3° (from solution in DMSO, c=2.1 mg/mL)

LC-MS (Method 2): $R_t$=1.09 min; MS (ESIpos): m/z=438 $[M+H]^+$ $^1$H-NMR (400 MHz, DMSO-$d_6$): δ [ppm]=12.10 (s, 1H), 10.77 (s, 1H), 8.45 (dd, 1H), 8.42-8.38 (m, 1H), 8.36 (s, 1H), 8.26 (d, 1H), 8.12 (d, 1H), 7.90-7.82 (m, 2H), 7.47-7.39 (m, 2H), 7.30-7.23 (m, 2H), 7.21-7.14 (m, 2H), 7.11 (dd, 1H), 4.05 (q, 1H), 1.39 (d, 3H)

Example 8

(−)-2-(4-fluorophenyl)-N-{4-[3-(pyridin-2-yl)-1H-pyrrolo[3,2-b]pyridin-2-yl]pyridin-2-yl}propanamide (Enantiomer 2)

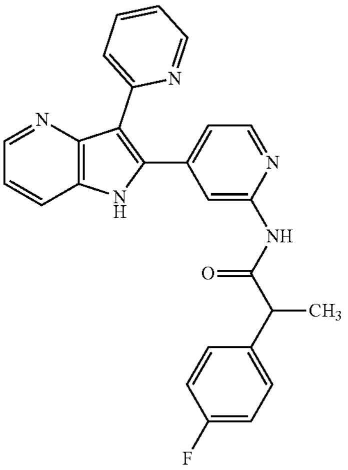 [SMILES: CC(C(=O)Nc1cc(-c2[nH]c3cccnc3c2-c2ccccn2)ccn1)c1ccc(F)cc1]

For the preparation of the racemic title compound see Example 6. Separation of enantiomers by preparative chiral HPLC (method see Example 7) followed by trituration with a mixture of dichloromethane and hexane gave the title compound (46 mg, 97.8% ee).

Analytical Chiral HPLC (method see Example 7): $R_t$=6.89 min.

$[\alpha]_D$=−173.7° (from solution in DMSO, c=2.1 mg/mL)

LC-MS (Method 2): $R_t$=1.09 min; MS (ESIpos): m/z=438 $[M+H]^+$ $^1$H-NMR (400 MHz, DMSO-$d_6$): δ [ppm]=12.09 (s, 1H), 10.76 (s, 1H), 8.45 (dd, 1H), 8.41-8.38 (m, 1H), 8.35 (s, 1H), 8.28-8.23 (m, 1H), 8.17-8.08 (m, 1H), 7.90-7.83 (m, 2H), 7.46-7.39 (m, 2H), 7.29-7.23 (m, 2H), 7.21-7.14 (m, 2H), 7.11 (dd, 1H), 4.05 (q, 1H), 1.39 (d, 3H).

Example 9

2-(4-fluorophenyl)-N-{4-[6-fluoro-3-(pyridin-2-yl)-1H-pyrrolo[3,2-b]pyridin-2-yl]pyridin-2-yl}acetamide

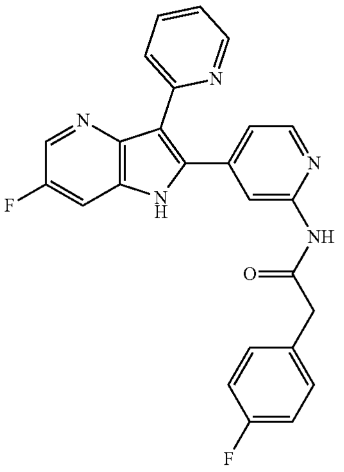 [SMILES: O=C(Cc1ccc(F)cc1)Nc1cc(-c2[nH]c3cc(F)cnc3c2-c2ccccn2)ccn1]

To a stirred solution of 4-[6-fluoro-3-(pyridin-2-yl)-1H-pyrrolo[3,2-b]pyridin-2-yl]pyridin-2-amine (see Intermediate 17, 60.0 mg, 197 μmol) in DMA (1.4 mL) was added N,N-diisopropylethylamine (210 μl, 1.2 mmol; CAS-RN: [7087-68-5]), (4-fluorophenyl)acetic acid (75.7 mg, 491 μmol) and PyBOP (511 mg, 983 μmol; CAS-RN:[128625-52-5]). The mixture was stirred at r.t. for 40 h. Water was added, the mixture was stirred for 30 minutes and the mixture was extracted with ethyl acetate. The organic phase was washed with half-saturated sodium chloride solution (three times), dried (sodium sulfate), filtered and the solvent was removed in vacuum. Aminophase-silicagel chromatography (Gradient: dichloromethane/ethanol 0-15%) gave a solid that was triturated with dichloromethane to give 14.0 mg of the title compound.

LC-MS (Method 2): $R_t$=1.12 min; MS (ESIpos): m/z=442 $[M+H]^+$ $^1$H-NMR (400 MHz, DMSO-$d_6$): δ [ppm]=12.22 (s, 1H), 10.83 (s, 1H), 8.45 (dd, 1H), 8.43 (dd, 1H), 8.31 (s, 1H), 8.29 (d, 1H), 8.04 (d, 1H), 7.86 (td, 1H), 7.73 (dd, 1H), 7.41-7.34 (m, 2H), 7.26 (ddd, 1H), 7.20-7.13 (m, 2H), 7.12 (dd, 1H), 3.71 (s, 2H).

Example 10

2-(4-fluorophenyl)-N-[4-(6-fluoro-3-phenyl-1H-pyrrolo[3,2-b]pyridin-2-yl)pyridin-2-yl]acetamide

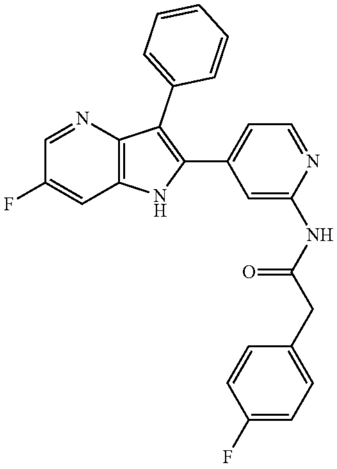 [SMILES: O=C(Cc1ccc(F)cc1)Nc1cc(-c2[nH]c3cc(F)cnc3c2-c2ccccc2)ccn1]

To a stirred solution of 4-(6-fluoro-3-phenyl-1H-pyrrolo[3,2-b]pyridin-2-yl)pyridin-2-amine (see, Intermediate 19, 90.0 mg, 75% purity, 222 μmol) in DMA (1.6 mL) was added N,N-diisopropylethylamine (230 μl, 1.3 mmol; CAS-RN:[7087-68-5]), (4-fluorophenyl)acetic acid (85.5 mg, 554 μmol) and PyBOP (577 mg, 1.11 mmol; CAS-RN:[128625-52-5]). The mixture was stirred at r.t. for 16 h. Water was added, the mixture was stirred for 30 minutes and the mixture was extracted with ethyl acetate. The organic phase was washed with half-saturated sodium chloride solution (three times), dried (sodium sulfate), filtered and the solvent was removed in vacuum.

Aminophase-silicagel chromatography (Gradient: dichloromethane/ethanol 0-15%) followed by silicagel chromatography (Gradient: dichloromethane/ethanol 0-25%) gave a solid that was triturated with a mixture of dichloromethane and hexane to give 8.00 mg of the title compound.

LC-MS (Method 2): $R_t$=1.27 min; MS (ESIpos): m/z=441 $[M+H]^+$ $^1$H-NMR (400 MHz, DMSO-d6): δ [ppm]=12.09 (s, 1H), 10.86 (s, 1H), 8.40 (dd, 1H), 8.35 (s, 1H), 8.29-8.23 (m, 1H), 7.70 (dd, 1H), 7.49-7.44 (m, 2H), 7.41-7.34 (m, 4H), 7.32-7.27 (m, 1H), 7.21-7.13 (m, 2H), 7.00 (dd, 1H), 3.72 (s, 2H).

Example 11

2-(4-fluorophenyl)-N-[4-(3-phenyl-1H-pyrrolo[3,2-b]pyridin-2-yl)pyridin-2-yl]propanamide (Racemate)

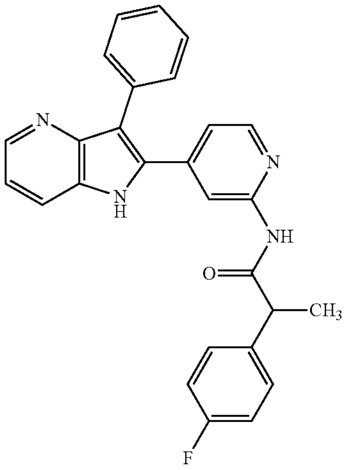 [SMILES: CC(C(=O)Nc1cc(-c2[nH]c3cccnc3c2-c2ccccc2)ccn1)c1ccc(F)cc1]

To a stirred solution of 4-(3-phenyl-1H-pyrrolo[3,2-b]pyridin-2-yl)pyridin-2-amine (see Intermediate 21, 200 mg, 698 μmol) in DMA (4.0 mL) was added N,N-diisopropylethylamine (0.73 ml, 4.19 mmol; CAS-RN:[7087-68-5]), (rac)-2-(4-fluorophenyl)propanoic acid (164 mg, 0.98 mmol) and PyBOP (1.09 g, 2.09 mmol; CAS-RN:[128625-52-5]). The mixture was stirred at r.t. for 48 h. Further N,N-diisopropylethylamine (0.37 ml, 2.11 mmol; CAS-RN: [7087-68-5]), (rac)-2-(4-fluorophenyl)propanoic acid (164 mg, 0.98 mmol) and PyBOP (0.73 g, 1.40 mmol; CAS-RN: [128625-52-5]) were added and the mixture was stirred at r.t. for further 4 days. An aqueous solution of sodium bicarbonate was added, the mixture was stirred for 5 minutes and the mixture was extracted with ethyl acetate. The organic phase was washed with half-saturated sodium chloride solution (three times), dried (sodium sulfate), filtered and the solvent was removed in vacuum. Aminophase-silicagel chromatography (Gradient: dichloromethane/ethanol 0-25%) followed by silicagel chromatography (Gradient: dichloromethane/ethanol 0-25%) gave a solid that was triturated with a mixture of dichloromethane and hexane to give 280 mg of the title compound.

LC-MS (Method 2): $R_t$=1.23 min; MS (ESIpos): m/z=437 $[M+H]^+$ $^1$H-NMR (400 MHz, DMSO-$d_6$): δ [ppm]=11.95 (s, 1H), 10.81 (s, 1H), 8.47-8.33 (m, 2H), 8.23 (d, 1H), 7.84 (dd, 1H), 7.51-7.46 (m, 2H), 7.46-7.41 (m, 2H), 7.39-7.33 (m, 2H), 7.32-7.27 (m, 1H), 7.23 (dd, 1H), 7.20-7.14 (m, 2H), 6.98 (dd, 1H), 4.10-4.00 (m, 1H), 1.44-1.36 (m, 3H).

Example 12

(−)-2-(4-fluorophenyl)-N-[4-(3-phenyl-1H-pyrrolo[3,2-b]pyridin-2-yl)pyridin-2-yl]propanamide (Enantiomer 1)

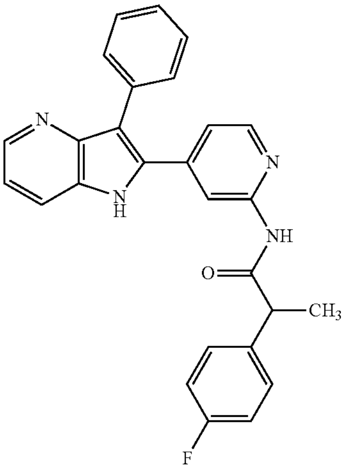 [SMILES: CC(C(=O)Nc1cc(-c2[nH]c3cccnc3c2-c2ccccc2)ccn1)c1ccc(F)cc1]

The racemic compound (see Example 11, 280 mg) was separated into enantiomers by preparative chiral HPLC. Crude enantiomer 1 was triturated with a mixture of dichloromethane and hexane to give enantiomer 1 (54 mg, >99% ee, see Example 12). Crude enantiomer 2 was triturated with a mixture of dichloromethane and hexane to give enantiomer 2 (51 mg, >99% ee, see Example 13).

Preparative Chiral HPLC Method:

Instrument: PrepCon Labomatic HPLC-3; Column: YMC Cellulose SB 10p, 250×50; eluent A: hexane+0.1 vol % diethylamine; eluent B: ethanol+0.1 vol % diethylamine; isocratic: 90% A+10% B; flow: 100 mL/min; temperature: 25° C.; UV: 254 nm Analytical Chiral HPLC Method:

Instrument: Waters Alliance 2695; Column: YMC Cellulose SB 3P, 100×4.6; eluent A: hexane+0.1 vol % diethylamine; eluent B: ethanol; isocratic: 90% A+10% B; flow: 1.4 ml/min; temperature: 25° C.; UV: 254 nm Analytical Chiral HPLC (method see Example 12 Intermediate 7): $R_t$=2.40 min.

$[\alpha]_D$=−196.7° (from solution in DMSO, c=3.0 mg/mL)

LC-MS (Method 2): $R_t$=1.26 min; MS (ESIpos): m/z=437 $[M+H]^+$ $^1$H-NMR (400 MHz, DMSO-d6): δ [ppm]=11.95 (s, 1H), 10.81 (s, 1H), 8.43-8.31 (m, 2H), 8.23 (dd, 1H), 7.84 (dd, 1H), 7.50-7.46 (m, 2H), 7.46-7.40 (m, 2H), 7.39-7.33 (m, 2H), 7.32-7.26 (m, 1H), 7.23 (dd, 1H), 7.20-7.14 (m, 2H), 7.01-6.96 (m, 1H), 4.05 (q, 1H), 1.46-1.35 (m, 3H).

Example 13

(+)-2-(4-fluorophenyl)-N-[4-(3-phenyl-1H-pyrrolo[3,2-b]pyridin-2-yl)pyridin-2-yl]propanamide (Enantiomer 2)

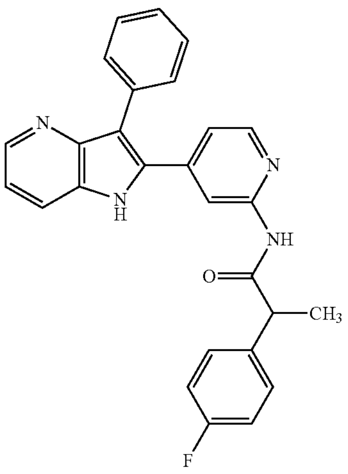 [SMILES: CC(C(=O)Nc1cc(-c2[nH]c3cccnc3c2-c2ccccc2)ccn1)c1ccc(F)cc1]

For the preparation of the racemic title compound see Example 11. Separation of enantiomers by preparative chiral HPLC (method see Example 12) followed by trituration with a mixture of dichloromethane and hexane gave the title compound (51 mg, >99% ee).

Analytical Chiral HPLC (method see Example 12): $R_t$=4.34 min-.

$[\alpha]_D$=+195.4° (from solution in DMSO, c=3.0 mg/mL)

LC-MS (Method 2): $R_t$=1.26 min; MS (ESIpos): m/z=437 $[M+H]^+$ $^1$H-NMR (400 MHz, DMSO-$d_6$): δ [ppm]=11.95 (s, 1H), 10.81 (s, 1H), 8.44-8.34 (m, 2H), 8.23 (d, 1H), 7.84 (dd, 1H), 7.50-7.46 (m, 2H), 7.46-7.41 (m, 2H), 7.39-7.33 (m, 2H), 7.32-7.26 (m, 1H), 7.23 (dd, 1H), 7.20-7.14 (m, 2H), 6.98 (dd, 1H), 4.05 (q, 1H), 1.40 (d, 3H).

Example 14

2-(4-fluorophenyl)-N-[4-(3-phenyl-1H-pyrrolo[3,2-b]pyridin-2-yl)pyridin-2-yl]acetamide

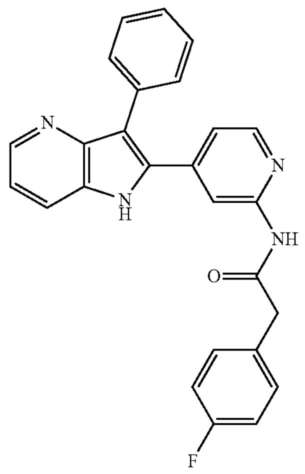 [SMILES: O=C(Cc1ccc(F)cc1)Nc1cc(-c2[nH]c3cccnc3c2-c2ccccc2)ccn1]

A mixture of 2,2,2-trifluoro-N-[2-({2-[2-(4-fluorophenyl)acetamido]pyridin-4-yl}ethynyl)pyridin-3-yl]acetamide (200 mg, 99% purity, 448 μmol, see Intermediate 9), iodobenzene (110 mg, 537 μmol), tetrakis(triphenylphosphine)palladium(0) (51.7 mg, 44.8 μmol) and dicaesium carbonate (437 mg, 1.34 mmol) in acetonitrile (5.0 ml) was purged with nitrogen. The mixture was then heated at 100° C. in a sealed vial for 2 hours, and then cooled to room temperature. The mixture was filtered. The filtrate was concentrated in vacuum. The residue was purified by flash silica gel chromatography (4 g, ethyl acetate in petroleum ether=0% to 50%) to give 2-(4-fluorophenyl)-N-[4-(3-phenyl-1H-pyrrolo[3,2-b]pyridin-2-yl)pyridin-2-yl]acetamide (38.8 mg, 96% purity, 20% yield) as a white solid.

LC-MS (Method C): R, =0.827 min; MS (ESIpos): m/z=423.1 $[M+H]^+$ $^1$H NMR (400 MHz, DMSO-$d_6$): δ [ppm]=12.00 (s, 1H), 10.86 (s, 1H), 8.41 (d, J=3.6 Hz, 1H), 8.37 (s, 1H), 8.27 (d, J=5.2 Hz, 1H), 7.87 (d, J=8.0 Hz, 1H), 7.51-7.49 (m, 2H), 7.40-7.36 (m, 4H), 7.32-7.30 (m, 1H), 7.27-7.23 (m, 1H), 7.19-7.15 (m, 2H), 7.02 (dd, J=5.2 Hz, 1.2 Hz, 1H), 7.34 (s, 2H).

Example 15

2-(4-fluorophenyl)-N-{4-[3-(3-fluorophenyl)-1H-pyrrolo[3,2-b]pyridin-2-yl]pyridin-2-yl}acetamide

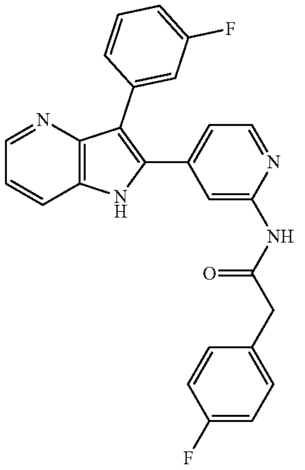 [SMILES: O=C(Cc1ccc(F)cc1)Nc1cc(-c2[nH]c3cccnc3c2-c2cccc(F)c2)ccn1]

A mixture of A mixture of 2,2,2-trifluoro-N-[2-({2-[2-(4-fluorophenyl)acetamido]pyridin-4-yl}ethynyl)pyridin-3-yl] acetamide (150 mg, 0.34 mmol, see Intermediate 9), 1-fluoro-3-iodobenzene (113 mg, 0.51 mmol) and dicaesium carbonate (331 mg, 1.02 mmol) in 1-methyl-2-pyrrolidinone (3 ml) was purged with nitrogen. Then methanesulfonato(2-dicyclohexylphosphino-2',4',6'-tri-i-propyl-1,1'-biphenyl) (2'-amino-1,1'-biphenyl-2-yl)palladium(II) (14.3 mg, 0.017 mmol) was added to the mixture and the mixture was purged with nitrogen at room temperature. The mixture was then heated at 100° C. for 16 hours. The mixture was cooled to room temperature. The solid was filtered off, and the filtrate was concentrated. The residue was purified by silica gel chromatography (100-200 mesh, petroleum ether:ethyl acetate=10:1, then 3:1, then 1:1, then 0:1) to give a crude product. The crude product was then purified by preparative HPLC [Instrument: ACSWH-GX-L; Column: Unisil 3-100 C18 Ultra 150*50 mm*3 μm; eluent A: water (0.225% formic acid in water), eluent B: acetonitrile; gradient: 10 minutes 25-45% B; flow 25 ml/minute; temperature: room temperature; Detector: UV 220/254 nm] and then lyophilization to give 2-(4-fluorophenyl)-N-{4-[3-(3-fluorophenyl)-1H-pyrrolo[3,2-b]pyridin-2-yl]pyridin-2-yl}acetamide (13.1 mg, 93% purity, 8% yield, NMR contained 0.21eq formic acid) as yellow solid.

LC-MS (Method C): $R_t$=0.883 min; MS (ESIpos): m/z=441.3 $[M+H]^+$.

$^1H$ NMR (400 MHz, DMSO-$d_6$): δ [ppm]=12.06 (s, 1H), 10.87 (s, 1H), 8.42 (dd, J=4.4, 1.2 Hz, 1H), 8.34 (s, 1H), 8.32-8.31 (m, 1H), 7.84 (dd, J=8.0, 1.2 Hz, 1H), 7.40-7.35 (m, 4H), 7.28-7.23 (m, 2H), 7.18-7.07 (m, 4H), 3.72 (s, 2H).

Example 16 formic acid salt of 2-(4-fluorophenyl)-N-{4-[3-(pyrimidin-2-yl)-1H-pyrrolo[3,2-b]pyridin-2-yl]pyridin-2-yl}acetamide

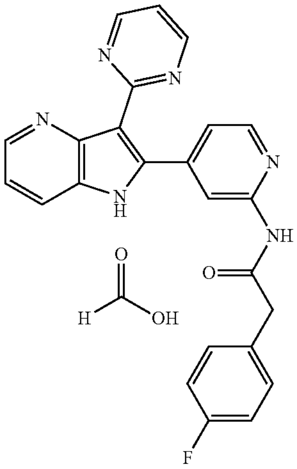

A mixture of 2,2,2-trifluoro-N-[2-({2-[2-(4-fluorophenyl) acetamido]pyridin-4-yl}ethynyl)pyridin-3-yl]acetamide (150 mg, 99% purity, 0.34 mmol, see Intermediate 9), 2-iodopyrimidine (105 mg, 50.51 mmol) and dicaesium carbonate (331 mg, 1.02 mmol) in 1-methyl-2-pyrrolidinone (3.0 ml) was purged with nitrogen. Then methanesulfonato (2-dicyclohexylphosphino-2',4',6'-tri-i-propyl-1,1'-biphenyl)(2'-amino-1,1'-biphenyl-2-yl)palladium(II) (14.3 mg, 0.017 mmol) was added to the mixture and the mixture was purged with nitrogen at room temperature. The mixture was then heated at 100° C. for 16 hours. The mixture was cooled to room temperature. The solid was filtered off, and the filtrate was concentrated. The residue was purified by silica gel chromatography (100~200 mesh, petroleum ether:ethyl acetate=10:1, then 3:1, then 1:1, then 0:1) to give a crude product. The crude product was then purified by preparative HPLC [Instrument: ACSWH-GX-L; Column: Unisil 3-100 C18 Ultra 150*50 mm*3 μm; eluent A: water (0.225% formic acid in water), eluent B: acetonitrile; gradient: 10 minutes 15-35% B; flow 25 ml/minute; temperature: room temperature; Detector: UV 220/254 nm] and then lyophilization to give formic acid-2-(4-fluorophenyl)-N-{4-[3-(pyrimidin-2-yl)-1H-pyrrolo[3,2-b]pyridin-2-yl]pyridin-2-yl}acetamide (1/1) (4.00 mg, 93% purity, 2% yield) as a yellow solid.

LC-MS (Method C): $R_t$=0.849 min; MS (ESIpos): m/z=425.3 $[M+H]^+$.

$^1H$ NMR (400 MHz, DMSO-$d_6$): δ [ppm]=12.24 (s, 1H), 10.80 (s, 1H), 8.82 (d, J=4.8 Hz, 2H), 8.41 (dd, J=4.4, 1.2 Hz, 1H), 8.38 (s, 1H), 8.32 (d, J=5.2 Hz, 1H), 8.22 (s, 1H), 7.88 (d, J=8.0 Hz, 1H), 7.41-7.36 (m, 3H), 7.27-7.23 (m, 1H), 7.20-7.15 (m, 2H), 7.13-7.12 (m, 1H), 3.71 (s, 2H).

Example 17

N-{4-[3-(5-chlorothiophen-2-yl)-1H-pyrrolo[3,2-b]pyridin-2-yl]pyridin-2-yl}-2-(4-fluorophenyl)acetamide

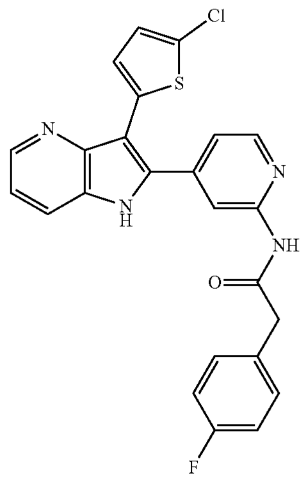 [SMILES: O=C(Cc1ccc(F)cc1)Nc1cc(-c2[nH]c3cccnc3c2-c2ccc(Cl)s2)ccn1]

A mixture of 2,2,2-trifluoro-N-[2-({2-[2-(4-fluorophenyl)acetamido]pyridin-4-yl}ethynyl)pyridin-3-yl]acetamide (200 mg, 99% purity, 448 μmol, see Intermediate 9), 2-bromo-5-chlorothiophene (106 mg, 537 μmol), tetrakis(triphenylphosphine)palladium(0) (51.7 mg, 44.8 μmol) and dicaesium carbonate (437 mg, 1.34 mmol) in acetonitrile (5.0 ml) was purged with nitrogen. The mixture was then heated at 100° C. in a sealed vial for 2 hours, and then cooled to room temperature. The mixture was filtered. The filtrate was concentrated in vacuum. The residue was purified by flash silica gel chromatography (4 g, ethyl acetate in petroleum ether=0% to 50%) to give N-{4-[3-(5-chlorothiophen-2-yl)-1H-pyrrolo[3,2-b]pyridin-2-yl]pyridin-2-yl}-2-(4-fluorophenyl)acetamide (22.8 mg, 92% purity, 10% yield) as a yellow solid.

LC-MS (Method C): $R_t$=0.858 min; MS (ESIpos): m/z=463.1 $[M+H]^+$ $^1$H NMR (400 MHz, DMSO-$d_6$): δ [ppm]=12.20 (s, 1H), 11.00 (s, 1H), 8.52 (dd, J=4.4 Hz, 1.2 Hz, 1H), 8.49 (d, J=5.2 Hz, 1H), 8.46 (s, 1H), 7.91 (dd, J=8.4 Hz, 1.2 Hz, 1H), 7.46-7.43 (m, 2H), 7.37 (dd, J=5.2 Hz, 1.6 Hz, 1H), 7.39-7.32 (m, 1H), 7.24-7.19 (m, 2H), 7.16-7.15 (m, 1H), 7.11-7.10 (m, 1H), 3.81 (s, 2H).

Example 18

2-(4-fluorophenyl)-N-[4-(7-phenyl-5H-pyrrolo[2,3-b]pyrazin-6-yl)pyridin-2-yl]acetamide

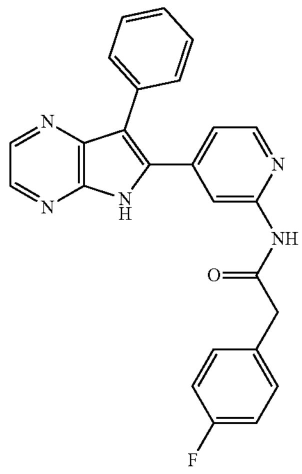 [SMILES: O=C(Cc1ccc(F)cc1)Nc1cc(-c2[nH]c3nccnc3c2-c2ccccc2)ccn1]

To a solution of N-[4-(7-bromo-5H-pyrrolo[2,3-b]pyrazin-6-yl)pyridin-2-yl]-2-(4-fluorophenyl)acetamide (see Intermediate 26, 100 mg, 0.24 mmol) and phenylboronic acid (85.8 mg, 0.70 mmol) in tetrahydrofuran were added methanesulfonato(2-dicyclohexylphosphino-2',4',6'-tri-i-propyl-1,1'-biphenyl)(2'-amino-1,1'-biphenyl-2-yl)palladium(II) (19.9 mg, 0.024 mmol, Xphos-Pd-G3) and potassium phosphate (0.47 ml, 0.7 mmol, 1.5 M in water) in one portion at room temperature. The reaction mixture was stirred at 70° C. for 16 hours under nitrogen atmosphere. The reaction mixture was diluted with water and extracted with ethyl acetate. The organic phase was washed with brine, dried over anhydrous sodium sulfate and filtered. The filtrate was concentrated and purified by preparative HPLC (Instrument: Gilson-281; Column: Phenomenex Synergi C18 150*25*10 μm; eluent A: water (0.225% formic acid), eluent B: acetonitrile; gradient: 0-10 min 18-48% B; flow 25 ml/min; temperature: room temperature; Detector: UV 220/254 nm) to give 2-(4-fluorophenyl)-N-[4-(7-phenyl-5H-pyrrolo[2,3-b]pyrazin-6-yl)pyridin-2-yl]acetamide as a yellow solid.

LC-MS (Method C): $R_t$=0.896 min; MS (ESIpos): m/z=424.2 $[M+H]^+$.

$^1$H NMR (400 MHz, DMSO-$d_6$): δ [ppm]=10.87 (s, 1H), 8.47 (d, J=2.4 Hz, 1H), 8.37-8.34 (m, 2H), 8.32 (d, J=5.2 Hz, 1H), 7.47 (d, J=7.2 Hz, 2H), 7.40-7.28 (m, 5H), 7.18-7.10 (m, 3H), 3.72 (s, 2H).

Example 19

2-(4-fluorophenyl)-N-{4-[7-(pyridin-2-yl)-5H-pyrrolo[2,3-b]pyrazin-6-yl]pyridin-2-yl}acetamide

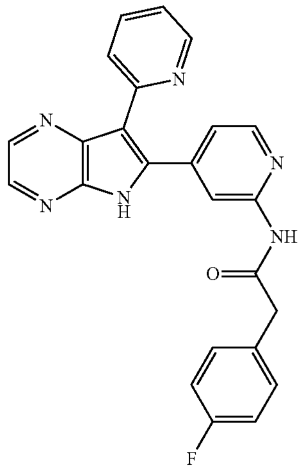 [SMILES: O=C(Cc1ccc(F)cc1)Nc1cc(-c2[nH]c3nccnc3c2-c2ccccn2)ccn1]

To a solution of N-[4-(7-bromo-5H-pyrrolo[2,3-b]pyrazin-6-yl)pyridin-2-yl]-2-(4-fluorophenyl)acetamide (see Intermediate 26, 100 mg, 0.24 mmol) and 2-(tributylstannyl)pyridine (173 mg, 0.47 mmol) in 1,4-dioxane (10 ml) was added bis(triphenylphosphine)palladium(II) chloride (16.5 mg, 0.024 mmol) in one portion at room temperature. The reaction mixture was stirred at 110° C. for 16 hours under nitrogen atmosphere. The reaction mixture (combined with a batch starting from 30 mg Intermediate 26) was concentrated in reduced pressure to give a residue. The residue was diluted with water and extracted with ethyl acetate. The organic phase was washed with brine, dried over anhydrous sodium sulfate and filtered. The filtrate was concentrated and purified by preparative HPLC (Instrument: Gilson-281; Column: Phenomenex Synergi C18 150*25*10 μm; eluent A: water (0.225% formic acid), eluent B: acetonitrile; gradient: 0-10 min 18-48% B; flow 25 ml/min; temperature: room temperature; Detector: UV 220/254 nm) to give 2-(4-fluorophenyl)-N-{4-[7-(pyridin-2-yl)-5H-pyrrolo[2,3-b]pyrazin-6-yl]pyridin-2-yl}acetamide (15.6 mg, 99% purity, 16% yield) as a off-white solid.

LC-MS (Method C): $R_t$=0.666 min; MS (ESIpos): m/z=425.1 $[M+H]^+$.

$^1H$ NMR (400 MHz, DMSO-$d_6$): δ [ppm]=12.86 (brs, 1H), 10.85 (s, 1H), 8.53 (d, J=2.8 Hz, 1H), 8.44-8.42 (m, 1H), 8.40 (d, J=2.4 Hz, 1H), 8.34 (d, J=5.6 Hz, 1H), 8.32 (s, 1H), 8.04 (d, J=8.0 Hz, 1H), 7.88 (dt, J=7.6, 2.0 Hz, 1H), 7.39-7.34 (m, 2H), 7.30-7.26 (m, 1H), 7.21 (dd, J=5.2, 1.6 Hz, 1H), 7.19-7.14 (m, 2H), 3.71 (s, 2H).

Example 20

2-(4-fluorophenyl)-N-[4-(7-phenyl-5H-pyrrolo[3,2-c]pyridazin-6-yl)pyridin-2-yl]acetamide

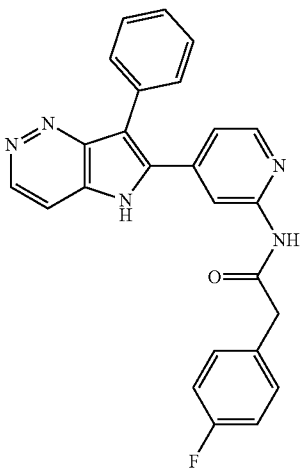 [SMILES: O=C(Cc1ccc(F)cc1)Nc1cc(-c2[nH]c3ccnnc3c2-c2ccccc2)ccn1]

To a solution of N-[4-(7-bromo-5H-pyrrolo[3,2-c]pyridazin-6-yl)pyridin-2-yl]-2-(4-fluorophenyl)acetamide (see Intermediate 30, 60.0 mg, 0.14 mmol) and phenylboronic acid (34.3 mg, 0.28 mmol) in tetrahydrofuran (10 ml) were added methanesulfonato(2-dicyclohexylphosphino-2',4',6'-tri-i-propyl-1,1'-biphenyl)(2'-amino-1,1'-biphenyl-2-yl)palladium(II) (XPhos-Pd-G3) (11.9 mg, 0.014 mmol) and potassium phosphate (0.28 ml, 1.5 M in water, 0.42 mmol) in one portion at room temperature. The reaction mixture was stirred at 70° C. for 16 hours under nitrogen atmosphere. The reaction was poured into water and the mixture was extracted with ethyl acetat. The organic phase was dried over anhydrous sodium sulfate, filtered and concentrated to give a residue. The residue was purified by preparative TLC (ethyl acetate:methanol=10:1) to give a crude product. The crude product was purified by preparative HPLC (Instrument: ACSWH-GX-J; Column: Unisil 3-100 C18 Ultra 150*50 mm*3 μm; eluent A: water (0.225% formic acid), eluent B: acetonitrile; gradient: 0-10 min 18-45% B; flow 25 ml/min; temperature: room temperature; Detector: UV 220/254 nm) to give 2-(4-fluorophenyl)-N-[4-(7-phenyl-5H-pyrrolo[3,2-c]pyridazin-6-yl)pyridin-2-yl]acetamide (4.6 mg, 99% purity, 8% yield) as a yellow solid.

LC-MS (Method C): $R_t$=0.802 min; MS (ESIpos): m/z=424.1 $[M+H]^+$.

$^1H$ NMR (400 MHz, DMSO-d6): δ [ppm]=11.43 (brs, 1H), 10.91 (s, 1H), 8.99 (d, J=6 Hz, 1H), 8.38 (s, 1H), 8.32 (d, J=5.2 Hz, 1H), 7.67 (d, J=5.6 Hz, 1H), 7.57-7.55 (m, 2H), 7.43-7.34 (m, 5H), 7.18-7.13 (m, 2H), 7.08 (dd, J=5.2, 1.2 Hz, 1H), 3.73 (s, 2H).

Example 21

2-(4-fluorophenyl)-N-{4-[7-(pyridin-2-yl)-5H-pyrrolo[3,2-c]pyridazin-6-yl]pyridin-2-yl}acetamide

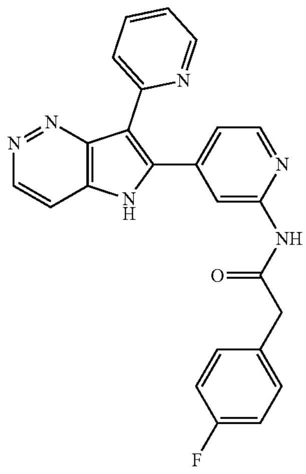 [SMILES: O=C(Cc1ccc(F)cc1)Nc1cc(-c2[nH]c3ccnnc3c2-c2ccccn2)ccn1]

A mixture of 2-(4-fluorophenyl)-N-{4-[7-(pyridin-2-yl)-5-{[2-(trimethylsilyl)ethoxy]methyl}-5H-pyrrolo[3,2-c]pyridazin-6-yl]pyridin-2-yl}acetamide (see Intermediate 32, 50.0 mg, 0.09 mmol) in Hydrochloric acid\dioxane (10 ml, 4.0 M, 40 mmol) and methanol (1.0 ml) was stirred at room temperature for 16 hours. The mixture was concentrated by evaporation in vacuum. The residue was purified by preparative-HPLC (Instrument: ACSWH-GX-K; Column: Phenomenex Gemini-NX C18 75*30 mm*3 μm; eluent A: water (0.225% formic acid), eluent B: acetonitrile; gradient: 0-7 min 10-40% B; flow 2 ml/min; temperature: room temperature; Detector: UV 220/254 nm) to give 2-(4-fluorophenyl)-N-{4-[7-(pyridin-2-yl)-5H-pyrrolo[3,2-c]pyridazin-6-yl]pyridin-2-yl}acetamide (13.6 mg, 91% purity, 32% yield) as a yellow solid.

LC-MS (Method C): Rt=0.648 min; MS (ESIpos): m/z=425.1 $[M+H]^+$.

$^1$H NMR (400 MHz, DMSO-$d_6$): δ [ppm]=10.88 (s, 1H), 9.02 (d, J=6.0 Hz, 1H), 8.45-8.44 (m, 1H), 8.35-8.34 (m, 2H), 8.21 (d, J=7.6 Hz, 1H), 7.93-7.89 (td, J=8.0, 2.0 Hz, 1H), 7.70 (d, J=6 Hz, 1H), 7.38-7.35 (m, 2H), 7.32-7.29 (m, 1H), 7.20-7.13 (m, 3H), 3.72 (s, 2H).

Example 22

N-{4-[7-chloro-3-(pyridin-2-yl)-1H-pyrrolo[3,2-b]pyridin-2-yl]pyridin-2-yl}-2-(4-fluorophenyl)acetamide

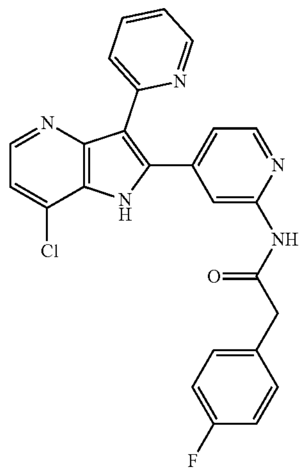 [SMILES: O=C(Cc1ccc(F)cc1)Nc1cc(-c2[nH]c3c(Cl)ccnc3c2-c2ccccn2)ccn1]

A mixture of N-[4-chloro-2-({2-[2-(4-fluorophenyl)acetamido]pyridin-4-yl}ethynyl)pyridin-3-yl]-2,2,2-trifluoroacetamide (see Intermediate 34, 300 mg, 0.63 mmol), 2-iodopyridine (155 mg, 0.76 mmol), Methanesulfonato(2-dicyclohexylphosphino-2',4',6'-tri-i-propyl-1,1'-biphenyl)(2'-amino-1,1'-biphenyl-2-yl)palladium(II) (53.1 mg, 0.063 mmol) and cesium carbonate (615 mg, 1.89 mmol) in 1-methyl-2-pyrrolidinone (3.0 ml) was purged with nitrogen. The mixture was stirred at 100° C. for 16 hours under nitrogen. The reaction mixture was poured into water and the mixture was extracted with ethyl acetate. The organic phase was washed with brine, dried over anhydrous sodium sulfate and concentrated by evaporation in vacuum. The residue was purified by silica gel chromatography (40 g, ethyl acetate:methanol=10:1 in petroleum ether=0% to 100%) to give a crude product (50 mg). The crude product was purified by preparative HPLC (Instrument: ACSWH-GX-Q; Column: Shim-pack C18 150*25*10 μm; eluent A: water (0.225% formic acid), eluent B: acetonitrile; gradient: 0-8 min 27-43% B; flow 2 ml/min; temperature: room temperature; Detector: UV 220/254 nm) to give N-{4-[7-chloro-3-(pyridin-2-yl)-1H-pyrrolo[3,2-b]pyridin-2-yl]pyridin-2-yl}-2-(4-fluorophenyl)acetamide (12.5 mg, 96% purity, 4% yield) as a yellow solid.

LC-MS (Method C): $R_t$=0.816 min; MS (ESIpos): m/z=457.9 $[M+H]^+$.

$^1$H NMR (400 MHz, DMSO-d6): δ [ppm]=12.59 (s, 1H), 10.81 (s, 1H), 8.39 (d, J=4.8 Hz, 2H), 8.30-8.29 (m, 2H), 8.07 (d, J=8.0 Hz, 1H), 7.85 (dt, J=7.6, 2.0 Hz, 1H), 7.41 (d, J=5.2 Hz, 1H), 7.39-7.35 (m, 2H), 7.27-7.22 (m, 1H), 7.18-7.13 (m, 3H), 3.71 (s, 2H).

Example 23

N-{4-[5-chloro-3-(pyridin-2-yl)-1H-pyrrolo[3,2-b]pyridin-2-yl]pyridin-2-yl}-2-(4-fluorophenyl)acetamide

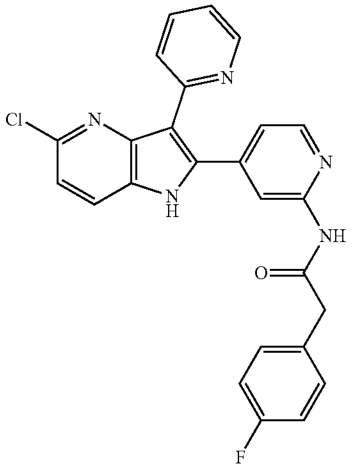 [SMILES: O=C(Cc1ccc(F)cc1)Nc1cc(-c2[nH]c3ccc(Cl)nc3c2-c2ccccn2)ccn1]

To a mixture of N-[4-(3-bromo-5-chloro-1H-pyrrolo[3,2-b]pyridin-2-yl)pyridin-2-yl]-2-(4-fluorophenyl)acetamide (see Intermediate 37, 100 mg, 0.22 mmol), 2-(tributylstannyl)pyridine (160 mg, 0.44 mmol) in 1,4-Dioxane was added dichlorobis(triphenylphosphine)palladium(II) (15.3 mg, 0.022 mmol in one portion at room temperature. The reaction mixture was stirred at 100° C. for 16 hours under nitrogen atmosphere. The reaction mixture was diluted with water, and then extracted with ethyl acetate. The organic layer was washed by saturated brine, dried over sodium sulfate, filtered and the filtrate was concentrated in vacuum to give a mixture. The mixture was purified by preparative TLC (petroleum ether:ethyl acetate=0:1) to give a crude product. The crude product was further purified by preparative HPLC (Instrument: ACSWH-GX-Q; Column: Shim-pack C18 150*25*10 μm; eluent A: water (0.225% formic acid), eluent B: acetonitrile; gradient: 0-10 min 24-44% B; flow 2 mi/min; temperature: room temperature; Detector: UV 220/254 nm) to give N-{4-[5-chloro-3-(pyridin-2-yl)-1H-pyrrolo[3,2-b]pyridin-2-yl]pyridin-2-yl}-2-(4-fluorophenyl)acetamide (6.7 mg) as a white solid and further N-{4-[5-chloro-3-(pyridin-2-yl)-1H-pyrrolo[3,2-b]pyridin-2-yl]pyridin-2-yl)-2-(4-fluorophenyl)acetamide (15 mg) as a white solid.

LC-MS (Method C): $R_t$=0.747 min; MS (ESIpos): m/z=458.1 $[M+H]^+$.

$^1$H NMR (400 MHz, DMSO-$d_6$): δ [ppm]=10.82 (s, 1H), 8.45-8.43 (m, 1H), 8.30-8.28 (m, 2H), 7.95-7.87 (m, 3H), 7.39-7.34 (m, 2H), 7.30-7.26 (m, 2H), 7.18-7.10 (m, 3H), 3.71 (s, 2H).

Example 24

2-(4-fluorophenyl)-N-{4-[5-fluoro-3-(pyridin-2-yl)-1H-pyrrolo[3,2-b]pyridin-2-yl]pyridin-2-yl}-3-methylbutanamide

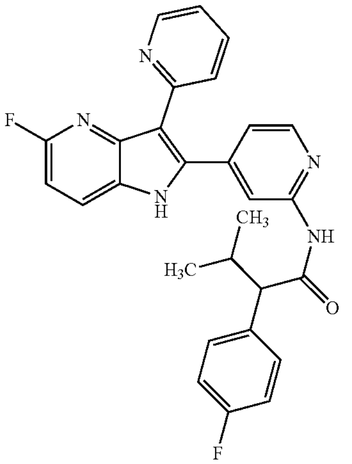 [SMILES: CC(C)C(C(=O)Nc1cc(-c2[nH]c3ccc(F)nc3c2-c2ccccn2)ccn1)c1ccc(F)cc1]

4-[5-Fluoro-3-(pyridin-2-yl)-1H-pyrrolo[3,2-b]pyridin-2-yl]pyridin-2-amine (Intermediate 4,150 mg, 0.49 mmol), 2-(4-fluorophenyl)-3-methylbutanoic acid (125 mg, 639 μmol, CAS-RN:[51632-33-8]), PyBOP (639 mg, 1.23 mmol), and N,N-diisopropylethylamine (510 μL, 2.9 mmol) were dissolved in 0.82 mL DMA and stirred at 60° C. for 5 days. Additional 2-(4-fluorophenyl)-3-methylbutanoic acid (125 mg, 639 μmol) and PyBOP (639 mg, 1.23 mmol) were added to the reaction mixture and stirring was continued for another day. The reaction mixture was diluted with dichloromethane and aqueous sodium hydrogencarbonate solution. The layers were separated and the aqueous layer was extracted with dichloromethane. The combined organic layers were washed with aqueous half-concentrated sodium chloride solution twice, filtered through a water impermeable filter and were concentrated under vacuum. The crude was purified by flash chromatography (silica gel; dichloromethane/ethanol 0%-15%) followed by preparative HPLC (method K, gradient: 0.00-0.50 min 30% B, 0.50-6.00 min 30-70% B) to provide 75 mg of the target compound in 95% purity.

LC-MS (Method 2): $R_t$=1.15 min; MS (ESIpos): m/z=485 $[M+H]^+$ $^1$H-NMR (400 MHz, DMSO-d6) δ[ppm]=0.64 (d, 3H), 0.99 (d, 3H), 2.21-2.37 (m, 1H), 3.50 (d, 1H), 7.00 (dd, 1H), 7.09 (dd, 1H), 7.12-7.22 (m, 2H), 7.25-7.30 (m, 1H), 7.38-7.46 (m, 2H), 7.84-7.97 (m, 2H), 8.04 (dd, 1H), 8.23-8.29 (m, 1H), 8.34 (s, 1H), 8.38-8.44 (m, 1H), 10.80 (s, 1H), 12.31 (s, 1H).

Example 25

(−)-2-(4-fluorophenyl)-N-{4-[5-fluoro-3-(pyridin-2-yl)-1H-pyrrolo[3,2-b]pyridin-2-yl]pyridin-2-yl}-3-methylbutanamide (Enantiomer 1)

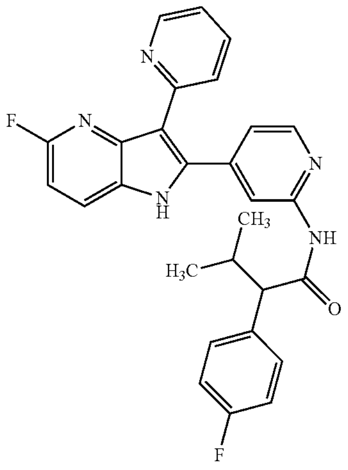 [SMILES: CC(C)C(C(=O)Nc1cc(-c2[nH]c3ccc(F)nc3c2-c2ccccn2)ccn1)c1ccc(F)cc1]

The racemic title compound from Example 24 (75 mg) was separated into enantiomers by preparative chiral HPLC to give title compound (enantiomer 1, 26 mg, 96.7% ee) and enantiomer 2 (30 mg, 99.9% ee, see Example 26).

Preparative Chiral HPLC Method:

Instrument: PrepCon Labomatic HPLC-4; Column: YMC Cellulose SB 10 μ, 250×50; eluent A: hexane+0.1 vol % diethylamine; eluent B: 2-propanol; isocratic: 70% A+30% B; flow: 100 mL/min; temperature: 25° C.; UV: 254 nm;

Analytical Chiral HPLC Method:

Instrument: Thermo Fisher UltiMate 3000; Column: YMC Cellulose SB 3 μ, 100×4.6; eluent A: hexane+0.1 vol % diethylamine; eluent B: 2-propanol; isocratic: 70% A+30% B; flow: 1.4 mL/min; temperature: 25° C.; UV: 254 nm;

Analytical Chiral HPLC: $R_t$=3.64 min.

$[\alpha]_D$=−180.1° (from solution in DMSO, c=5.2 mg/mL)

$^1$H-NMR (400 MHz, DMSO-d6) δ[ppm]0.64 (d, 3H), 0.99 (d, 3H), 2.17-2.36 (m, 1H), 3.50 (d, 1H), 7.00 (dd, 1H), 7.04-7.12 (m, 1H), 7.14-7.23 (m, 2H), 7.27 (ddd, 1H), 7.33-7.49 (m, 2H), 7.81-7.98 (m, 2H), 8.04 (dd, 1H), 8.26 (dd, 1H), 8.34 (s, 1H), 8.36-8.45 (m, 1H), 10.80 (s, 1H), 12.31 (s, 1H).

Example 1

(+)-2-(4-fluorophenyl)-N-{4-[5-fluoro-3-(pyridin-2-yl)-1H-pyrrolo[3,2-b]pyridin-2-yl]pyridin-2-yl}-3-methylbutanamide (Enantiomer 2)

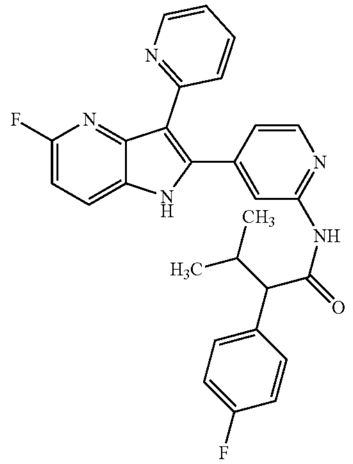 [SMILES: CC(C)C(C(=O)Nc1cc(-c2[nH]c3ccc(F)nc3c2-c2ccccn2)ccn1)c1ccc(F)cc1]

For the preparation of the racemic title compound see Example 24. Separation of enantiomers by preparative chiral HPLC (method see Example 25) gave the title compound (30 mg).

Analytical Chiral HPLC (method see Example 25): $R_t$=5.03 min.

$[\alpha]_D$=+177.4° (from solution in DMSO, c=5.5 mg/mL)

$^1$H-NMR (400 MHz, DMSO-d6) δ[ppm]=0.64 (d, 3H), 0.99 (d, 3H), 2.24-2.37 (m, 1H), 3.50 (d, 1H), 7.00 (dd, 1H), 7.09 (dd, 1H), 7.13-7.21 (m, 2H), 7.27 (ddd, 1H), 7.37-7.48 (m, 2H), 7.82-7.91 (m, 1H), 7.92-7.97 (m, 1H), 8.04 (dd, 1H), 8.26 (dd, 1H), 8.34 (s, 1H), 8.38-8.43 (m, 1H), 10.80 (s, 1H), 12.31 (s, 1H).

Example 27

N-{4-[5-fluoro-6-methyl-3-(pyridin-2-yl)-1H-pyrrolo[3,2-b]pyridin-2-yl]pyridin-2-yl}-2-(4-fluorophenyl)acetamide

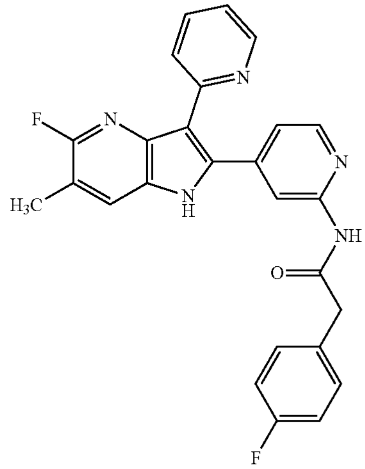 [SMILES: Cc1cc2[nH]c(-c3ccnc(NC(=O)Cc4ccc(F)cc4)c3)c(-c3ccccn3)c2nc1F]

2-(2-Bromopyridin-4-yl)-5-fluoro-6-methyl-3-(pyridin-2-yl)-1H-pyrrolo[3,2-b]pyridine (Intermediate 43, 250 mg), 2-(4-fluorophenyl)acetamide (150 mg, 979 μmol, CAS-RN: [332-29-6]), cesium carbonate (638 mg, 1.96 mmol), di-tert-butyl(2',4',6'-triisopropyl-3,6-dimethoxy-[1,1'-biphenyl]-2-yl)phosphine (63.2 mg, 130 μmol; CAS-RN:[1160861-53-9]) and [(2-di-tert-butylphosphino-3,6-dimethoxy-2',4',6'-triisopropyl-1,1'-biphenyl)-2-(2'-amino-1,1'-biphenyl)] palladium(II) methanesulfonate (55.7 mg, 65.2 μmol; CAS-RN:[1536473-72-9]) were dissolved in 5.6 mL 1,4-dioxane and stirred at 100° C. for 1 hour under a nitrogen atmosphere. The reaction mixture was diluted with ethyl acetate and water. The layers were separated and the aqueous layer was extracted with ethyl acetate. The combined organic layers were dried using a water resistant filter and the clear filtrate was concentrated under reduced pressure. The crude product was purified by flash chromatography (amine functionalized silica gel, gradient dichloromethane/ethanol 0-8%) to provide 295 mg of the target compound in 91% purity.

LC-MS (Method 2): $R_t$=1.18 min; MS (ESIpos): m/z=456 $[M+H]^+$ $^1$H-NMR (400 MHz, DMSO-$d_6$) δ [ppm]=2.36 (s, 3H), 3.71 (s, 2H), 7.06-7.11 (m, 1H), 7.13-7.20 (m, 2H), 7.21-7.29 (m, 1H), 7.34-7.41 (m, 2H), 7.82-7.90 (m, 2H), 7.90-7.98 (m, 1H), 8.24-8.34 (m, 2H), 8.38-8.47 (m, 1H), 10.81 (s, 1H), 12.14 (s, 1H).

Example 2

N-{4-[5-fluoro-6-methyl-3-(pyridin-2-yl)-1H-pyrrolo[3,2-b]pyridin-2-yl]pyridin-2-yl)-2-(4-fluorophenyl)propanamide (Racemate)

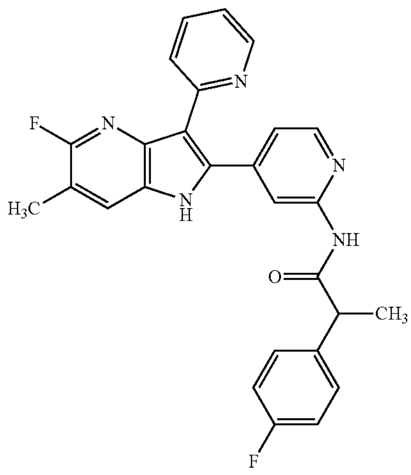 [SMILES: Cc1cc2[nH]c(-c3ccnc(NC(=O)C(C)c4ccc(F)cc4)c3)c(-c3ccccn3)c2nc1F]

2-(2-Bromopyridin-4-yl)-5-fluoro-6-methyl-3-(pyridin-2-yl)-1H-pyrrolo[3,2-b]pyridine (Intermediate 43, 250 mg 0.65 mmol), (2-(4-fluorophenyl)propanamide (Intermediate 44, 164 mg, 0.98 mmol), cesium carbonate (638 mg, 1.96 mmol), di-tert-butyl(2',4',6'-triisopropyl-3,6-dimethoxy-[1,1'-biphenyl]-2-yl)phosphine (63.2 mg, 130 μmol; CAS-RN: [1160861-53-9]) and [(2-di-tert-butylphosphino-3,6-dimethoxy-2',4',6'-triisopropyl-1,1'-biphenyl)-2-(2'-amino-1,1'-biphenyl)]palladium(II) methanesulfonate (55.7 mg, 65.2 μmol; CAS-RN:[1536473-72-9]) were dissolved in 1,4-dioxane (5.6 mL) and stirred at 100° C. for 1 hour under a nitrogen atmosphere. The mixture was diluted with ethyl acetate and water. The layers were separated and the aqueous layer was extracted with ethyl acetate three times. The combined organic layer was filtered through a water impermeable filter and concentrated under reduced pressure. The crude product was purified by flash chromatography (10 g aminophase column, gradient DCM/ethanol 0-8%) followed by preparative HPLC (method K, gradient: 0.00-0.50 min 30% B, 0.50-6.00 min 30-70% B) to provide the 85 mg (27% yield) of the target compound in 97% purity.

LC-MS (Method 2): $R_t$=1.26 min; MS (ESIpos): m/z=471 $[M+H]^+$ $^1$H-NMR (400 MHz, DMSO-$d_6$) δ [ppm]1.38 (d, 3H), 2.37 (s, 3H), 4.04 (q, 1H), 7.07 (dd, 1H), 7.13-7.22 (m, 2H), 7.26 (ddd, 1H), 7.37-7.48 (m, 2H), 7.82-7.91 (m, 2H), 7.92-7.99 (m, 1H), 8.24 (dd, 1H), 8.32 (d, 1H), 8.37-8.44 (m, 1H), 10.76 (s, 1H), 12.15 (s, 1H).

Example 3

(+)—N-{4-[5-fluoro-6-methyl-3-(pyridin-2-yl)-1H-pyrrolo[3,2-b]pyridin-2-yl]pyridin-2-yl}-2-(4-fluorophenyl)propanamide (Enantiomer 1)

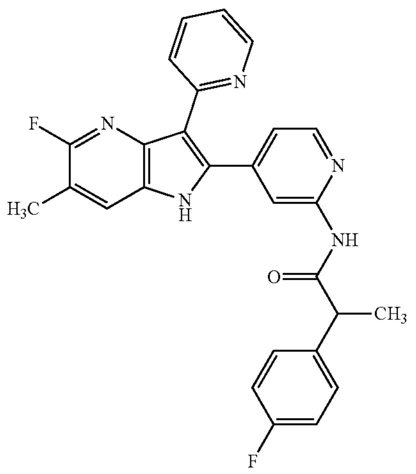 [SMILES: Cc1cc2[nH]c(-c3ccnc(NC(=O)C(C)c4ccc(F)cc4)c3)c(-c3ccccn3)c2nc1F]

The racemic title compound from example 28 (77 mg) was separated into enantiomers by preparative chiral HPLC to give title compound (enantiomer 1, 28 mg, 100% ee) and enantiomer 2 (31 mg, 91.1% ee, see Example 30).

Preparative Chiral HPLC Method:

Instrument: PrepCon Labomatic HPLC-1; Column: YMC Cellulose SB 5 p, 250×30; eluent A: hexane+0.1 vol % diethylamine; eluent B: ethanol+0.1 vol % diethylamine; isocratic: 60% A+40% B; flow: 50 mL/min; temperature: 25° C.; UV: 254 nm;

Analytical Chiral HPLC Method:

Instrument: Thermo Fisher UltiMate 3000; Column: YMC Cellulose SB 3 p, 100×4.6; eluent A: hexane+0.1 vol % diethylamine; eluent B: ethanol; isocratic: 60% A+40% B; flow: 1.4 mL/min; temperature: 25° C.; UV: 254 nm;

Analytical Chiral HPLC: $R_t$=2.21 min.

$[\alpha]_D$=205.54° (from solution in DMSO, c=5.2 mg/mL)

$^1$H-NMR (400 MHz, DMSO-d6) δ[ppm]12.15 (br s, 1H), 10.75 (s, 1H), 8.45-8.37 (m, 1H), 8.32 (d, 1H), 8.24 (dd, 1H), 7.98-7.91 (m, 1H), 7.91-7.83 (m, 2H), 7.47-7.37 (m, 2H), 7.26 (ddd, 1H), 7.21-7.13 (m, 2H), 7.07 (dd, 1H), 4.04 (q, 1H), 2.37 (s, 3H), 1.38 (d, 3H).

Example 4

(−)—N-{4-[5-fluoro-6-methyl-3-(pyridin-2-yl)-1H-pyrrolo[3,2-b]pyridin-2-yl]pyridin-2-yl}-2-(4-fluorophenyl)propanamide (Enantiomer 2)

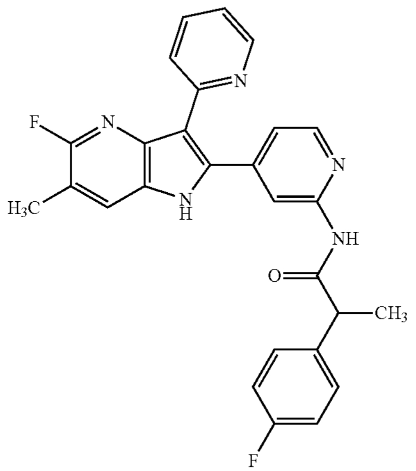 [SMILES: Cc1cc2[nH]c(-c3ccnc(NC(=O)C(C)c4ccc(F)cc4)c3)c(-c3ccccn3)c2nc1F]

For the preparation of the racemic title compound see Example 28. Separation of enantiomers by preparative chiral HPLC (method see Example 29) gave the title compound (31 mg).

Analytical Chiral HPLC (method see Example 29): $R_t$=2.74 min.

$[\alpha]_D$=−176.4° (from solution in DMSO, c=5.4 mg/mL)

$^1$H-NMR (400 MHz, DMSO-$d_6$) δ [ppm]12.44-11.87 (m, 1H), 10.75 (s, 1H), 8.44-8.37 (m, 1H), 8.32 (s, 1H), 8.27-8.21 (m, 1H), 7.97-7.91 (m, 1H), 7.90-7.81 (m, 2H), 7.48-7.37 (m, 2H), 7.26 (ddd, 1H), 7.21-7.14 (m, 2H), 7.07 (dd, 1H), 4.04 (q, 1H), 2.37 (s, 3H), 1.38 (d, 3H).

Example 31

2-(4-fluorophenyl)-N-{4-[7-methoxy-3-(pyridin-2-yl)-1H-pyrrolo[3,2-b]pyridin-2-yl]pyridin-2-yl}acetamide

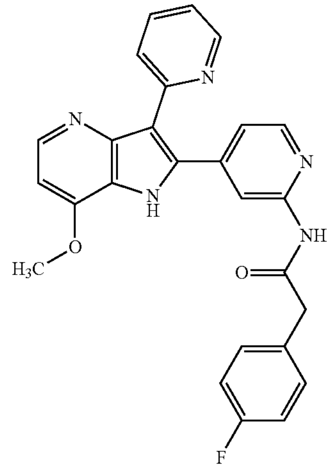 [SMILES: COc1ccnc2c(-c3ccccn3)c(-c3ccnc(NC(=O)Cc4ccc(F)cc4)c3)[nH]c12]

A mixture of 2-(4-fluorophenyl)-N-{4-[7-methoxy-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 50, 46.0 mg, 0.079 mmol) in a mixed solvent of trifluoroacetic acid (5.0 ml) and dichloromethane (5.0 ml) was stirred at room temperature for 16 hours. The mixture was concentrated to give a residue. The residue was purified by preparative HPLC (Instrument: ACSWH-GX-L; Column: Unisil 3-100 $C_{18}$ Ultra 150*50 mm*3 μm; eluent A: water (0.225% formic acid), eluent B: acetonitrile; gradient: 0-10 min 18-38% B; flow 25 ml/min; temperature: room temperature; Detector: UV 220/254 nm) to give 2-(4-fluorophenyl)-N-{4-[7-methoxy-3-(pyridin-2-yl)-1H-pyrrolo[3,2-b]pyridin-2-yl]pyridin-2-yl}acetamide (15 mg, 96% purity, 40% yield) as a yellow solid.

LC-MS (Method C): $R_t$=0.807 min; MS (ESIpos): m/z=454.3 $[M+H]^+$.

$^1$H NMR (400 MHz, $CD_3OD$): δ [ppm]=8.59 (d, J=4.8 Hz, 1H), 8.35 (d, J=6 Hz, 1H), 8.30 (d, J=4.8 Hz, 1H), 8.23 (s, 1H), 7.86-7.81 (m, 1H), 7.56 (d, J=7.6 Hz, 1H), 7.38-7.34 (m, 3H), 7.16 (dd, J=5.2, 1.6 Hz, 1H), 7.09-7.04 (m, 3H), 4.18 (s, 3H), 3.72 (s, 2H).

Example 32

2-(4-fluorophenyl)-N-{4-[5-methoxy-3-(pyridin-2-yl)-1H-pyrrolo[3,2-b]pyridin-2-yl]pyridin-2-yl}acetamide

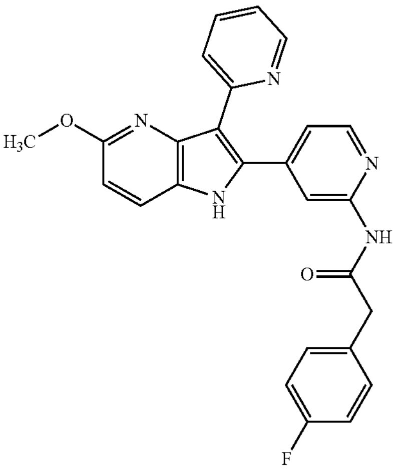 [SMILES: COc1ccc2[nH]c(-c3ccnc(NC(=O)Cc4ccc(F)cc4)c3)c(-c3ccccn3)c2n1]

A solution of 2-(4-fluorophenyl)-N-{4-[5-methoxy-3-(pyridin-2-yl)-1-{[2-(trimethylsilyl)ethoxy]methyl}-1H-pyrrolo[3,2-b]pyridin-2-yl]pyridin-2-yl}acetamide (see Intermediate 57, 28.0 mg, 0.05 mmol) in a mixed solvent of trifluoroacetic acid (1 ml) and dichloromethane (3 ml) was stirred at room temperature for 16 hours. The reaction mixture was concentrated to give a residue. The residue was purified by preparative HPLC (Instrument: Gilson-281; Column: Phenomenex Synergi C18 150*25*10 μm; eluent A: water (0.225% formic acid), eluent B: acetonitrile; gradient: 0-10 min 18-48% B; flow 25 ml/min; temperature: room temperature; Detector: UV 220/254 nm) to give 2-(4-fluorophenyl)-N-{4-[5-methoxy-3-(pyridin-2-yl)-1H-pyrrolo[3,2-b]pyridin-2-yl]pyridin-2-yl)acetamide (18.9 mg, 94% purity, 82% yield) as a yellow solid.

LC-MS (Method H): $R_t$=0.815 min; MS (ESIpos): m/z=453.9 $[M+H]^+$.

$^1$H NMR (400 MHz, DMSO-$d_6$): δ [ppm]=11.93 (s, 1H), 10.77 (s, 1H), 8.39-8.37 (m, 1H), 8.29 (s, 1H), 8.26 (d, J=8.4 Hz, 1H), 8.20 (d, J=8.0 Hz, 1H), 7.86 (td, J=8.0, 2.0 Hz, 1H), 7.79 (d, J=8.8 Hz, 1H), 7.39-7.35 (m, 2H), 7.23-7.20 (m, 1H), 7.18-7.14 (m, 2H), 7.11 (dd, J=5.2, 1.6 Hz, 2H), 6.71 (d, J=8.8 Hz, 1H), 3.90 (s, 3H), 3.72 (s, 2H).

Example 33

N-{4-[7-ethenyl-3-(pyridin-2-yl)-1H-pyrrolo[3,2-b]pyridin-2-yl]pyridin-2-yl}-2-(4-fluorophenyl)acetamide

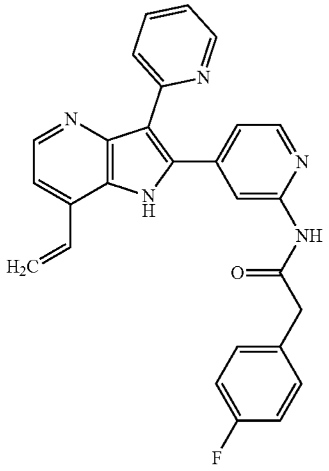

To a solution of 4-[7-ethenyl-3-(pyridin-2-yl)-1H-pyrrolo[3,2-b]pyridin-2-yl]pyridin-2-amine (see Intermediate 60, 100 mg, 86% purity, 0.274 mmol) and (4-fluorophenyl) acetic acid (50.6 mg, 0.329 μmol) in N,N-dimethylformamide (4.0 ml) were added propanephosphonic anhydride (4.0 ml, 50% purity in N,N-dimethylformamide, 550 mmol) and N,N-diisopropylethylamine (0.14 ml, 0.820 mmol). The mixture was stirred at 80° C. for 16 hours. The mixture was poured into water, the organic layer was separated. The aqueous layer was extracted with ethyl acetate. The combined organic layer was washed with brine, dried over anhydrous sodium sulfate, filtered and concentrated to give a residue. The residue was purified by preparative HPLC (Instrument: ACSWH-GX-L; Column: Unisil 3-100 C18 Ultra 150*50 mm*3 μm; eluent A: water (0.225% formic acid), eluent B: acetonitrile; gradient: 0-10 min 20-40% B; flow 25 ml/min; temperature: room temperature; Detector: UV 220/254 nm) to give a crude product. The crude product was purified by preparative HPLC (Instrument: GX-A; Column: Phenomenex Gemini-NX C18 75*30 mm*3 μm; eluent A: water (0.05% ammonia hydroxide), eluent B: acetonitrile; gradient: 0-7 min 26-56% B; flow 25 ml/min; temperature: room temperature; Detector: UV 220/254 nm) to give 2-(4-fluorophenyl)-N-{4-[3-(pyridin-2-yl)-7-vinyl-1H-pyrrolo[3,2-b]pyridin-2-yl]pyridin-2-yl}acetamide (2.5 mg, 92% purity, 2% yield) as a yellow solid.

LC-MS (Method C): $R_t$=0.721 min; MS (ESIpos): m/z=450.1 [M+H]$^+$. $^1$H-NMR (400 MHz, $CD_3OD$): δ [ppm] =12.02 (s, 1H), 10.82 (s, 1H), 8.42 (d, J=4.8 Hz, 1H), 8.38 (d, J=4.8 Hz, 1H), 8.31-8.30 (m, 2H), 8.14 (d, J=7.6 Hz, 1H), 7.86-7.82 (m, 1H), 7.49-7.48 (m, 1H), 7.44-7.35 (m, 3H), 7.24-7.21 (m, 1H), 7.18-7.13 (m, 3H), 6.24 (d, J=17.6 Hz, 1H), 5.66 (d, J=11.2 Hz, 1H), 3.71 (s, 2H).

Example 34

N-{4-[7-ethyl-3-(pyridin-2-yl)-1H-pyrrolo[3,2-b]pyridin-2-yl]pyridin-2-yl}-2-(4-fluorophenyl)acetamide

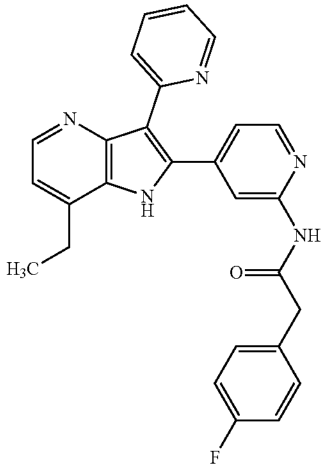

A mixture of N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide (see Intermediate 63, 100 mg, 0.17 mmol) in trifluoroacetic acid (3.0 ml) and dichloromethane (3.0 ml) was stirred at room temperature for 16 hours. The mixture was concentrated, purified by preparative HPLC (Instrument: ACSWH-GX-L; Column: Unisil 3-100 C18 Ultra 150*50 mm*3 μm; eluent A: water (0.225% formic acid), eluent B: acetonitrile; gradient: 0-10 min 23-43% B; flow 25 ml/min; temperature: room temperature; Detector: UV 220/254 nm) to give N-{4-[7-ethyl-3-(pyridin-2-yl)-1H-pyrrolo[3,2-b]pyridin-2-yl]pyridin-2-yl}-2-(4-fluorophenyl)acetamide (62.9 mg, 92% purity, 74% yield) as a yellow solid.

LC-MS (method C): $R_t$=0.824 min; MS (ESIpos): m/z=452.3 [M+H]$^+$.

$^1$H-NMR (400 MHz, MeOD): δ [ppm]=8.68 (d, J=4.4 Hz, 1H), 8.45 (d, J=5.6 Hz, 1H), 8.41 (d, J=5.2 Hz, 1H), 8.36 (s, 1H), 7.83-7.78 (m, 1H), 7.48 (s, 1H), 7.47-7.46 (m, 1H), 7.38-7.35 (m, 3H), 7.27-7.25 (dd, J=5.2 Hz, 1.6 Hz, 1H), 7.08-7.04 (m, 2H), 3.74 (s, 2H), 3.21-3.15 (q, J=7.6 Hz, 2H), 1.45 (t, J=7.6 Hz, 3H).

Example 55

N-{4-[7-cyclopropyl-3-(pyridin-2-yl)-1H-pyrrolo[3,2-b]pyridin-2-yl]pyridin-2-yl}-2-(4-fluorophenyl) acetamide

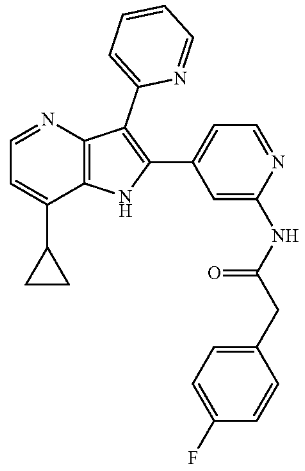 [SMILES: O=C(Cc1ccc(F)cc1)Nc1cc(-c2[nH]c3c(C4CC4)ccnc3c2-c2ccccn2)ccn1]

A mixture of N-{4-[7-cyclopropyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide (see Intermediate 66, 35.0 mg, 0.0589 mmol) in a mixed solvent of trifluoroacetic acid (1.0 ml) and dichloromethane (1.0 ml) was stirred at room temperature for 16 hours. The mixture was concentrated, purified by preparative HPLC (Instrument: GX-R; Column: Waters Xbridge 150*25 mm*5 μm; eluent A: water (10 mM ammonium bicarbonate), eluent B: acetonitrile; gradient: 0-9 min 33-63% B; flow 25 ml/min; temperature: room temperature; Detector: UV 220/254 nm) to give N-{4-[7-cyclopropyl-3-(pyridin-2-yl)-1H-pyrrolo[3,2-b]pyridin-2-yl]pyridin-2-yl}-2-(4-fluorophenyl) acetamide (4.5 mg, 99% purity, 16% yield) as a yellow solid.

LC-MS (method C): $R_t$=0.827 min; MS (ESIpos): m/z=464.3 $[M+H]^+$.

$^1$H-NMR (400 MHz, MeOD): 5 [ppm]=8.51 (d, J=3.6 Hz, 1H), 8.23 (d, J=4.8 Hz, 3H), 7.93-7.89 (m, 1H), 7.69 (d, J=7.6 Hz, 1H), 7.39-7.35 (m, 3H), 7.12-7.05 (m, 3H), 6.79 (d, J=4.8 Hz, 1H), 3.71 (s, 2H), 2.52-2.48 (m, 1H), 1.29-1.22 (m, 2H), 1.01-0.97 (m, 2H).

Example 36

2-(4-fluorophenyl)-N-{4-[7-(2-methoxyethyl)-3-(pyridin-2-yl)-1H-pyrrolo[3,2-b]pyridin-2-yl]pyridin-2-yl}acetamide

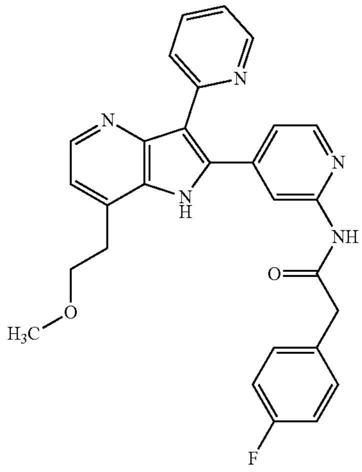 [SMILES: COCCc1ccnc2c(-c3ccccn3)c(-c3ccnc(NC(=O)Cc4ccc(F)cc4)c3)[nH]c12]

2-(4-fluorophenyl)-N-{4-[7-(2-methoxyethyl)-3-(pyridin-2-yl)-1-{[2-(trimethylsilyl)ethoxy]methyl}-1H-pyrrolo[3,2-b]pyridin-2-yl]pyridin-2-yl}acetamide containing a small amount of N-{4-[7-ethyl-3-(pyridin-2-yl)-1-{[2-(trimethylsilyl)ethoxy]methyl}-1H-pyrrolo[3,2-b]pyridin-2-yl]pyridin-2-yl}-2-(4-fluorophenyl)acetamide as an impurity (see Intermediate 69, 30.0 mg) in a mixed solvent of trifluoroacetic acid (3.0 ml) and dichloromethane (3.0 ml) was stirred at room for 16 hours. The mixture was concentrated, purified by preparative HPLC (Instrument: ACSWH-GX-L; Column: Unisil 3-100 $C_{18}$ Ultra 150*50 mm*3 μm; eluent A: water (0.225% formic acid), eluent B: acetonitrile; gradient: 0-10 min 25-43% B; flow 25 ml/min; temperature: room temperature; Detector: UV 220/254 nm) to give 2-(4-fluorophenyl)-N-{4-[7-(2-methoxyethyl)-3-(pyridin-2-yl)-1H-pyrrolo[3,2-b]pyridin-2-yl]pyridin-2-yl}acetamide (2 mg, 84% purity) as a yellow solid.

LC-MS (method C): $R_t$=0.811 min; MS (ESIpos): m/z=482.0 $[M+H]^+$.

$^1$H-NMR (400 MHz, $CD_3OD$): δ [ppm]=8.64-8.63 (m, 1H), 8.40 (d, J=4.4 Hz, 1H), 8.36 (d, J=5.2 Hz, 1H), 8.25 (s, 1H), 7.89-7.86 (m, 1H), 7.55-7.53 (m, 1H), 7.42-7.35 (m, 4H), 7.25-7.23 (m, 1H), 7.10-7.06 (m, 2H), 3.86 (t, J=6.4 Hz, 2H), 3.75 (s, 2H), 3.39-3.36 (m, 5H).

Example 37

N-{4-[7-(cyclopropylmethyl)-5-fluoro-3-(pyridin-2-yl)-1H-pyrrolo[3,2-b]pyridin-2-yl]pyridin-2-yl}-2-(4-fluorophenyl)acetamide

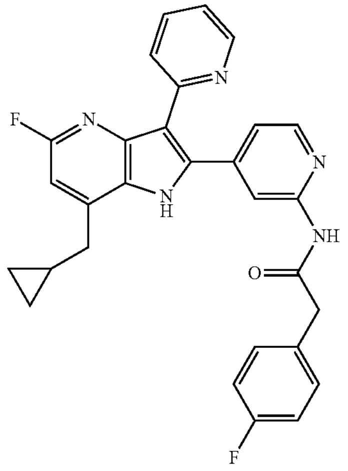 [SMILES: O=C(Cc1ccc(F)cc1)Nc1cc(-c2[nH]c3c(CC4CC4)cc(F)nc3c2-c2ccccn2)ccn1]

To a mixture of 2-(2-bromopyridin-4-yl)-7-(cyclopropylmethyl)-5-fluoro-3-(pyridin-2-yl)-1H-pyrrolo[3,2-b]pyridine (see Intermediate 78, 100 mg, 0.236 mmol) and 2-(4-fluorophenyl)acetamide (see Intermediate 79, 72.4 mg, 0.472 mmol) in N,N-dimethylformamide (5.0 ml) were added (9,9-dimethyl-9H-xanthene-4,5-diyl)bis(diphenylphosphine) (13.7 mg, 0.0236 mmol), palladium(II) acetate (5.30 mg, 0.0236 mmol) and cesium carbonate (154 mg, 0.472 mmol) at 25° C. After stirring at 100° C. for 16 hours under nitrogen atmosphere, the reaction mixture (combined with a batch starting from 20 mg Example 37) was poured into water and extracted with ethyl acetate. The organic phase was washed with brine, dried over anhydrous sodium sulfate, filtered and concentrated to give a residue. The residue was purified by flash silica gel column (10% methanol in ethyl acetate:petroleum ether=1:1 to 2:1) to give a crude product. The crude product was further purified by preparative HPLC (Instrument:ACSWH-GX-L; Column: Unisil 3-100 C18 Ultra 150*50 mm*3 μm; eluent A: water (0.225% formic acid), eluent B: acetonitrile; gradient: 0-10 min 28-48% B; flow 25 ml/min; temperature: room temperature; Detector: UV 220/254 nm) to give N-{4-[7-(cyclopropylmethyl)-5-fluoro-3-(pyridin-2-yl)-1H-pyrrolo[3,2-b]pyridin-2-yl]pyridin-2-yl}-2-(4-fluorophenyl)acetamide (10.9 mg, 98% purity) as a white solid.

LC-MS (Method C): $R_t$=0.774 min; MS (ESIpos): m/z=596.1 $[M+H]^+$ $^1$H NMR (400 MHz, $CD_3OD$): δ [ppm]=8.47 (d, J=4.8 Hz, 1H), 8.23 (d, J=5.2 Hz, 1H), 8.21 (s, 1H), 7.90 (td, J=7.6, 1.6 Hz, 1H), 7.74 (d, J=7.6 Hz, 1H), 7.38-7.33 (m, 3H), 7.09-7.07 (m, 3H), 6.95 (s, 1H), 3.71 (s, 2H), 2.97 (d, J=7.2 Hz, 2H), 1.29-1.23 (m, 1H), 0.67-0.62 (m, 2H), 0.36-0.32 (m, 2H).

Example 38

2-(4-fluorophenyl)-N-{4-[7-(4-methylpiperazin-1-yl)-3-(pyridin-2-yl)-1H-pyrrolo[3,2-b]pyridin-2-yl]pyridin-2-yl}acetamide

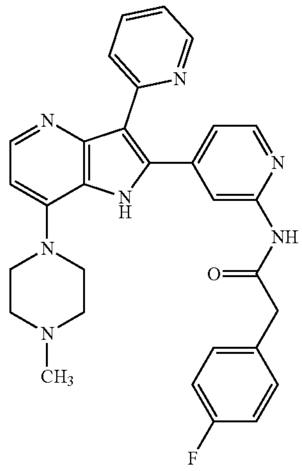 [SMILES: CN1CCN(c2ccnc3c(-c4ccccn4)c(-c4ccnc(NC(=O)Cc5ccc(F)cc5)c4)[nH]c23)CC1]

To a solution of 4-[7-(4-methylpiperazin-1-yl)-3-(pyridin-2-yl)-1H-pyrrolo[3,2-b]pyridin-2-yl]pyridin-2-amine (see Intermediate 80, 100 mg, 0.259 mmol) and (4-fluorophenyl) acetic acid (80.0 mg, 0.519 mmol) in N,N-dimethylformamide (3.0 ml) were added 2-(7-azabenzotriazol-1-yl)-N,N,N',N'-tetramethyluronium hexafluorophosphate (HATU, 296 mg, 0.778 mmol) and N,N-diisopropylethylamine (0.450 ml, 1.3 mmol) at 25° C. After stirring at room temperature for 16 hours, the mixture was poured into water and extracted with ethyl acetate. The combined organic layers were washed with brine, dried over anhydrous sodium sulfate, filtered and concentrated to give a residue. The residue was purified by flash column chromatography (10% methanol in ethyl acetate:petroleum ether=1:9~1:0, then ethyl acetate:methanol=5:1) to give 2-(4-fluorophenyl)-N-{4-[7-(4-methylpiperazin-1-yl)-3-(pyridin-2-yl)-1H-pyrrolo[3,2-b]pyridin-2-yl]pyridin-2-yl}acetamide (54.6 mg, 98% purity, 39% yield) as a yellow solid.

LC-MS (Method C): $R_t$=0.744 min; MS (ESIpos): m/z=522.1 $[M+H]^+$.

$^1$H NMR (400 MHz, $CD_3OD$): δ [ppm]=8.53 (d, J=4.4 Hz, 1H), 8.25-8.22 (m, 2H), 8.15 (d, J=6.0 Hz, 1H), 7.85-7.81 (m, 1H), 7.56 (d, J=7.6 Hz, 1H), 7.38-7.30 (m, 3H), 7.12 (dd, J=5.2, 1.2 Hz, 1H), 7.09-7.04 (m, 2H), 6.81 (d, J=6.0 Hz, 1H), 3.71 (s, 2H), 3.58-3.53 (m, 4H), 2.74 (t, J=4.8 Hz, 4H), 2.40 (s, 3H).

Example 39

2-(4-fluorophenyl)-N-(4-{7-[methyl(1-methylpiperidin-4-yl)amino]-3-(pyridin-2-yl)-1H-pyrrolo[3,2-b]pyridin-2-yl}pyridin-2-yl)acetamide

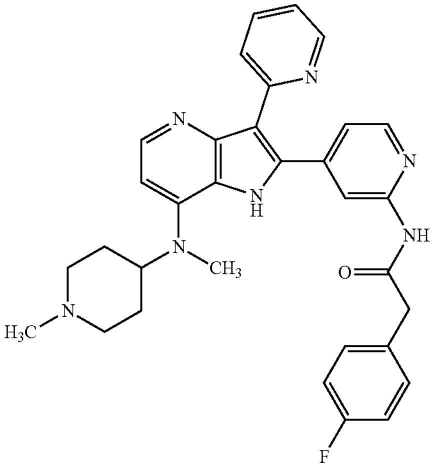 [SMILES: CN1CCC(N(C)c2ccnc3c(-c4ccccn4)c(-c4ccnc(NC(=O)Cc5ccc(F)cc5)c4)[nH]c23)CC1]

To a solution of 2-(2-aminopyridin-4-yl)-N-methyl-N-(1-methylpiperidin-4-yl)-3-(pyridin-2-yl)-1H-pyrrolo[3,2-b]pyridin-7-amine (see Intermediate 81, 60.0 mg, 77% purity, 0.11 mmol) and (4-fluorophenyl)acetic acid (51.7 mg, 0.34 mmol) in N,N-dimethylformamide (2.0 ml) were added 2-(7-azabenzotriazol-1-yl)-N,N,N',N'-tetramethyluronium hexafluorophosphate (HATU, 170 mg, 0.45 mmol) and N,N-diisopropylethylamine (0.160 ml, 0.89 mmol) at 25° C. After stirring at room temperature for 16 hours, the mixture was poured into water, extracted with ethyl acetate. The combined organic layers were washed with brine, dried over anhydrous sodium sulfate, filtered and concentrated to give a residue. The residue was purified by flash column chromatography (10% methanol in ethyl acetate:petroleum ether=0:1 to 1:0, then ethyl acetate:methanol:ammonium hydroxide=5:1:1) to give a crude product. The crude product was purified by preparative HPLC (Instrument: ACSWH-GX-L; Column: Unisil 3-100 C18 Ultra 150*50 mm*3 μm; eluent A: water (0.225% formic acid), eluent B: acetonitrile; gradient: 0-10 min 13-33% B; flow 25 ml/min; temperature: room temperature; Detector: UV 220/254 nm) to give 2-(4-fluorophenyl)-N-(4-{7-[methyl(1-methylpiperidin-4-yl)amino]-3-(pyridin-2-yl)-1H-pyrrolo[3,2-b]pyridin-2-yl}pyridin-2-yl)acetamide (14.5 mg, 94% purity, 22% yield) as a yellow solid.

LC-MS (Method C): $R_t$=0.740 min; MS (ESIpos): m/z=550.5 $[M+H]^+$.

$^1$H-NMR (400 MHz, DMSO-$d_6$): δ [ppm]=10.65 (s, 1H), 8.52 (d, J=7.6 Hz, 2H), 8.25-8.24 (m, 2H), 7.89-7.70 (m, 1H), 7.66-7.53 (m, 1H), 7.39-7.35 (m, 2H), 7.25 (d, J=4.8 Hz, 1H), 7.16-7.11 (m, 2H), 7.08-7.03 (m, 1H), 6.48-6.27 (m, 1H), 3.72 (s, 2H), 3.09 (s, 3H), 2.83 (d, J=10.8 Hz, 2H), 2.14-2.11 (m, 5H), 1.89-1.86 (m, 2H), 1.74-1.71 (m, 2H).

Example 40

2-(4-fluorophenyl)-N-{4-[7-(2-oxopyrrolidin-1-yl)-3-(pyridin-2-yl)-1H-pyrrolo[3,2-b]pyridin-2-yl]pyridin-2-yl}acetamide

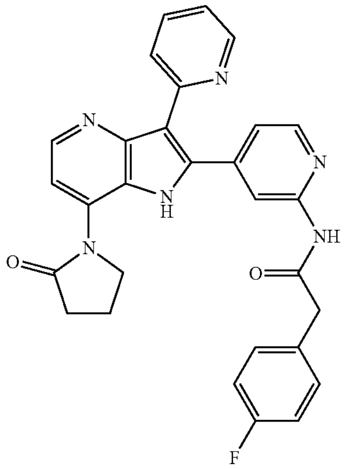 [SMILES: O=C(Cc1ccc(F)cc1)Nc1cc(-c2[nH]c3c(N4CCCC4=O)ccnc3c2-c2ccccn2)ccn1]

To a solution of 1-[2-(2-aminopyridin-4-yl)-3-(pyridin-2-yl)-1H-pyrrolo[3,2-b]pyridin-7-yl]pyrrolidin-2-one (see Intermediate 84, 90 mg, 0.24 mmol) and (4-fluorophenyl)acetic acid (44.9 mg, 0.30 mmol) in N,N-dimethylformamide (2.0 ml) were added 2-(7-Azabenzotriazol-1-yl)-N,N,N',N'-tetramethyluronium hexafluorophosphate (HATU, 185 mg, 49 mmol) and N,N-diisopropylethylamine (0.130 ml, 0.73 mmol) at 25° C. After stirring at 25° C. for 16 hours, water and ethyl acetate were added and separated. The organic phase was dried over anhydrous sodium sulfate, filtered and concentrated to give a residue. The residue was purified by preparative HPLC (Instrument: ACSWH-GX-k; Column: Phenomenex Gemini-NX C18 75*30 mm*3 μm; eluent A: water (0.225% formic acid), eluent B: acetonitrile; gradient: 0-7 min 15-45% B; flow 25 ml/min; temperature: room temperature; Detector: UV 220/254 nm) to give 2-(4-fluorophenyl)-N-{4-[7-(2-oxopyrrolidin-1-yl)-3-(pyridin-2-yl)-1H-pyrrolo[3,2-b]pyridin-2-yl]pyridin-2-yl}acetamide (1 mg, 97% purity) as a yellow solid.

LC-MS (Method C): $R_t$=0.817 min; MS (ESIpos): m/z=507.4 $[M+H]^+$.

$^1$H NMR (400 MHz, DMSO-d6): δ [ppm]=11.37 (s, 1H), 10.80 (s, 1H), 8.42 (d, J=5.2 Hz, 1H), 8.39 (d, J=4.4 Hz, 1H), 8.31 (d, J=5.2 Hz, 1H), 8.26 (s, 1H), 8.12 (d, J=8 Hz, 1H), 7.87-7.82 (m, 1H), 7.38-7.34 (m, 2H), 7.25-7.22 (m, 1H), 7.17-7.12 (m, 4H), 3.99-3.96 (m, 2H), 3.71 (s, 2H), 2.60-2.56 (m, 2H), 2.23-2.17 (m, 2H).

Example 41

2-(4-fluoro-3-methylphenyl)-N-{4-[3-(pyridin-2-yl)-1H-pyrrolo[3,2-b]pyridin-2-yl]pyridin-2-yl}acetamide

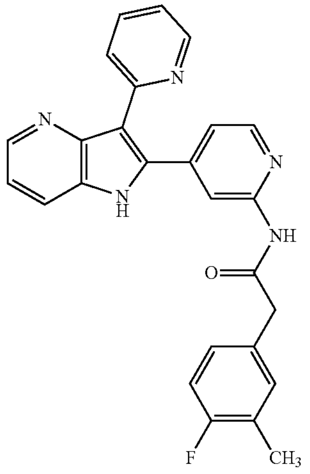 [SMILES: Cc1cc(CC(=O)Nc2cc(-c3[nH]c4cccnc4c3-c3ccccn3)ccn2)ccc1F]

4-[3-(pyridin-2-yl)-1H-pyrrolo[3,2-b]pyridin-2-yl]pyridin-2-amine (see Intermediate 13, 150 mg, 522 μmol), (4-fluoro-3-methylphenyl)acetic acid (105 mg, 626 μmol) and PyBOP (326 mg, 626 μmol; CAS-RN:[128625-52-5]) in dichloromethane (6.0 ml) was treated with N,N-diisopropylethylamine (360 μl, 2.1 mmol; CAS-RN:[7087-68-5]) and stirred at r.t. for 96 h. The reaction mixture was partitioned between dichloromethane and water. The aqueous layer was extracted with dichloromethane twice. The combined organic layer was washed with half-saturated brine three times, dried over a hydrophobic filter paper, concentrated and purified by preparative HPLC (Instrument: Waters Acquity UPLC SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm). The crude product was dissolved in dichloromethane, washed with aqueous sodium hydrogencarbonate solution (1.0 M), dried over a hydrophobic filter paper and evaporated to give 18.0 mg (95% purity, 7% yield) of the title compound as a white solid.

LC-MS (Method 1): $R_t$=0.92 min; MS (ESIneg): m/z=436 $[M-H]^-$ $^1$H-NMR (400 MHz, DMSO-d6): δ [ppm]=12.38-11.87 (m, 1H), 10.83-10.57 (m, 1H), 8.43-8.32 (m, 3H), 8.24 (br d, 1H), 8.15 (d, 1H), 7.87-7.76 (m, 2H), 7.26-7.21 (m, 1H), 7.21-7.13 (m, 4H), 7.08 (dd, 1H), 3.66 (s, 2H), 2.22 (d, 3H).

Example 46

2-(4-chlorophenyl)-N-{4-[3-(pyridin-2-yl)-1H-pyrrolo[3,2-b]pyridin-2-yl]pyridin-2-yl}acetamide

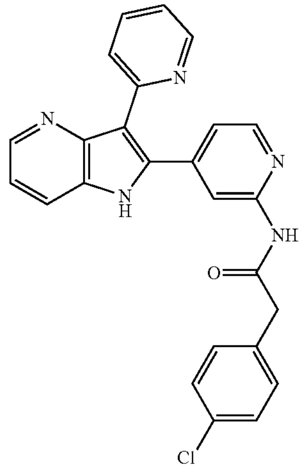

4-[3-(pyridin-2-yl)-1H-pyrrolo[3,2-b]pyridin-2-yl]pyridin-2-amine (see Intermediate 13, 200 mg, 696 μmol), (4-chlorophenyl)acetic acid (142 mg, 835 μmol) and PyBOP (435 mg, 835 μmol; CAS-RN:[128625-52-5]) in a mixture of dichloromethane (4.0 ml) and DMF (1.0 ml) was treated with N,N-diisopropylethylamine (480 μl, 2.8 mmol; CAS-RN:[7087-68-5]) and stirred at r.t. for 18 h. The reaction mixture was partitioned between dichloromethane and water. The aqueous layer was extracted with dichloromethane twice. The combined organic layer was washed with half-saturated brine three times, dried over a hydrophobic filter paper, concentrated and purified by silica gel flash chromatography (gradient hexane/ethyl acetate 10-90%) and preparative HPLC (Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm) to give 12.0 mg (95% purity, 4% yield) of the title compound.

LC-MS (Method 1): $R_t$=0.89 min; MS (ESIneg): m/z=438 $[M-H]^-$ $^1$H-NMR (400 MHz, DMSO-d6): δ [ppm]=12.07 (s, 1H), 10.84 (s, 1H), 8.44 (dd, 1H), 8.42-8.39 (m, 1H), 8.32 (s, 1H), 8.30-8.27 (m, 1H), 8.15-8.09 (m, 1H), 7.89-7.82 (m, 2H), 7.43-7.33 (m, 4H), 7.28-7.21 (m, 2H), 7.14 (dd, 1H), 3.73 (s, 2H).

Example 43

(2RS)—2-(4-fluorophenyl)-3-methoxy-N-(4-(3-(pyridin-2-yl)-1H-pyrrolo[3,2-b]pyridin-2-yl)pyridin-2-yl)propanamide (Racemate)

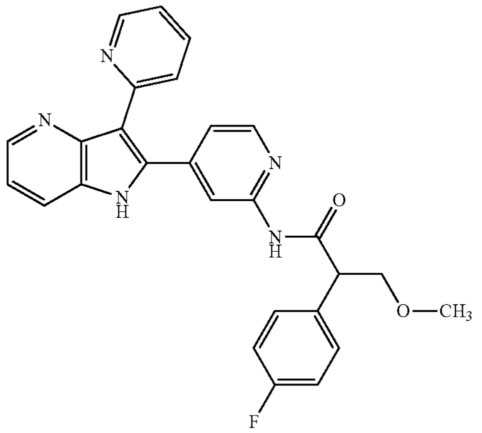 [SMILES: COCC(C(=O)Nc1cc(-c2[nH]c3cccnc3c2-c2ccccn2)ccn1)c1ccc(F)cc1]

2-(4-fluorophenyl)-3-methoxy-propanoic acid (see Intermediate 86, 82.8 mg, 417 μmol) was dissolved in pyridine (1 mL). 4-[3-(pyridin-2-yl)-1H-pyrrolo[3,2-b]pyridin-2-yl]pyridin-2-amine (see Intermediate 13, 60.0 mg, 208 μmol) and 1-ethyl-3-(3-dimethylaminopropyl)carbodiimide (120 mg, 626 μmol, CAS-RN: [1892-57-5]) were added in one portion. The reaction mixture was stirred at 25° C. for 12 h. The reaction mixture was diluted by the addition of water (1 mL), and then extracted with ethyl acetate three times. The combined organic layers were washed with brine three times, dried over sodium sulfate, filtered, and concentrated under reduced pressure to give a residue. The crude residue was purified by reverse phase preparative-HPLC (column: Phenomenex luna C18 150*25 mm*10 μm; mobile phase: [water (0.225% FA)-ACN]; B %: 12%-42%, 11.5 min) to provide 18.0 mg of the title compound (97% purity, 18% yield).

LC-MS (Method 3): $R_t$=1.26 min; MS (ESIpos): m/z=467 $[M+H]^+$.

$^1$H-NMR (400 MHz, DMSO-d6) δ[ppm]12.09 (s, 1H), 10.83 (s, 1H), 8.45 (d, J=4.0 Hz, 1H), 8.42-8.35 (m, 2H), 8.26 (d, J=5.2 Hz, 1H), 8.16-8.10 (m, 1H), 7.92-7.81 (m, 2H), 7.43 (dd, J=5.6, 8.4 Hz, 2H), 7.29-7.22 (m, 2H), 7.18 (t, J=8.8 Hz, 2H), 7.12 (br d, J=4.4 Hz, 1H), 4.24 (br dd, J=5.2, 9.2 Hz, 1H), 3.95 (t, J=9.2 Hz, 1H), 3.48 (br d, J=5.2 Hz, 1H), 3.26 (s, 3H).

Example 44

(2RS)-4-methoxy-2-phenyl-N-(4-(3-(pyridin-2-yl)-1H-pyrrolo[3,2-b]pyridin-2-yl)pyridin-2-yl)butanamide (Racemate)

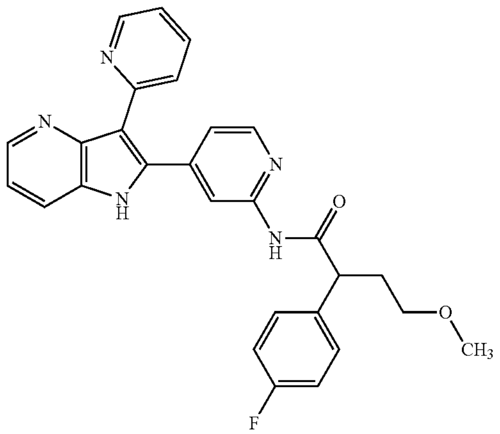 [SMILES: COCCC(C(=O)Nc1cc(-c2[nH]c3cccnc3c2-c2ccccn2)ccn1)c1ccc(F)cc1]

2-(4-fluorophenyl)-4-methoxy-butanoic acid (see Intermediate 87, 36.9 mg, 174 μmol) and 4-[3-(pyridin-2-yl)-1H-pyrrolo[3,2-b]pyridin-2-yl]pyridin-2-amine (see Intermediate 13, 50.0 mg, 174 μmol) were dissolved in pyridine (0.5 mL). T3P (332 mg, 522 μmol, 50% purity, CAS-RN: [68957-94-8]) was added, and the reaction mixture was stirred at 25° C. for 16 h. The reaction mixture was concentrated under reduced pressure, and the crude residue was directly purified by reverse phase preparative-HPLC (column: Phenomenex luna C18 150*25 mm*10 μm; mobile phase: [water (0.225% FA)-ACN]; B %: 12%-42%, 11.5 min) to provide 29 mg of the title compound (98% purity, 31% yield).

LC-MS (Method 3): $R_t$=1.287 min; MS (ESIpos): m/z=482 $[M+H]^+$.

$^1$H-NMR (400 MHz, DMSO-d6) δ[ppm]12.28-12.10 (m, 1H), 10.79 (s, 1H), 8.47 (dd, J=1.2, 4.4 Hz, 1H), 8.45-8.40 (m, 1H), 8.35 (s, 1H), 8.28 (d, J=5.2 Hz, 1H), 8.10-8.04 (m, 1H), 7.93 (br d, J=8.4 Hz, 1H), 7.87 (dt, J=1.6, 7.6 Hz, 1H), 7.47-7.40 (m, 2H), 7.34-7.25 (m, 2H), 7.23-7.11 (m, 3H), 4.06 (br dd, J=6.8, 8.8 Hz, 1H), 3.25 (br d, J=6.4 Hz, 2H), 3.20 (s, 3H), 2.31-2.20 (m, 1H), 1.93-1.78 (m, 1H), 1.74-1.60 (m, 3H), 1.58-1.45 (m, 4H), 0.99-0.91 (m, 5H).

Example 45

(2RS)—2-(4-fluorophenyl)-N-[4-[6-fluoro-3-(2-pyridyl)-1H-pyrrolo[3,2-b]pyridin-2-yl]-2-pyridyl]-3-methoxy-propanamide (Racemate)

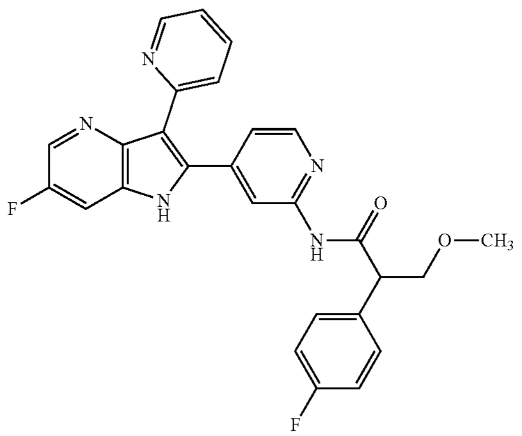 [SMILES: COCC(C(=O)Nc1cc(-c2[nH]c3cc(F)cnc3c2-c2ccccn2)ccn1)c1ccc(F)cc1]

4-[6-fluoro-3-(pyridin-2-yl)-1H-pyrrolo[3,2-b]pyridin-2-yl]pyridin-2-amine (see Intermediate 17, 60.0 mg, 196 μmol) and 2-(4-fluorophenyl)-3-methoxy-propanoic acid (see Intermediate 86, 116 mg, 589 μmol) were dissolved in pyridine (1 mL). 1-Ethyl-3-(3-dimethylaminopropyl)carbodiimide (113 mg, 589 μmol, CAS-RN: [1892-57-5]) was added in one portion. The reaction mixture was stirred at 25° C. for 16 h, then the reaction mixture was quenched by the addition of saturated aqueous ammonium chloride, and extracted with ethyl acetate three times. The combined organic layers were washed with brine three times, dried over sodium sulfate, filtered, and concentrated under reduced pressure to give a crude residue. The crude mixture was purified by reverse phase preparative-HPLC (column: Phenomenex luna C18 150*25 mm*10 μm; mobile phase: [water (0.225% FA)-ACN]; B %: 15%-45% over 11.5 min) to provide 22.7 mg of the title compound (98% purity, 24% yield).

LC-MS (Method 3): $R_t$=1.31 min; MS (ESIpos): m/z=486 $[M+H]^+$.

$^1$H-NMR (400 MHz, DMSO-d6) δ=12.24 (s, 1H), 10.84 (s, 1H), 8.46 (dd, J=1.2, 2.4 Hz, 1H), 8.43-8.39 (m, 1H), 8.37 (s, 1H), 8.26 (d, J=5.2 Hz, 1H), 8.04 (d, J=8.0 Hz, 1H), 7.86 (dt, J=2.0, 7.6 Hz, 1H), 7.75 (dd, J=2.4, 9.2 Hz, 1H), 7.46-7.38 (m, 2H), 7.27 (ddd, J=1.2, 5.6, 6.8 Hz, 1H), 7.22-7.14 (m, 2H), 7.10 (dd, J=1.2, 5.2 Hz, 1H), 4.23 (dd, J=5.2, 9.6 Hz, 1H), 3.95 (t, J=9.2 Hz, 1H), 3.47 (dd, J=5.2, 9.2 Hz, 1H), 3.26 (s, 3H).

Example 46

2-phenyl-N-(4-(3-(pyridin-2-yl)-1H-pyrrolo[3,2-b]pyridin-2-yl)pyridin-2-yl)acetamide

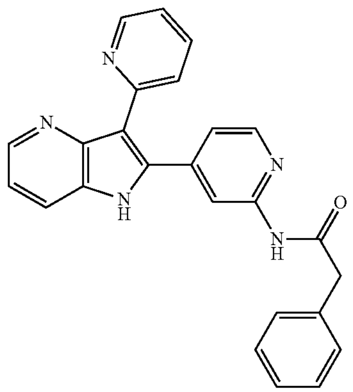 [SMILES: O=C(Cc1ccccc1)Nc1cc(-c2[nH]c3cccnc3c2-c2ccccn2)ccn1]

4-[3-(2-pyridyl)-1H-pyrrolo[3,2-b]pyridin-2-yl]pyridin-2-amine (see Intermediate 13, 50.0 mg, 174 μmol) and phenylacetic acid (28.4 mg, 208 μmol, CAS-RN: [103-82-2]) were dissolved in 0.5 mL of DMF. N,N,-diisopropylethylamine (60.6 μL, 348 μmol, CAS-RN: [7087-68-5]) and PyBOP (136 mg, 261 μmol, CAS-RN: [128625-52-5]) were added. The reaction mixture was stirred at 25° C. for 2 h. The reaction mixture was diluted by the addition of 1 mL of H2O, and then extracted with EtOAc (3×3 mL). The combined organic layers were dried over Na2SO4, filtered, and concentrated under reduced pressure to give a residue. The crude residue was purified by reverse phase preparative-HPLC (column: Shim-pack C18 150*25*10 μm; mobile phase: [water (0.225% FA)-ACN]; B %: 20%-40%, 10 min) and lyophilized to provide the title compound in 98% purity: 8.13 mg, 11% yield.

LC-MS (Method 4): $R_t$=0.956 min; MS (ESIpos): m/z=406.0 $[M+H]^+$.

1H NMR (400 MHz, DMSO-d6) δ[ppm]12.08 (s, 1H), 10.81 (s, 1H), 8.46-8.44 (m, 1H), 8.43-8.40 (m, 1H), 8.34 (s, 1H), 8.29 (d, J=5.2 Hz, 1H), 8.13 (d, J=8.0 Hz, 1H), 7.89-7.83 (m, 2H), 7.37-7.31 (m, 4H), 7.28-7.23 (m, 3H), 7.15-7.13 (m, 1H), 3.73 (s, 2H).

Example 47

4,4-difluoro-N-{4-[5-fluoro-3-(5-fluoropyridin-2-yl)-1H-pyrrolo[3,2-b]pyridin-2-yl]pyridin-2-yl}-2-(4-fluorophenyl)butanamide

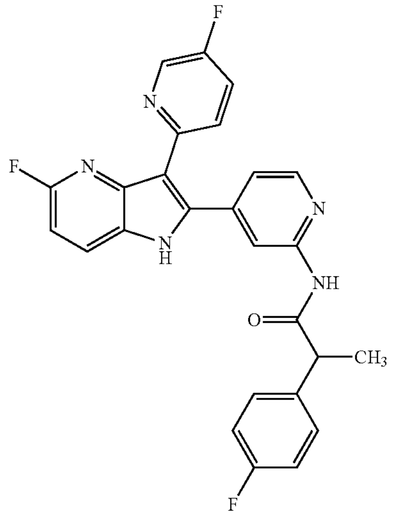 [SMILES: CC(C(=O)Nc1cc(-c2[nH]c3ccc(F)nc3c2-c2ccc(F)cn2)ccn1)c1ccc(F)cc1]

4-[5-Fluoro-3-(5-fluoropyridin-2-yl)-1H-pyrrolo[3,2-b]pyridin-2-yl]pyridin-2-amine (Intermediate 46, 100 mg, 309 μmol), 2-(4-fluorophenyl)propanoic acid (78.0 mg, 464 μmol, CAS RN:[75908-73-5]), N,N-diisopropylethylamine (320 μl, 1.9 mmol) and PyBOP (483 mg, 928 μmol; CAS-RN:[128625-52-5]) were dissolved in DMA (1.8 ml) and stirred at rt under an Argon atmosphere over night. The reaction mixture was diluted with DCM and half saturated sodium hydrogencarbonate solution. The mixture was stirred for 10 minutes, phases were separated and the aqueous layer extracted with DCM. The combined organic layer was filtered through a water impermeable filter and concentrated under reduced pressure. The crude product was purified by HPLC chromatography (method K, gradient: 0.00-0.50 min 30% B, 0.50-6.00 min 30-70% B) to yield 62 mg (98% purity, 41% yield) of the title compound.

LC-MS (Method 2): $R_t$=1.25 min; MS (ESIpos): m/z=474.3 $[M+H]^+$ $^1$H NMR (400 MHz, DMSO-$d_6$) δ [ppm]ppm 1.38 (d, 3H), 4.04 (q, 1H), 7.01 (dd, 1H), 7.10 (dd, 1H), 7.13-7.20 (m, 2H), 7.38-7.45 (m, 2H), 7.83 (dt, 1H), 8.00 (dd, 1H), 8.04 (dd 1H), 8.27-8.31 (m, 2H), 8.41 (d, 1H), 10.78 (s, 1H), 12.35 (s, 1H).

Example 48

(+)—N-{4-[5-fluoro-3-(5-fluoropyridin-2-yl)-1H-pyrrolo[3,2-b]pyridin-2-yl]pyridin-2-yl}-2-(4-fluorophenyl)propanamide (Enantiomer 1)

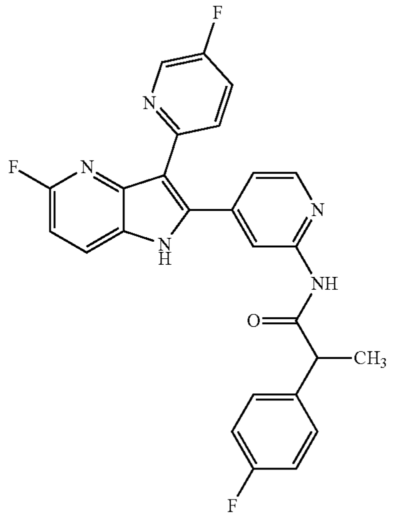 [SMILES: CC(C(=O)Nc1cc(-c2[nH]c3ccc(F)nc3c2-c2ccc(F)cn2)ccn1)c1ccc(F)cc1]

The racemic title compound from example 47 (51 mg) was separated into enantiomers by preparative chiral HPLC to give title compound (enantiomer 1, 18 mg, 99% ee) and enantiomer 2 (17 mg, 99% ee, see example 49).

Preparative Chiral HPLC Method:

Instrument: PrepCon Labomatic HPLC-4; Column: YMC Cellulose SB 10p, 250×50; eluent A: hexane+0.1 vol % diethylamine; eluent B: ethanol; isocratic: 70% A+30% B; flow: 90 ml/min; temperature: 25° C.; UV: 254 nm.

Analytical Chiral HPLC Method:

Instrument: Thermo Fisher UltiMate 3000; Column: YMC Cellulose SB 3p, 100×4.6; eluent A: hexane+0.1 vol % diethylamine; eluent B: ethanol; isocratic: 70% A+30% B; flow: 1.4 ml/min; temperature: 60° C.; UV: 254 nm.

Analytical Chiral HPLC: $R_t$=3.96 min.

$[\alpha]_D$=+166,1° (from solution in DMSO, c=6.1 mg/mL).

$^1$H NMR (400 MHz, DMSO-$d_6$) δ [ppm]1.38 (d, 3H), 4.04 (q, 1H), 7.01 (dd, 1H), 7.10 (dd, 1H), 7.13-7.19 (m, 2H), 7.39-7.44 (m, 2H), 7.83 (dt, 1H), 8.00 (dd, 1H), 8.04 (dd, 1H), 8.29 (dd, 1H), 8.29 (s, 1H), 8.41 (d, 1H), 10.78 (s, 1H), 12.35 (br s, 1H).

Example 49

(−)—N-{4-[5-fluoro-3-(5-fluoropyridin-2-yl)-1H-pyrrolo[3,2-b]pyridin-2-yl]pyridin-2-yl}-2-(4-fluorophenyl)propanamide (Enantiomer 2)

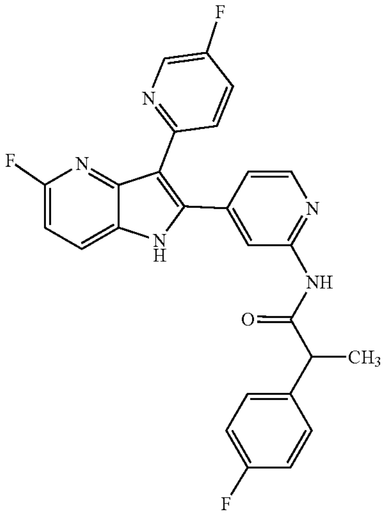 [SMILES: CC(C(=O)Nc1cc(-c2[nH]c3ccc(F)nc3c2-c2ccc(F)cn2)ccn1)c1ccc(F)cc1]

For the preparation of the racemic title compound see Example 47. Separation of enantiomers by preparative chiral HLPC (method see Example 48) gave the title compound (17 mg, 99% ee).

Analytical Chiral HPLC (method see Example 48): $R_t$=1.67 min.

$[\alpha]_D$=−182.4 (from solution in DMSO, c=5.4 mg/mL).

$^1$H NMR (400 MHz, DMSO-$d_6$) δ [ppm]1.38 (d, 3H), 4.04 (q, 1H), 7.01 (dd, 1H), 7.10 (dd, 1H), 7.12-7.19 (m, 2H), 7.36-7.45 (m, 2H), 7.83 (dt, 1H), 8.00 (dd, 1H), 8.04 (dd, 1H), 8.26-8.31 (m, 2H), 8.41 (d, 1H), 10.78 (s, 1H), 12.35 (br s, 1H).

Example 50

N-{4-[5-fluoro-3-(5-fluoropyridin-2-yl)-1H-pyrrolo[3,2-b]pyridin-2-yl]pyridin-2-yl}-2-(4-fluorophenyl)acetamide

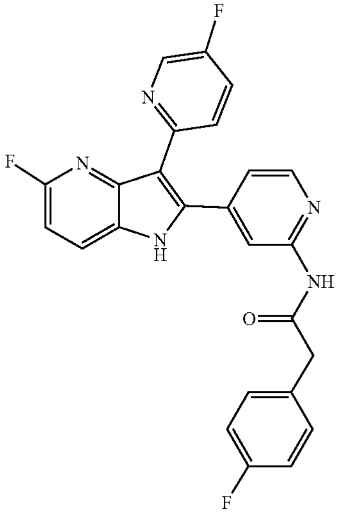 [SMILES: O=C(Cc1ccc(F)cc1)Nc1cc(-c2[nH]c3ccc(F)nc3c2-c2ccc(F)cn2)ccn1]

4-[5-Fluoro-3-(5-fluoropyridin-2-yl)-1H-pyrrolo[3,2-b]pyridin-2-yl]pyridin-2-amine (Intermediate 46, 100 mg, 309 μmol), (4-fluorophenyl)acetic acid (71.5 mg, 464 μmol, CAS-RN:[405-50-5]), N,N-diisopropylethylamine (320 μl, 1.9 mmol) and PyBOP (483 mg, 928 μmol; CAS-RN: [128625-52-5]) were dissolved in DMA (1.8 ml) and stirred at rt under an Argon atmosphere over night. The reaction mixture was diluted with DCM and half saturated sodium hydrogencarbonate solution. Phases were separated and the aqueous layer extracted with DCM. The combined organic layer was filtered through a water impermeable filter and concentrated under reduced pressure. The crude product was purified by HPLC chromatography (method K, gradient: 0.00-0.50 min 30% B, 0.50-6.00 min 30-70% B) to yield 54 mg (97% purity, 37% yield) of the title compound.

LC-MS (Method 2): $R_t$=1.17 min; MS (ESIpos): m/z=460 $[M+H]^+$ $^1$H NMR (400 MHz, DMSO-$d_6$) δ [ppm]3.71 (s, 2H), 7.00 (dd, 1H), 7.12 (dd, 1H), 7.13-7.18 (m, 2H), 7.33-7.39 (m, 2H), 7.82 (dt, 1H), 8.00 (dd, 1H), 8.03 (dd, 1H), 8.27 (s, 1H), 8.31 (dd, 1H), 8.43 (d, 1H), 10.83 (s, 1H), 12.34 (s, 1H).

Example 51

2-(4-fluorophenyl)-N-{4-[3-(pyrimidin-2-yl)-1H-pyrrolo[3,2-b]pyridin-2-yl]pyridin-2-yl}acetamide

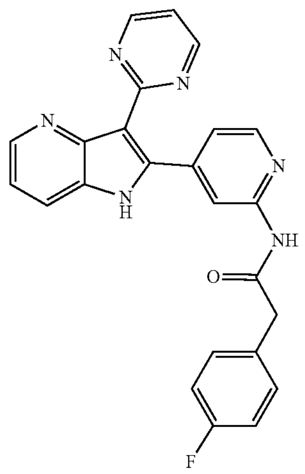 [SMILES: O=C(Cc1ccc(F)cc1)Nc1cc(-c2[nH]c3cccnc3c2-c2ncccn2)ccn1]

4-(3-pyrimidin-2-yl-1H-pyrrolo[3,2-b]pyridin-2-yl)pyridin-2-amine (Intermediate 93, 50.0 mg, 173.4 μmol) and 2-(4-fluorophenyl)acetic acid (53.46 mg, 346.85 μmol, CAS-RN: [405-50-5]) were dissolved in 1 mL of pyridine. A solution of T3P (331.09 mg, 0.520 mmol, 50% in DMF, CAS-RN: [68957-94-8]) was added. The reaction mixture was stirred at 25° C. for 2 h. The reaction was concentrated under reduced pressure to give a residue. The crude residue was purified by reverse phase preparative-HPLC (column: Phenomenex Gemini 150*25 mm*10 μm; mobile phase: [water (0.05% NH3H2O)-ACN]; B %: 15%-45%, 10 min) to provide the title compound in 95% purity: 16.89 mg, 37.8 μmol.

LC-MS (Method 3): $R_t$=1.144 min; MS (ESIpos): m/z=424.9 $[M+H]^+$ $^1$H NMR (400 MHz, DMSO-$d_6$) δ [ppm]=12.15 (s, 1H), 10.79 (s, 1H), 8.81 (d, J=4.8 Hz, 2H), 8.40 (dd, J=1.2, 4.6 Hz, 1H), 8.30 (d, J=5.2 Hz, 1H), 8.21 (s, 1H), 7.86 (dd, J=1.2, 8.0 Hz, 1H), 7.41-7.34 (m, 3H), 7.24 (dd, J=4.6, 8.4 Hz, 1H), 7.16 (t, J=8.8 Hz, 2H), 7.09 (dd, J=1.6, 5.2 Hz, 1H), 3.70 (s, 2H).

Example 52

N-{4-[6-chloro-3-(pyridin-2-yl)-1H-pyrrolo[3,2-b]pyridin-2-yl]pyridin-2-yl}-2-(4-fluorophenyl)propanamide

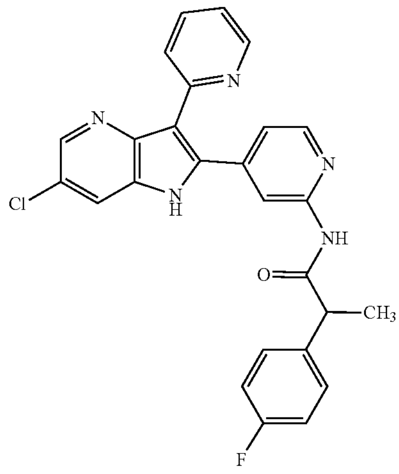 [SMILES: CC(C(=O)Nc1cc(-c2[nH]c3cc(Cl)cnc3c2-c2ccccn2)ccn1)c1ccc(F)cc1]

To a mixture of 2-(2-bromopyridin-4-yl)-6-chloro-3-(pyridin-2-yl)-1H-pyrrolo[3,2-b]pyridine (intermediate 96, 75.0 mg, 194 μmol) and 6-chloro-2-(2-chloropyridin-4-yl)-3-(pyridin-2-yl)-1H-pyrrolo[3,2-b]pyridine was added 2-(4-fluorophenyl)propanamide (intermediate 44, 48.8 mg, 292 μmol), cesium carbonate (190 mg, 583 μmol), tBuBrettPhos (18.9 mg, 38.9 μmol) and tBuBrettPhos Pd G3 (16.6 mg, 19.4 μmol). The mixture was dissolved in 1,4-dioxane (1.7 ml) and stirred at 100° C. under Ar atmosphere for 3 hours. The reaction mixture was diluted with methylene chloride and water. It was extracted three times with methylene chloride and the combined organic layer was washed once with water and brine, filtered through a silicone coated filter and concentrated under reduced pressure. The crude product was purified by HPLC chromatography (method K, gradient: 0.00-0.50 min 30% B, 0.50-6.00 min 30-70% B) followed by silica gel chromatography (hexane/ethyl acetate 50 to 100%, then ethyl acetate/ethanol 0 to 10%) to afford the title compound (11 mg, 12% yield).

LC-MS (Method 2): $R_t$=1.23 min; MS (ESIpos): m/z=472.2 $[M+H]^+$ $^1$H NMR (400 MHz, DMSO-$d_6$) δ [ppm 1.39 (d, 3H) 4.04 (q, 1H) 7.10 (dd, 1H) 7.14-7.21 (m, 2H) 7.28 (ddd, 1H) 7.36-7.47 (m, 2H) 7.87 (dt, 1H) 7.95 (d, 1H) 8.03 (td, 1H) 8.27 (dd, 1H) 8.35 (br s, 1H) 8.39-8.43 (m, 1H) 8.45 (d, 1H) 10.78 (s, 1H) 12.29 (s, 1H).

Experimental Section—Biological Assays

The following assays can be used to illustrate the commercial utility of the compounds according to the present invention.

Examples were tested in selected biological assays one or more times. When tested more than once, data are reported as either average values or as median values or single individual measurements, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Individual measurements are shown when median or average values cannot be computed.

Examples were synthesized one or more times. When synthesized more than once, data from biological assays represent average values calculated utilizing data sets obtained from testing of one or more synthetic batch.

The in vitro activity of the compounds of the present invention can be demonstrated in the following assays:

CSNK1A1 Assay 1

CSNK1A1-inhibitory activity of compounds of the present invention in presence of 1 μM adenosine-tri-phosphate (ATP) was quantified employing the CSNK1A1 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide Btn-Ahx-SGSEGDSESGEEEG (C-terminus in amide form) (SEQ ID NO: 1) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 μM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentration is 0.15 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1A1 Assay 2

CSNK1A1-inhibitory activity of compounds of the present invention in presence of 1 μM adenosine-tri-phosphate (ATP) was quantified employing the CSNK1A1 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Gio-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) (SEQ ID NO: 2) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 PM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentrations are about 0.0375 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1A1 High ATP Assay

CSNK1A1-inhibitory activity of compounds of the present invention in presence of 1 mM adenosine-tri-phosphate (ATP) was quantified employing the CSNK1A1-high-ATP-assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) (SEQ ID NO: 2) was used which can be purchased e.g. from the company Biosyntan (Berlin-Buch, Germany).

For the assay 50 nl of a 100 fold concentrated solution of the test compound in DMSO was pipetted into a white low volume 384-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 mM=>final conc. in the 5 μL assay volume is 1 mM) and peptide substrate (167 μM=>final conc. in the 5 μL assay volume is 100 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentration is about 0.4 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1D Assay

CSNK1 D-inhibitory activity of compounds of the present invention in presence of 1 μM adenosine-tri-phosphate (ATP) was quantified employing the CSNK1 D assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1 D, expressed by baculovirus infected insect cells and purified via Glutathion affinity chromatography, was purchased from Life Technologies (product no. PV3665) and used as enzyme. As substrate for the kinase reaction the biotinylated peptide Btn-Ahx-SGSEGDSESGEEEG (C-terminus in amide form) (SEQ ID NO: 1) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1 D in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 PM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1 D was adjusted depending of the activity of the enzyme lot and was chosen appropriate to have the assay in the linear range, a typical concentration is about 0.5 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1 D.

The data were normalised (enzyme reaction without inhibitor=0% inhibition, all other assay components but no enzyme=100% inhibition). Usually the test compounds were tested on the same microtiterplate in 11 different concentrations in the range of 20 PM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1G3 Assay

CSNK1G3-inhibitory activity of compounds of the present invention in presence of 1 μM adenosine-tri-phosphate (ATP) was quantified employing the CSNK1G3 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1G3, expressed by baculovirus infected insect cells and purified via Glutathion affinity chromatography, was purchased from Life Technologies (product no. PV3838) and used as enzyme. As substrate for the kinase reaction the biotinylated peptide biotin-Ahx-KRRRAL-pS-VASLPGL (C-terminus in amide form) (SEQ ID NO: 2) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1G3 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 μM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1G3 was adjusted depending of the activity of the enzyme lot and was chosen appropriate to have the assay in the linear range, a typical concentration is about 0.06 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1G3.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

WT-EGFR Kinase Assay

Inhibitory activity of compounds of the present invention against wild-type Epidermal Growth Factor Receptor (EGFR) was quantified employing the TR-FRET based EGFR assay as described in the following paragraphs.

Recombinant fusion protein of N-terminal Glutathion-S-Transferase (GST) and a fragment of human EGFR (amino acids R669 to A1210), expressed in Sf9 insect cells and purified via affinity chromatography using Glutathion Sepharose as described above, was used as kinase. As substrate for the kinase reaction the biotinylated peptide biotin-Ahx-AEEEEYFELVAKKK (C-terminus in amide form) (SEQ ID NO: 3) was used which can be purchased e.g. form the company Biosynthan GmbH (Berlin-Buch, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 μL of a solution of EGFR in aqueous assay buffer [50 mM Hepes pH 7.0, 10 mM $MgCl_2$, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 3.33 mM=>final conc. in the 5 μL assay volume is 2 mM) and substrate (1.67 μM=>final conc. in the 5 μL assay volume is 1 μM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 7.6 pg/μL. The reaction was stopped by the addition of 3 μL of a solution of HTRF detection reagents (83.3 nM streptavidine-XL665 [Cisbio Bioassays, Codolet, France] and 1.67 nM PT66-Tb-Cryptate, a terbium-cryptate labelled anti-phospho-tyrosine antibody from Cisbio Bioassays [instead of the PT66-Tb-cryptate PT66-Eu-Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

Bub1 Kinase Assay

Bub1-inhibitory activity of compounds of the present invention was quantified employing the Bub1 TR-FRET assay as described in the following paragraphs.

N-terminally $His_6$-tagged recombinant catalytic domain ("$His_6$" disclosed as SEQ ID NO: 5) of human Bub1 (amino acids 704-1085), expressed in insect cells (Hi5) and purified by Ni-NTA affinity chromatography and subsequent size exclusion chromatography, was used as enzyme.

As substrate for the kinase reaction the biotinylated peptide biotin-Ahx-VLLPKKSFAEPG (C-terminus in amid form) (SEQ ID NO: 4) was used which can be purchased e.g. form the company Biosyntan (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 μL of a solution of Bub1 in aqueous. assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 16.7 μM=>final conc. in the 5 μL assay volume is 10 μM) and substrate (1.67 μM=>final conc. in the 5 μL assay volume is 1 μM) in assay buffer and the resulting mixture was incubated for a reaction time of 60 min at 22° C. The concentration of Bub1 was adjusted depending of the activity of the enzyme lot and was chosen appropriate to have the assay in the linear range, typical concentrations were in the range of 200 ng/mL. The reaction was stopped by the addition of 5 μL of a solution of TR-FRET detection reagents (0.2 μM streptavidine-XL665 [Cisbio Bioassays, Codolet, France] and 1 nM anti-phosho-Serine antibody [Merck Millipore, cat. #35-002] and 0.4 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (50 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). The test compounds were tested on the same microtiterplate, usually in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions, the exact concentrations and the number of tested concentrations may vary depending on the liquid handling instrumentation used for test sample preparation) in duplicate values for each concentration and $IC_{50}$ values were calculated by a 4 parameter fit.

Bub1 High ATP Kinase Assay

Bub1-inhibitory activity of compounds of the present invention at a high ATP concentration was quantified employing the Bub1 TR-FRET high ATP kinase assay as described in the following paragraphs.

N-terminally $His_6$-tagged recombinant catalytic domain ("$His_6$" disclosed as SEQ ID NO: 5) of human Bub1 (amino acids 704-1085), expressed in insect cells (Hi5) and purified by Ni-NTA affinity chromatography and subsequent size exclusion chromatography, was used as enzyme.

As substrate for the kinase reaction the biotinylated peptide biotin-Ahx-VLLPKKSFAEPG (C-terminus in amid form) (SEQ ID NO: 4) was used which can be purchased e.g. form the company Biosyntan (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 3 μL of a solution of adenosine-tri-phosphate (ATP, 3.33 mM=>final conc. in the 5 μL assay volume is 2 mM) and substrate (1.67 μM=>final conc. in the 5 μL assay volume is 1 μM) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added. Then the kinase reaction was started by the addition of 2 μL of a solution of Bub1 in assay buffer and the resulting mixture was incubated for a reaction time of 60 min at 22° C. The concentration of Bub1 was adjusted depending of the activity of the enzyme lot and was chosen appropriate to have the assay in the linear range, a typical concentration is about 200 ng/mL. The reaction was stopped by the addition of 3 μL of a solution of TR-FRET detection reagents (0.167 μM streptavidine-XL665 [Cisbio Bioassays, Codolet, France] and 1.67 nM anti-phosho-Serine antibody [Merck Millipore, cat. #35-002] and 0.67 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (83.3 mM EDTA, 0.2% (w/v) bovine serum albumin in 100 mM HEPES pH 7.5).

The resulting mixture was incubated 1 h at 22° C. to allow the formation of complex between the phpsphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665-nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.0.7 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated by a 4 parameter fit.

Cellular Mechanistic Assays

P—RPS6 (Ser244/247) Ribosomal protein S6 The kinase CSNK1A phosphorylates Ribosomal protein S6 at Ser247. In-cell Western assay simultaneously detects two targets at 700 and 800 nm using two spectrally distinct near-infrared dyes. With a specific antibody, Ser244/247-phosphorylated RPS6 (Thermo Fisher 44-923) can be quantified and the samples can be normalized with cell stains Draq5 (Cell signaling, 4084L) and Sapphire700 (LiCor, 928-40022) in parallel.

2000 HCT 116 cells were seeded in growth medium (DMEM/Ham's F12, 10% FCS) in 96 well plate (Falcon 353075) over night at 37° C. Cells were treated with varying concentrations of test compounds at 37° C. for 4 h. Cells were fixed with 4% paraformaldehyde, washed (Sigma-Aldrich, AB351787, Tween 20, 1%) and blocked with buffer (Odyssey blocking buffer, LiCor, 927-40000) before incubating with the primary antibody (Ser244/247-phosphorylated RPS6 (Thermo Fisher 44-923) overnight at 2-8° C. After washing, secondary IRDye-labeled antibody mix with cell stains was added for 1 h and washed again. Plates were scanned with LiCor Odyssey Infrared Imager CLX at 800 nm for pRPS6 and at 700 nm for cell stains Draq5/Sapphire. The quotient of 800 nm and 700 nm for standard compound-treated cells was set as 0% and the quotient of 800 nm and 700 nm of DMSO treated cells was set as 100%. The results given as % reflecting the inhibition of Casein kinase activity compared to control and normalized according to cell number.

The $IC_{50}$ values were determined by means of a 4 parameter fit.

P—β-Catenin (Ser45)

50,000 DLD-1 cells were seeded in 96 well plates (nunc #161093) in RPMI 1640 (Biochrom; #FG 1215, 10% FCS, 2 mM L-Glutamine). After 24 h, cells were treated with varying concentrations of test compounds at 37° C. for 30 min. Cells were washed twice with ice-cold PBS buffer, treated with lysis buffer and all next steps were performed to the supplier's manual (β-Catenin pS45 ELISA Kit; ab205703). The content of pS45 was measured with ELISA at 450 nm, calculated with calibration curve and normalized to protein content. The normalized quotient of control compound-treated cells treated cells was set as 0% and the normalized quotient of untreated cells was set as 100%. The results given as % reflecting the content of β-Catenin pS45 compared to control. The $IC_{50}$ values were determined by means of a 4 parameter fit.

Proliferation Assays

HCT 116

400 HCT 116 cells/30 µL/well were plated in growth medium (DMEM/Ham's F12, 10% FCS) in a 384-well plate (CORNING #3571) at day 1. Reference plate was seeded for time zero determination. All plates were incubated overnight 37° C. Day 2: test compound was added in 7-step dilution and incubate at 37° C. for 96 h. Day 2: time zero plate: 30 µL/well CTG solution (Promega Cell Titer Glo solution; catalog #G755B and G756B) were added, incubated for 30 minutes, read luminescence on PheraStar. Day 6: compound treated plates: 30 µL/well CTG solution (Promega Cell Titer Glo solution; catalog #G755B and G756B) were added, incubated for 30 minutes, luminescence was read on PheraStar. Proliferation was calculated after subtracting time zero luminescence values from day 6 values and comparing to untreated wells.

The $IC_{50}$ values were determined using the four parameter fit.

A549

400 A549 cells/30 µL/well were plated in growth medium (DMEM/Ham's F12, 10% FCS) in a 384-well plate (CORNING #3571) at day 1. Reference plate was seeded for time zero determination. All plates were incubated overnight 37° C. Day 2: test compound was added in 7-step dilution and incubated at 37° C. for 96 h. Day 2: time zero plate: 30 µL/well CTG solution were added (Promega Cell Titer Glo solution; catalog #G755B and G756B), incubated for 30 minutes, luminescence was read on PheraStar. Day 6: compound treated plates: 30 µL/well CTG solution (Promega Cell Titer Glo solution; catalog #G755B and G756B) were added, incubated for 30 minutes, luminescence was read on PheraStar. Proliferation was calculated after subtracting time zero luminescence values from day 6 values and comparing to untreated wells.

The $IC_{50}$ values were determined using the four parameter fit.

TMD8

400 TMD8 cells/30 µL/well were plated in growth medium (RPM11640, 20% FCS) in a 384-well plate (CORNING #3571) at day 1. Reference plate was seeded for time zero determination. All plates were incubated overnight 37° C. Day 2: test compound was added in 7-step dilution and incubated at 37° C. for 96 h. Day 2: time zero plate: 30 L/well CTG solution (Promega Cell Titer Glo solution; catalog #G755B and G756B) were added, incubated 30 minutes, luminescence was read on PheraStar. Day 6: compound treated plates: 30 L/well CTG solution (Promega Cell Titer Glo solution; catalog #G755B and G756B) were added, incubated 30 minutes, luminescence was read on PheraStar. Proliferation was calculated after subtracting time zero luminescence values from day 6 values and comparing to untreated wells.

The $IC_{50}$ values were determined using the four parameter fit.

Results:

Table 2 shows the results of the inhibition in the CSNK1A1 and CSNK1 D biochemical assays.

TABLE 2

| Example No | CSNK1A1 Assay 1 $IC_{50}$ [mol/l] (median) | CSNK1A1 Assay 2 $IC_{50}$ [mol/l] (median) | CSNK1D $IC_{50}$ [mol/l] (median) | CSNK1A1 high ATP assay $IC_{50}$ [mol/l] (median) |
|---|---|---|---|---|
| 1 | | 1.66E−9 | 4.58E−9 | 1.60E−8 |
| 2 | | 1.09E−8 | 3.22E−8 | 8.86E−7 |
| 3 | | 1.00E−9 | 2.87E−9 | 1.20E−8 |
| 4 | | 7.39E−10 | 2.33E−9 | 5.72E−9 |
| 5 | | 1.06E−9 | 2.68E−9 | 6.10E−9 |
| 6 | | 1.73E−9 | 3.37E−9 | 8.47E−9 |
| 7 | | 9.49E−10 | 2.10E−9 | 4.32E−9 |
| 8 | | 7.53E−9 | 1.46E−8 | 3.34E−7 |
| 9 | | 1.68E−9 | 4.76E−9 | 3.36E−8 |
| 10 | | 3.83E−9 | 4.27E−9 | 3.02E−7 |
| 11 | | 6.11E−9 | 7.02E−9 | 3.21E−7 |
| 12 | | 3.70E−8 | | 2.51E−6 |
| 13 | | 1.66E−9 | | 9.16E−8 |
| 14 | | 1.04E−9 | 2.64E−9 | 4.55E−8 |
| 15 | | 1.87E−9 | 3.40E−9 | 8.77E−8 |
| 16 | | 4.77E−9 | 9.02E−9 | 9.79E−8 |
| 17 | | 1.88E−9 | 3.15E−9 | 8.73E−8 |
| 18 | | 3.33E−9 | | 2.60E−7 |
| 19 | | 1.02E−9 | | 3.31E−8 |
| 20 | | 1.30E−9 | | 7.79E−8 |
| 21 | | 1.66E−9 | 3.96E−9 | 2.51E−8 |
| 22 | | 1.60E−9 | 5.84E−9 | 2.18E−8 |
| 23 | | 9.41E−10 | 3.18E−9 | 4.09E−8 |
| 24 | | 4.79E−9 | 1.04E−8 | 4.30E−8 |
| 25 | | 2.39E−8 | 5.63E−8 | 2.32E−6 |
| 26 | | 3.50E−9 | 7.62E−9 | 4.86E−8 |
| 27 | | 1.60E−9 | 5.11E−9 | 1.12E−8 |
| 28 | | 4.61E−9 | 1.13E−8 | 5.91E−8 |
| 29 | | 1.38E−8 | 3.02E−8 | 1.14E−6 |
| 30 | | 1.69E−9 | 4.65E−9 | 2.37E−8 |
| 31 | | 2.50E−9 | 4.40E−9 | 5.63E−9 |
| 32 | | 2.50E−9 | 7.52E−9 | 2.33E−8 |
| 33 | | 3.97E−9 | 9.16E−9 | 2.90E−8 |
| 34 | | 3.08E−9 | 3.84E−9 | 1.35E−8 |
| 35 | | 2.79E−9 | 4.19E−9 | 6.39E−9 |
| 36 | | 1.48E−8 | 1.48E−8 | 3.18E−8 |
| 37 | | 4.00E−9 | 5.76E−9 | 9.53E−9 |
| 38 | | 3.32E−9 | 5.59E−9 | 1.98E−8 |
| 39 | | 3.49E−9 | 1.36E−8 | 3.29E−8 |
| 40 | | 6.26E−9 | 1.03E−8 | 3.01E−8 |
| 41 | | 4.03E−9 | 1.21E−8 | 1.90E−8 |
| 42 | | 1.23E−9 | 3.33E−9 | 7.14E−9 |
| 43 | | 3.51E−9 | 6.46E−9 | 4.01E−8 |
| 44 | | 4.97E−9 | 9.84E−9 | 5.92E−8 |
| 45 | | 4.83E−9 | 1.20E−8 | 3.88E−8 |
| 46 | | 2.25E−9 | 5.77E−9 | 1.46E−8 |
| 47 | | 2.79E−9 | 7.39E−9 | 1.58E−7 |
| 48 | | 1.69E−9 | 3.96E−9 | 3.61E−8 |
| 49 | | 3.45E−8 | 3.31E−8 | 2.58E−6 |
| 50 | | 1.42E−9 | 3.15E−9 | 4.16E−8 |
| 51 | | 7.93E−9 | 2.00E−8 | 1.80E−7 |
| 52 | | 6.26E−9 | 2.05E−8 | 3.82E−7 |

TABLE 3

| Example No | EGFR Wildtype 2 mM ATP $IC_{50}$ [mol/l] (median) |
|---|---|
| 1 | >2.00E−5 |
| 2 | >2.00E−5 |
| 3 | >2.00E−5 |
| 4 | >2.00E−5 |
| 5 | >2.00E−5 |
| 6 | >2.00E−5 |
| 7 | >2.00E−5 |
| 8 | >2.00E−5 |
| 9 | >2.00E−5 |
| 10 | >2.00E−5 |
| 11 | >2.00E−5 |
| 12 | >2.00E−5 |

TABLE 3-continued

| Example No | EGFR Wildtype 2 mM ATP $IC_{50}$ [mol/l] (median) |
|---|---|
| 13 | >2.00E−5 |
| 14 | 1.91E−5 |
| | >2.00E−5 |
| 15 | >2.00E−5 |
| 16 | >2.00E−5 |
| | 1.75E−5 |
| 17 | >2.00E−5 |
| 18 | >2.00E−5 |
| 19 | >2.00E−5 |
| 20 | >2.00E−5 |
| 21 | >2.00E−5 |
| 22 | >2.00E−5 |
| 23 | >2.00E−5 |
| 24 | >2.00E−5 |
| 25 | >2.00E−5 |
| 26 | >2.00E−5 |
| 27 | >2.00E−5 |
| 28 | >2.00E−5 |
| 29 | >2.00E−5 |
| 30 | >2.00E−5 |
| 31 | >2.00E−5 |
| 32 | >2.00E−5 |
| 33 | 1.51E−5 |
| 34 | >2.00E−5 |
| 35 | >2.00E−5 |
| 36 | >2.00E−5 |
| 37 | >2.00E−5 |
| 38 | >2.00E−5 |
| 39 | 1.09E−6 |
| 40 | >2.00E−5 |
| 41 | >2.00E−5 |
| 42 | >2.00E−5 |
| 43 | >2.00E−5 |
| 44 | >2.00E−5 |
| 45 | >2.00E−5 |
| 46 | >2.00E−5 |
| 47 | |
| 48 | |
| 49 | |
| 50 | |
| 51 | >2.00E−5 |
| 52 | >2.00E−5 |

It has now been found that compounds of the present invention have surprising and advantageous combined properties. In particular, compounds of the present invention have surprisingly been found to effectively inhibit CSNK1A1. Furthermore, in certain embodiments, compounds of the present invention additionally show low inhibition of wild type-EGFR kinase. In certain embodiments, compounds of the present invention display an $IC_{50}$ below 100 nM in a CSNK1A1 kinase assay in the presence of 1 μM ATP and are less potent than 600 nM in a wild type-EGFR kinase assay in the presence of 2 mM ATP.

In certain embodiments, compounds of the present invention display an $IC_{50}$ below 125 nM in a CSNK1A1 kinase assay in the presence of 1 mM ATP and are less potent than 100 nM in a wild type-EGFR kinase assay in the presence of 2 mM ATP.

In contrast to the claimed compounds of this invention the compounds claimed in WO 2016/120196 do not show the advantageous combined properties described above. This can be seen in Table 4.

TABLE 4

| WO 2016/120196 Example No. | CSNK1A1 Assay 1 $IC_{50}$ [mol/l] (median) | CSNK1A1 Assay 2 $IC_{50}$ [mol/l] (median) | EGFR Wildtype-2 mM ATP $IC_{50}$ [mol/l] (median) |
|---|---|---|---|
| 14 | 2.03E−8 | | 1.04E−7 |
| 23 | | 1.14E−8 | 1.50E−7 |
| 24 | <3.43E−9 | 4.51E−9 | 4.26E−8 |
| | 9.32E−9 | | |
| | 1.01E−8 | | |
| | 5.57E−9 | | |
| | 4.38E−9 | | |
| 25 | 6.25E−8 | | 3.21E−7 |
| 40 | 2.41E−8 | | 8.55E−8 |

The invention claimed is:

1. A compound of formula (I)

(I)

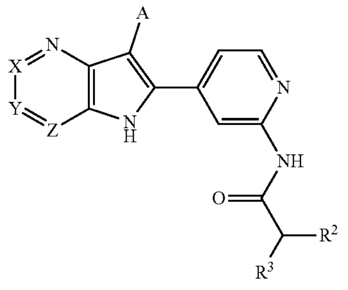

wherein:

A represents a group selected from:

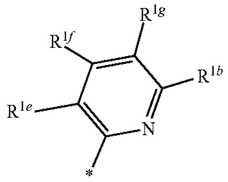

and

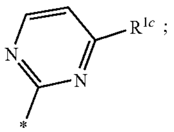

;

X represents N, C—H, C—F, $C_1$-$C_1$, or C-Me;

Y represents N or C—$R^{4a}$;

Z represents N or C—$R^{4b}$, wherein none or one of X, Y, and Z represents N;

$R^{1b}$ represents hydrogen or halogen;

$R^{1c}$ represents hydrogen or fluoro;

$R^{1e}$ represents hydrogen or fluoro;

$R^{1f}$ represents hydrogen or fluoro;

$R^{1g}$ represents hydrogen or fluoro;

$R^2$ represents hydrogen, halogen, methoxy, cyano, $C_1$-$C_2$-alkyl, or $C_1$-$C_3$-alkoxy-$C_1$-$C_3$-alkyl-;

$R^3$ represents phenyl, wherein said phenyl is independently optionally substituted, one or more times, with halogen, methyl, methoxy, $C_1$-$C_2$-haloalkyl, or $C_1$-$C_2$-haloalkoxy;

$R^{4a}$ represents hydrogen, halogen, $C_1$-$C_3$-alkyl, $C_2$-alkenyl, methoxy, difluoromethoxy, $C_3$-cycloalkyl, 4-membered heterocycloalkyl, cyclopropyloxy, 4-membered heterocycloalkyl-O—, or $R^{5a}R^{6a}N$—;

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_5$-cycloalkyl, $C_3$-$C_5$-cycloalkyl-$C_1$-$C_2$-alkyl, $C_3$-$C_5$-cycloalkyl-O—, $C_3$-$C_5$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl, or $C_1$-$C_4$-hydroxyalkyl-O—, wherein said $C_3$-$C_5$-cycloalkyl, $C_3$-$C_5$-cycloalkyl $C_1$-$C_2$-alkyl, $C_3$-$C_5$-cycloalkyl-O—, $C_3$-$C_5$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_1$-$C_3$-alkyl-, $C_1$-$C_3$-alkoxy-$C_2$-$C_3$-alkoxy-, $C_1$-$C_4$-hydroxyalkyl, and $C_1$-$C_4$-hydroxyalkyl-O— groups are optionally substituted, one, two or three times, with halogen, methyl, or methoxy;

$R^{5a}$ represents hydrogen or methyl;

$R^{6a}$ represents hydrogen or methyl, or $R^{5a}$ and $R^{6a}$, together with the nitrogen atom to which they are attached, represent a 4-membered heterocyclic ring, wherein said heterocyclic ring is optionally substituted with methyl;

or an N-oxide, a salt, a tautomer or a stereoisomer of said compound, or a salt of said N-oxide, tautomer or stereoisomer.

2. The compound of formula (I) according to claim 1, wherein:

A represents a group selected from:

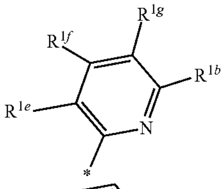

and

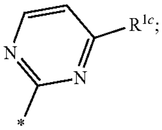

;

X represents N, C—H, C—F, or C—Cl;

Y represents N or C—$R^{4a}$;

Z represents N or C—$R^{4b}$, wherein none or one of X, Y and Z represents N;

$R^{1b}$ represents hydrogen or fluoro;

$R^{1c}$ represents hydrogen;

$R^{1e}$ represents hydrogen;

$R^{1f}$ represents hydrogen or fluoro;

$R^{1g}$ represents hydrogen or fluoro;

$R^2$ represents hydrogen, $C_1$-$C_2$-alkyl, or $C_1$-$C_2$-alkoxy-$C_1$-$C_2$-alkyl-;

$R^3$ represents phenyl, wherein said phenyl is independently optionally substituted, one or more times, with halogen, methyl, or $C_1$-haloalkyl;

$R^{4a}$ represents hydrogen, halogen, $C_1$-alkyl, $C_2$-alkenyl, $C_3$-cycloalkyl, 4-membered heterocycloalkyl, or $R^{5a}R^{6a}N$—;

$R^{4b}$ represents hydrogen, halogen, $C_1$-$C_4$-alkyl, $C_2$-$C_4$-alkenyl, $C_1$-$C_3$-haloalkyl-$CH_2$—, $C_1$-$C_3$-alkoxy, $C_1$-$C_3$-haloalkoxy, $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—, wherein said $C_3$-$C_4$-cycloalkyl, $C_3$-$C_4$-cycloalkyl-$C_1$-$C_2$-alkyl, $C_3$-$C_4$-cycloalkyl-O—, $C_3$-$C_4$-cycloalkyl-$CH_2$—O—, 3- to 6-membered heterocycloalkyl, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, piperazin-1-yl, morpholin-4-yl, $C_1$-$C_3$-alkoxy-$C_2$-$C_3$-alkoxy-, $C_1$-$C_4$-hydroxyalkyl and $C_1$-$C_4$-hydroxyalkyl-O— groups are optionally substituted, one or two times, with halogen or methyl;

$R^{5a}$ represents hydrogen or methyl;

$R^{6a}$ represents hydrogen or methyl, or $R^{5a}$ and $R^{6a}$, together with the nitrogen atom to which they are attached, represent a 4-membered heterocyclic ring;

or an N-oxide, a salt, a tautomer or a stereoisomer of said compound, or a salt of said N-oxide, tautomer or stereoisomer.

3. The compound of formula (I) according to claim 2, wherein:

A represents:

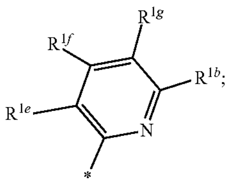

X represents C—H, C—F;

Y represents N or C—$R^{4a}$;

Z represents N or C—$R^{4b}$;

wherein none or one of Y and Z represents N;

$R^{1b}$ represents hydrogen or fluoro;

$R^{1e}$ represents hydrogen;

$R^{1f}$ represents hydrogen;

$R^{1g}$ represents hydrogen or fluoro;

$R^2$ represents hydrogen, methyl, or $C_1$-alkoxy-$C_1$-$C_2$-alkyl-;

$R^3$ represents phenyl, wherein said phenyl is independently optionally substituted, one or more times, with halogen or methyl;

$R^{4a}$ represents hydrogen, halogen, or methyl;

$R^{4b}$ represents hydrogen, halogen, $C_1$-$C_4$-alkyl, $C_1$-$C_3$-haloalkyl-$CH_2$—, $C_1$-$C_3$-alkoxy, $C_1$-$C_3$-haloalkoxy, $C_3$-cycloalkyl, $C_3$-cycloalkyl-$C_1$-$C_2$-alkyl, $C_3$-cycloalkyl-O—, $C_3$-cycloalkyl-$CH_2$—O—, piperazin-1-yl, morpholin-4-yl, 3- to 6-membered heterocycloalkyl connected via a carbon atom thereof, pyrrolidin-2-one, piperidin-2-one, morpholin-3-one, 4-methylpiperazin-2-one, 3- to 6-membered heterocycloalkyl-O—, 3- to 6-membered heterocycloalkyl-$CH_2$—O—, $C_1$-$C_3$-alkoxy-$C_2$-$C_3$-alkoxy-, $C_1$-$C_4$-hydroxyalkyl, or $C_1$-$C_4$-hydroxyalkyl-O—;

or an N-oxide, a salt, a tautomer or a stereoisomer of said compound, or a salt of said N-oxide, tautomer or stereoisomer.

4. A compound selected from:

2-(4-fluorophenyl)-N-{4-[5-fluoro-3-(pyridin-2-yl)-1H-pyrrolo[3,2-b]pyridin-2-yl]pyridin-2-yl}propanamide;

(2R)-2-(4-fluorophenyl)-N-{4-[5-fluoro-3-(pyridin-2-yl)-1H-pyrrolo[3,2-b]pyridin-2-yl]pyridin-2-yl}propanamide;

(2S)-2-(4-fluorophenyl)-N-{4-[5-fluoro-3-(pyridin-2-yl)-1H-pyrrolo[3,2-b]pyridin-2-yl]pyridin-2-yl}propanamide;

2-(4-fluorophenyl)-N-{4-[5-fluoro-3-(pyridin-2-yl)-1H-pyrrolo[3,2-b]pyridin-2-yl]pyridin-2-yl}acetamide;

2-(4-fluorophenyl)-N-{4-[3-(pyridin-2-yl)-1H-pyrrolo[3,2-b]pyridin-2-yl]pyridin-2-yl}acetamide 2-(4-fluorophenyl)-N-{4-[3-(pyridin-2-yl)-1H-pyrrolo[3,2-b]pyridin-2-yl]pyridin-2-yl}propanamide;

(2R)-2-(4-fluorophenyl)-N-{4-[3-(pyridin-2-yl)-1H-pyrrolo[3,2-b]pyridin-2-yl]pyridin-2-yl}propanamide;

(2S)-2-(4-fluorophenyl)-N-{4-[3-(pyridin-2-yl)-1H-pyrrolo[3,2-b]pyridin-2-yl]pyridin-2-yl}propanamide;

2-(4-fluorophenyl)-N-{4-[6-fluoro-3-(pyridin-2-yl)-1H-pyrrolo[3,2-b]pyridin-2-yl]pyridin-2-yl}acetamide;

2-(4-fluorophenyl)-N-[4-(6-fluoro-3-phenyl-1H-pyrrolo[3,2-b]pyridin-2-yl)pyridin-2-yl]acetamide;

2-(4-fluorophenyl)-N-[4-(3-phenyl-1H-pyrrolo[3,2-b]pyridin-2-yl)pyridin-2-yl]propanamide;

(2R)-2-(4-fluorophenyl)-N-[4-(3-phenyl-1H-pyrrolo[3,2-b]pyridin-2-yl)pyridin-2-yl]propanamide;

(2S)-2-(4-fluorophenyl)-N-[4-(3-phenyl-1H-pyrrolo[3,2-b]pyridin-2-yl)pyridin-2-yl]propanamide;

2-(4-fluorophenyl)-N-[4-(3-phenyl-1H-pyrrolo[3,2-b]pyridin-2-yl)pyridin-2-yl]acetamide;

2-(4-fluorophenyl)-N-{4-[3-(3-fluorophenyl)-1H-pyrrolo[3,2-b]pyridin-2-yl]pyridin-2-yl}acetamide;

formic acid salt of 2-(4-fluorophenyl)-N-{4-[3-(pyrimidin-2-yl)-1H-pyrrolo[3,2-b]pyridin-2-yl]pyridin-2-yl}acetamide;

N-{4-[3-(5-chlorothiophen-2-yl)-1H-pyrrolo[3,2-b]pyridin-2-yl]pyridin-2-yl}-2-(4-fluorophenyl)acetamide;

2-(4-fluorophenyl)-N-[4-(7-phenyl-5H-pyrrolo[2,3-b]pyrazin-6-yl)pyridin-2-yl]acetamide;

2-(4-fluorophenyl)-N-{4-[7-(pyridin-2-yl)-5H-pyrrolo[2,3-b]pyrazin-6-yl]pyridin-2-yl}acetamide;

2-(4-fluorophenyl)-N-[4-(7-phenyl-5H-pyrrolo[3,2-c]pyridazin-6-yl)pyridin-2-yl]acetamide;

2-(4-fluorophenyl)-N-{4-[7-(pyridin-2-yl)-5H-pyrrolo[3,2-c]pyridazin-6-yl]pyridin-2-yl}acetamide;

N-{4-[7-chloro-3-(pyridin-2-yl)-1H-pyrrolo[3,2-b]pyridin-2-yl]pyridin-2-yl}-2-(4-fluorophenyl)acetamide;

N-{4-[5-chloro-3-(pyridin-2-yl)-1H-pyrrolo[3,2-b]pyridin-2-yl]pyridin-2-yl}-2-(4-fluorophenyl)acetamide;

(2RS)-2-(4-fluorophenyl)-N-{4-[5-fluoro-3-(pyridin-2-yl)-1H-pyrrolo[3,2-b]pyridin-2-yl]pyridin-2-yl}-3-methylbutanamide;

(2R)-2-(4-fluorophenyl)-N-{4-[5-fluoro-3-(pyridin-2-yl)-1H-pyrrolo[3,2-b]pyridin-2-yl]pyridin-2-yl}-3-methylbutanamide;

(2S)-2-(4-fluorophenyl)-N-{4-[5-fluoro-3-(pyridin-2-yl)-1H-pyrrolo[3,2-b]pyridin-2-yl]pyridin-2-yl}-3-methylbutanamide;

N-{4-[5-fluoro-6-methyl-3-(pyridin-2-yl)-1H-pyrrolo[3,2-b]pyridin-2-yl]pyridin-2-yl}-2-(4-fluorophenyl)acetamide;

(2RS)—N-{4-[5-fluoro-6-methyl-3-(pyridin-2-yl)-1H-pyrrolo[3,2-b]pyridin-2-yl]pyridin-2-yl}-2-(4-fluorophenyl)propanamide;

(2R)—N-{4-[5-fluoro-6-methyl-3-(pyridin-2-yl)-1H-pyrrolo[3,2-b]pyridin-2-yl]pyridin-2-yl}-2-(4-fluorophenyl)propanamide;

(2S)—N-{4-[5-fluoro-6-methyl-3-(pyridin-2-yl)-1H-pyrrolo[3,2-b]pyridin-2-yl]pyridin-2-yl}-2-(4-fluorophenyl)propanamide;

2-(4-fluorophenyl)-N-{4-[7-methoxy-3-(pyridin-2-yl)-1H-pyrrolo[3,2-b]pyridin-2-yl]pyridin-2-yl}acetamide;
2-(4-fluorophenyl)-N-{4-[5-methoxy-3-(pyridin-2-yl)-1H-pyrrolo[3,2-b]pyridin-2-yl]pyridin-2-yl}acetamide;
N-{4-[7-ethenyl-3-(pyridin-2-yl)-1H-pyrrolo[3,2-b]pyridin-2-yl]pyridin-2-yl}-2-(4-fluorophenyl)acetamide;
N-{4-[7-ethyl-3-(pyridin-2-yl)-1H-pyrrolo[3,2-b]pyridin-2-yl]pyridin-2-yl}-2-(4-fluorophenyl)acetamide;
N-{4-[7-cyclopropyl-3-(pyridin-2-yl)-1H-pyrrolo[3,2-b]pyridin-2-yl]pyridin-2-yl}-2-(4-fluorophenyl)acetamide;
2-(4-fluorophenyl)-N-{4-[7-(2-methoxyethyl)-3-(pyridin-2-yl)-1H-pyrrolo[3,2-b]pyridin-2-yl]pyridin-2-yl}acetamide;
N-{4-[7-(cyclopropylmethyl)-5-fluoro-3-(pyridin-2-yl)-1H-pyrrolo[3,2-b]pyridin-2-yl]pyridin-2-yl}-2-(4-fluorophenyl)acetamide;
2-(4-fluorophenyl)-N-{4-[7-(4-methylpiperazin-1-yl)-3-(pyridin-2-yl)-1H-pyrrolo[3,2-b]pyridin-2-yl]pyridin-2-yl}acetamide;
2-(4-fluorophenyl)-N-(4-{7-[methyl(1-methylpiperidin-4-yl)amino]-3-(pyridin-2-yl)-1H-pyrrolo[3,2-b]pyridin-2-yl}pyridin-2-yl)acetamide;
2-(4-fluorophenyl)-N-{4-[7-(2-oxopyrrolidin-1-yl)-3-(pyridin-2-yl)-1H-pyrrolo[3,2-b]pyridin-2-yl]pyridin-2-yl}acetamide;
2-(4-fluoro-3-methylphenyl)-N-{4-[3-(pyridin-2-yl)-1H-pyrrolo[3,2-b]pyridin-2-yl]pyridin-2-yl}acetamide;
2-(4-chlorophenyl)-N-{4-[3-(pyridin-2-yl)-1H-pyrrolo[3,2-b]pyridin-2-yl]pyridin-2-yl}acetamide;
(2RS)-2-(4-fluorophenyl)-3-methoxy-N-(4-(3-(pyridin-2-yl)-1H-pyrrolo[3,2-b]pyridin-2-yl)pyridin-2-yl)propanamide;
(2RS)-4-methoxy-2-phenyl-N-(4-(3-(pyridin-2-yl)-1H-pyrrolo[3,2-b]pyridin-2-yl)pyridin-2-yl)butanamide;
(2RS)-2-(4-fluorophenyl)-N-[4-[6-fluoro-3-(2-pyridyl)-1H-pyrrolo[3,2-b]pyridin-2-yl]-2-pyridyl]-3-methoxypropanamide;
2-phenyl-N-(4-(3-(pyridin-2-yl)-1H-pyrrolo[3,2-b]pyridin-2-yl)pyridin-2-yl)acetamide;
(2RS)-4,4-difluoro-N-{4-[5-fluoro-3-(5-fluoropyridin-2-yl)-1H-pyrrolo[3,2-b]pyridin-2-yl]pyridin-2-yl}-2-(4-fluorophenyl)butanamide;
(2R)—N-{4-[5-fluoro-3-(5-fluoropyridin-2-yl)-1H-pyrrolo[3,2-b]pyridin-2-yl]pyridin-2-yl}-2-(4-fluorophenyl)propanamide;
(2S)—N-{4-[5-fluoro-3-(5-fluoropyridin-2-yl)-1H-pyrrolo[3,2-b]pyridin-2-yl]pyridin-2-yl}-2-(4-fluorophenyl)propanamide;
N-{4-[5-fluoro-3-(5-fluoropyridin-2-yl)-1H-pyrrolo[3,2-b]pyridin-2-yl]pyridin-2-yl}-2-(4-fluorophenyl)acetamide;
2-(4-fluorophenyl)-N-{4-[3-(pyrimidin-2-yl)-1H-pyrrolo[3,2-b]pyridin-2-yl]pyridin-2-yl}acetamide;
N-{4-[6-chloro-3-(pyridin-2-yl)-1H-pyrrolo[3,2-b]pyridin-2-yl]pyridin-2-yl}-2-(4-fluorophenyl)propanamide;

or an N-oxide, a salt, a tautomer or a stereoisomer of said compound, or a salt of said N-oxide, tautomer or stereoisomer.

5. A method of preparing a compound of general formula (I) according to claim 1, said method comprising reacting an intermediate compound of general formula (VII-A):

(VII-A)

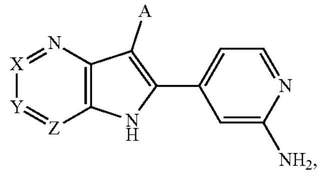

in which A, X, Y and Z are as defined for the compound of general formula (I) according to claim 1, with an acylating reagent selected from:

a) a carboxylic acid of formula

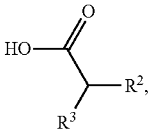

b) an acyl halide of formula

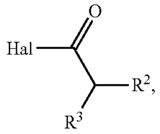

wherein Hal represents F, Cl, or Br, or c) an anhydride of formula

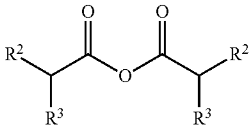 or

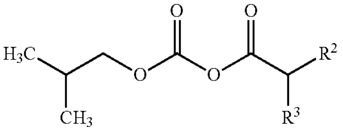

in which $R^2$ and $R^3$ are as defined for the compound of general formula (I) according to claim 1, to give a compound of general formula (I):

(I)

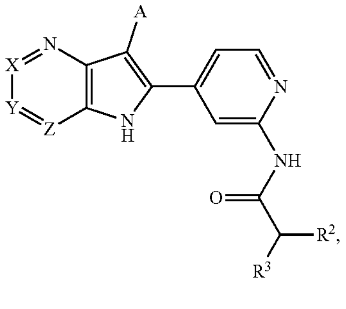

in which $R^2$, $R^3$, A, X, Y and Z are as defined for the compound of general formula (I) according to claim 1.

6. A method of treating or preventing a hyperproliferative disease and/or a disorder responsive to induction of cell death in a subject, comprising administering a compound of general formula (I) according to claim 1 to the subject.

7. The method according to claim 6, wherein the hyperproliferative disease and/or disorder responsive to induction of cell death are haematological tumours, solid tumours and/or metastases thereof.

8. The method according to claim 7, wherein the haematological tumour is a lymphoma and/or metastases thereof.

9. The method according to claim 8, wherein the lymphoma is diffuse large B-cell lymphoma and/or metastases thereof.

10. The method according to claim 7, wherein the solid tumour is a cervical tumour, a lung tumour, a colon tumour and/or metastases thereof.

11. The method according to claim 10, wherein the lung tumour is a lung carcinoma and/or metastases thereof.

12. The method according to claim 10, wherein the colon tumour is a colorectal carcinoma and/or metastases thereof.

13. A pharmaceutical composition comprising at least one compound of general formula (I) according to claim 1, together with at least one pharmaceutically acceptable auxiliary.

14. A combination comprising one or more first active ingredients selected from a compound of general formula (I) according to claim 1, and one or more second active ingredients selected from chemotherapeutic anti-cancer agents and target-specific anti-cancer agents.

15. An intermediate compound of general formula (IX-Q), (IX-A), (XIV-Q) or (XVII), or a salt thereof:

(IX-Q)

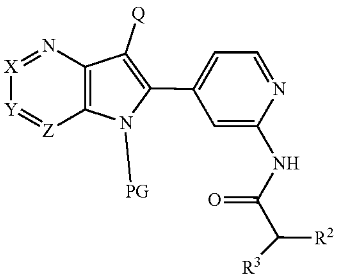

(IX-A)

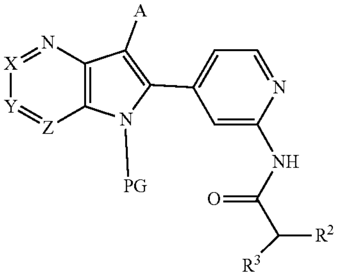

(XIV-Q)

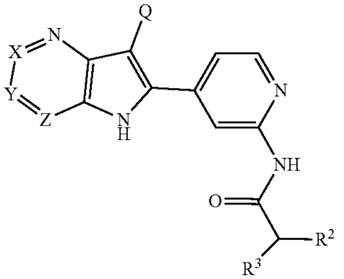

-continued (XVII)

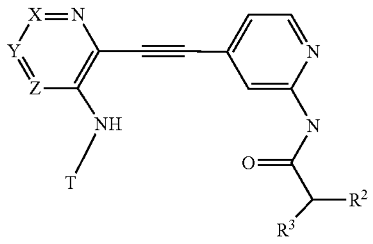

wherein $R^2$, $R^3$, X, Y and Z are as defined for the compound of general formula (I) according to claim 1 Q represents a chloro, a bromo or an iodo, PG represents a protecting group and T represents $CF_3$—C(O)—, mesylate, tosylate or Ph-$SO_2$—, wherein Ph can be substituted one, two or three times with halogen or a methyl-group or a nitro-group.

16. A method of preparing a compound of general formula (I) according to claim 1, said method comprising reacting an intermediate compound of general formula (XIV-Q):

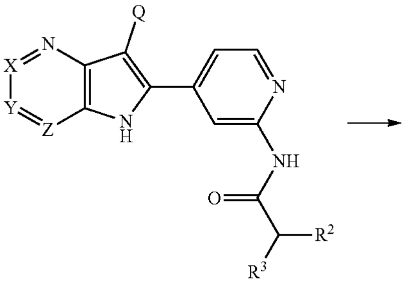

(XIV-Q)

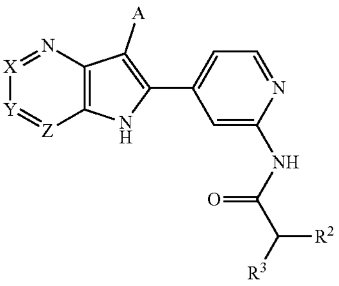

(I)

wherein $R^2$, $R^3$, X, Y and Z are as defined for the compound of general formula (I) according to claim 1, and Q represents a chloro, a bromo or an iodo, with a stannane or a boronic acid A-B$(OH)_2$ or a boronic acid ester thereof, in which A is as defined for the compound of general formula (I), in the presence of a palladium catalyst, to prepare compounds of general formula (I).

17. A method of preparing a compound of general formula (I) according to claim 1, said method comprising reacting an intermediate compound of general formula (XVII):

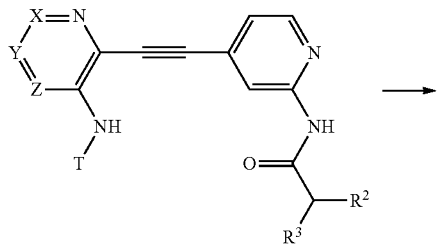

(XVII)

-continued

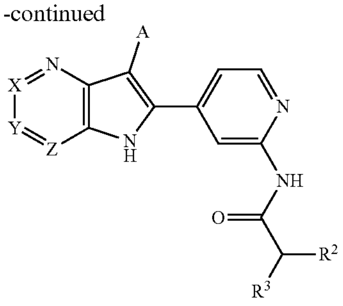

(I)

wherein $R^2$, $R^3$, X, Y and Z are as defined for the compound of general formula (I) according to claim 1, and T represents $CF_3$—C(O)—, mesylate, tosylate or Ph-$SO_2$—, wherein Ph can be substituted one, two or three times with halogen, methyl, or nitro, with A-Br or A-I, in which A is as defined for the compound of general formula (I), in the presence of a palladium catalyst, in a Cacchi reaction, to directly provide compounds of general formula (I) or to provide compounds of general formula (I) after removal of the group T.

* * * * *

SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Biotin-6-Aminohexanoic Acid
<220> FEATURE:
<223> OTHER INFORMATION: C-term amidated

<400> SEQUENCE: 1

Xaa Ser Gly Ser Glu Gly Asp Ser Glu Ser Gly Glu Glu Glu Gly
1               5                   10                  15

<210> SEQ ID NO 2
<211> LENGTH: 15
<212> TYPE: PRT

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Biotin-6-Aminohexanoic Acid
<220> FEATURE:
<221> NAME/KEY: MOD_RES
<222> LOCATION: (8)..(8)
<223> OTHER INFORMATION: phospho-Serine

<400> SEQUENCE: 2

```
Xaa Lys Arg Arg Arg Ala Leu Ser Val Ala Ser Leu Pro Gly Leu
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Biotin-6-Aminohexanoic Acid

<400> SEQUENCE: 3

```
Xaa Ala Glu Glu Glu Glu Tyr Phe Glu Leu Val Ala Lys Lys Lys
1               5                   10                  15
```

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Biotin-6-Aminohexanoic Acid

<400> SEQUENCE: 4

```
Xaa Val Leu Leu Pro Lys Lys Ser Phe Ala Glu Pro Gly
1               5                   10
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

```
His His His His His His
1               5
```